US011826013B2

(12) United States Patent
Parks

(10) Patent No.: US 11,826,013 B2
(45) Date of Patent: Nov. 28, 2023

(54) SURGICAL INSTRUMENTS WITH FIRING MEMBER CLOSURE FEATURES

(71) Applicant: Cilag GmbH International, Zug (CH)

(72) Inventor: Darryl A. Parks, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/360,139

(22) Filed: Jun. 28, 2021

(65) Prior Publication Data

US 2022/0031322 A1 Feb. 3, 2022

Related U.S. Application Data

(60) Provisional application No. 63/057,430, filed on Jul. 28, 2020, provisional application No. 63/057,432, filed on Jul. 28, 2020.

(51) Int. Cl.
*A61B 17/072* (2006.01)
*F16H 55/22* (2006.01)
(Continued)

(52) U.S. Cl.
CPC .... *A61B 17/0686* (2013.01); *A61B 17/00234* (2013.01); *A61B 17/068* (2013.01); *A61B 17/072* (2013.01); *A61B 17/07207* (2013.01); *A61B 17/29* (2013.01); *A61B 17/320092* (2013.01); *A61B 34/30* (2016.02); *A61B 2017/00314* (2013.01);
(Continued)

(58) Field of Classification Search
CPC ........... A61B 2017/320094; F61H 1/16; F61H 25/2015; F61H 2055/0893; F61H 55/22; F61H 55/24; F16H 1/16; F16H 25/2015; F16H 2055/0893; F16H 55/22; F16H 55/24; F16H 55/26
See application file for complete search history.

(56) References Cited

U.S. PATENT DOCUMENTS 66,052 A 6/1867 Smith
662,587 A 11/1900 Blake
(Continued)

FOREIGN PATENT DOCUMENTS

AU 2012200594 A1 2/2012
AU 2012203035 A1 6/2012
(Continued)

OTHER PUBLICATIONS

ASTM procedure D2240-00, "Standard Test Method for Rubber Property-Durometer Hardness," (Published Aug. 2000).
(Continued)

*Primary Examiner* — Thanh K Truong
*Assistant Examiner* — Patrick B Fry
(74) *Attorney, Agent, or Firm* — Frost Brown Todd LLP

(57) ABSTRACT

Surgical end effectors with first and second jaws that are opened and closed with an axially movable firing member. The firing member is configured to apply a first closure motion to the second jaw to move the second jaw from an open position to a closed position as the firing member is moved in a distal direction from a home position to an ending position. The firing member is further configured to move the second jaw towards the first jaw when the firing member is moved in a proximal direction from the home position.

32 Claims, 59 Drawing Sheets

(51) Int. Cl.

| | |
|---|---|
| ***A61B 17/068*** | (2006.01) |
| ***A61B 17/32*** | (2006.01) |
| ***A61B 17/29*** | (2006.01) |
| ***A61B 34/30*** | (2016.01) |
| ***A61B 17/00*** | (2006.01) |

(52) U.S. Cl.
CPC ............... *A61B 2017/00323* (2013.01); *A61B 2017/00336* (2013.01); *A61B 2017/00367* (2013.01); *A61B 2017/00389* (2013.01); *A61B 2017/00398* (2013.01); *A61B 2017/00477* (2013.01); *A61B 2017/07214* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01); *A61B 2017/320071* (2017.08); *A61B 2017/320093* (2017.08); *A61B 2017/320094* (2017.08); *A61B 2017/320095* (2017.08); *A61B 2017/320097* (2017.08); *A61B 2034/301* (2016.02)

(56) References Cited

U.S. PATENT DOCUMENTS

| | | | |
|---|---|---|---|
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |
| 1,306,107 | A | 6/1919 | Elliott |
| 1,314,601 | A | 9/1919 | McCaskey |
| 1,677,337 | A | 7/1928 | Grove |
| 1,794,907 | A | 3/1931 | Kelly |
| 1,849,427 | A | 3/1932 | Hook |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,882 | A | 12/1940 | Peck |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,608,549 | A | 9/1971 | Merrill |
| 3,618,842 | A | 11/1971 | Bryan |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,688,966 | A | 9/1972 | Perkins et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |

(56) References Cited

U.S. PATENT DOCUMENTS 3,955,581 A 5/1976 Spasiano et al.
3,959,879 A 6/1976 Sellers
RE28,932 E 8/1976 Noiles et al.
3,972,734 A 8/1976 King
3,973,179 A 8/1976 Weber et al.
3,981,051 A 9/1976 Brumlik
3,999,110 A 12/1976 Ramstrom et al.
4,025,216 A 5/1977 Hives
4,027,746 A 6/1977 Kine
4,034,143 A 7/1977 Sweet
4,038,987 A 8/1977 Komiya
4,054,108 A 10/1977 Gill
4,060,089 A 11/1977 Noiles
4,066,133 A 1/1978 Voss
4,085,337 A 4/1978 Moeller
4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale
4,154,122 A 5/1979 Severin
4,160,857 A 7/1979 Nardella et al.
4,169,990 A 10/1979 Lerdman
4,180,285 A 12/1979 Reneau
4,185,701 A 1/1980 Boys
4,190,042 A 2/1980 Sinnreich
4,198,734 A 4/1980 Brumlik
4,198,982 A 4/1980 Fortner et al.
4,203,444 A 5/1980 Bonnell et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A 11/1982 Kochera
4,366,544 A 12/1982 Shima et al.
4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier

(56) References Cited

U.S. PATENT DOCUMENTS 4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A * 2/1988 Hormann ............ F16H 19/0636 74/424.6
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A * 4/1989 Hormann ............ F16H 19/0636 74/424.78
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.

(56) References Cited

U.S. PATENT DOCUMENTS 4,909,789 A 3/1990 Taguchi et al.
4,915,100 A 4/1990 Green
4,919,679 A 4/1990 Averill et al.
4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,222 A 4/1991 Her
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth

(56) References Cited

U.S. PATENT DOCUMENTS

| | | | |
|---|---|---|---|
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller et al. |
| 5,314,466 | A | 5/1994 | Stern et al. |
| 5,318,221 | A | 6/1994 | Green et al. |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,250 | A | 10/1994 | Christensen |
| 5,354,303 | A | 10/1994 | Spaeth et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |

(56) References Cited

U.S. PATENT DOCUMENTS 5,382,247 A 1/1995 Cimino et al.
5,383,460 A 1/1995 Jang et al.
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,645 A 7/1995 Smith et al.
5,431,654 A 7/1995 Nic
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.

(56) References Cited

U.S. PATENT DOCUMENTS

| | | | |
|---|---|---|---|
| 5,507,425 | A | 4/1996 | Ziglioli |
| 5,507,426 | A | 4/1996 | Young et al. |
| 5,507,773 | A | 4/1996 | Huitema et al. |
| 5,509,596 | A | 4/1996 | Green et al. |
| 5,509,916 | A | 4/1996 | Taylor |
| 5,509,918 | A | 4/1996 | Romano |
| 5,511,564 | A | 4/1996 | Wilk |
| 5,514,129 | A | 5/1996 | Smith |
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,601 | A | 3/1997 | Kolesa et al. |
| 5,611,709 | A | 3/1997 | McAnulty |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,289 | A | 4/1997 | Curry |
| 5,620,326 | A | 4/1997 | Younker |
| 5,620,452 | A | 4/1997 | Yoon |
| 5,624,398 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |
| 5,633,374 | A | 5/1997 | Humphrey et al. |
| 5,634,584 | A | 6/1997 | Okorocha et al. |
| 5,636,779 | A | 6/1997 | Palmer |
| 5,636,780 | A | 6/1997 | Green et al. |
| 5,638,582 | A | 6/1997 | Klatt et al. |

(56) References Cited

U.S. PATENT DOCUMENTS 5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,186 A 6/1998 Faraz et al.
5,766,188 A 6/1998 Igaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.

(56) References Cited

U.S. PATENT DOCUMENTS

| | | | |
|---|---|---|---|
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Gelb et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,878 | A | 4/1999 | Pierce |
| 5,894,979 | A | 4/1999 | Powell |
| 5,897,552 | A | 4/1999 | Edwards et al. |
| 5,897,562 | A | 4/1999 | Bolanos et al. |
| 5,899,824 | A | 5/1999 | Kurtz et al. |
| 5,899,914 | A | 5/1999 | Zirps et al. |
| 5,901,895 | A | 5/1999 | Heaton et al. |
| 5,902,312 | A | 5/1999 | Frater et al. |
| 5,903,117 | A | 5/1999 | Gregory |
| 5,904,647 | A | 5/1999 | Ouchi |
| 5,904,693 | A | 5/1999 | Dicesare et al. |
| 5,904,702 | A | 5/1999 | Ek et al. |
| 5,906,577 | A | 5/1999 | Beane et al. |
| 5,906,625 | A | 5/1999 | Bito et al. |
| 5,907,211 | A | 5/1999 | Hall et al. |
| 5,907,664 | A | 5/1999 | Wang et al. |
| 5,908,402 | A | 6/1999 | Blythe |
| 5,908,427 | A | 6/1999 | McKean et al. |
| 5,909,062 | A | 6/1999 | Krietzman |
| 5,911,353 | A | 6/1999 | Bolanos et al. |
| 5,915,616 | A | 6/1999 | Viola et al. |
| 5,916,225 | A | 6/1999 | Kugel |
| 5,918,791 | A | 7/1999 | Sorrentino et al. |
| 5,919,198 | A | 7/1999 | Graves, Jr. et al. |
| 5,921,956 | A | 7/1999 | Grinberg et al. |
| 5,924,864 | A | 7/1999 | Loge et al. |
| 5,928,137 | A | 7/1999 | Green |
| 5,928,256 | A | 7/1999 | Riza |
| 5,931,847 | A | 8/1999 | Bittner et al. |
| 5,931,853 | A | 8/1999 | McEwen et al. |
| 5,937,951 | A | 8/1999 | Izuchukwu et al. |
| 5,938,667 | A | 8/1999 | Peyser et al. |
| 5,941,442 | A | 8/1999 | Geiste et al. |
| 5,941,890 | A | 8/1999 | Voegele et al. |
| 5,944,172 | A | 8/1999 | Hannula |
| 5,944,715 | A | 8/1999 | Goble et al. |
| 5,946,978 | A | 9/1999 | Yamashita |
| 5,947,984 | A | 9/1999 | Whipple |
| 5,947,996 | A | 9/1999 | Logeman |
| 5,948,030 | A | 9/1999 | Miller et al. |
| 5,948,429 | A | 9/1999 | Bell et al. |
| 5,951,301 | A | 9/1999 | Younker |
| 5,951,516 | A | 9/1999 | Bunyan |

(56) References Cited

U.S. PATENT DOCUMENTS

| | | | |
|---|---|---|---|
| 5,951,552 | A | 9/1999 | Long et al. |
| 5,951,574 | A | 9/1999 | Stefanchik et al. |
| 5,951,575 | A | 9/1999 | Bolduc et al. |
| 5,951,581 | A | 9/1999 | Saadat et al. |
| 5,954,259 | A | 9/1999 | Viola et al. |
| 5,957,831 | A | 9/1999 | Adair |
| 5,964,394 | A | 10/1999 | Robertson |
| 5,964,774 | A | 10/1999 | McKean et al. |
| 5,966,126 | A | 10/1999 | Szabo |
| 5,971,916 | A | 10/1999 | Koren |
| 5,973,221 | A | 10/1999 | Collyer et al. |
| D416,089 | S | 11/1999 | Barton et al. |
| 5,976,122 | A | 11/1999 | Madhani et al. |
| 5,977,746 | A | 11/1999 | Hershberger et al. |
| 5,980,248 | A | 11/1999 | Kusakabe et al. |
| 5,984,949 | A | 11/1999 | Levin |
| 5,988,479 | A | 11/1999 | Palmer |
| 5,990,379 | A | 11/1999 | Gregory |
| 5,993,466 | A | 11/1999 | Yoon |
| 5,997,528 | A | 12/1999 | Bisch et al. |
| 5,997,552 | A | 12/1999 | Person et al. |
| 6,001,108 | A | 12/1999 | Wang et al. |
| 6,003,517 | A | 12/1999 | Sheffield et al. |
| 6,004,319 | A | 12/1999 | Goble et al. |
| 6,004,335 | A | 12/1999 | Vaitekunas et al. |
| 6,007,521 | A | 12/1999 | Bidwell et al. |
| 6,010,054 | A | 1/2000 | Johnson et al. |
| 6,010,513 | A | 1/2000 | Tormala et al. |
| 6,010,520 | A | 1/2000 | Pattison |
| 6,012,494 | A | 1/2000 | Balazs |
| 6,013,076 | A | 1/2000 | Goble et al. |
| 6,013,991 | A | 1/2000 | Philipp |
| 6,015,406 | A | 1/2000 | Goble et al. |
| 6,015,417 | A | 1/2000 | Reynolds, Jr. |
| 6,017,322 | A | 1/2000 | Snoke et al. |
| 6,017,354 | A | 1/2000 | Culp et al. |
| 6,017,356 | A | 1/2000 | Frederick et al. |
| 6,018,227 | A | 1/2000 | Kumar et al. |
| 6,019,745 | A | 2/2000 | Gray |
| 6,019,780 | A | 2/2000 | Lombardo et al. |
| 6,022,352 | A | 2/2000 | Vandewalle |
| 6,023,641 | A | 2/2000 | Thompson |
| 6,024,708 | A | 2/2000 | Bales et al. |
| 6,024,741 | A | 2/2000 | Williamson, IV et al. |
| 6,024,748 | A | 2/2000 | Manzo et al. |
| 6,024,750 | A | 2/2000 | Mastri et al. |
| 6,024,764 | A | 2/2000 | Schroeppel |
| 6,027,501 | A | 2/2000 | Goble et al. |
| 6,030,384 | A | 2/2000 | Nezhat |
| 6,032,849 | A | 3/2000 | Mastri et al. |
| 6,033,105 | A | 3/2000 | Barker et al. |
| 6,033,378 | A | 3/2000 | Lundquist et al. |
| 6,033,399 | A | 3/2000 | Gines |
| 6,033,427 | A | 3/2000 | Lee |
| 6,036,641 | A | 3/2000 | Taylor et al. |
| 6,036,667 | A | 3/2000 | Manna et al. |
| 6,037,724 | A | 3/2000 | Buss et al. |
| 6,037,927 | A | 3/2000 | Rosenberg |
| 6,039,126 | A | 3/2000 | Hsieh |
| 6,039,733 | A | 3/2000 | Buysse et al. |
| 6,039,734 | A | 3/2000 | Goble |
| 6,042,601 | A | 3/2000 | Smith |
| 6,042,607 | A | 3/2000 | Williamson, IV et al. |
| 6,043,626 | A | 3/2000 | Snyder et al. |
| 6,045,560 | A | 4/2000 | McKean et al. |
| 6,047,861 | A | 4/2000 | Vidal et al. |
| 6,049,145 | A | 4/2000 | Austin et al. |
| 6,050,172 | A | 4/2000 | Corves et al. |
| 6,050,472 | A | 4/2000 | Shibata |
| 6,050,989 | A | 4/2000 | Fox et al. |
| 6,050,990 | A | 4/2000 | Tankovich et al. |
| 6,050,996 | A | 4/2000 | Schmaltz et al. |
| 6,053,390 | A | 4/2000 | Green et al. |
| 6,053,899 | A | 4/2000 | Slanda et al. |
| 6,053,922 | A | 4/2000 | Krause et al. |
| 6,054,142 | A | 4/2000 | Li et al. |
| 6,055,062 | A | 4/2000 | Dina et al. |
| RE36,720 | E | 5/2000 | Green et al. |
| 6,056,735 | A | 5/2000 | Okada et al. |
| 6,056,746 | A | 5/2000 | Goble et al. |
| 6,059,806 | A | 5/2000 | Hoegerle |
| 6,062,360 | A | 5/2000 | Shields |
| 6,063,020 | A | 5/2000 | Jones et al. |
| 6,063,025 | A | 5/2000 | Bridges et al. |
| 6,063,050 | A | 5/2000 | Manna et al. |
| 6,063,095 | A | 5/2000 | Wang et al. |
| 6,063,097 | A | 5/2000 | Oi et al. |
| 6,063,098 | A | 5/2000 | Houser et al. |
| 6,065,679 | A | 5/2000 | Levie et al. |
| 6,065,919 | A | 5/2000 | Peck |
| 6,066,132 | A | 5/2000 | Chen et al. |
| 6,066,151 | A | 5/2000 | Miyawaki et al. |
| 6,068,627 | A | 5/2000 | Orszulak et al. |
| 6,071,233 | A | 6/2000 | Ishikawa et al. |
| 6,072,299 | A | 6/2000 | Kurle et al. |
| 6,074,386 | A | 6/2000 | Goble et al. |
| 6,074,401 | A | 6/2000 | Gardiner et al. |
| 6,075,441 | A | 6/2000 | Maloney |
| 6,077,280 | A | 6/2000 | Fossum |
| 6,077,286 | A | 6/2000 | Cuschieri et al. |
| 6,077,290 | A | 6/2000 | Marini |
| 6,079,606 | A | 6/2000 | Milliman et al. |
| 6,080,181 | A | 6/2000 | Jensen et al. |
| 6,082,577 | A | 7/2000 | Coates et al. |
| 6,083,191 | A | 7/2000 | Rose |
| 6,083,223 | A | 7/2000 | Baker |
| 6,083,234 | A | 7/2000 | Nicholas et al. |
| 6,083,242 | A | 7/2000 | Cook |
| 6,086,544 | A | 7/2000 | Hibner et al. |
| 6,086,600 | A | 7/2000 | Kortenbach |
| 6,090,106 | A | 7/2000 | Goble et al. |
| 6,090,123 | A | 7/2000 | Culp et al. |
| 6,093,186 | A | 7/2000 | Goble |
| D429,252 | S | 8/2000 | Haitani et al. |
| 6,099,537 | A | 8/2000 | Sugai et al. |
| 6,099,551 | A | 8/2000 | Gabbay |
| 6,102,271 | A | 8/2000 | Longo et al. |
| 6,102,926 | A | 8/2000 | Tartaglia et al. |
| 6,104,162 | A | 8/2000 | Sainsbury et al. |
| 6,104,304 | A | 8/2000 | Clark et al. |
| 6,106,511 | A | 8/2000 | Jensen |
| 6,109,500 | A | 8/2000 | Alli et al. |
| 6,110,187 | A | 8/2000 | Donlon |
| 6,113,618 | A | 9/2000 | Nic |
| 6,117,148 | A | 9/2000 | Ravo et al. |
| 6,117,158 | A | 9/2000 | Measamer et al. |
| 6,119,913 | A | 9/2000 | Adams et al. |
| 6,120,433 | A | 9/2000 | Mizuno et al. |
| 6,120,462 | A | 9/2000 | Hibner et al. |
| 6,123,241 | A | 9/2000 | Walter et al. |
| 6,123,701 | A | 9/2000 | Nezhat |
| H1904 | H | 10/2000 | Yates et al. |
| RE36,923 | E | 10/2000 | Hiroi et al. |
| 6,126,058 | A | 10/2000 | Adams et al. |
| 6,126,359 | A | 10/2000 | Dittrich et al. |
| 6,126,670 | A | 10/2000 | Walker et al. |
| 6,131,789 | A | 10/2000 | Schulze et al. |
| 6,131,790 | A | 10/2000 | Piraka |
| 6,132,368 | A | 10/2000 | Cooper |
| 6,134,962 | A | 10/2000 | Sugitani |
| 6,139,546 | A | 10/2000 | Koenig et al. |
| 6,142,149 | A | 11/2000 | Steen |
| 6,142,933 | A | 11/2000 | Longo et al. |
| 6,147,135 | A | 11/2000 | Yuan et al. |
| 6,149,660 | A | 11/2000 | Laufer et al. |
| 6,151,323 | A | 11/2000 | O'Connell et al. |
| 6,152,935 | A | 11/2000 | Kammerer et al. |
| 6,155,473 | A | 12/2000 | Tompkins et al. |
| 6,156,056 | A | 12/2000 | Kearns et al. |
| 6,157,169 | A | 12/2000 | Lee |
| 6,159,146 | A | 12/2000 | El Gazayerli |
| 6,159,200 | A | 12/2000 | Verdura et al. |
| 6,159,224 | A | 12/2000 | Yoon |
| 6,162,208 | A | 12/2000 | Hipps |

(56) References Cited

U.S. PATENT DOCUMENTS 6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.

(56) References Cited

U.S. PATENT DOCUMENTS

| | | | |
|---|---|---|---|
| 6,416,486 | B1 | 7/2002 | Wampler |
| 6,416,509 | B1 | 7/2002 | Goble et al. |
| 6,419,695 | B1 | 7/2002 | Gabbay |
| 6,423,079 | B1 | 7/2002 | Blake, III |
| 6,424,885 | B1 | 7/2002 | Niemeyer et al. |
| RE37,814 | E | 8/2002 | Allgeyer |
| 6,428,070 | B1 | 8/2002 | Takanashi et al. |
| 6,428,487 | B1 | 8/2002 | Burdorff et al. |
| 6,429,611 | B1 | 8/2002 | Li |
| 6,430,298 | B1 | 8/2002 | Kettl et al. |
| 6,432,065 | B1 | 8/2002 | Burdorff et al. |
| 6,436,097 | B1 | 8/2002 | Nardella |
| 6,436,107 | B1 | 8/2002 | Wang et al. |
| 6,436,110 | B2 | 8/2002 | Bowman et al. |
| 6,436,115 | B1 | 8/2002 | Beaupre |
| 6,436,122 | B1 | 8/2002 | Frank et al. |
| 6,439,439 | B1 | 8/2002 | Rickard et al. |
| 6,439,446 | B1 | 8/2002 | Perry et al. |
| 6,440,146 | B2 | 8/2002 | Nicholas et al. |
| 6,441,577 | B2 | 8/2002 | Blumenkranz et al. |
| D462,758 | S | 9/2002 | Epstein et al. |
| 6,443,973 | B1 | 9/2002 | Whitman |
| 6,445,530 | B1 | 9/2002 | Baker |
| 6,447,518 | B1 | 9/2002 | Krause et al. |
| 6,447,523 | B1 | 9/2002 | Middleman et al. |
| 6,447,799 | B1 | 9/2002 | Ullman |
| 6,447,864 | B2 | 9/2002 | Johnson et al. |
| 6,450,391 | B1 | 9/2002 | Kayan et al. |
| 6,450,989 | B2 | 9/2002 | Dubrul et al. |
| 6,454,781 | B1 | 9/2002 | Witt et al. |
| 6,457,338 | B1 | 10/2002 | Frenken |
| 6,457,625 | B1 | 10/2002 | Tormala et al. |
| 6,458,077 | B1 | 10/2002 | Boebel et al. |
| 6,458,142 | B1 | 10/2002 | Faller et al. |
| 6,458,147 | B1 | 10/2002 | Cruise et al. |
| 6,460,627 | B1 | 10/2002 | Below et al. |
| 6,468,275 | B1 | 10/2002 | Wampler et al. |
| 6,468,286 | B2 | 10/2002 | Mastri et al. |
| 6,471,106 | B1 | 10/2002 | Reining |
| 6,471,659 | B2 | 10/2002 | Eggers et al. |
| 6,478,210 | B2 | 11/2002 | Adams et al. |
| 6,482,200 | B2 | 11/2002 | Shippert |
| 6,482,217 | B1 | 11/2002 | Pintor et al. |
| 6,485,490 | B2 | 11/2002 | Wampler et al. |
| 6,485,503 | B2 | 11/2002 | Jacobs et al. |
| 6,485,667 | B1 | 11/2002 | Tan |
| 6,486,286 | B1 | 11/2002 | McGall et al. |
| 6,488,196 | B1 | 12/2002 | Fenton, Jr. |
| 6,488,197 | B1 | 12/2002 | Whitman |
| 6,488,659 | B1 | 12/2002 | Rosenman |
| 6,491,201 | B1 | 12/2002 | Whitman |
| 6,491,690 | B1 | 12/2002 | Goble et al. |
| 6,491,701 | B2 | 12/2002 | Tierney et al. |
| 6,491,702 | B2 | 12/2002 | Heilbrun et al. |
| 6,492,785 | B1 | 12/2002 | Kasten et al. |
| 6,494,882 | B1 | 12/2002 | Lebouitz et al. |
| 6,494,885 | B1 | 12/2002 | Dhindsa |
| 6,494,888 | B1 | 12/2002 | Laufer et al. |
| 6,494,896 | B1 | 12/2002 | D'Alessio et al. |
| 6,498,480 | B1 | 12/2002 | Manara |
| 6,500,176 | B1 | 12/2002 | Truckai et al. |
| 6,500,189 | B1 | 12/2002 | Lang et al. |
| 6,500,194 | B2 | 12/2002 | Benderev et al. |
| D468,749 | S | 1/2003 | Friedman |
| 6,503,139 | B2 | 1/2003 | Coral |
| 6,503,257 | B2 | 1/2003 | Grant et al. |
| 6,503,259 | B2 | 1/2003 | Huxel et al. |
| 6,505,768 | B2 | 1/2003 | Whitman |
| 6,506,197 | B1 | 1/2003 | Rollero et al. |
| 6,506,399 | B2 | 1/2003 | Donovan |
| 6,510,854 | B2 | 1/2003 | Goble |
| 6,511,468 | B1 | 1/2003 | Cragg et al. |
| 6,512,360 | B1 | 1/2003 | Goto et al. |
| 6,514,252 | B2 | 2/2003 | Nezhat et al. |
| 6,516,073 | B1 | 2/2003 | Schulz et al. |
| 6,517,528 | B1 | 2/2003 | Pantages et al. |
| 6,517,535 | B2 | 2/2003 | Edwards |
| 6,517,565 | B1 | 2/2003 | Whitman et al. |
| 6,517,566 | B1 | 2/2003 | Hovland et al. |
| 6,520,971 | B1 | 2/2003 | Perry et al. |
| 6,520,972 | B2 | 2/2003 | Peters |
| 6,522,101 | B2 | 2/2003 | Malackowski |
| 6,524,180 | B1 | 2/2003 | Simms et al. |
| 6,525,499 | B2 | 2/2003 | Naganuma |
| D471,206 | S | 3/2003 | Buzzard et al. |
| 6,527,782 | B2 | 3/2003 | Hogg et al. |
| 6,527,785 | B2 | 3/2003 | Sancoff et al. |
| 6,530,942 | B2 | 3/2003 | Fogarty et al. |
| 6,532,958 | B1 | 3/2003 | Buan et al. |
| 6,533,157 | B1 | 3/2003 | Whitman |
| 6,533,723 | B1 | 3/2003 | Lockery et al. |
| 6,533,784 | B2 | 3/2003 | Truckai et al. |
| 6,535,764 | B2 | 3/2003 | Imran et al. |
| 6,539,297 | B2 | 3/2003 | Weiberle et al. |
| D473,239 | S | 4/2003 | Cockerill |
| 6,539,816 | B2 | 4/2003 | Kogiso et al. |
| 6,540,737 | B2 | 4/2003 | Bacher et al. |
| 6,543,456 | B1 | 4/2003 | Freeman |
| 6,545,384 | B1 | 4/2003 | Pelrine et al. |
| 6,547,786 | B1 | 4/2003 | Goble |
| 6,550,546 | B2 | 4/2003 | Thurler et al. |
| 6,551,333 | B2 | 4/2003 | Kuhns et al. |
| 6,554,844 | B2 | 4/2003 | Lee et al. |
| 6,554,861 | B2 | 4/2003 | Knox et al. |
| 6,555,770 | B2 | 4/2003 | Kawase |
| 6,558,378 | B2 | 5/2003 | Sherman et al. |
| 6,558,379 | B1 | 5/2003 | Batchelor et al. |
| 6,558,429 | B2 | 5/2003 | Taylor |
| 6,561,187 | B2 | 5/2003 | Schmidt et al. |
| 6,565,560 | B1 | 5/2003 | Goble et al. |
| 6,566,619 | B2 | 5/2003 | Gillman et al. |
| 6,569,085 | B2 | 5/2003 | Kortenbach et al. |
| 6,569,171 | B2 | 5/2003 | DeGuillebon et al. |
| 6,578,751 | B2 | 6/2003 | Hartwick |
| 6,582,364 | B2 | 6/2003 | Butler et al. |
| 6,582,427 | B1 | 6/2003 | Goble et al. |
| 6,582,441 | B1 | 6/2003 | He et al. |
| 6,583,533 | B2 | 6/2003 | Pelrine et al. |
| 6,585,144 | B2 | 7/2003 | Adams et al. |
| 6,585,664 | B2 | 7/2003 | Burdorff et al. |
| 6,586,898 | B2 | 7/2003 | King et al. |
| 6,587,750 | B2 | 7/2003 | Gerbi et al. |
| 6,588,277 | B2 | 7/2003 | Giordano et al. |
| 6,588,643 | B2 | 7/2003 | Bolduc et al. |
| 6,588,931 | B2 | 7/2003 | Betzner et al. |
| 6,589,118 | B1 | 7/2003 | Soma et al. |
| 6,589,164 | B1 | 7/2003 | Flaherty |
| 6,592,538 | B1 | 7/2003 | Hotchkiss et al. |
| 6,592,572 | B1 | 7/2003 | Suzuta |
| 6,592,597 | B2 | 7/2003 | Grant et al. |
| 6,594,552 | B1 | 7/2003 | Nowlin et al. |
| 6,595,914 | B2 | 7/2003 | Kato |
| 6,596,296 | B1 | 7/2003 | Nelson et al. |
| 6,596,304 | B1 | 7/2003 | Bayon et al. |
| 6,596,432 | B2 | 7/2003 | Kawakami et al. |
| 6,599,295 | B1 | 7/2003 | Tornier et al. |
| 6,599,323 | B2 | 7/2003 | Melican et al. |
| D478,665 | S | 8/2003 | Isaacs et al. |
| D478,986 | S | 8/2003 | Johnston et al. |
| 6,601,749 | B2 | 8/2003 | Sullivan et al. |
| 6,602,252 | B2 | 8/2003 | Mollenauer |
| 6,602,262 | B2 | 8/2003 | Griego et al. |
| 6,603,050 | B2 | 8/2003 | Heaton |
| 6,605,078 | B2 | 8/2003 | Adams |
| 6,605,669 | B2 | 8/2003 | Awokola et al. |
| 6,605,911 | B1 | 8/2003 | Klesing |
| 6,607,475 | B2 | 8/2003 | Doyle et al. |
| 6,611,793 | B1 | 8/2003 | Burnside et al. |
| 6,613,069 | B2 | 9/2003 | Boyd et al. |
| 6,616,686 | B2 | 9/2003 | Coleman et al. |
| 6,619,529 | B2 | 9/2003 | Green et al. |
| 6,620,111 | B2 | 9/2003 | Stephens et al. |
| 6,620,161 | B2 | 9/2003 | Schulze et al. |
| 6,620,166 | B1 | 9/2003 | Wenstrom, Jr. et al. |

(56) References Cited

U.S. PATENT DOCUMENTS

| | | | |
|---|---|---|---|
| 6,625,517 | B1 | 9/2003 | Bogdanov et al. |
| 6,626,834 | B2 | 9/2003 | Dunne et al. |
| H2086 | H | 10/2003 | Amsler |
| 6,629,630 | B2 | 10/2003 | Adams |
| 6,629,974 | B2 | 10/2003 | Penny et al. |
| 6,629,988 | B2 | 10/2003 | Weadock |
| 6,635,838 | B1 | 10/2003 | Kornelson |
| 6,636,412 | B2 | 10/2003 | Smith |
| 6,638,108 | B2 | 10/2003 | Tachi |
| 6,638,285 | B2 | 10/2003 | Gabbay |
| 6,638,297 | B1 | 10/2003 | Huitema |
| RE38,335 | E | 11/2003 | Aust et al. |
| 6,641,528 | B2 | 11/2003 | Torii |
| 6,644,532 | B2 | 11/2003 | Green et al. |
| 6,645,201 | B1 | 11/2003 | Utley et al. |
| 6,646,307 | B1 | 11/2003 | Yu et al. |
| 6,648,816 | B2 | 11/2003 | Irion et al. |
| 6,648,901 | B2 | 11/2003 | Fleischman et al. |
| 6,652,595 | B1 | 11/2003 | Nicolo |
| D484,243 | S | 12/2003 | Ryan et al. |
| D484,595 | S | 12/2003 | Ryan et al. |
| D484,596 | S | 12/2003 | Ryan et al. |
| 6,656,177 | B2 | 12/2003 | Truckai et al. |
| 6,656,193 | B2 | 12/2003 | Grant et al. |
| 6,659,940 | B2 | 12/2003 | Adler |
| 6,660,008 | B1 | 12/2003 | Foerster et al. |
| 6,663,623 | B1 | 12/2003 | Oyama et al. |
| 6,663,641 | B1 | 12/2003 | Kovac et al. |
| 6,666,854 | B1 | 12/2003 | Lange |
| 6,666,860 | B1 | 12/2003 | Takahashi |
| 6,666,875 | B1 | 12/2003 | Sakurai et al. |
| 6,667,825 | B2 | 12/2003 | Lu et al. |
| 6,669,073 | B2 | 12/2003 | Milliman et al. |
| 6,670,806 | B2 | 12/2003 | Wendt et al. |
| 6,671,185 | B2 | 12/2003 | Duval |
| D484,977 | S | 1/2004 | Ryan et al. |
| 6,676,660 | B2 | 1/2004 | Wampler et al. |
| 6,677,687 | B2 | 1/2004 | Ho et al. |
| 6,679,269 | B2 | 1/2004 | Swanson |
| 6,679,410 | B2 | 1/2004 | Wursch et al. |
| 6,681,978 | B2 | 1/2004 | Geiste et al. |
| 6,681,979 | B2 | 1/2004 | Whitman |
| 6,682,527 | B2 | 1/2004 | Strul |
| 6,682,528 | B2 | 1/2004 | Frazier et al. |
| 6,682,544 | B2 | 1/2004 | Mastri et al. |
| 6,685,698 | B2 | 2/2004 | Morley et al. |
| 6,685,727 | B2 | 2/2004 | Fisher et al. |
| 6,689,153 | B1 | 2/2004 | Skiba |
| 6,692,507 | B2 | 2/2004 | Pugsley et al. |
| 6,692,692 | B2 | 2/2004 | Stetzel |
| 6,695,198 | B2 | 2/2004 | Adams et al. |
| 6,695,199 | B2 | 2/2004 | Whitman |
| 6,695,774 | B2 | 2/2004 | Hale et al. |
| 6,695,849 | B2 | 2/2004 | Michelson |
| 6,696,814 | B2 | 2/2004 | Henderson et al. |
| 6,697,048 | B2 | 2/2004 | Rosenberg et al. |
| 6,698,643 | B2 | 3/2004 | Whitman |
| 6,699,177 | B1 | 3/2004 | Wang et al. |
| 6,699,214 | B2 | 3/2004 | Gellman |
| 6,699,235 | B2 | 3/2004 | Wallace et al. |
| 6,704,210 | B1 | 3/2004 | Myers |
| 6,705,503 | B1 | 3/2004 | Pedicini et al. |
| 6,709,445 | B2 | 3/2004 | Boebel et al. |
| 6,712,773 | B1 | 3/2004 | Viola |
| 6,716,215 | B1 | 4/2004 | David et al. |
| 6,716,223 | B2 | 4/2004 | Leopold et al. |
| 6,716,232 | B1 | 4/2004 | Vidal et al. |
| 6,716,233 | B1 | 4/2004 | Whitman |
| 6,720,734 | B2 | 4/2004 | Norris |
| 6,722,550 | B1 | 4/2004 | Ricordi et al. |
| 6,722,552 | B2 | 4/2004 | Fenton, Jr. |
| 6,723,087 | B2 | 4/2004 | O'Neill et al. |
| 6,723,091 | B2 | 4/2004 | Goble et al. |
| 6,723,106 | B1 | 4/2004 | Charles et al. |
| 6,723,109 | B2 | 4/2004 | Solingen |
| 6,726,651 | B1 | 4/2004 | Robinson et al. |
| 6,726,697 | B2 | 4/2004 | Nicholas et al. |
| 6,726,705 | B2 | 4/2004 | Peterson et al. |
| 6,726,706 | B2 | 4/2004 | Dominguez |
| 6,729,119 | B2 | 5/2004 | Schnipke et al. |
| 6,731,976 | B2 | 5/2004 | Penn et al. |
| 6,736,810 | B2 | 5/2004 | Hoey et al. |
| 6,736,825 | B2 | 5/2004 | Blatter et al. |
| 6,736,854 | B2 | 5/2004 | Vadurro et al. |
| 6,740,030 | B2 | 5/2004 | Martone et al. |
| 6,743,230 | B2 | 6/2004 | Lutze et al. |
| 6,744,385 | B2 | 6/2004 | Kazuya et al. |
| 6,747,121 | B2 | 6/2004 | Gogolewski |
| 6,747,300 | B2 | 6/2004 | Nadd et al. |
| 6,749,560 | B1 | 6/2004 | Konstorum et al. |
| 6,749,600 | B1 | 6/2004 | Levy |
| 6,752,768 | B2 | 6/2004 | Burdorff et al. |
| 6,752,816 | B2 | 6/2004 | Culp et al. |
| 6,754,959 | B1 | 6/2004 | Guiette, III et al. |
| 6,755,195 | B1 | 6/2004 | Lemke et al. |
| 6,755,338 | B2 | 6/2004 | Hahnen et al. |
| 6,755,825 | B2 | 6/2004 | Shoenman et al. |
| 6,755,843 | B2 | 6/2004 | Chung et al. |
| 6,756,705 | B2 | 6/2004 | Pulford, Jr. |
| 6,758,846 | B2 | 7/2004 | Goble et al. |
| 6,761,685 | B2 | 7/2004 | Adams et al. |
| 6,762,339 | B1 | 7/2004 | Klun et al. |
| 6,763,307 | B2 | 7/2004 | Berg et al. |
| 6,764,445 | B2 | 7/2004 | Ramans et al. |
| 6,766,957 | B2 | 7/2004 | Matsuura et al. |
| 6,767,352 | B2 | 7/2004 | Field et al. |
| 6,767,356 | B2 | 7/2004 | Kanner et al. |
| 6,769,590 | B2 | 8/2004 | Vresh et al. |
| 6,769,594 | B2 | 8/2004 | Orban, III |
| 6,770,027 | B2 | 8/2004 | Banik et al. |
| 6,770,070 | B1 | 8/2004 | Balbierz |
| 6,770,072 | B1 | 8/2004 | Truckai et al. |
| 6,770,078 | B2 | 8/2004 | Bonutti |
| 6,773,409 | B2 | 8/2004 | Truckai et al. |
| 6,773,437 | B2 | 8/2004 | Ogilvie et al. |
| 6,773,438 | B1 | 8/2004 | Knodel et al. |
| 6,775,575 | B2 | 8/2004 | Bommannan et al. |
| 6,777,838 | B2 | 8/2004 | Miekka et al. |
| 6,778,846 | B1 | 8/2004 | Martinez et al. |
| 6,780,151 | B2 | 8/2004 | Grabover et al. |
| 6,780,180 | B1 | 8/2004 | Goble et al. |
| 6,783,524 | B2 | 8/2004 | Anderson et al. |
| 6,784,775 | B2 | 8/2004 | Mandell et al. |
| 6,786,382 | B1 | 9/2004 | Hoffman |
| 6,786,864 | B2 | 9/2004 | Matsuura et al. |
| 6,786,896 | B1 | 9/2004 | Madhani et al. |
| 6,788,018 | B1 | 9/2004 | Blumenkranz |
| 6,790,173 | B2 | 9/2004 | Saadat et al. |
| 6,793,652 | B1 | 9/2004 | Whitman et al. |
| 6,793,661 | B2 | 9/2004 | Hamilton et al. |
| 6,793,663 | B2 | 9/2004 | Kneifel et al. |
| 6,793,669 | B2 | 9/2004 | Nakamura et al. |
| 6,796,921 | B1 | 9/2004 | Buck et al. |
| 6,799,669 | B2 | 10/2004 | Fukumura et al. |
| 6,801,009 | B2 | 10/2004 | Makaran et al. |
| 6,802,822 | B1 | 10/2004 | Dodge |
| 6,802,843 | B2 | 10/2004 | Truckai et al. |
| 6,802,844 | B2 | 10/2004 | Ferree |
| 6,805,273 | B2 | 10/2004 | Bilotti et al. |
| 6,806,808 | B1 | 10/2004 | Watters et al. |
| 6,806,867 | B1 | 10/2004 | Arruda et al. |
| 6,808,525 | B2 | 10/2004 | Latterell et al. |
| 6,810,359 | B2 | 10/2004 | Sakaguchi |
| 6,814,154 | B2 | 11/2004 | Chou |
| 6,814,741 | B2 | 11/2004 | Bowman et al. |
| 6,817,508 | B1 | 11/2004 | Racenet et al. |
| 6,817,509 | B2 | 11/2004 | Geiste et al. |
| 6,817,974 | B2 | 11/2004 | Cooper et al. |
| 6,818,018 | B1 | 11/2004 | Sawhney |
| 6,820,791 | B2 | 11/2004 | Adams |
| 6,821,273 | B2 | 11/2004 | Mollenauer |
| 6,821,282 | B2 | 11/2004 | Perry et al. |
| 6,821,284 | B2 | 11/2004 | Sturtz et al. |
| 6,827,246 | B2 | 12/2004 | Sullivan et al. |

(56) References Cited

U.S. PATENT DOCUMENTS 6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,007,176 B2 2/2006 Goodfellow et al.
7,008,433 B2 3/2006 Voellmicke et al.
7,008,435 B2 3/2006 Cummins

(56) References Cited

U.S. PATENT DOCUMENTS 7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,161,036 B2 1/2007 Oikawa et al.

(56) References Cited

U.S. PATENT DOCUMENTS 7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,205,959 B2 4/2007 Henriksson
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,313,430 B2 12/2007 Urquhart et al.
7,314,473 B2 1/2008 Jinno et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.

(56) References Cited

U.S. PATENT DOCUMENTS 7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.

(56) References Cited

U.S. PATENT DOCUMENTS

| | | | |
|---|---|---|---|
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,575,144 | B2 | 8/2009 | Ortiz et al. |
| 7,578,825 | B2 | 8/2009 | Huebner |
| D600,712 | S | 9/2009 | LaManna et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |
| 7,591,818 | B2 | 9/2009 | Bertolero et al. |
| 7,593,766 | B2 | 9/2009 | Faber et al. |
| 7,595,642 | B2 | 9/2009 | Doyle |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Iio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |
| 7,617,961 | B2 | 11/2009 | Viola |
| 7,618,427 | B2 | 11/2009 | Ortiz et al. |
| D605,201 | S | 12/2009 | Lorenz et al. |
| D606,992 | S | 12/2009 | Liu et al. |
| D607,010 | S | 12/2009 | Kocmick |
| 7,624,902 | B2 | 12/2009 | Marczyk et al. |
| 7,624,903 | B2 | 12/2009 | Green et al. |
| 7,625,370 | B2 | 12/2009 | Hart et al. |
| 7,625,388 | B2 | 12/2009 | Boukhny et al. |
| 7,630,841 | B2 | 12/2009 | Comisky et al. |
| 7,631,793 | B2 | 12/2009 | Rethy et al. |
| 7,631,794 | B2 | 12/2009 | Rethy et al. |
| 7,635,074 | B2 | 12/2009 | Olson et al. |
| 7,635,922 | B2 | 12/2009 | Becker |
| 7,637,409 | B2 | 12/2009 | Marczyk |
| 7,637,410 | B2 | 12/2009 | Marczyk |
| 7,638,958 | B2 | 12/2009 | Philipp et al. |
| 7,641,091 | B2 | 1/2010 | Olson et al. |
| 7,641,092 | B2 | 1/2010 | Kruszynski et al. |
| 7,641,093 | B2 | 1/2010 | Doll et al. |
| 7,641,095 | B2 | 1/2010 | Viola |
| 7,641,671 | B2 | 1/2010 | Crainich |
| 7,644,783 | B2 | 1/2010 | Roberts et al. |
| 7,644,848 | B2 | 1/2010 | Swayze et al. |
| 7,645,230 | B2 | 1/2010 | Mikkaichi et al. |
| 7,648,055 | B2 | 1/2010 | Marczyk |
| 7,648,457 | B2 | 1/2010 | Stefanchik et al. |
| 7,648,519 | B2 | 1/2010 | Lee et al. |
| 7,650,185 | B2 | 1/2010 | Maile et al. |
| 7,651,017 | B2 | 1/2010 | Ortiz et al. |
| 7,651,498 | B2 | 1/2010 | Shifrin et al. |
| 7,654,431 | B2 | 2/2010 | Hueil et al. |
| 7,655,003 | B2 | 2/2010 | Lorang et al. |
| 7,655,004 | B2 | 2/2010 | Long |
| 7,655,288 | B2 | 2/2010 | Bauman et al. |
| 7,655,584 | B2 | 2/2010 | Biran et al. |
| 7,656,131 | B2 | 2/2010 | Embrey et al. |
| 7,658,311 | B2 | 2/2010 | Boudreaux |
| 7,658,312 | B2 | 2/2010 | Vidal et al. |
| 7,658,705 | B2 | 2/2010 | Melvin et al. |
| 7,659,219 | B2 | 2/2010 | Biran et al. |
| 7,661,448 | B2 | 2/2010 | Kim et al. |
| 7,662,161 | B2 | 2/2010 | Briganti et al. |
| 7,665,646 | B2 | 2/2010 | Prommersberger |
| 7,665,647 | B2 | 2/2010 | Shelton, IV et al. |
| 7,666,195 | B2 | 2/2010 | Kelleher et al. |
| 7,669,746 | B2 | 3/2010 | Shelton, IV |
| 7,669,747 | B2 | 3/2010 | Weisenburgh, II et al. |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,674,253 | B2 | 3/2010 | Fisher et al. |
| 7,674,255 | B2 | 3/2010 | Braun |
| 7,674,263 | B2 | 3/2010 | Ryan |
| 7,674,270 | B2 | 3/2010 | Layer |
| 7,678,121 | B1 | 3/2010 | Knodel |
| 7,682,307 | B2 | 3/2010 | Danitz et al. |
| 7,682,367 | B2 | 3/2010 | Shah et al. |
| 7,682,686 | B2 | 3/2010 | Curro et al. |
| 7,686,201 | B2 | 3/2010 | Csiky |
| 7,686,804 | B2 | 3/2010 | Johnson et al. |
| 7,686,826 | B2 | 3/2010 | Lee et al. |
| 7,688,028 | B2 | 3/2010 | Phillips et al. |
| 7,690,547 | B2 | 4/2010 | Racenet et al. |
| 7,691,098 | B2 | 4/2010 | Wallace et al. |
| 7,691,103 | B2 | 4/2010 | Fernandez et al. |
| 7,691,106 | B2 | 4/2010 | Schenberger et al. |
| 7,694,864 | B2 | 4/2010 | Okada et al. |
| 7,694,865 | B2 | 4/2010 | Scirica |
| 7,695,485 | B2 | 4/2010 | Whitman et al. |
| 7,695,493 | B2 | 4/2010 | Saadat et al. |
| 7,699,204 | B2 | 4/2010 | Viola |
| 7,699,835 | B2 | 4/2010 | Lee et al. |
| 7,699,844 | B2 | 4/2010 | Utley et al. |
| 7,699,846 | B2 | 4/2010 | Ryan |
| 7,699,856 | B2 | 4/2010 | Van Wyk et al. |
| 7,699,859 | B2 | 4/2010 | Bombard et al. |
| 7,699,860 | B2 | 4/2010 | Huitema et al. |
| 7,699,868 | B2 | 4/2010 | Frank et al. |
| 7,703,653 | B2 | 4/2010 | Shah et al. |
| 7,705,559 | B2 | 4/2010 | Powell et al. |
| 7,706,853 | B2 | 4/2010 | Hacker et al. |
| 7,708,180 | B2 | 5/2010 | Murray et al. |
| 7,708,181 | B2 | 5/2010 | Cole et al. |
| 7,708,182 | B2 | 5/2010 | Viola |
| 7,708,758 | B2 | 5/2010 | Lee et al. |
| 7,708,768 | B2 | 5/2010 | Danek et al. |
| 7,709,136 | B2 | 5/2010 | Touchton et al. |
| 7,712,182 | B2 | 5/2010 | Zeiler et al. |
| 7,713,190 | B2 | 5/2010 | Brock et al. |
| 7,713,542 | B2 | 5/2010 | Xu et al. |
| 7,714,239 | B2 | 5/2010 | Smith |
| 7,714,334 | B2 | 5/2010 | Lin |

(56) References Cited

U.S. PATENT DOCUMENTS 7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,614 B1 8/2010 McGonagle et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,782,382 B2 8/2010 Fujimura
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.

(56) References Cited

U.S. PATENT DOCUMENTS 7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,879,063 B2 2/2011 Khosravi
7,879,070 B2 2/2011 Ortiz et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,025 B2 7/2011 Pool et al.
7,981,102 B2 7/2011 Patel et al.
7,981,132 B2 7/2011 Dubrul et al.
7,987,405 B2 7/2011 Turner et al.
7,988,015 B2 8/2011 Mason, II et al.
7,988,026 B2 8/2011 Knodel et al.

(56) References Cited

U.S. PATENT DOCUMENTS 7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.
8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,882 B2 10/2011 Viola
8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,636 B2 11/2011 Moll et al.
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.
8,074,858 B2 12/2011 Marczyk
8,074,859 B2 12/2011 Kostrzewski
8,074,861 B2 12/2011 Ehrenfels et al.
8,075,476 B2 12/2011 Vargas
8,075,571 B2 12/2011 Vitali et al.
8,079,950 B2 12/2011 Stern et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,102,138 B2 1/2012 Sekine et al.
8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,114,345 B2 2/2012 Dlugos, Jr. et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.

(56) References Cited

U.S. PATENT DOCUMENTS 8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,472 B2 6/2012 Lau et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stopek
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.

(56) References Cited

U.S. PATENT DOCUMENTS

| | | | |
|---|---|---|---|
| 8,286,845 | B2 | 10/2012 | Perry et al. |
| 8,286,846 | B2 | 10/2012 | Smith et al. |
| 8,286,847 | B2 | 10/2012 | Taylor |
| 8,287,487 | B2 | 10/2012 | Estes |
| 8,287,522 | B2 | 10/2012 | Moses et al. |
| 8,287,561 | B2 | 10/2012 | Nunez et al. |
| 8,288,984 | B2 | 10/2012 | Yang |
| 8,289,403 | B2 | 10/2012 | Dobashi et al. |
| 8,290,883 | B2 | 10/2012 | Takeuchi et al. |
| 8,292,147 | B2 | 10/2012 | Viola |
| 8,292,148 | B2 | 10/2012 | Viola |
| 8,292,150 | B2 | 10/2012 | Bryant |
| 8,292,151 | B2 | 10/2012 | Viola |
| 8,292,152 | B2 | 10/2012 | Milliman et al. |
| 8,292,155 | B2 | 10/2012 | Shelton, IV et al. |
| 8,292,157 | B2 | 10/2012 | Smith et al. |
| 8,292,158 | B2 | 10/2012 | Sapienza |
| 8,292,801 | B2 | 10/2012 | Dejima et al. |
| 8,292,888 | B2 | 10/2012 | Whitman |
| 8,292,906 | B2 | 10/2012 | Taylor et al. |
| 8,294,399 | B2 | 10/2012 | Suzuki et al. |
| 8,298,161 | B2 | 10/2012 | Vargas |
| 8,298,189 | B2 | 10/2012 | Fisher et al. |
| 8,298,233 | B2 | 10/2012 | Mueller |
| 8,298,677 | B2 | 10/2012 | Wiesner et al. |
| 8,302,323 | B2 | 11/2012 | Fortier et al. |
| 8,303,621 | B2 | 11/2012 | Miyamoto et al. |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |
| 8,308,046 | B2 | 11/2012 | Prommersberger |
| 8,308,659 | B2 | 11/2012 | Scheibe et al. |
| 8,308,725 | B2 | 11/2012 | Bell et al. |
| 8,310,188 | B2 | 11/2012 | Nakai |
| 8,313,496 | B2 | 11/2012 | Sauer et al. |
| 8,313,499 | B2 | 11/2012 | Magnusson et al. |
| 8,313,509 | B2 | 11/2012 | Kostrzewski |
| 8,317,070 | B2 | 11/2012 | Hueil et al. |
| 8,317,071 | B1 | 11/2012 | Knodel |
| 8,317,074 | B2 | 11/2012 | Ortiz et al. |
| 8,317,437 | B2 | 11/2012 | Merkley et al. |
| 8,317,744 | B2 | 11/2012 | Kirschenman |
| 8,317,790 | B2 | 11/2012 | Bell et al. |
| 8,319,002 | B2 | 11/2012 | Daniels et al. |
| D672,784 | S | 12/2012 | Clanton et al. |
| 8,322,455 | B2 | 12/2012 | Shelton, IV et al. |
| 8,322,589 | B2 | 12/2012 | Boudreaux |
| 8,322,590 | B2 | 12/2012 | Patel et al. |
| 8,322,901 | B2 | 12/2012 | Michelotti |
| 8,323,271 | B2 | 12/2012 | Humayun et al. |
| 8,323,789 | B2 | 12/2012 | Rozhin et al. |
| 8,324,585 | B2 | 12/2012 | McBroom et al. |
| 8,327,514 | B2 | 12/2012 | Kim |
| 8,328,061 | B2 | 12/2012 | Kasvikis |
| 8,328,062 | B2 | 12/2012 | Viola |
| 8,328,063 | B2 | 12/2012 | Milliman et al. |
| 8,328,064 | B2 | 12/2012 | Racenet et al. |
| 8,328,065 | B2 | 12/2012 | Shah |
| 8,328,802 | B2 | 12/2012 | Deville et al. |
| 8,328,823 | B2 | 12/2012 | Aranyi et al. |
| 8,333,313 | B2 | 12/2012 | Boudreaux et al. |
| 8,333,691 | B2 | 12/2012 | Schaaf |
| 8,333,764 | B2 | 12/2012 | Francischelli et al. |
| 8,333,779 | B2 | 12/2012 | Smith et al. |
| 8,334,468 | B2 | 12/2012 | Palmer et al. |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,343,150 | B2 | 1/2013 | Artale |
| 8,347,978 | B2 | 1/2013 | Forster et al. |
| 8,348,118 | B2 | 1/2013 | Segura |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,348,837 | B2 | 1/2013 | Wenchell |
| 8,348,959 | B2 | 1/2013 | Wolford et al. |
| 8,348,972 | B2 | 1/2013 | Soltz et al. |
| 8,349,987 | B2 | 1/2013 | Kapiamba et al. |
| 8,352,004 | B2 | 1/2013 | Mannheimer et al. |
| 8,353,437 | B2 | 1/2013 | Boudreaux |
| 8,353,438 | B2 | 1/2013 | Baxter, III et al. |
| 8,353,439 | B2 | 1/2013 | Baxter, III et al. |
| 8,356,740 | B1 | 1/2013 | Knodel |
| 8,357,144 | B2 | 1/2013 | Whitman et al. |
| 8,357,158 | B2 | 1/2013 | McKenna et al. |
| 8,357,161 | B2 | 1/2013 | Mueller |
| 8,359,174 | B2 | 1/2013 | Nakashima et al. |
| 8,360,296 | B2 | 1/2013 | Zingman |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,361,501 | B2 | 1/2013 | DiTizio et al. |
| D676,866 | S | 2/2013 | Chaudhri |
| 8,365,972 | B2 | 2/2013 | Aranyi et al. |
| 8,365,973 | B1 | 2/2013 | White et al. |
| 8,365,975 | B1 | 2/2013 | Manoux et al. |
| 8,365,976 | B2 | 2/2013 | Hess et al. |
| 8,366,559 | B2 | 2/2013 | Papenfuss et al. |
| 8,366,719 | B2 | 2/2013 | Markey et al. |
| 8,366,787 | B2 | 2/2013 | Brown et al. |
| 8,368,327 | B2 | 2/2013 | Benning et al. |
| 8,369,056 | B2 | 2/2013 | Senriuchi et al. |
| 8,371,393 | B2 | 2/2013 | Higuchi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,371,494 | B2 | 2/2013 | Racenet et al. |
| 8,372,094 | B2 | 2/2013 | Bettuchi et al. |
| 8,374,723 | B2 | 2/2013 | Zhao et al. |
| 8,376,865 | B2 | 2/2013 | Forster et al. |
| 8,377,029 | B2 | 2/2013 | Nagao et al. |
| 8,377,044 | B2 | 2/2013 | Coe et al. |
| 8,377,059 | B2 | 2/2013 | Deville et al. |
| 8,381,828 | B2 | 2/2013 | Whitman et al. |
| 8,382,773 | B2 | 2/2013 | Whitfield et al. |
| 8,382,790 | B2 | 2/2013 | Uenohara et al. |
| D677,273 | S | 3/2013 | Randall et al. |
| 8,387,848 | B2 | 3/2013 | Johnson et al. |
| 8,388,633 | B2 | 3/2013 | Rousseau et al. |
| 8,389,588 | B2 | 3/2013 | Ringeisen et al. |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,397,832 | B2 | 3/2013 | Blickle et al. |
| 8,397,971 | B2 | 3/2013 | Yates et al. |
| 8,397,972 | B2 | 3/2013 | Kostrzewski |
| 8,397,973 | B1 | 3/2013 | Hausen |
| 8,398,633 | B2 | 3/2013 | Mueller |
| 8,398,669 | B2 | 3/2013 | Kim |
| 8,398,673 | B2 | 3/2013 | Hinchliffe et al. |
| 8,398,674 | B2 | 3/2013 | Prestel |
| 8,400,108 | B2 | 3/2013 | Powell et al. |
| 8,400,851 | B2 | 3/2013 | Byun |
| 8,403,138 | B2 | 3/2013 | Weisshaupt et al. |
| 8,403,195 | B2 | 3/2013 | Beardsley et al. |
| 8,403,196 | B2 | 3/2013 | Beardsley et al. |
| 8,403,198 | B2 | 3/2013 | Sorrentino et al. |
| 8,403,832 | B2 | 3/2013 | Cunningham et al. |
| 8,403,926 | B2 | 3/2013 | Nobis et al. |
| 8,403,945 | B2 | 3/2013 | Whitfield et al. |
| 8,403,946 | B2 | 3/2013 | Whitfield et al. |
| 8,403,950 | B2 | 3/2013 | Palmer et al. |
| D680,646 | S | 4/2013 | Hunt et al. |
| 8,408,439 | B2 | 4/2013 | Huang et al. |
| 8,408,442 | B2 | 4/2013 | Racenet et al. |

(56) References Cited

U.S. PATENT DOCUMENTS

| | | | |
|---|---|---|---|
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,423,182 | B2 | 4/2013 | Robinson et al. |
| 8,424,737 | B2 | 4/2013 | Scirica |
| 8,424,739 | B2 | 4/2013 | Racenet et al. |
| 8,424,740 | B2 | 4/2013 | Shelton, IV et al. |
| 8,424,741 | B2 | 4/2013 | McGuckin, Jr. et al. |
| 8,425,600 | B2 | 4/2013 | Maxwell |
| 8,427,430 | B2 | 4/2013 | Lee et al. |
| 8,430,292 | B2 | 4/2013 | Patel et al. |
| 8,430,892 | B2 | 4/2013 | Bindra et al. |
| 8,430,898 | B2 | 4/2013 | Wiener et al. |
| 8,435,257 | B2 | 5/2013 | Smith et al. |
| 8,439,246 | B1 | 5/2013 | Knodel |
| 8,439,830 | B2 | 5/2013 | McKinley et al. |
| 8,444,036 | B2 | 5/2013 | Shelton, IV |
| 8,444,037 | B2 | 5/2013 | Nicholas et al. |
| 8,444,549 | B2 | 5/2013 | Viola et al. |
| 8,449,536 | B2 | 5/2013 | Selig |
| 8,449,560 | B2 | 5/2013 | Roth et al. |
| 8,453,904 | B2 | 6/2013 | Eskaros et al. |
| 8,453,906 | B2 | 6/2013 | Huang et al. |
| 8,453,907 | B2 | 6/2013 | Laurent et al. |
| 8,453,908 | B2 | 6/2013 | Bedi et al. |
| 8,453,912 | B2 | 6/2013 | Mastri et al. |
| 8,453,914 | B2 | 6/2013 | Laurent et al. |
| 8,454,495 | B2 | 6/2013 | Kawano et al. |
| 8,454,551 | B2 | 6/2013 | Allen et al. |
| 8,454,628 | B2 | 6/2013 | Smith et al. |
| 8,454,640 | B2 | 6/2013 | Johnston et al. |
| 8,457,757 | B2 | 6/2013 | Cauller et al. |
| 8,459,520 | B2 | 6/2013 | Giordano et al. |
| 8,459,521 | B2 | 6/2013 | Zemlok et al. |
| 8,459,524 | B2 | 6/2013 | Pribanic et al. |
| 8,459,525 | B2 | 6/2013 | Yates et al. |
| 8,464,922 | B2 | 6/2013 | Marczyk |
| 8,464,923 | B2 | 6/2013 | Shelton, IV |
| 8,464,924 | B2 | 6/2013 | Gresham et al. |
| 8,464,925 | B2 | 6/2013 | Hull et al. |
| 8,465,475 | B2 | 6/2013 | Isbell, Jr. |
| 8,465,502 | B2 | 6/2013 | Zergiebel |
| 8,465,515 | B2 | 6/2013 | Drew et al. |
| 8,469,254 | B2 | 6/2013 | Czernik et al. |
| 8,469,946 | B2 | 6/2013 | Sugita |
| 8,469,973 | B2 | 6/2013 | Meade et al. |
| 8,470,355 | B2 | 6/2013 | Skalla et al. |
| D686,240 | S | 7/2013 | Lin |
| D686,244 | S | 7/2013 | Moriya et al. |
| 8,474,677 | B2 | 7/2013 | Woodard, Jr. et al. |
| 8,475,453 | B2 | 7/2013 | Marczyk et al. |
| 8,475,454 | B1 | 7/2013 | Alshemari |
| 8,475,474 | B2 | 7/2013 | Bombard et al. |
| 8,479,968 | B2 | 7/2013 | Hodgkinson et al. |
| 8,479,969 | B2 | 7/2013 | Shelton, IV |
| 8,480,703 | B2 | 7/2013 | Nicholas et al. |
| 8,483,509 | B2 | 7/2013 | Matsuzaka |
| 8,485,412 | B2 | 7/2013 | Shelton, IV et al. |
| 8,485,413 | B2 | 7/2013 | Scheib et al. |
| 8,485,970 | B2 | 7/2013 | Widenhouse et al. |
| 8,487,199 | B2 | 7/2013 | Palmer et al. |
| 8,487,487 | B2 | 7/2013 | Dietz et al. |
| 8,490,851 | B2 | 7/2013 | Blier et al. |
| 8,490,852 | B2 | 7/2013 | Viola |
| 8,490,853 | B2 | 7/2013 | Criscuolo et al. |
| 8,491,581 | B2 | 7/2013 | Deville et al. |
| 8,491,603 | B2 | 7/2013 | Yeung et al. |
| 8,496,153 | B2 | 7/2013 | Demmy et al. |
| 8,496,154 | B2 | 7/2013 | Marczyk et al. |
| 8,496,156 | B2 | 7/2013 | Sniffin et al. |
| 8,496,683 | B2 | 7/2013 | Prommersberger et al. |
| 8,498,691 | B2 | 7/2013 | Moll et al. |
| 8,499,673 | B2 | 8/2013 | Keller |
| 8,499,966 | B2 | 8/2013 | Palmer et al. |
| 8,499,992 | B2 | 8/2013 | Whitman et al. |
| 8,499,993 | B2 | 8/2013 | Shelton, IV et al. |
| 8,499,994 | B2 | 8/2013 | D'Arcangelo |
| 8,500,721 | B2 | 8/2013 | Jinno |
| 8,500,762 | B2 | 8/2013 | Sholev et al. |
| 8,502,091 | B2 | 8/2013 | Palmer et al. |
| 8,505,799 | B2 | 8/2013 | Viola et al. |
| 8,505,801 | B2 | 8/2013 | Ehrenfels et al. |
| 8,506,555 | B2 | 8/2013 | Ruiz Morales |
| 8,506,557 | B2 | 8/2013 | Zemlok et al. |
| 8,506,580 | B2 | 8/2013 | Zergiebel et al. |
| 8,506,581 | B2 | 8/2013 | Wingardner, III et al. |
| 8,511,308 | B2 | 8/2013 | Hecox et al. |
| 8,512,359 | B2 | 8/2013 | Whitman et al. |
| 8,512,402 | B2 | 8/2013 | Marczyk et al. |
| 8,517,239 | B2 | 8/2013 | Scheib et al. |
| 8,517,241 | B2 | 8/2013 | Nicholas et al. |
| 8,517,243 | B2 | 8/2013 | Giordano et al. |
| 8,517,244 | B2 | 8/2013 | Shelton, IV et al. |
| 8,517,938 | B2 | 8/2013 | Eisenhardt et al. |
| 8,518,024 | B2 | 8/2013 | Williams et al. |
| 8,521,273 | B2 | 8/2013 | Kliman |
| 8,523,042 | B2 | 9/2013 | Masiakos et al. |
| 8,523,043 | B2 | 9/2013 | Ullrich et al. |
| 8,523,787 | B2 | 9/2013 | Ludwin et al. |
| 8,523,881 | B2 | 9/2013 | Cabiri et al. |
| 8,523,900 | B2 | 9/2013 | Jinno et al. |
| 8,529,588 | B2 | 9/2013 | Ahlberg et al. |
| 8,529,599 | B2 | 9/2013 | Holsten |
| 8,529,600 | B2 | 9/2013 | Woodard, Jr. et al. |
| 8,529,819 | B2 | 9/2013 | Ostapoff et al. |
| 8,532,747 | B2 | 9/2013 | Nock et al. |
| 8,534,527 | B2 | 9/2013 | Brendel et al. |
| 8,534,528 | B2 | 9/2013 | Shelton, IV |
| 8,535,304 | B2 | 9/2013 | Sklar et al. |
| 8,535,340 | B2 | 9/2013 | Allen |
| 8,539,866 | B2 | 9/2013 | Nayak et al. |
| 8,540,128 | B2 | 9/2013 | Shelton, IV et al. |
| 8,540,129 | B2 | 9/2013 | Baxter, III et al. |
| 8,540,130 | B2 | 9/2013 | Moore et al. |
| 8,540,131 | B2 | 9/2013 | Swayze |
| 8,540,133 | B2 | 9/2013 | Bedi et al. |
| 8,540,646 | B2 | 9/2013 | Mendez-Coll |
| 8,540,733 | B2 | 9/2013 | Whitman et al. |
| 8,540,735 | B2 | 9/2013 | Mitelberg et al. |
| 8,550,984 | B2 | 10/2013 | Takemoto |
| 8,551,076 | B2 | 10/2013 | Duval et al. |
| 8,555,660 | B2 | 10/2013 | Takenaka et al. |
| 8,556,151 | B2 | 10/2013 | Viola |
| 8,556,918 | B2 | 10/2013 | Bauman et al. |
| 8,556,935 | B1 | 10/2013 | Knodel et al. |
| 8,560,147 | B2 | 10/2013 | Taylor et al. |
| 8,561,617 | B2 | 10/2013 | Lindh et al. |
| 8,561,870 | B2 | 10/2013 | Baxter, III et al. |
| 8,561,871 | B2 | 10/2013 | Rajappa et al. |
| 8,561,873 | B2 | 10/2013 | Ingmanson et al. |
| 8,562,592 | B2 | 10/2013 | Conlon et al. |
| 8,562,598 | B2 | 10/2013 | Falkenstein et al. |
| 8,567,656 | B2 | 10/2013 | Shelton, IV et al. |

(56) References Cited

U.S. PATENT DOCUMENTS 8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.

(56) References Cited

U.S. PATENT DOCUMENTS

| | | | |
|---|---|---|---|
| 8,740,034 | B2 | 6/2014 | Morgan et al. |
| 8,740,037 | B2 | 6/2014 | Shelton, IV et al. |
| 8,740,038 | B2 | 6/2014 | Shelton, IV et al. |
| 8,740,987 | B2 | 6/2014 | Geremakis et al. |
| 8,746,529 | B2 | 6/2014 | Shelton, IV et al. |
| 8,746,530 | B2 | 6/2014 | Giordano et al. |
| 8,746,533 | B2 | 6/2014 | Whitman et al. |
| 8,746,535 | B2 | 6/2014 | Shelton, IV et al. |
| 8,747,238 | B2 | 6/2014 | Shelton, IV et al. |
| 8,747,441 | B2 | 6/2014 | Konieczynski et al. |
| 8,752,264 | B2 | 6/2014 | Ackley et al. |
| 8,752,699 | B2 | 6/2014 | Morgan et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,753,664 | B2 | 6/2014 | Dao et al. |
| 8,757,287 | B2 | 6/2014 | Mak et al. |
| 8,757,465 | B2 | 6/2014 | Woodard, Jr. et al. |
| 8,758,235 | B2 | 6/2014 | Jaworek |
| 8,758,366 | B2 | 6/2014 | McLean et al. |
| 8,758,391 | B2 | 6/2014 | Swayze et al. |
| 8,758,438 | B2 | 6/2014 | Boyce et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,764,732 | B2 | 7/2014 | Hartwell |
| 8,765,942 | B2 | 7/2014 | Feraud et al. |
| 8,770,458 | B2 | 7/2014 | Scirica |
| 8,770,459 | B2 | 7/2014 | Racenet et al. |
| 8,770,460 | B2 | 7/2014 | Belzer |
| 8,771,169 | B2 | 7/2014 | Whitman et al. |
| 8,771,260 | B2 | 7/2014 | Conlon et al. |
| 8,777,004 | B2 | 7/2014 | Shelton, IV et al. |
| 8,777,082 | B2 | 7/2014 | Scirica |
| 8,777,083 | B2 | 7/2014 | Racenet et al. |
| 8,777,898 | B2 | 7/2014 | Suon et al. |
| 8,783,541 | B2 | 7/2014 | Shelton, IV et al. |
| 8,783,542 | B2 | 7/2014 | Riestenberg et al. |
| 8,783,543 | B2 | 7/2014 | Shelton, IV et al. |
| 8,784,304 | B2 | 7/2014 | Mikkaichi et al. |
| 8,784,404 | B2 | 7/2014 | Doyle et al. |
| 8,784,415 | B2 | 7/2014 | Malackowski et al. |
| 8,789,737 | B2 | 7/2014 | Hodgkinson et al. |
| 8,789,739 | B2 | 7/2014 | Swensgard |
| 8,789,740 | B2 | 7/2014 | Baxter, III et al. |
| 8,789,741 | B2 | 7/2014 | Baxter, III et al. |
| 8,790,658 | B2 | 7/2014 | Cigarini et al. |
| 8,790,684 | B2 | 7/2014 | Dave et al. |
| D711,905 | S | 8/2014 | Morrison et al. |
| 8,794,496 | B2 | 8/2014 | Scirica |
| 8,794,497 | B2 | 8/2014 | Zingman |
| 8,795,159 | B2 | 8/2014 | Moriyama |
| 8,795,276 | B2 | 8/2014 | Dietz et al. |
| 8,795,308 | B2 | 8/2014 | Valin |
| 8,795,324 | B2 | 8/2014 | Kawai et al. |
| 8,796,995 | B2 | 8/2014 | Cunanan et al. |
| 8,800,681 | B2 | 8/2014 | Rousson et al. |
| 8,800,837 | B2 | 8/2014 | Zemlok |
| 8,800,838 | B2 | 8/2014 | Shelton, IV |
| 8,800,839 | B2 | 8/2014 | Beetel |
| 8,800,840 | B2 | 8/2014 | Jankowski |
| 8,800,841 | B2 | 8/2014 | Ellerhorst et al. |
| 8,801,710 | B2 | 8/2014 | Ullrich et al. |
| 8,801,734 | B2 | 8/2014 | Shelton, IV et al. |
| 8,801,735 | B2 | 8/2014 | Shelton, IV et al. |
| 8,801,752 | B2 | 8/2014 | Fortier et al. |
| 8,801,801 | B2 | 8/2014 | Datta et al. |
| 8,806,973 | B2 | 8/2014 | Ross et al. |
| 8,807,414 | B2 | 8/2014 | Ross et al. |
| 8,808,161 | B2 | 8/2014 | Gregg et al. |
| 8,808,164 | B2 | 8/2014 | Hoffman et al. |
| 8,808,274 | B2 | 8/2014 | Hartwell |
| 8,808,294 | B2 | 8/2014 | Fox et al. |
| 8,808,308 | B2 | 8/2014 | Boukhny et al. |
| 8,808,311 | B2 | 8/2014 | Heinrich et al. |
| 8,808,325 | B2 | 8/2014 | Hess et al. |
| 8,810,197 | B2 | 8/2014 | Juergens |
| 8,811,017 | B2 | 8/2014 | Fujii et al. |
| 8,813,866 | B2 | 8/2014 | Suzuki |
| 8,814,024 | B2 | 8/2014 | Woodard, Jr. et al. |
| 8,814,025 | B2 | 8/2014 | Miller et al. |
| 8,814,836 | B2 | 8/2014 | Ignon et al. |
| 8,815,594 | B2 | 8/2014 | Harris et al. |
| 8,818,523 | B2 | 8/2014 | Olson et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,820,608 | B2 | 9/2014 | Miyamoto |
| 8,821,514 | B2 | 9/2014 | Aranyi |
| 8,822,934 | B2 | 9/2014 | Sayeh et al. |
| 8,825,164 | B2 | 9/2014 | Tweden et al. |
| 8,827,133 | B2 | 9/2014 | Shelton, IV et al. |
| 8,827,134 | B2 | 9/2014 | Viola et al. |
| 8,827,903 | B2 | 9/2014 | Shelton, IV et al. |
| 8,828,046 | B2 | 9/2014 | Stefanchik et al. |
| 8,831,779 | B2 | 9/2014 | Ortmaier et al. |
| 8,833,219 | B2 | 9/2014 | Pierce |
| 8,833,630 | B2 | 9/2014 | Milliman |
| 8,833,632 | B2 | 9/2014 | Swensgard |
| 8,834,353 | B2 | 9/2014 | Dejima et al. |
| 8,834,465 | B2 | 9/2014 | Ramstein et al. |
| 8,834,498 | B2 | 9/2014 | Byrum et al. |
| 8,834,518 | B2 | 9/2014 | Faller et al. |
| 8,840,003 | B2 | 9/2014 | Morgan et al. |
| 8,840,603 | B2 | 9/2014 | Shelton, IV et al. |
| 8,840,609 | B2 | 9/2014 | Stuebe |
| 8,840,876 | B2 | 9/2014 | Eemeta et al. |
| 8,844,789 | B2 | 9/2014 | Shelton, IV et al. |
| 8,844,790 | B2 | 9/2014 | Demmy et al. |
| 8,845,622 | B2 | 9/2014 | Paik et al. |
| 8,851,215 | B2 | 10/2014 | Goto |
| 8,851,354 | B2 | 10/2014 | Swensgard et al. |
| 8,851,355 | B2 | 10/2014 | Aranyi et al. |
| 8,852,174 | B2 | 10/2014 | Burbank |
| 8,852,185 | B2 | 10/2014 | Twomey |
| 8,852,199 | B2 | 10/2014 | Deslauriers et al. |
| 8,852,218 | B2 | 10/2014 | Hughett, Sr. et al. |
| 8,857,693 | B2 | 10/2014 | Schuckmann et al. |
| 8,857,694 | B2 | 10/2014 | Shelton, IV et al. |
| 8,858,538 | B2 | 10/2014 | Belson et al. |
| 8,858,547 | B2 | 10/2014 | Brogna |
| 8,858,571 | B2 | 10/2014 | Shelton, IV et al. |
| 8,858,590 | B2 | 10/2014 | Shelton, IV et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,864,750 | B2 | 10/2014 | Ross et al. |
| 8,869,912 | B2 | 10/2014 | Roβkamp et al. |
| 8,869,913 | B2 | 10/2014 | Matthias et al. |
| 8,870,050 | B2 | 10/2014 | Hodgkinson |
| 8,870,867 | B2 | 10/2014 | Walberg et al. |
| 8,870,912 | B2 | 10/2014 | Brisson et al. |
| 8,875,971 | B2 | 11/2014 | Hall et al. |
| 8,875,972 | B2 | 11/2014 | Weisenburgh, II et al. |
| 8,876,857 | B2 | 11/2014 | Burbank |
| 8,876,858 | B2 | 11/2014 | Braun |
| 8,882,660 | B2 | 11/2014 | Phee et al. |
| 8,882,792 | B2 | 11/2014 | Dietz et al. |
| 8,884,560 | B2 | 11/2014 | Ito |
| 8,887,979 | B2 | 11/2014 | Mastri et al. |
| 8,888,688 | B2 | 11/2014 | Julian et al. |
| 8,888,695 | B2 | 11/2014 | Piskun et al. |
| 8,888,792 | B2 | 11/2014 | Harris et al. |
| 8,888,809 | B2 | 11/2014 | Davison et al. |
| 8,893,946 | B2 | 11/2014 | Boudreaux et al. |
| 8,893,949 | B2 | 11/2014 | Shelton, IV et al. |
| 8,894,647 | B2 | 11/2014 | Beardsley et al. |
| 8,894,654 | B2 | 11/2014 | Anderson |
| 8,899,460 | B2 | 12/2014 | Wojcicki |
| 8,899,461 | B2 | 12/2014 | Farascioni |
| 8,899,462 | B2 | 12/2014 | Kostrzewski et al. |
| 8,899,463 | B2 | 12/2014 | Schall et al. |

(56) References Cited

U.S. PATENT DOCUMENTS

| | | | |
|---|---|---|---|
| 8,899,464 | B2 | 12/2014 | Hueil et al. |
| 8,899,465 | B2 | 12/2014 | Shelton, IV et al. |
| 8,899,466 | B2 | 12/2014 | Baxter, III et al. |
| 8,900,267 | B2 | 12/2014 | Woolfson et al. |
| 8,905,287 | B2 | 12/2014 | Racenet et al. |
| 8,905,977 | B2 | 12/2014 | Shelton et al. |
| 8,910,846 | B2 | 12/2014 | Viola |
| 8,910,847 | B2 | 12/2014 | Nalagatla et al. |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,915,842 | B2 | 12/2014 | Weisenburgh, II et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,936,614 | B2 | 1/2015 | Allen, IV |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |
| 9,050,084 | B2 | 6/2015 | Schmid et al. |
| 9,050,089 | B2 | 6/2015 | Orszulak |
| 9,050,100 | B2 | 6/2015 | Yates et al. |
| 9,050,120 | B2 | 6/2015 | Swarup et al. |
| 9,050,123 | B2 | 6/2015 | Krause et al. |
| 9,050,176 | B2 | 6/2015 | Datta et al. |
| 9,050,192 | B2 | 6/2015 | Mansmann |

(56) References Cited

U.S. PATENT DOCUMENTS 9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV

(56) References Cited

U.S. PATENT DOCUMENTS 9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,223 B2 6/2016 Scirica
9,364,226 B2 6/2016 Zemlok et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.

(56) References Cited

U.S. PATENT DOCUMENTS 9,381,058 B2 7/2016 Houser et al.
9,383,881 B2 7/2016 Day et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,540 B2 10/2016 Stokes et al.
9,475,180 B2 10/2016 Eshleman et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,549,750 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,561,072 B2 2/2017 Ko
9,566,061 B2 2/2017 Aronhalt et al.
9,566,062 B2 2/2017 Boudreaux

(56) References Cited

U.S. PATENT DOCUMENTS 9,566,065 B2 2/2017 Knodel
9,566,067 B2 2/2017 Milliman et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,074 B2 3/2017 Felder et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.
9,610,412 B2 4/2017 Zemlok et al.
9,614,258 B2 4/2017 Takahashi et al.
9,615,826 B2 4/2017 Shelton, IV et al.
9,622,745 B2 4/2017 Ingmanson et al.
9,622,746 B2 4/2017 Simms et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.
9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,116 B2 5/2017 Smith et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,872 B2 6/2017 Jankowski et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.

(56) References Cited

U.S. PATENT DOCUMENTS 9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,731,410 B2 8/2017 Hirabayashi et al.
9,733,663 B2 8/2017 Leimbach et al.
9,737,297 B2 8/2017 Racenet et al.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow

(56) References Cited

U.S. PATENT DOCUMENTS

| | | |
|---|---|---|
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czemik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,630 B2 | 5/2018 | Larkin et al. |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |

(56) References Cited

U.S. PATENT DOCUMENTS

| | | | |
|---|---|---|---|
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |

(56) References Cited

U.S. PATENT DOCUMENTS 10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,363 B2 4/2019 Worrell et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.
10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,292,701 B2 5/2019 Scheib et al.
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,578 B2 6/2019 Leimbach et al.
10,314,580 B2 6/2019 Scheib et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 * 7/2019 Shelton, IV ......... A61B 17/072
10,357,247 B2 7/2019 Shelton, IV et al.
10,357,248 B2 7/2019 Dalessandro et al.
10,357,252 B2 7/2019 Harris et al.
10,363,031 B2 7/2019 Alexander, III et al.
10,363,033 B2 7/2019 Timm et al.
10,363,036 B2 7/2019 Yates et al.
10,363,037 B2 7/2019 Aronhalt et al.
D855,634 S 8/2019 Kim
D856,359 S 8/2019 Huang et al.
10,368,838 B2 8/2019 Williams et al.
10,368,861 B2 8/2019 Baxter, III et al.
10,368,863 B2 8/2019 Timm et al.
10,368,864 B2 8/2019 Harris et al.
10,368,865 B2 8/2019 Harris et al.
10,368,867 B2 8/2019 Harris et al.
10,368,892 B2 8/2019 Stulen et al.
10,376,263 B2 8/2019 Morgan et al.
10,383,626 B2 8/2019 Soltz
10,383,628 B2 8/2019 Kang et al.
10,383,629 B2 8/2019 Ross et al.

(56) References Cited

U.S. PATENT DOCUMENTS

| | | | |
|---|---|---|---|
| 10,383,630 | B2 | 8/2019 | Shelton, IV et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,470,770 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,309 | B2 | 12/2019 | Shah et al. |
| 10,508,720 | B2 | 12/2019 | Nicholas |
| 10,512,461 | B2 | 12/2019 | Gupta et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,531,874 | B2 | 1/2020 | Morgan et al. |
| 10,531,887 | B2 | 1/2020 | Shelton, IV et al. |
| 10,537,324 | B2 | 1/2020 | Shelton, IV et al. |

(56) References Cited

U.S. PATENT DOCUMENTS

| | | | |
|---|---|---|---|
| 10,537,325 | B2 | 1/2020 | Bakos et al. |
| 10,537,351 | B2 | 1/2020 | Shelton, IV et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |
| 10,582,928 | B2 | 3/2020 | Hunter et al. |
| 10,588,231 | B2 | 3/2020 | Sgroi, Jr. et al. |
| 10,588,623 | B2 | 3/2020 | Schmid et al. |
| 10,588,625 | B2 | 3/2020 | Weaner et al. |
| 10,588,626 | B2 | 3/2020 | Overmyer et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,595,835 | B2 | 3/2020 | Kerr et al. |
| 10,595,862 | B2 | 3/2020 | Shelton, IV et al. |
| 10,595,882 | B2 | 3/2020 | Parfett et al. |
| 10,595,887 | B2 | 3/2020 | Shelton, IV et al. |
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,117 | B2 | 3/2020 | Schings et al. |
| 10,603,128 | B2 | 3/2020 | Zergiebel et al. |
| 10,610,224 | B2 | 4/2020 | Shelton, IV et al. |
| 10,610,236 | B2 | 4/2020 | Baril |
| 10,610,313 | B2 | 4/2020 | Bailey et al. |
| 10,610,346 | B2 | 4/2020 | Schwartz |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,617,438 | B2 | 4/2020 | O'Keefe et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,089 | B2 | 5/2020 | Manwaring et al. |
| 10,639,115 | B2 | 5/2020 | Shelton, IV et al. |
| 10,645,905 | B2 | 5/2020 | Gandola et al. |
| 10,646,220 | B2 | 5/2020 | Shelton, IV et al. |
| 10,646,292 | B2 | 5/2020 | Solomon et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |
| 10,667,408 | B2 | 5/2020 | Sgroi, Jr. et al. |
| D888,953 | S | 6/2020 | Baxter, III et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,818 | B2 | 6/2020 | McLain et al. |
| 10,674,895 | B2 | 6/2020 | Yeung et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,675,102 | B2 | 6/2020 | Forgione et al. |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,812 | B2 | 6/2020 | Shelton, IV et al. |
| 10,687,813 | B2 | 6/2020 | Shelton, IV et al. |
| 10,687,817 | B2 | 6/2020 | Shelton, IV et al. |
| 10,687,819 | B2 | 6/2020 | Stokes et al. |
| 10,687,904 | B2 | 6/2020 | Harris et al. |
| 10,695,053 | B2 | 6/2020 | Hess et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,062 | B2 | 6/2020 | Leimbach et al. |
| 10,695,063 | B2 | 6/2020 | Morgan et al. |
| 10,695,074 | B2 | 6/2020 | Carusillo |
| 10,695,081 | B2 | 6/2020 | Shelton, IV et al. |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |

(56) References Cited

U.S. PATENT DOCUMENTS

| | | | |
|---|---|---|---|
| D893,717 | S | 8/2020 | Messerly et al. |
| 10,729,432 | B2 | 8/2020 | Shelton, IV et al. |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,743,849 | B2 | 8/2020 | Shelton, IV et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,053 | B2 | 8/2020 | Harris et al. |
| 10,751,076 | B2 | 8/2020 | Laurent et al. |
| 10,751,138 | B2 | 8/2020 | Giordano et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,910 | B2 | 11/2020 | Gasparovich et al. |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| D904,612 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,395 | B2 | 1/2021 | Merchant et al. |
| 10,881,396 | B2 | 1/2021 | Shelton, IV et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |

(56) References Cited

U.S. PATENT DOCUMENTS

| | | | |
|---|---|---|---|
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Blasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,727 | B2 | 3/2021 | Hunter et al. |
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,197 | B2 | 6/2021 | Shelton, IV et al. |
| 11,045,270 | B2 | 6/2021 | Shelton, IV et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,048 | B2 | 7/2021 | Messerly et al. |
| 11,069,012 | B2 | 7/2021 | Shelton, IV et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 * | 9/2021 | Beardsley .............. A61B 34/71 |

(56) References Cited

U.S. PATENT DOCUMENTS

| | | | |
|---|---|---|---|
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,202,570 | B2 | 12/2021 | Shelton, IV et al. |
| 11,202,631 | B2 | 12/2021 | Shelton, IV et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Rogosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,699 | B2 | 4/2022 | Shelton, IV et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,342 | B2 | 4/2022 | Parihar et al. |
| 11,317,910 | B2 | 5/2022 | Miller et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,976 | B2 | 5/2022 | Johnson et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| 11,350,843 | B2 | 6/2022 | Shelton, IV et al. |
| 11,350,916 | B2 | 6/2022 | Shelton, IV et al. |

(56) References Cited

U.S. PATENT DOCUMENTS

| | | | |
|---|---|---|---|
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |
| 11,361,176 | B2 | 6/2022 | Shelton, IV et al. |
| 11,364,027 | B2 | 6/2022 | Harris et al. |
| 11,364,046 | B2 | 6/2022 | Shelton, IV et al. |
| 11,369,368 | B2 | 6/2022 | Shelton, IV et al. |
| 11,369,376 | B2 | 6/2022 | Simms et al. |
| 11,369,377 | B2 | 6/2022 | Boudreaux et al. |
| 11,373,755 | B2 | 6/2022 | Shelton, IV et al. |
| 11,376,001 | B2 | 7/2022 | Shelton, IV et al. |
| 11,376,098 | B2 | 7/2022 | Shelton, IV et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,628 | B2 | 7/2022 | Baxter, III et al. |
| 11,382,638 | B2 | 7/2022 | Harris et al. |
| 11,382,697 | B2 | 7/2022 | Shelton, IV et al. |
| 11,389,160 | B2 | 7/2022 | Shelton, IV et al. |
| 11,389,161 | B2 | 7/2022 | Shelton, IV et al. |
| 11,389,162 | B2 | 7/2022 | Baber et al. |
| 11,389,164 | B2 | 7/2022 | Yates et al. |
| 11,395,651 | B2 | 7/2022 | Shelton, IV et al. |
| 11,395,652 | B2 | 7/2022 | Parihar et al. |
| 11,399,836 | B2 | 8/2022 | Cabrera et al. |
| 11,638,582 | B2 | 5/2023 | Bakos et al. |
| 11,660,090 | B2 | 5/2023 | Bakos et al. |
| 2001/0000531 | A1 | 4/2001 | Casscells et al. |
| 2001/0025183 | A1 | 9/2001 | Shahidi |
| 2001/0025184 | A1 | 9/2001 | Messerly |
| 2001/0034530 | A1 | 10/2001 | Malackowski et al. |
| 2002/0014510 | A1 | 2/2002 | Richter et al. |
| 2002/0022810 | A1 | 2/2002 | Urich |
| 2002/0022836 | A1 | 2/2002 | Goble et al. |
| 2002/0022861 | A1 | 2/2002 | Jacobs et al. |
| 2002/0029032 | A1 | 3/2002 | Arkin |
| 2002/0029036 | A1 | 3/2002 | Goble et al. |
| 2002/0042620 | A1 | 4/2002 | Julian et al. |
| 2002/0087048 | A1 | 7/2002 | Brock et al. |
| 2002/0091374 | A1 | 7/2002 | Cooper |
| 2002/0095175 | A1 | 7/2002 | Brock et al. |
| 2002/0103494 | A1 | 8/2002 | Pacey |
| 2002/0111624 | A1 | 8/2002 | Witt et al. |
| 2002/0116063 | A1 | 8/2002 | Giannetti et al. |
| 2002/0117534 | A1 | 8/2002 | Green et al. |
| 2002/0127265 | A1 | 9/2002 | Bowman et al. |
| 2002/0128633 | A1 | 9/2002 | Brock et al. |
| 2002/0134811 | A1 | 9/2002 | Napier et al. |
| 2002/0135474 | A1 | 9/2002 | Sylliassen |
| 2002/0138086 | A1 | 9/2002 | Sixto et al. |
| 2002/0143340 | A1 | 10/2002 | Kaneko |
| 2002/0151770 | A1 | 10/2002 | Noll et al. |
| 2002/0158593 | A1 | 10/2002 | Henderson et al. |
| 2002/0177848 | A1 | 11/2002 | Truckai et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0009193 | A1 | 1/2003 | Corsaro |
| 2003/0011245 | A1 | 1/2003 | Fiebig |
| 2003/0012805 | A1 | 1/2003 | Chen et al. |
| 2003/0039689 | A1 | 2/2003 | Chen et al. |
| 2003/0040670 | A1 | 2/2003 | Govari |
| 2003/0045835 | A1 | 3/2003 | Anderson et al. |
| 2003/0047230 | A1 | 3/2003 | Kim |
| 2003/0050654 | A1 | 3/2003 | Whitman et al. |
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0094356 | A1 | 5/2003 | Waldron |
| 2003/0096158 | A1 | 5/2003 | Takano et al. |
| 2003/0114851 | A1 | 6/2003 | Truckai et al. |
| 2003/0121586 | A1 | 7/2003 | Mitra et al. |
| 2003/0139741 | A1 | 7/2003 | Goble et al. |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0163085 | A1 | 8/2003 | Tanner et al. |
| 2003/0164172 | A1 | 9/2003 | Chumas et al. |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0260315 | A1 | 12/2004 | Dell et al. |
| 2004/0267310 | A1 | 12/2004 | Racenet et al. |

(56) References Cited

U.S. PATENT DOCUMENTS

| | | | |
|---|---|---|---|
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |

(56) References Cited

U.S. PATENT DOCUMENTS

| | | | |
|---|---|---|---|
| 2007/0090788 | A1 | 4/2007 | Hansford et al. |
| 2007/0093869 | A1 | 4/2007 | Bloom et al. |
| 2007/0102472 | A1 | 5/2007 | Shelton |
| 2007/0103437 | A1 | 5/2007 | Rosenberg |
| 2007/0106113 | A1 | 5/2007 | Ravo |
| 2007/0106317 | A1 | 5/2007 | Shelton et al. |
| 2007/0118115 | A1 | 5/2007 | Artale et al. |
| 2007/0134251 | A1 | 6/2007 | Ashkenazi et al. |
| 2007/0135686 | A1 | 6/2007 | Pruitt et al. |
| 2007/0135803 | A1 | 6/2007 | Belson |
| 2007/0152612 | A1 | 7/2007 | Chen et al. |
| 2007/0152829 | A1 | 7/2007 | Lindsay et al. |
| 2007/0155010 | A1 | 7/2007 | Farnsworth et al. |
| 2007/0170225 | A1 | 7/2007 | Shelton et al. |
| 2007/0173687 | A1 | 7/2007 | Shima et al. |
| 2007/0173813 | A1 | 7/2007 | Odom |
| 2007/0173872 | A1 | 7/2007 | Neuenfeldt |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0179477 | A1 | 8/2007 | Danger |
| 2007/0185545 | A1 | 8/2007 | Duke |
| 2007/0187857 | A1 | 8/2007 | Riley et al. |
| 2007/0190110 | A1 | 8/2007 | Pameijer et al. |
| 2007/0191868 | A1 | 8/2007 | Theroux et al. |
| 2007/0194079 | A1 | 8/2007 | Hueil et al. |
| 2007/0194082 | A1 | 8/2007 | Morgan et al. |
| 2007/0197954 | A1 | 8/2007 | Keenan |
| 2007/0198039 | A1 | 8/2007 | Jones et al. |
| 2007/0203510 | A1 | 8/2007 | Bettuchi |
| 2007/0207010 | A1 | 9/2007 | Caspi |
| 2007/0208359 | A1 | 9/2007 | Hoffman |
| 2007/0208375 | A1 | 9/2007 | Nishizawa et al. |
| 2007/0213750 | A1 | 9/2007 | Weadock |
| 2007/0225562 | A1 | 9/2007 | Spivey et al. |
| 2007/0233163 | A1 | 10/2007 | Bombard et al. |
| 2007/0243227 | A1 | 10/2007 | Gertner |
| 2007/0244471 | A1 | 10/2007 | Malackowski |
| 2007/0244496 | A1 | 10/2007 | Hellenkamp |
| 2007/0246505 | A1 | 10/2007 | Pace-Floridia et al. |
| 2007/0260132 | A1 | 11/2007 | Sterling |
| 2007/0262592 | A1 | 11/2007 | Hwang et al. |
| 2007/0270660 | A1 | 11/2007 | Caylor et al. |
| 2007/0275035 | A1 | 11/2007 | Herman et al. |
| 2007/0276409 | A1 | 11/2007 | Ortiz et al. |
| 2007/0279011 | A1 | 12/2007 | Jones et al. |
| 2007/0286892 | A1 | 12/2007 | Herzberg et al. |
| 2007/0290027 | A1 | 12/2007 | Maatta et al. |
| 2007/0296286 | A1 | 12/2007 | Avenell |
| 2008/0003196 | A1 | 1/2008 | Jonn et al. |
| 2008/0015598 | A1 | 1/2008 | Prommersberger |
| 2008/0021486 | A1 | 1/2008 | Oyola et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0030170 | A1 | 2/2008 | Dacquay et al. |
| 2008/0039746 | A1 | 2/2008 | Hissong et al. |
| 2008/0042861 | A1 | 2/2008 | Dacquay et al. |
| 2008/0051833 | A1 | 2/2008 | Gramuglia et al. |
| 2008/0064920 | A1 | 3/2008 | Bakos et al. |
| 2008/0064921 | A1 | 3/2008 | Larkin et al. |
| 2008/0065153 | A1 | 3/2008 | Allard et al. |
| 2008/0069736 | A1 | 3/2008 | Mingerink et al. |
| 2008/0071328 | A1 | 3/2008 | Haubrich et al. |
| 2008/0077158 | A1 | 3/2008 | Haider et al. |
| 2008/0078802 | A1 | 4/2008 | Hess et al. |
| 2008/0081948 | A1 | 4/2008 | Weisenburgh et al. |
| 2008/0082114 | A1 | 4/2008 | McKenna et al. |
| 2008/0082125 | A1 | 4/2008 | Murray et al. |
| 2008/0082126 | A1 | 4/2008 | Murray et al. |
| 2008/0083807 | A1 | 4/2008 | Beardsley et al. |
| 2008/0083811 | A1 | 4/2008 | Marczyk |
| 2008/0085296 | A1 | 4/2008 | Powell et al. |
| 2008/0086078 | A1 | 4/2008 | Powell et al. |
| 2008/0091072 | A1 | 4/2008 | Omori et al. |
| 2008/0108443 | A1 | 5/2008 | Jinno et al. |
| 2008/0114250 | A1 | 5/2008 | Urbano et al. |
| 2008/0125634 | A1 | 5/2008 | Ryan et al. |
| 2008/0125749 | A1 | 5/2008 | Olson |
| 2008/0128469 | A1 | 6/2008 | Dalessandro et al. |
| 2008/0129253 | A1 | 6/2008 | Shiue et al. |
| 2008/0135600 | A1 | 6/2008 | Hiranuma et al. |
| 2008/0140115 | A1 | 6/2008 | Stopek |
| 2008/0140159 | A1 | 6/2008 | Bornhoft et al. |
| 2008/0149682 | A1 | 6/2008 | Uhm |
| 2008/0154299 | A1 | 6/2008 | Livneh |
| 2008/0154335 | A1 | 6/2008 | Thrope et al. |
| 2008/0169328 | A1 | 7/2008 | Shelton |
| 2008/0169332 | A1 | 7/2008 | Shelton et al. |
| 2008/0169333 | A1 | 7/2008 | Shelton et al. |
| 2008/0172087 | A1 | 7/2008 | Fuchs et al. |
| 2008/0177392 | A1 | 7/2008 | Williams et al. |
| 2008/0190989 | A1 | 8/2008 | Crews et al. |
| 2008/0196253 | A1 | 8/2008 | Ezra et al. |
| 2008/0196419 | A1 | 8/2008 | Dube |
| 2008/0197167 | A1 | 8/2008 | Viola et al. |
| 2008/0200755 | A1 | 8/2008 | Bakos |
| 2008/0200762 | A1 | 8/2008 | Stokes et al. |
| 2008/0200835 | A1 | 8/2008 | Monson et al. |
| 2008/0200911 | A1 | 8/2008 | Long |
| 2008/0200933 | A1 | 8/2008 | Bakos et al. |
| 2008/0200934 | A1 | 8/2008 | Fox |
| 2008/0206186 | A1 | 8/2008 | Butler et al. |
| 2008/0208058 | A1 | 8/2008 | Sabata et al. |
| 2008/0234709 | A1 | 9/2008 | Houser |
| 2008/0242939 | A1 | 10/2008 | Johnston |
| 2008/0243088 | A1 | 10/2008 | Evans |
| 2008/0249536 | A1 | 10/2008 | Stahler et al. |
| 2008/0249608 | A1 | 10/2008 | Dave |
| 2008/0255413 | A1 | 10/2008 | Zemlok et al. |
| 2008/0255420 | A1 | 10/2008 | Lee et al. |
| 2008/0255663 | A1 | 10/2008 | Akpek et al. |
| 2008/0262654 | A1 | 10/2008 | Omori et al. |
| 2008/0269596 | A1 | 10/2008 | Revie et al. |
| 2008/0281171 | A1 | 11/2008 | Fennell et al. |
| 2008/0281332 | A1 | 11/2008 | Taylor |
| 2008/0287944 | A1 | 11/2008 | Pearson et al. |
| 2008/0293910 | A1 | 11/2008 | Kapiamba et al. |
| 2008/0294179 | A1 | 11/2008 | Balbierz et al. |
| 2008/0296346 | A1 | 12/2008 | Shelton, IV et al. |
| 2008/0297287 | A1 | 12/2008 | Shachar et al. |
| 2008/0298784 | A1 | 12/2008 | Kastner |
| 2008/0308602 | A1 | 12/2008 | Timm et al. |
| 2008/0308603 | A1 | 12/2008 | Shelton et al. |
| 2008/0312686 | A1 | 12/2008 | Ellingwood |
| 2008/0312687 | A1 | 12/2008 | Blier |
| 2008/0315829 | A1 | 12/2008 | Jones et al. |
| 2009/0001121 | A1 | 1/2009 | Hess et al. |
| 2009/0001130 | A1 | 1/2009 | Hess et al. |
| 2009/0004455 | A1 | 1/2009 | Gravagna et al. |
| 2009/0005809 | A1 | 1/2009 | Hess et al. |
| 2009/0012534 | A1 | 1/2009 | Madhani et al. |
| 2009/0015195 | A1 | 1/2009 | Loth-Krausser |
| 2009/0020958 | A1 | 1/2009 | Soul |
| 2009/0048583 | A1 | 2/2009 | Williams et al. |
| 2009/0048589 | A1 | 2/2009 | Takashino et al. |
| 2009/0076506 | A1 | 3/2009 | Baker |
| 2009/0078736 | A1 | 3/2009 | Van Lue |
| 2009/0081313 | A1 | 3/2009 | Aghion et al. |
| 2009/0088659 | A1 | 4/2009 | Graham et al. |
| 2009/0090763 | A1 | 4/2009 | Zemlok et al. |
| 2009/0099579 | A1 | 4/2009 | Nentwick et al. |
| 2009/0099876 | A1 | 4/2009 | Whitman |
| 2009/0110533 | A1 | 4/2009 | Jinno |
| 2009/0112234 | A1 | 4/2009 | Crainich et al. |
| 2009/0118762 | A1 | 5/2009 | Crainch et al. |
| 2009/0119011 | A1 | 5/2009 | Kondo et al. |
| 2009/0131819 | A1 | 5/2009 | Ritchie et al. |
| 2009/0132400 | A1 | 5/2009 | Conway |
| 2009/0143855 | A1 | 6/2009 | Weber et al. |
| 2009/0149871 | A9 | 6/2009 | Kagan et al. |
| 2009/0171147 | A1 | 7/2009 | Lee et al. |
| 2009/0177218 | A1 | 7/2009 | Young et al. |

(56) References Cited

U.S. PATENT DOCUMENTS

2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0261141 A1 10/2009 Stratton et al.
2009/0262078 A1 10/2009 Pizzi
2009/0270895 A1 10/2009 Churchill et al.
2009/0277288 A1 11/2009 Doepker et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0005035 A1 1/2010 Carpenter et al.
2010/0012703 A1 1/2010 Calabrese et al.
2010/0015104 A1 1/2010 Fraser et al.
2010/0016853 A1 1/2010 Burbank
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0036370 A1 2/2010 Mirel et al.
2010/0051668 A1 3/2010 Milliman et al.
2010/0057118 A1 3/2010 Dietz et al.
2010/0065604 A1 3/2010 Weng
2010/0069833 A1 3/2010 Wenderow et al.
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094340 A1 4/2010 Stopek et al.
2010/0100123 A1 4/2010 Bennett
2010/0100124 A1 4/2010 Calabrese et al.
2010/0116519 A1 5/2010 Gareis
2010/0122339 A1 5/2010 Boccacci
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0179022 A1 7/2010 Shirokoshi
2010/0180711 A1 7/2010 Kilibarda et al.
2010/0191262 A1 7/2010 Harris et al.
2010/0191292 A1 7/2010 DeMeo et al.
2010/0193566 A1 8/2010 Scheib et al.
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0228250 A1 9/2010 Brogna
2010/0234687 A1 9/2010 Azarbarzin et al.
2010/0241137 A1 9/2010 Doyle et al.
2010/0245102 A1 9/2010 Yokoi
2010/0249497 A1 9/2010 Peine et al.
2010/0249947 A1 9/2010 Lesh et al.
2010/0256675 A1 10/2010 Romans
2010/0258327 A1 10/2010 Esenwein et al.
2010/0267662 A1 10/2010 Fielder et al.
2010/0274160 A1 10/2010 Yachi et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0331856 A1 12/2010 Carlson et al.
2011/0006101 A1 1/2011 Hall et al.
2011/0009694 A1 1/2011 Schultz et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0029270 A1 2/2011 Mueglitz
2011/0036891 A1 2/2011 Zemlok et al.
2011/0046667 A1 2/2011 Culligan et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0095067 A1 4/2011 Ohdaira
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0118708 A1 5/2011 Burbank et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0225105 A1 9/2011 Scholer et al.
2011/0230713 A1 9/2011 Kleemann et al.
2011/0235168 A1 9/2011 Sander
2011/0238044 A1 9/2011 Main et al.
2011/0241597 A1 10/2011 Zhu et al.
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278343 A1 11/2011 Knodel et al.
2011/0279268 A1 11/2011 Konishi et al.
2011/0285507 A1 11/2011 Nelson
2011/0290856 A1 12/2011 Shelton, IV et al.
2011/0290858 A1 12/2011 Whitman et al.
2011/0293690 A1 12/2011 Griffin et al.
2011/0295295 A1 12/2011 Shelton, IV et al.
2011/0313894 A1 12/2011 Dye et al.
2011/0315413 A1 12/2011 Fisher et al.

(56) References Cited

U.S. PATENT DOCUMENTS

| | | | |
|---|---|---|---|
| 2012/0004636 | A1 | 1/2012 | Lo |
| 2012/0007442 | A1 | 1/2012 | Rhodes et al. |
| 2012/0008880 | A1 | 1/2012 | Toth |
| 2012/0016239 | A1 | 1/2012 | Barthe et al. |
| 2012/0016413 | A1 | 1/2012 | Timm et al. |
| 2012/0016467 | A1 | 1/2012 | Chen et al. |
| 2012/0029272 | A1 | 2/2012 | Shelton, IV et al. |
| 2012/0033360 | A1 | 2/2012 | Hsu |
| 2012/0059286 | A1 | 3/2012 | Hastings et al. |
| 2012/0064483 | A1 | 3/2012 | Lint et al. |
| 2012/0074200 | A1 | 3/2012 | Schmid et al. |
| 2012/0078243 | A1 | 3/2012 | Worrell et al. |
| 2012/0078244 | A1 | 3/2012 | Worrell et al. |
| 2012/0080336 | A1 | 4/2012 | Shelton, IV et al. |
| 2012/0080344 | A1 | 4/2012 | Shelton, IV |
| 2012/0080478 | A1 | 4/2012 | Morgan et al. |
| 2012/0080498 | A1 | 4/2012 | Shelton, IV et al. |
| 2012/0086276 | A1 | 4/2012 | Sawyers |
| 2012/0095458 | A1 | 4/2012 | Cybulski et al. |
| 2012/0109186 | A1 | 5/2012 | Parrott et al. |
| 2012/0116261 | A1 | 5/2012 | Mumaw et al. |
| 2012/0116262 | A1 | 5/2012 | Houser et al. |
| 2012/0116265 | A1 | 5/2012 | Houser et al. |
| 2012/0116266 | A1 | 5/2012 | Houser et al. |
| 2012/0116381 | A1 | 5/2012 | Houser et al. |
| 2012/0118595 | A1 | 5/2012 | Pellenc |
| 2012/0123463 | A1 | 5/2012 | Jacobs |
| 2012/0125792 | A1 | 5/2012 | Cassivi |
| 2012/0130217 | A1 | 5/2012 | Kauphusman et al. |
| 2012/0132286 | A1 | 5/2012 | Lim et al. |
| 2012/0171539 | A1 | 7/2012 | Rejman et al. |
| 2012/0175398 | A1 | 7/2012 | Sandborn et al. |
| 2012/0190964 | A1 | 7/2012 | Hyde et al. |
| 2012/0197239 | A1 | 8/2012 | Smith et al. |
| 2012/0197272 | A1 | 8/2012 | Oray et al. |
| 2012/0211542 | A1 | 8/2012 | Racenet |
| 2012/0220990 | A1 | 8/2012 | Mckenzie et al. |
| 2012/0234895 | A1 | 9/2012 | O'Connor et al. |
| 2012/0234897 | A1 | 9/2012 | Shelton, IV et al. |
| 2012/0239068 | A1 | 9/2012 | Morris et al. |
| 2012/0248169 | A1 | 10/2012 | Widenhouse et al. |
| 2012/0251861 | A1 | 10/2012 | Liang et al. |
| 2012/0253328 | A1 | 10/2012 | Cunningham et al. |
| 2012/0271327 | A1 | 10/2012 | West et al. |
| 2012/0283707 | A1 | 11/2012 | Giordano et al. |
| 2012/0289811 | A1 | 11/2012 | Viola et al. |
| 2012/0289979 | A1 | 11/2012 | Eskaros et al. |
| 2012/0292367 | A1 | 11/2012 | Morgan et al. |
| 2012/0296342 | A1 | 11/2012 | Haglund Wendelschafer |
| 2012/0298722 | A1 | 11/2012 | Hess et al. |
| 2012/0301498 | A1 | 11/2012 | Altreuter et al. |
| 2012/0316424 | A1 | 12/2012 | Stopek |
| 2012/0330329 | A1 | 12/2012 | Harris et al. |
| 2013/0006227 | A1 | 1/2013 | Takashino |
| 2013/0008937 | A1 | 1/2013 | Viola |
| 2013/0012983 | A1 | 1/2013 | Kleyman |
| 2013/0018400 | A1 | 1/2013 | Milton et al. |
| 2013/0020375 | A1 | 1/2013 | Shelton, IV et al. |
| 2013/0020376 | A1 | 1/2013 | Shelton, IV et al. |
| 2013/0023861 | A1 | 1/2013 | Shelton, IV et al. |
| 2013/0023910 | A1 | 1/2013 | Solomon et al. |
| 2013/0026208 | A1 | 1/2013 | Shelton, IV et al. |
| 2013/0026210 | A1 | 1/2013 | Shelton, IV et al. |
| 2013/0030462 | A1 | 1/2013 | Keating et al. |
| 2013/0041292 | A1 | 2/2013 | Cunningham |
| 2013/0057162 | A1 | 3/2013 | Pollischansky |
| 2013/0068816 | A1 | 3/2013 | Mandakolathur Vasudevan et al. |
| 2013/0087597 | A1 | 4/2013 | Shelton, IV et al. |
| 2013/0090534 | A1 | 4/2013 | Burns et al. |
| 2013/0096568 | A1 | 4/2013 | Justis |
| 2013/0098970 | A1 | 4/2013 | Racenet et al. |
| 2013/0106352 | A1 | 5/2013 | Nagamine |
| 2013/0116669 | A1 | 5/2013 | Shelton, IV et al. |
| 2013/0123816 | A1 | 5/2013 | Hodgkinson et al. |
| 2013/0126202 | A1 | 5/2013 | Oomori et al. |
| 2013/0131476 | A1 | 5/2013 | Siu et al. |
| 2013/0131651 | A1 | 5/2013 | Strobl et al. |
| 2013/0136969 | A1 | 5/2013 | Yasui et al. |
| 2013/0153641 | A1 | 6/2013 | Shelton, IV et al. |
| 2013/0158390 | A1 | 6/2013 | Tan et al. |
| 2013/0162198 | A1 | 6/2013 | Yokota et al. |
| 2013/0169217 | A1 | 7/2013 | Watanabe et al. |
| 2013/0172713 | A1 | 7/2013 | Kirschenman |
| 2013/0172878 | A1 | 7/2013 | Smith |
| 2013/0175317 | A1 | 7/2013 | Yates et al. |
| 2013/0183769 | A1 | 7/2013 | Tajima |
| 2013/0211244 | A1 | 8/2013 | Nathaniel |
| 2013/0214025 | A1 | 8/2013 | Zemlok et al. |
| 2013/0215449 | A1 | 8/2013 | Yamasaki |
| 2013/0231681 | A1 | 9/2013 | Robinson et al. |
| 2013/0233906 | A1 | 9/2013 | Hess et al. |
| 2013/0238021 | A1 | 9/2013 | Gross et al. |
| 2013/0248578 | A1 | 9/2013 | Arteaga Gonzalez |
| 2013/0253480 | A1 | 9/2013 | Kimball et al. |
| 2013/0256373 | A1 | 10/2013 | Schmid et al. |
| 2013/0256380 | A1 | 10/2013 | Schmid et al. |
| 2013/0267978 | A1 | 10/2013 | Trissel |
| 2013/0270322 | A1 | 10/2013 | Scheib et al. |
| 2013/0277410 | A1 | 10/2013 | Fernandez et al. |
| 2013/0293353 | A1 | 11/2013 | McPherson et al. |
| 2013/0306704 | A1 | 11/2013 | Balbierz et al. |
| 2013/0327552 | A1 | 12/2013 | Lovelass et al. |
| 2013/0333910 | A1 | 12/2013 | Tanimoto et al. |
| 2013/0334280 | A1 | 12/2013 | Krehel et al. |
| 2013/0334283 | A1 | 12/2013 | Swayze et al. |
| 2013/0334285 | A1 | 12/2013 | Swayze et al. |
| 2013/0341374 | A1 | 12/2013 | Shelton, IV et al. |
| 2014/0001231 | A1 | 1/2014 | Shelton, IV et al. |
| 2014/0001234 | A1 | 1/2014 | Shelton, IV et al. |
| 2014/0005640 | A1 | 1/2014 | Shelton, IV et al. |
| 2014/0005678 | A1 | 1/2014 | Shelton, IV et al. |
| 2014/0005702 | A1 | 1/2014 | Timm et al. |
| 2014/0005718 | A1 | 1/2014 | Shelton, IV et al. |
| 2014/0008289 | A1 | 1/2014 | Williams et al. |
| 2014/0014704 | A1 | 1/2014 | Onukuri et al. |
| 2014/0014705 | A1 | 1/2014 | Baxter, III |
| 2014/0014707 | A1 | 1/2014 | Onukuri et al. |
| 2014/0018832 | A1 | 1/2014 | Shelton, IV |
| 2014/0022283 | A1 | 1/2014 | Chan et al. |
| 2014/0039549 | A1 | 2/2014 | Belsky et al. |
| 2014/0041191 | A1 | 2/2014 | Knodel |
| 2014/0048580 | A1 | 2/2014 | Merchant et al. |
| 2014/0081176 | A1 | 3/2014 | Hassan |
| 2014/0094681 | A1 | 4/2014 | Valentine et al. |
| 2014/0100558 | A1 | 4/2014 | Schmitz et al. |
| 2014/0107697 | A1 | 4/2014 | Patani et al. |
| 2014/0115229 | A1 | 4/2014 | Kothamasu et al. |
| 2014/0131418 | A1 | 5/2014 | Kostrzewski |
| 2014/0135832 | A1 | 5/2014 | Park et al. |
| 2014/0151433 | A1 | 6/2014 | Shelton, IV et al. |
| 2014/0155916 | A1 | 6/2014 | Hodgkinson et al. |
| 2014/0158747 | A1 | 6/2014 | Measamer et al. |
| 2014/0166723 | A1 | 6/2014 | Beardsley et al. |
| 2014/0166724 | A1 | 6/2014 | Schellin et al. |
| 2014/0166725 | A1 | 6/2014 | Schellin et al. |
| 2014/0166726 | A1 | 6/2014 | Schellin et al. |
| 2014/0175147 | A1 | 6/2014 | Manoux et al. |
| 2014/0175150 | A1 | 6/2014 | Shelton, IV et al. |
| 2014/0175152 | A1 | 6/2014 | Hess et al. |
| 2014/0181710 | A1 | 6/2014 | Baalu et al. |
| 2014/0183244 | A1 | 7/2014 | Duque et al. |
| 2014/0188091 | A1 | 7/2014 | Vidal et al. |
| 2014/0188159 | A1 | 7/2014 | Steege |
| 2014/0207124 | A1 | 7/2014 | Aldridge et al. |
| 2014/0209658 | A1 | 7/2014 | Skalla et al. |
| 2014/0224857 | A1 | 8/2014 | Schmid |
| 2014/0228632 | A1 | 8/2014 | Sholev et al. |
| 2014/0228867 | A1 | 8/2014 | Thomas et al. |
| 2014/0239047 | A1 | 8/2014 | Hodgkinson et al. |
| 2014/0243865 | A1 | 8/2014 | Swayze et al. |
| 2014/0246475 | A1 | 9/2014 | Hall et al. |
| 2014/0248167 | A1 | 9/2014 | Sugimoto et al. |
| 2014/0249557 | A1 | 9/2014 | Koch et al. |
| 2014/0249573 | A1 | 9/2014 | Arav |

(56) References Cited

U.S. PATENT DOCUMENTS

2014/0262408 A1 9/2014 Woodard
2014/0263541 A1 9/2014 Leimbach et al.
2014/0263552 A1 9/2014 Hall et al.
2014/0263558 A1 9/2014 Hausen et al.
2014/0276730 A1 9/2014 Boudreaux et al.
2014/0284371 A1 9/2014 Morgan et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0374130 A1 12/2014 Nakamura et al.
2014/0378950 A1 12/2014 Chiu
2015/0001272 A1 1/2015 Sniffin et al.
2015/0002089 A1 1/2015 Rejman et al.
2015/0025549 A1 1/2015 Kilroy et al.
2015/0025571 A1 1/2015 Suzuki et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209045 A1 7/2015 Hodgkinson et al.
2015/0222212 A1 8/2015 Iwata
2015/0223868 A1 8/2015 Brandt et al.
2015/0230697 A1 8/2015 Phee et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297228 A1 10/2015 Huitema et al.
2015/0297824 A1 10/2015 Cabiri et al.
2015/0303417 A1 10/2015 Koeder et al.
2015/0313594 A1 11/2015 Shelton, IV et al.
2015/0324317 A1 11/2015 Collins et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0000453 A1 1/2016 Yates et al.
2016/0030042 A1 2/2016 Heinrich et al.
2016/0030043 A1 2/2016 Fanelli et al.
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0082161 A1 3/2016 Zilberman et al.
2016/0135835 A1 5/2016 Onuma
2016/0135895 A1 5/2016 Faasse et al.
2016/0139666 A1 5/2016 Rubin et al.
2016/0183939 A1 6/2016 Shelton, IV et al.
2016/0183943 A1 6/2016 Shelton, IV
2016/0183944 A1 6/2016 Swensgard et al.
2016/0192960 A1 7/2016 Bueno et al.
2016/0199063 A1 7/2016 Mandakolathur Vasudevan et al.
2016/0199956 A1 7/2016 Shelton, IV et al.
2016/0235494 A1 8/2016 Shelton, IV et al.
2016/0242783 A1 8/2016 Shelton, IV et al.
2016/0249910 A1 9/2016 Shelton, IV et al.
2016/0249922 A1 9/2016 Morgan et al.
2016/0256159 A1 9/2016 Pinjala et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0367122 A1 12/2016 Ichimura et al.
2016/0374716 A1 12/2016 Kessler
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0055819 A1 3/2017 Hansen et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086842 A1 3/2017 Shelton, IV et al.
2017/0086930 A1 3/2017 Thompson et al.
2017/0105733 A1 4/2017 Scheib et al.
2017/0135711 A1 5/2017 Overmyer et al.
2017/0135717 A1 5/2017 Boudreaux et al.
2017/0135747 A1 5/2017 Broderick et al.
2017/0172382 A1 6/2017 Nir et al.
2017/0172549 A1 6/2017 Smaby et al.
2017/0172662 A1 6/2017 Panescu et al.
2017/0182195 A1 6/2017 Wagner
2017/0182211 A1 6/2017 Raxworthy et al.
2017/0196558 A1 7/2017 Morgan et al.
2017/0196649 A1 7/2017 Yates et al.
2017/0202770 A1 7/2017 Friedrich et al.
2017/0224332 A1 8/2017 Hunter et al.
2017/0231628 A1 8/2017 Shelton, IV et al.
2017/0231629 A1 8/2017 Stopek et al.
2017/0238962 A1 8/2017 Hansen et al.
2017/0242455 A1 8/2017 Dickens
2017/0249431 A1 8/2017 Shelton, IV et al.
2017/0255799 A1 9/2017 Zhao et al.
2017/0262110 A1 9/2017 Polishchuk et al.
2017/0265774 A1 9/2017 Johnson et al.
2017/0281161 A1* 10/2017 Shelton, IV ......... A61B 17/072

(56) References Cited

U.S. PATENT DOCUMENTS

| | | | |
|---|---|---|---|
| 2017/0281186 | A1 | 10/2017 | Shelton, IV et al. |
| 2017/0296173 | A1 | 10/2017 | Shelton, IV et al. |
| 2017/0296185 | A1 | 10/2017 | Swensgard et al. |
| 2017/0296213 | A1 | 10/2017 | Swensgard et al. |
| 2017/0312042 | A1 | 11/2017 | Giordano et al. |
| 2017/0319201 | A1 | 11/2017 | Morgan et al. |
| 2017/0333034 | A1 | 11/2017 | Morgan et al. |
| 2017/0333035 | A1 | 11/2017 | Morgan et al. |
| 2017/0348010 | A1 | 12/2017 | Chiang |
| 2017/0348043 | A1 | 12/2017 | Wang et al. |
| 2017/0354413 | A1 | 12/2017 | Chen et al. |
| 2017/0358052 | A1 | 12/2017 | Yuan |
| 2017/0360441 | A1 | 12/2017 | Sgroi |
| 2018/0049794 | A1 | 2/2018 | Swayze et al. |
| 2018/0051780 | A1 | 2/2018 | Shelton, IV et al. |
| 2018/0055501 | A1 | 3/2018 | Zemlok et al. |
| 2018/0085116 | A1 | 3/2018 | Yates et al. |
| 2018/0085117 | A1 | 3/2018 | Shelton, IV et al. |
| 2018/0092710 | A1 | 4/2018 | Bosisio et al. |
| 2018/0114591 | A1 | 4/2018 | Pribanic et al. |
| 2018/0116658 | A1 | 5/2018 | Aronhalt, IV et al. |
| 2018/0116662 | A1 | 5/2018 | Shelton, IV et al. |
| 2018/0125481 | A1 | 5/2018 | Yates et al. |
| 2018/0125487 | A1 | 5/2018 | Beardsley |
| 2018/0125488 | A1 | 5/2018 | Morgan et al. |
| 2018/0125594 | A1* | 5/2018 | Beardsley ........ A61B 17/07207 |
| 2018/0132845 | A1 | 5/2018 | Schmid et al. |
| 2018/0132849 | A1 | 5/2018 | Miller et al. |
| 2018/0132850 | A1 | 5/2018 | Leimbach et al. |
| 2018/0132926 | A1 | 5/2018 | Asher et al. |
| 2018/0132952 | A1 | 5/2018 | Spivey et al. |
| 2018/0133521 | A1 | 5/2018 | Frushour et al. |
| 2018/0140299 | A1 | 5/2018 | Weaner et al. |
| 2018/0146960 | A1 | 5/2018 | Shelton, IV et al. |
| 2018/0153542 | A1 | 6/2018 | Shelton, IV et al. |
| 2018/0153634 | A1 | 6/2018 | Zemlok et al. |
| 2018/0168574 | A1 | 6/2018 | Robinson et al. |
| 2018/0168575 | A1 | 6/2018 | Simms et al. |
| 2018/0168577 | A1 | 6/2018 | Aronhalt et al. |
| 2018/0168579 | A1 | 6/2018 | Aronhalt et al. |
| 2018/0168592 | A1 | 6/2018 | Overmyer et al. |
| 2018/0168598 | A1 | 6/2018 | Shelton, IV et al. |
| 2018/0168608 | A1 | 6/2018 | Shelton, IV et al. |
| 2018/0168609 | A1 | 6/2018 | Fanelli et al. |
| 2018/0168610 | A1 | 6/2018 | Shelton, IV et al. |
| 2018/0168615 | A1 | 6/2018 | Shelton, IV et al. |
| 2018/0168618 | A1 | 6/2018 | Scott et al. |
| 2018/0168619 | A1 | 6/2018 | Scott et al. |
| 2018/0168623 | A1 | 6/2018 | Simms et al. |
| 2018/0168625 | A1 | 6/2018 | Posada et al. |
| 2018/0168633 | A1 | 6/2018 | Shelton, IV et al. |
| 2018/0168647 | A1 | 6/2018 | Shelton, IV et al. |
| 2018/0168648 | A1 | 6/2018 | Shelton, IV et al. |
| 2018/0168650 | A1 | 6/2018 | Shelton, IV et al. |
| 2018/0168754 | A1 | 6/2018 | Overmyer |
| 2018/0228490 | A1 | 8/2018 | Richard et al. |
| 2018/0235609 | A1 | 8/2018 | Harris et al. |
| 2018/0236181 | A1 | 8/2018 | Marlin et al. |
| 2018/0242970 | A1 | 8/2018 | Mozdzierz |
| 2018/0271520 | A1 | 9/2018 | Shelton, IV et al. |
| 2018/0271604 | A1 | 9/2018 | Grout et al. |
| 2018/0273597 | A1 | 9/2018 | Stimson |
| 2018/0289371 | A1 | 10/2018 | Wang et al. |
| 2018/0296213 | A1* | 10/2018 | Strobl ................ A61B 18/1445 |
| 2018/0296216 | A1 | 10/2018 | Shelton, IV et al. |
| 2018/0333169 | A1 | 11/2018 | Leimbach et al. |
| 2018/0360446 | A1 | 12/2018 | Shelton, IV et al. |
| 2018/0360456 | A1 | 12/2018 | Shelton, IV et al. |
| 2018/0360473 | A1 | 12/2018 | Shelton, IV et al. |
| 2018/0368833 | A1 | 12/2018 | Shelton, IV et al. |
| 2018/0368844 | A1 | 12/2018 | Bakos et al. |
| 2019/0000459 | A1 | 1/2019 | Shelton, IV et al. |
| 2019/0000461 | A1 | 1/2019 | Shelton, IV et al. |
| 2019/0000462 | A1 | 1/2019 | Shelton, IV et al. |
| 2019/0000470 | A1 | 1/2019 | Yates et al. |
| 2019/0000475 | A1 | 1/2019 | Shelton, IV et al. |
| 2019/0000476 | A1 | 1/2019 | Shelton, IV et al. |
| 2019/0000477 | A1 | 1/2019 | Shelton, IV et al. |
| 2019/0000481 | A1 | 1/2019 | Harris et al. |
| 2019/0015102 | A1 | 1/2019 | Baber et al. |
| 2019/0015165 | A1 | 1/2019 | Giordano et al. |
| 2019/0029682 | A1 | 1/2019 | Huitema et al. |
| 2019/0029701 | A1 | 1/2019 | Shelton, IV et al. |
| 2019/0033955 | A1 | 1/2019 | Leimbach et al. |
| 2019/0038281 | A1 | 2/2019 | Shelton, IV et al. |
| 2019/0038282 | A1 | 2/2019 | Shelton, IV et al. |
| 2019/0038283 | A1 | 2/2019 | Shelton, IV et al. |
| 2019/0038285 | A1 | 2/2019 | Mozdzierz |
| 2019/0059986 | A1 | 2/2019 | Shelton, IV et al. |
| 2019/0076143 | A1 | 3/2019 | Smith |
| 2019/0090871 | A1 | 3/2019 | Shelton, IV et al. |
| 2019/0091183 | A1 | 3/2019 | Tomat et al. |
| 2019/0099179 | A1 | 4/2019 | Leimbach et al. |
| 2019/0099229 | A1 | 4/2019 | Spivey et al. |
| 2019/0104919 | A1 | 4/2019 | Shelton, IV et al. |
| 2019/0105035 | A1 | 4/2019 | Shelton, IV et al. |
| 2019/0105036 | A1 | 4/2019 | Morgan et al. |
| 2019/0105037 | A1 | 4/2019 | Morgan et al. |
| 2019/0105039 | A1 | 4/2019 | Morgan et al. |
| 2019/0105043 | A1 | 4/2019 | Jaworek et al. |
| 2019/0105044 | A1 | 4/2019 | Shelton, IV et al. |
| 2019/0110779 | A1 | 4/2019 | Gardner et al. |
| 2019/0110791 | A1 | 4/2019 | Shelton, IV et al. |
| 2019/0117224 | A1 | 4/2019 | Setser et al. |
| 2019/0125320 | A1 | 5/2019 | Shelton, IV et al. |
| 2019/0125335 | A1 | 5/2019 | Shelton, IV et al. |
| 2019/0125336 | A1 | 5/2019 | Deck et al. |
| 2019/0125338 | A1 | 5/2019 | Shelton, IV et al. |
| 2019/0125342 | A1 | 5/2019 | Beardsley et al. |
| 2019/0125358 | A1 | 5/2019 | Shelton, IV et al. |
| 2019/0125361 | A1 | 5/2019 | Shelton, IV et al. |
| 2019/0125377 | A1 | 5/2019 | Shelton, IV |
| 2019/0125378 | A1 | 5/2019 | Shelton, IV et al. |
| 2019/0125388 | A1 | 5/2019 | Shelton, IV et al. |
| 2019/0125430 | A1 | 5/2019 | Shelton, IV et al. |
| 2019/0125431 | A1 | 5/2019 | Shelton, IV et al. |
| 2019/0125432 | A1 | 5/2019 | Shelton, IV et al. |
| 2019/0125454 | A1 | 5/2019 | Stokes et al. |
| 2019/0125455 | A1 | 5/2019 | Shelton, IV et al. |
| 2019/0125458 | A1 | 5/2019 | Shelton, IV et al. |
| 2019/0125459 | A1 | 5/2019 | Shelton, IV et al. |
| 2019/0125476 | A1 | 5/2019 | Shelton, IV et al. |
| 2019/0133422 | A1 | 5/2019 | Nakamura |
| 2019/0138770 | A1 | 5/2019 | Compaijen et al. |
| 2019/0142421 | A1 | 5/2019 | Shelton, IV |
| 2019/0150925 | A1 | 5/2019 | Marczyk et al. |
| 2019/0151029 | A1 | 5/2019 | Robinson |
| 2019/0159778 | A1 | 5/2019 | Shelton, IV et al. |
| 2019/0183502 | A1 | 6/2019 | Shelton, IV et al. |
| 2019/0192141 | A1 | 6/2019 | Shelton, IV et al. |
| 2019/0192146 | A1 | 6/2019 | Widenhouse et al. |
| 2019/0192147 | A1 | 6/2019 | Shelton, IV et al. |
| 2019/0192148 | A1 | 6/2019 | Shelton, IV et al. |
| 2019/0192151 | A1 | 6/2019 | Shelton, IV et al. |
| 2019/0192153 | A1 | 6/2019 | Shelton, IV et al. |
| 2019/0192155 | A1 | 6/2019 | Shelton, IV et al. |
| 2019/0192157 | A1 | 6/2019 | Scott et al. |
| 2019/0200844 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0201024 | A1 | 7/2019 | Shelton, IV et al. |
| 2019/0201025 | A1 | 7/2019 | Shelton, IV et al. |
| 2019/0201026 | A1 | 7/2019 | Shelton, IV et al. |
| 2019/0201027 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201033 | A1 | 7/2019 | Yates et al. |
| 2019/0201034 | A1 | 7/2019 | Shelton, IV et al. |
| 2019/0201045 | A1 | 7/2019 | Yates et al. |
| 2019/0201046 | A1 | 7/2019 | Shelton, IV et al. |
| 2019/0201047 | A1 | 7/2019 | Yates et al. |
| 2019/0201104 | A1 | 7/2019 | Shelton, IV et al. |

(56) References Cited

U.S. PATENT DOCUMENTS

| | | | |
|---|---|---|---|
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201120 | A1 | 7/2019 | Shelton, IV et al. |
| 2019/0201136 | A1 | 7/2019 | Shelton, IV et al. |
| 2019/0201137 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201594 | A1 | 7/2019 | Shelton, IV et al. |
| 2019/0205001 | A1 | 7/2019 | Messerly et al. |
| 2019/0205567 | A1 | 7/2019 | Shelton, IV et al. |
| 2019/0206003 | A1 | 7/2019 | Harris et al. |
| 2019/0206551 | A1 | 7/2019 | Yates et al. |
| 2019/0206555 | A1 | 7/2019 | Morgan et al. |
| 2019/0206561 | A1 | 7/2019 | Shelton, IV et al. |
| 2019/0206562 | A1 | 7/2019 | Shelton, IV et al. |
| 2019/0206564 | A1 | 7/2019 | Shelton, IV et al. |
| 2019/0206565 | A1 | 7/2019 | Shelton, IV |
| 2019/0206569 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0216558 | A1 | 7/2019 | Giordano et al. |
| 2019/0261983 | A1 | 8/2019 | Granger et al. |
| 2019/0261984 | A1 | 8/2019 | Nelson et al. |
| 2019/0261987 | A1 | 8/2019 | Viola et al. |
| 2019/0269400 | A1 | 9/2019 | Mandakolathur Vasudevan et al. |
| 2019/0269402 | A1 | 9/2019 | Murray et al. |
| 2019/0269428 | A1 | 9/2019 | Allen et al. |
| 2019/0274685 | A1 | 9/2019 | Olson et al. |
| 2019/0282233 | A1 | 9/2019 | Burbank et al. |
| 2019/0290264 | A1 | 9/2019 | Morgan et al. |
| 2019/0290266 | A1 | 9/2019 | Scheib et al. |
| 2019/0290267 | A1 | 9/2019 | Baxter, III et al. |
| 2019/0290297 | A1 | 9/2019 | Haider et al. |
| 2019/0298340 | A1 | 10/2019 | Shelton, IV et al. |
| 2019/0298350 | A1 | 10/2019 | Shelton, IV et al. |
| 2019/0298352 | A1 | 10/2019 | Shelton, IV et al. |
| 2019/0298353 | A1 | 10/2019 | Shelton, IV et al. |
| 2019/0298360 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |
| 2019/0307456 | A1 | 10/2019 | Shelton, IV et al. |
| 2019/0321040 | A1 | 10/2019 | Shelton, IV |
| 2019/0328387 | A1 | 10/2019 | Overmyer et al. |
| 2019/0328390 | A1 | 10/2019 | Harris et al. |
| 2019/0343515 | A1 | 11/2019 | Morgan et al. |
| 2019/0350581 | A1 | 11/2019 | Baxter, III et al. |
| 2019/0357909 | A1 | 11/2019 | Huitema et al. |
| 2020/0000531 | A1 | 1/2020 | Giordano et al. |
| 2020/0008802 | A1 | 1/2020 | Aronhalt et al. |
| 2020/0008809 | A1 | 1/2020 | Shelton, IV et al. |
| 2020/0015819 | A1 | 1/2020 | Shelton, IV et al. |
| 2020/0015915 | A1 | 1/2020 | Swayze et al. |
| 2020/0038016 | A1 | 2/2020 | Shelton, IV et al. |
| 2020/0038018 | A1 | 2/2020 | Shelton, IV et al. |
| 2020/0038020 | A1 | 2/2020 | Yates et al. |
| 2020/0054321 | A1 | 2/2020 | Harris et al. |
| 2020/0054332 | A1 | 2/2020 | Shelton, IV et al. |
| 2020/0054333 | A1 | 2/2020 | Shelton, IV et al. |
| 2020/0054334 | A1 | 2/2020 | Shelton, IV et al. |
| 2020/0054355 | A1 | 2/2020 | Laurent et al. |
| 2020/0060523 | A1 | 2/2020 | Matsuda et al. |
| 2020/0060680 | A1 | 2/2020 | Shelton, IV et al. |
| 2020/0060713 | A1 | 2/2020 | Leimbach et al. |
| 2020/0085431 | A1 | 3/2020 | Swayze et al. |
| 2020/0085435 | A1 | 3/2020 | Shelton, IV et al. |
| 2020/0085438 | A1 | 3/2020 | Shelton, IV et al. |
| 2020/0085518 | A1 | 3/2020 | Giordano et al. |
| 2020/0093484 | A1 | 3/2020 | Shelton, IV et al. |
| 2020/0093485 | A1 | 3/2020 | Shelton, IV et al. |
| 2020/0093506 | A1 | 3/2020 | Leimbach et al. |
| 2020/0093550 | A1 | 3/2020 | Spivey et al. |
| 2020/0100783 | A1 | 4/2020 | Yates et al. |
| 2020/0107829 | A1 | 4/2020 | Shelton, IV et al. |
| 2020/0138436 | A1 | 5/2020 | Yates et al. |
| 2020/0138534 | A1 | 5/2020 | Garcia Kilroy et al. |
| 2020/0146741 | A1 | 5/2020 | Long et al. |
| 2020/0187943 | A1 | 6/2020 | Shelton, IV et al. |
| 2020/0197027 | A1 | 6/2020 | Hershberger et al. |
| 2020/0214706 | A1 | 7/2020 | Vendely et al. |
| 2020/0214731 | A1 | 7/2020 | Shelton, IV et al. |
| 2020/0222047 | A1 | 7/2020 | Shelton, IV et al. |
| 2020/0229812 | A1 | 7/2020 | Parihar et al. |
| 2020/0237371 | A1 | 7/2020 | Huitema et al. |
| 2020/0253605 | A1 | 8/2020 | Swayze et al. |
| 2020/0261078 | A1 | 8/2020 | Bakos et al. |
| 2020/0261086 | A1 | 8/2020 | Zeiner et al. |
| 2020/0261087 | A1 | 8/2020 | Timm et al. |
| 2020/0261106 | A1 | 8/2020 | Hess et al. |
| 2020/0268377 | A1 | 8/2020 | Schmid et al. |
| 2020/0275927 | A1 | 9/2020 | Shelton, IV et al. |
| 2020/0275928 | A1 | 9/2020 | Shelton, IV et al. |
| 2020/0275930 | A1 | 9/2020 | Harris et al. |
| 2020/0281585 | A1 | 9/2020 | Timm et al. |
| 2020/0281587 | A1 | 9/2020 | Schmid et al. |
| 2020/0281590 | A1 | 9/2020 | Shelton, IV et al. |
| 2020/0289112 | A1 | 9/2020 | Whitfield et al. |
| 2020/0297341 | A1 | 9/2020 | Yates et al. |
| 2020/0297346 | A1 | 9/2020 | Shelton, IV et al. |
| 2020/0305862 | A1 | 10/2020 | Yates et al. |
| 2020/0305863 | A1 | 10/2020 | Yates et al. |
| 2020/0305864 | A1 | 10/2020 | Yates et al. |
| 2020/0305870 | A1 | 10/2020 | Shelton, IV |
| 2020/0305871 | A1 | 10/2020 | Shelton, IV et al. |
| 2020/0305872 | A1 | 10/2020 | Weidner et al. |
| 2020/0305874 | A1 | 10/2020 | Huitema et al. |
| 2020/0315612 | A1 | 10/2020 | Shelton, IV et al. |
| 2020/0315625 | A1 | 10/2020 | Hall et al. |
| 2020/0315983 | A1 | 10/2020 | Widenhouse et al. |
| 2020/0323526 | A1 | 10/2020 | Huang et al. |
| 2020/0330092 | A1 | 10/2020 | Shelton, IV et al. |
| 2020/0330093 | A1 | 10/2020 | Shelton, IV et al. |
| 2020/0330094 | A1 | 10/2020 | Baxter, III et al. |
| 2020/0330096 | A1 | 10/2020 | Shelton, IV et al. |
| 2020/0337693 | A1 | 10/2020 | Shelton, IV et al. |
| 2020/0337791 | A1 | 10/2020 | Shelton, IV et al. |
| 2020/0345346 | A1 | 11/2020 | Shelton, IV et al. |
| 2020/0345352 | A1 | 11/2020 | Shelton, IV et al. |
| 2020/0345353 | A1 | 11/2020 | Leimbach et al. |
| 2020/0345354 | A1 | 11/2020 | Leimbach et al. |
| 2020/0345355 | A1 | 11/2020 | Baxter, III et al. |
| 2020/0345356 | A1 | 11/2020 | Leimbach et al. |
| 2020/0345357 | A1 | 11/2020 | Leimbach et al. |
| 2020/0345358 | A1 | 11/2020 | Jenkins |
| 2020/0345359 | A1 | 11/2020 | Baxter, III et al. |
| 2020/0345360 | A1 | 11/2020 | Leimbach et al. |
| 2020/0345435 | A1 | 11/2020 | Traina |
| 2020/0345446 | A1 | 11/2020 | Kimball et al. |
| 2020/0352562 | A1 | 11/2020 | Timm et al. |
| 2020/0367885 | A1 | 11/2020 | Yates et al. |
| 2020/0367886 | A1 | 11/2020 | Shelton, IV et al. |
| 2020/0375585 | A1 | 12/2020 | Swayze et al. |
| 2020/0375592 | A1 | 12/2020 | Hall et al. |
| 2020/0375593 | A1 | 12/2020 | Hunter et al. |
| 2020/0375597 | A1 | 12/2020 | Shelton, IV et al. |
| 2020/0390444 | A1 | 12/2020 | Harris et al. |
| 2020/0397433 | A1 | 12/2020 | Lytle, IV et al. |
| 2020/0397434 | A1 | 12/2020 | Overmyer et al. |
| 2020/0405290 | A1 | 12/2020 | Shelton, IV et al. |
| 2020/0405292 | A1 | 12/2020 | Shelton, IV et al. |
| 2020/0405293 | A1 | 12/2020 | Shelton, IV et al. |
| 2020/0405294 | A1 | 12/2020 | Shelton, IV |
| 2020/0405295 | A1 | 12/2020 | Shelton, IV et al. |
| 2020/0405296 | A1 | 12/2020 | Shelton, IV et al. |
| 2020/0405302 | A1 | 12/2020 | Shelton, IV et al. |
| 2020/0405306 | A1 | 12/2020 | Shelton, IV et al. |

(56) References Cited

U.S. PATENT DOCUMENTS

| | | | |
|---|---|---|---|
| 2020/0405307 | A1 | 12/2020 | Shelton, IV et al. |
| 2020/0405308 | A1 | 12/2020 | Shelton, IV |
| 2020/0405312 | A1 | 12/2020 | Shelton, IV et al. |
| 2020/0405314 | A1 | 12/2020 | Shelton, IV et al. |
| 2020/0405316 | A1 | 12/2020 | Shelton, IV et al. |
| 2020/0405341 | A1 | 12/2020 | Hess et al. |
| 2020/0405409 | A1 | 12/2020 | Shelton, IV et al. |
| 2020/0405410 | A1 | 12/2020 | Shelton, IV |
| 2020/0405416 | A1 | 12/2020 | Shelton, IV et al. |
| 2020/0405437 | A1 | 12/2020 | Shelton, IV et al. |
| 2020/0405439 | A1 | 12/2020 | Shelton, IV et al. |
| 2020/0410177 | A1 | 12/2020 | Shelton, IV |
| 2021/0000466 | A1 | 1/2021 | Leimbach et al. |
| 2021/0000467 | A1 | 1/2021 | Shelton, IV et al. |
| 2021/0000470 | A1 | 1/2021 | Leimbach et al. |
| 2021/0015480 | A1 | 1/2021 | Shelton, IV et al. |
| 2021/0030416 | A1 | 2/2021 | Shelton, IV et al. |
| 2021/0045742 | A1 | 2/2021 | Shelton, IV et al. |
| 2021/0052271 | A1 | 2/2021 | Harris et al. |
| 2021/0052332 | A1 | 2/2021 | Saulenas et al. |
| 2021/0059661 | A1 | 3/2021 | Schmid et al. |
| 2021/0059662 | A1 | 3/2021 | Shelton, IV |
| 2021/0059664 | A1 | 3/2021 | Hensel et al. |
| 2021/0059669 | A1 | 3/2021 | Yates et al. |
| 2021/0059670 | A1 | 3/2021 | Overmyer et al. |
| 2021/0059671 | A1 | 3/2021 | Shelton, IV et al. |
| 2021/0059672 | A1 | 3/2021 | Giordano et al. |
| 2021/0059673 | A1 | 3/2021 | Shelton, IV et al. |
| 2021/0068817 | A1 | 3/2021 | Shelton, IV et al. |
| 2021/0068818 | A1 | 3/2021 | Overmyer et al. |
| 2021/0068820 | A1 | 3/2021 | Parihar et al. |
| 2021/0068831 | A1 | 3/2021 | Baber et al. |
| 2021/0068832 | A1 | 3/2021 | Yates et al. |
| 2021/0068835 | A1 | 3/2021 | Shelton, IV et al. |
| 2021/0077099 | A1 | 3/2021 | Shelton, IV et al. |
| 2021/0077100 | A1 | 3/2021 | Shelton, IV et al. |
| 2021/0077109 | A1 | 3/2021 | Harris et al. |
| 2021/0085313 | A1 | 3/2021 | Morgan et al. |
| 2021/0085314 | A1 | 3/2021 | Schmid et al. |
| 2021/0085315 | A1 | 3/2021 | Aronhalt et al. |
| 2021/0085316 | A1 | 3/2021 | Harris et al. |
| 2021/0085317 | A1 | 3/2021 | Miller et al. |
| 2021/0085318 | A1 | 3/2021 | Swayze et al. |
| 2021/0085319 | A1 | 3/2021 | Swayze et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0085326 | A1 | 3/2021 | Vendely et al. |
| 2021/0093321 | A1 | 4/2021 | Auld et al. |
| 2021/0093323 | A1 | 4/2021 | Scirica et al. |
| 2021/0100541 | A1 | 4/2021 | Shelton, IV et al. |
| 2021/0100550 | A1 | 4/2021 | Shelton, IV et al. |
| 2021/0100982 | A1 | 4/2021 | Laby et al. |
| 2021/0106333 | A1 | 4/2021 | Shelton, IV et al. |
| 2021/0107031 | A1 | 4/2021 | Bales, Jr. et al. |
| 2021/0121175 | A1 | 4/2021 | Yates et al. |
| 2021/0128146 | A1 | 5/2021 | Shelton, IV et al. |
| 2021/0137522 | A1 | 5/2021 | Shelton, IV et al. |
| 2021/0186492 | A1 | 6/2021 | Shelton, IV et al. |
| 2021/0186493 | A1 | 6/2021 | Shelton, IV et al. |
| 2021/0186494 | A1 | 6/2021 | Shelton, IV et al. |
| 2021/0186495 | A1 | 6/2021 | Shelton, IV et al. |
| 2021/0186497 | A1 | 6/2021 | Shelton, IV et al. |
| 2021/0186498 | A1 | 6/2021 | Boudreaux et al. |
| 2021/0186499 | A1 | 6/2021 | Shelton, IV et al. |
| 2021/0186500 | A1 | 6/2021 | Shelton, IV et al. |
| 2021/0186501 | A1 | 6/2021 | Shelton, IV et al. |
| 2021/0186502 | A1 | 6/2021 | Shelton, IV et al. |
| 2021/0186504 | A1 | 6/2021 | Shelton, IV et al. |
| 2021/0186505 | A1 | 6/2021 | Shelton, IV et al. |
| 2021/0186507 | A1 | 6/2021 | Shelton, IV et al. |
| 2021/0204941 | A1 | 7/2021 | Dewaele et al. |
| 2021/0212691 | A1 | 7/2021 | Smith et al. |
| 2021/0219976 | A1 | 7/2021 | DiNardo et al. |
| 2021/0228209 | A1 | 7/2021 | Shelton, IV et al. |
| 2021/0236117 | A1 | 8/2021 | Morgan et al. |
| 2021/0236124 | A1 | 8/2021 | Shelton, IV et al. |
| 2021/0244406 | A1 | 8/2021 | Kerr et al. |
| 2021/0244407 | A1 | 8/2021 | Shelton, IV et al. |
| 2021/0244410 | A1 | 8/2021 | Swayze et al. |
| 2021/0244412 | A1 | 8/2021 | Vendely et al. |
| 2021/0259681 | A1 | 8/2021 | Shelton, IV et al. |
| 2021/0259687 | A1 | 8/2021 | Gonzalez et al. |
| 2021/0259986 | A1 | 8/2021 | Widenhouse et al. |
| 2021/0259987 | A1 | 8/2021 | Widenhouse et al. |
| 2021/0267589 | A1 | 9/2021 | Swayze et al. |
| 2021/0267594 | A1 | 9/2021 | Morgan et al. |
| 2021/0267595 | A1 | 9/2021 | Posada et al. |
| 2021/0267596 | A1 | 9/2021 | Fanelli et al. |
| 2021/0275053 | A1 | 9/2021 | Shelton, IV et al. |
| 2021/0275172 | A1 | 9/2021 | Harris et al. |
| 2021/0275173 | A1 | 9/2021 | Shelton, IV et al. |
| 2021/0275176 | A1 | 9/2021 | Beckman et al. |
| 2021/0282767 | A1 | 9/2021 | Shelton, IV et al. |
| 2021/0282769 | A1 | 9/2021 | Baxter, III et al. |
| 2021/0282776 | A1 | 9/2021 | Overmyer et al. |
| 2021/0290226 | A1 | 9/2021 | Mandakolathur Vasudevan et al. |
| 2021/0290231 | A1 | 9/2021 | Baxter, III et al. |
| 2021/0290232 | A1 | 9/2021 | Harris et al. |
| 2021/0290233 | A1 | 9/2021 | Shelton, IV et al. |
| 2021/0290236 | A1 | 9/2021 | Moore et al. |
| 2021/0290322 | A1 | 9/2021 | Traina |
| 2021/0353284 | A1 | 11/2021 | Yang et al. |
| 2022/0031313 | A1 | 2/2022 | Bakos et al. |
| 2022/0031314 | A1 | 2/2022 | Bakos et al. |
| 2022/0031315 | A1 | 2/2022 | Bakos et al. |
| 2022/0031319 | A1 | 2/2022 | Witte et al. |
| 2022/0031320 | A1 | 2/2022 | Hall et al. |
| 2022/0031323 | A1 | 2/2022 | Witte |
| 2022/0031324 | A1 | 2/2022 | Hall et al. |
| 2022/0031345 | A1 | 2/2022 | Witte |
| 2022/0031346 | A1 | 2/2022 | Parks |
| 2022/0031350 | A1 | 2/2022 | Witte |
| 2022/0031351 | A1 | 2/2022 | Moubarak et al. |
| 2022/0071632 | A1 | 3/2022 | Patel et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101721236 | A | 6/2010 |
| CN | 101756727 | A | 6/2010 |

(56) References Cited

FOREIGN PATENT DOCUMENTS

| | | | |
|---|---|---|---|
| CN | 101828940 | A | 9/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247183 | A | 11/2011 |
| CN | 101779977 | B | 12/2011 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |

(56) References Cited

FOREIGN PATENT DOCUMENTS

| | | | |
|---|---|---|---|
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3326548 | A1 | 5/2018 |
| EP | 3363378 | A1 | 8/2018 |
| EP | 3476334 | A1 | 5/2019 |
| EP | 3275378 | B1 | 7/2019 |
| EP | 383172 | A2 | 6/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H06237937 | A | 8/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |

(56) References Cited

FOREIGN PATENT DOCUMENTS

| | | | |
|---|---|---|---|
| JP | 2013541982 | A | 11/2013 |
| JP | 2013541983 | A | 11/2013 |
| JP | 2013541997 | A | 11/2013 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016512057 | A | 4/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| KR | 20100110134 | A | 10/2010 |
| KR | 20110003229 | A | 1/2011 |
| KR | 300631507 | | 3/2012 |
| KR | 300747646 | | 6/2014 |
| RU | 1814161 | A1 | 5/1993 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO 2007/078988 | A2 | 7/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2019036490 | A1 | 2/2019 |
| WO | Wo 2019/136041 | A1 | 7/2019 |
| WO | WO 2019/229158 | A2 | 12/2019 |
| WO | WO 2020/131418 | A1 | 6/2020 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

(56) References Cited

OTHER PUBLICATIONS

Breedveld et al., "A New, Easily Miniaturized Sterrable Endoscope," IEEE Engineering in Medicine and Biology Magazine (Nov./Dec. 2005).
Disclosed Anonymously, "Motor-Driven Surgical Stapler Improvements," Research Disclosure Database No. 526041, Published: Feb. 2008.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—-6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.

(56) References Cited

OTHER PUBLICATIONS

Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-5 DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
U.S. Appl. No. 17/360,162.
U.S. Appl. No. 17/360,176.
U.S. Appl. No. 17/360,192.
U.S. Appl. No. 17/360,197.
U.S. Appl. No. 17/360,199.
U.S. Appl. No. 17/360,211.
U.S. Appl. No. 17/360,220.
U.S. Appl. No. 17/360,244.
U.S. Appl. No. 17/360,249.
U.S. Appl. No. 18/085,137.
International Search Report and Written Opinion dated Oct. 28, 2021 for Application No. PCT/IB2021/056750, 12 pgs.
International Search Report and Written Opinion dated Nov. 5, 2021 for Application No. PCT/IB2021/056783, 15 pgs.
International Search Report and Written Opinion dated Jan. 5, 2022 for Application No. PCT/IB2021/056753, 23 pgs.

* cited by examiner

SURGICAL INSTRUMENTS WITH FIRING MEMBER CLOSURE FEATURES

CROSS-REFERENCE TO RELATED APPLICATIONS

This non-provisional application claims the benefit under 35 U.S.C. § 119(e) of U.S. Provisional Patent Application Ser. No. 63/057,430, entitled SURGICAL INSTRUMENTS WITH TORSION SPINE DRIVE ARRANGEMENTS, filed Jul. 28, 2020, of U.S. Provisional Patent Application Ser. No. 63/057,432, entitled ARTICULATION JOINT ARRANGEMENTS FOR SURGICAL INSTRUMENTS, filed Jul. 28, 2020, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings in which:

DETAILED DESCRIPTION

Figure 1:
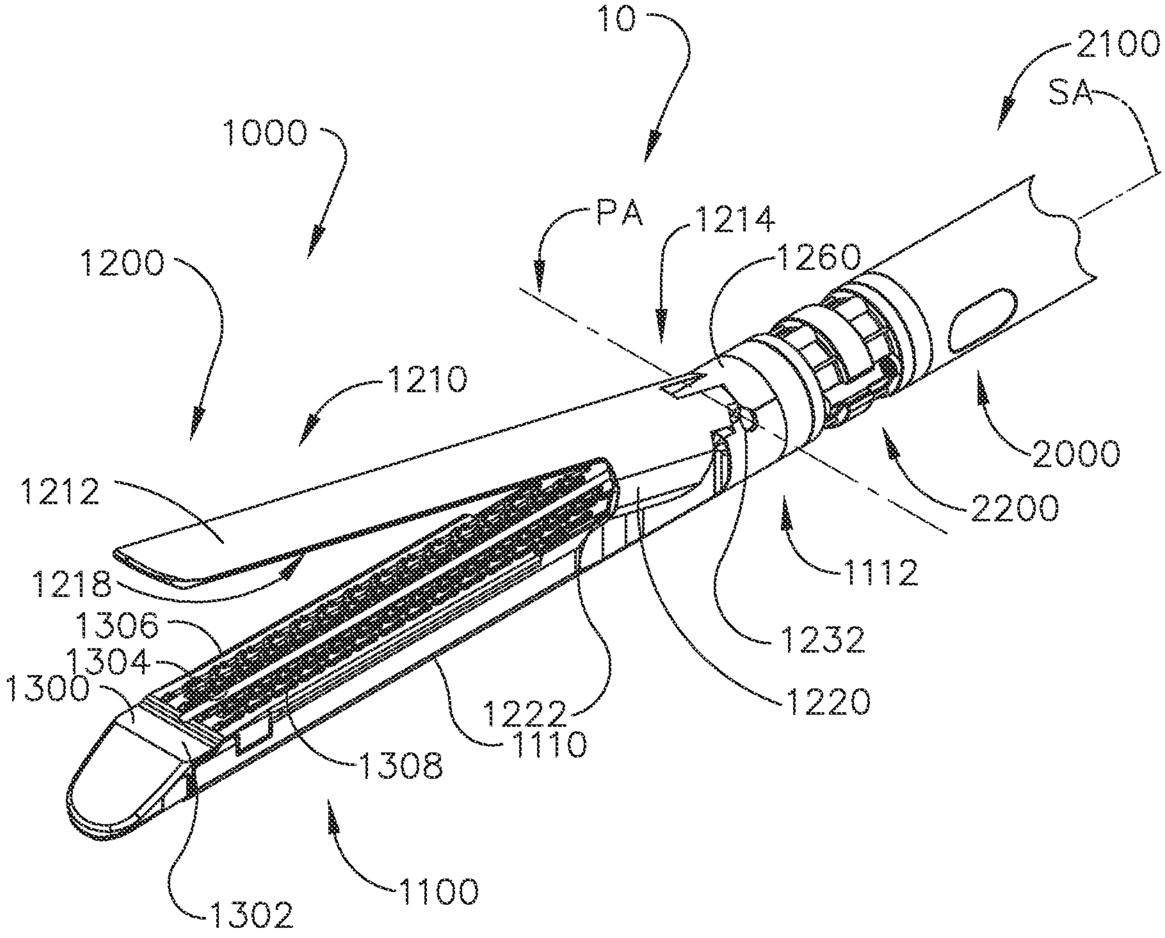
FIG. 1 is a perspective view of a surgical end effector portion of a surgical instrument in accordance with at least one aspect of the present disclosure.
Figure 2:
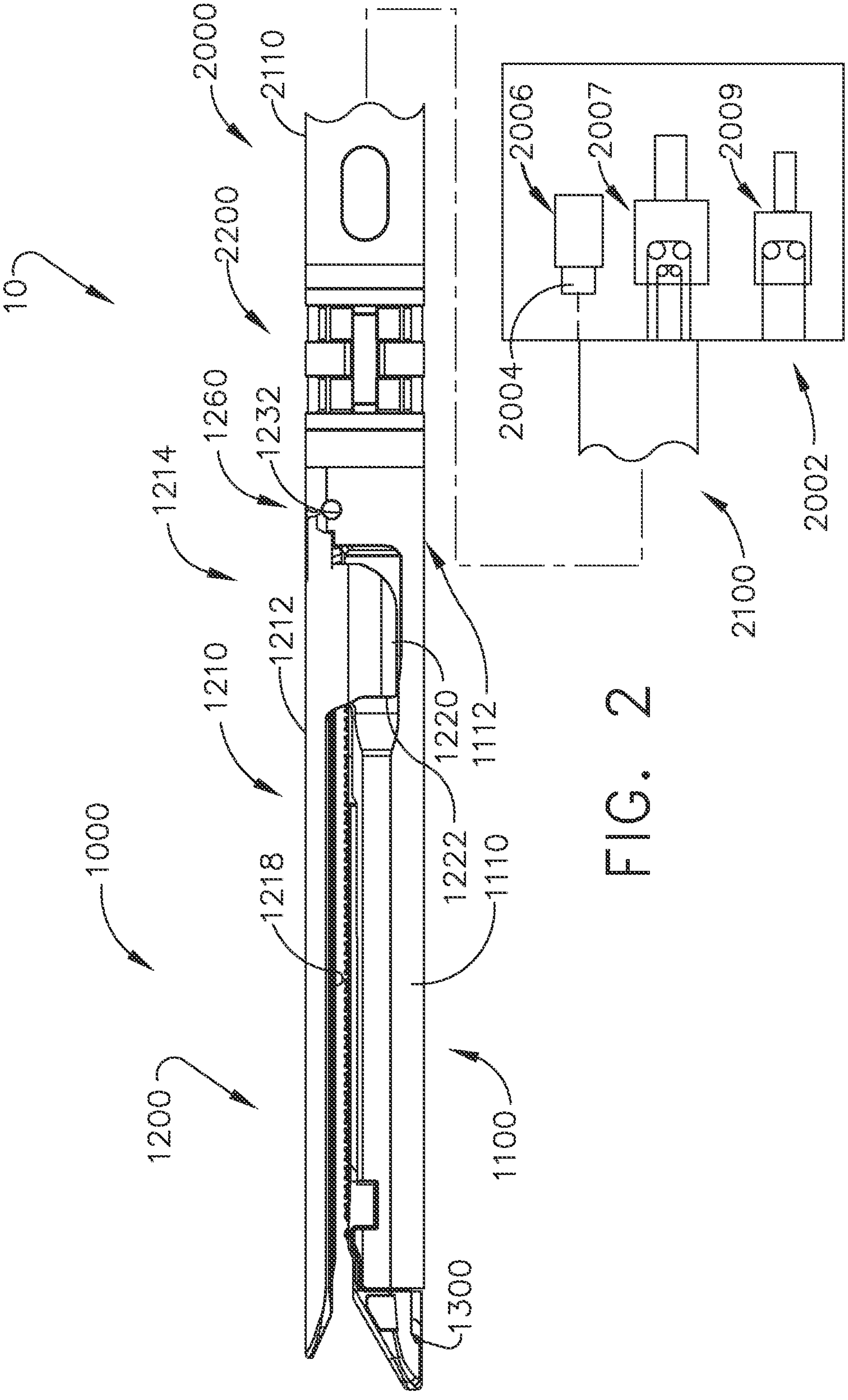
FIG. 2 is a side view of the surgical end effector portion instrument of FIG. 1 in a closed orientation.
Figure 3:
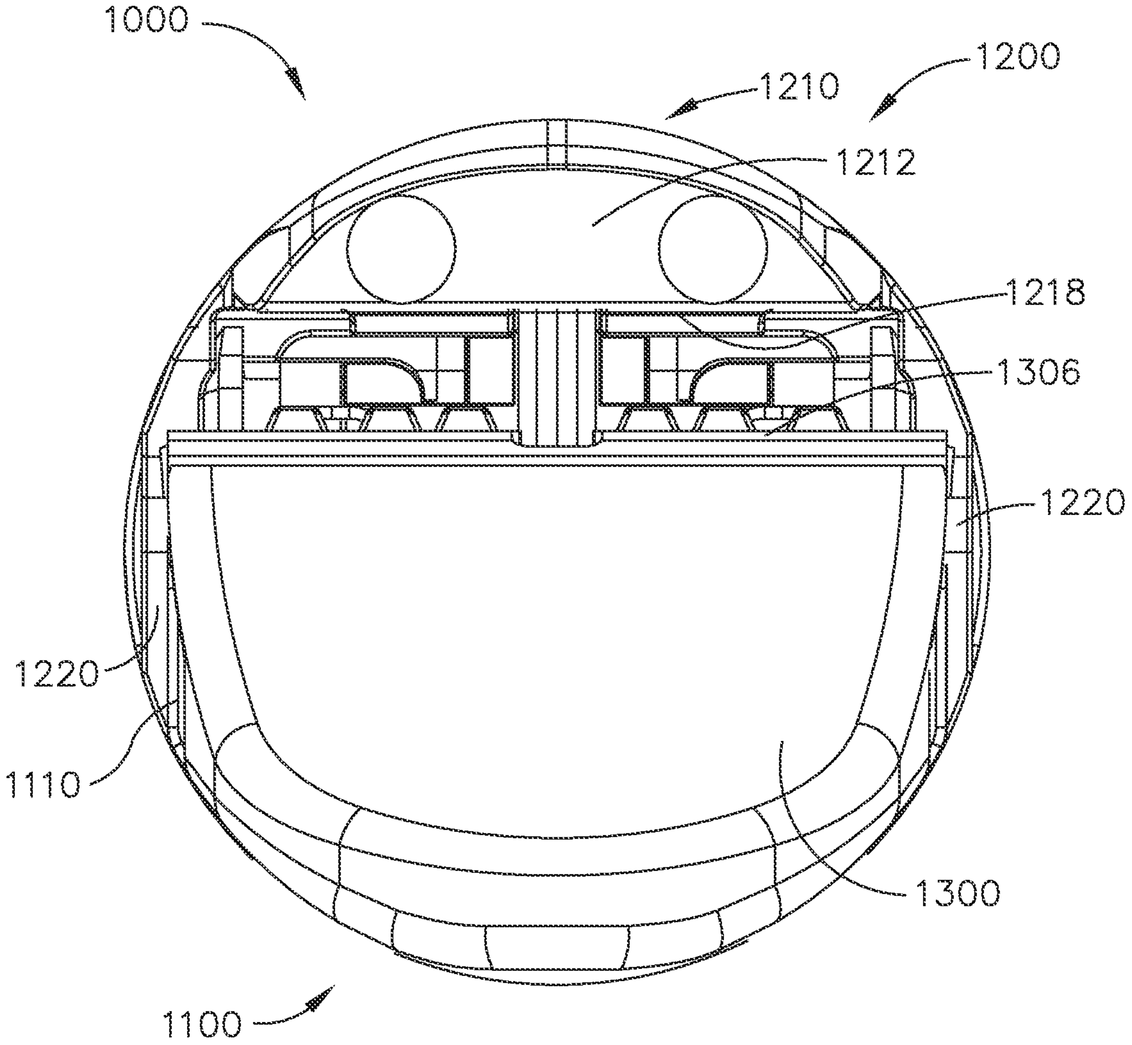
FIG. 3 is an end view of the surgical end effector of FIG. 2.
Figure 4:
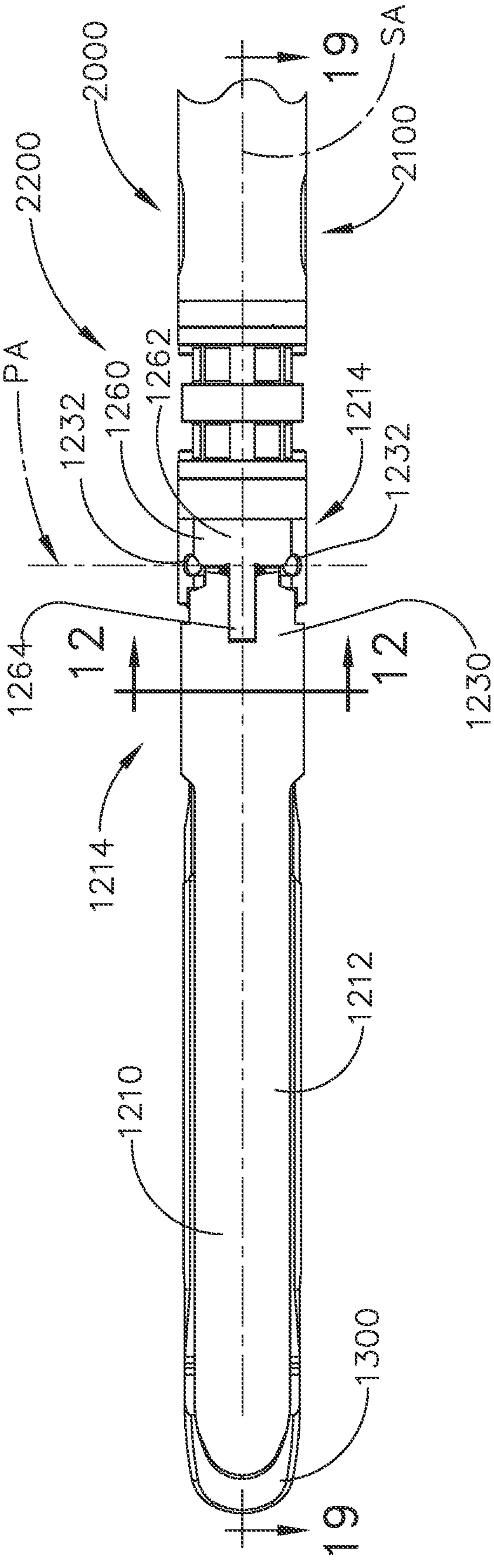
FIG. 4 is a top view of the surgical end effector of FIG. 2.

Applicant of the present application owns the following U.S. Patent Applications that were filed on Jun. 28, 2021 and which are each herein incorporated by reference in their respective entireties:

- U.S. patent application Ser. No. 17/360,133, entitled SURGICAL INSTRUMENTS WITH TORSION SPINE DRIVE ARRANGEMENTS, now U.S. Patent Application Publication No. 2022-0031313;
- U.S. patent application Ser. No. 17/360,149, entitled SURGICAL INSTRUMENTS WITH SEGMENTED FLEXIBLE DRIVE ARRANGEMENTS, now U.S. Patent Application Publication No. 2022-0031314;

- U.S. patent application Ser. No. 17/360,162, entitled SURGICAL INSTRUMENTS WITH FLEXIBLE BALL CHAIN DRIVE ARRANGEMENTS, now U.S. Patent Application Publication No. 2022-0031319;
- U.S. patent application Ser. No. 17/360,176, entitled SURGICAL INSTRUMENTS WITH DOUBLE SPHERICAL ARTICULATION JOINTS WITH PIVOTABLE LINKS, now U.S. Patent Application Publication No. 2022-0031345;
- U.S. patent application Ser. No. 17/360,192 entitled SURGICAL INSTRUMENTS WITH DOUBLE PIVOT ARTICULATION JOINT ARRANGEMENTS, now U.S. Patent Application Publication No. 2022-0031350;
- U.S. patent application Ser. No. 17/360,197, entitled SURGICAL INSTRUMENTS WITH COMBINATION FUNCTION ARTICULATION JOINT ARRANGEMENTS, now U.S. Patent Application Publication No. 2022-0031323;
- U.S. patent application Ser. No. 17/360,199, entitled METHOD OF OPERATING A SURGICAL INSTRUMENT, now U.S. Patent Application Publication No. 2022-0031315;
- U.S. patent application Ser. No. 17/360,211, entitled SURGICAL INSTRUMENTS WITH DUAL SPHERICAL ARTICULATION JOINT ARRANGEMENTS, now U.S. Patent Application Publication No. 2022-0031324;
- U.S. patent application Ser. No. 17/360,220, entitled SURGICAL INSTRUMENTS WITH FLEXIBLE FIRING MEMBER ACTUATOR CONSTRAINT ARRANGEMENTS, now U.S. Patent Application Publication No. 2022-0031320;
- U.S. patent application Ser. No. 17/360,244, entitled ARTICULATABLE SURGICAL INSTRUMENTS WITH ARTICULATION JOINTS COMPRISING FLEXIBLE EXOSKELETON ARRANGEMENTS, now U.S. Patent Application Publication No. 2022-0031346;
- U.S. patent application Ser. No. 17/360,249, entitled SURGICAL INSTRUMENTS WITH DIFFERENTIAL ARTICULATION JOINT ARRANGEMENTS FOR ACCOMMODATING FLEXIBLE ACTUATORS, now U.S. Patent Application Publication No. 2022-0031351.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

Recitation of ranges of values herein are not intended to be limiting, referring instead individually to any and all values falling within the range, unless otherwise indicated herein, and each separate value within such a range is incorporated into the disclosure as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be construed to contemplate a range of deviations that would be appreciated by one of ordinary skill in the art to operate satisfactorily for a corresponding use, function, purpose or the like.

The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

FIGS. 1-4 illustrate one form of a surgical instrument 10 that may address many of the challenges facing surgical instruments with articulatable end effectors that are configured to cut and fasten tissue. In various embodiments, the surgical instrument 10 may comprise a handheld device. In other embodiments, the surgical instrument 10 may comprises an automated system sometimes referred to as a robotically-controlled system, for example. In various forms, the surgical instrument 10 comprises a surgical end effector 1000 that is operably coupled to an elongate shaft assembly 2000. The elongate shaft assembly 2000 may be operably attached to a housing 2002. In one embodiment, the housing 2002 may comprise a handle that is configured to be grasped, manipulated, and actuated by the clinician. In other embodiments, the housing 2002 may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

In one form, the surgical end effector 1000 comprises a first jaw 1100 and a second jaw 1200. In the illustrated arrangement, the first jaw 1100 comprises an elongate channel 1110 that comprises a proximal end 1112 and a distal end 1114 and is configured to operably support a surgical staple cartridge 1300 therein. The surgical staple cartridge 1300 comprises a cartridge body 1302 that has an elongate slot 1304 therein. A plurality of surgical staples or fasteners 1305 are stored therein on drivers 1303 that are arranged in rows on each side of the elongate slot 1304. The drivers 1303 are each associated with corresponding staple cavities 1308 that open through a cartridge deck surface 1306 and are driven therein upon contact with a sled 1312. The surgical staple cartridge 1300 may be replaced after the staples/fasteners 1305 have been discharged therefrom. See FIG. 6. Other embodiments are contemplated wherein the elongate channel 1110 and/or the entire surgical end effector 1000 may is discarded after the surgical staple cartridge 1300 has been used. Such end effector arrangements may be referred to as "disposable loading units", for example.

In the illustrated arrangement, the second jaw 1200 comprises an anvil 1210 that comprises an elongate anvil body 1212 that comprises a proximal end 1214 and a distal end 1216. In one arrangement, a pair of stiffening rods or members 1213 may be supported in the anvil body 1212 to provide the anvil body 1212 with added stiffness and rigidity. The anvil body 1212 comprises a staple-forming undersurface 1218 that faces the first jaw 1100 and may include a series of staple-forming pockets (not shown) that corresponds to each of the staples or fasteners in the surgical staple cartridge 1300. The anvil body 1212 may further include a pair of downwardly extending tissue stop features 1220 that are formed adjacent the proximal end 1214 of the anvil body 1212. One tissue stop feature 1220 extends from each side of the anvil body 1212 such that a distal end 1222 on each tissue stop corresponds to the proximal-most staples/fasteners in the surgical staple cartridge 1300. When the anvil 1210 is moved to a closed position onto tissue positioned between the staple-forming undersurface 1218 of the anvil 1210 and the cartridge deck surface 1306 of the surgical staple cartridge 1300, the tissue contacts the distal ends 1222 of the tissue stop features 1220 to prevent the tissue from migrating proximally past the proximal-most staples/fasteners to thereby ensure that the tissue that is cut is also stapled. When the surgical staple cartridge is "fired" as will be discussed in further detail below, the staples/fasteners supported within each staple cavity are driven out of the staple cavity 1308 through the clamped tissue and into forming contact with the staple-forming undersurface 1218 of the anvil 1210.

Figure 5:
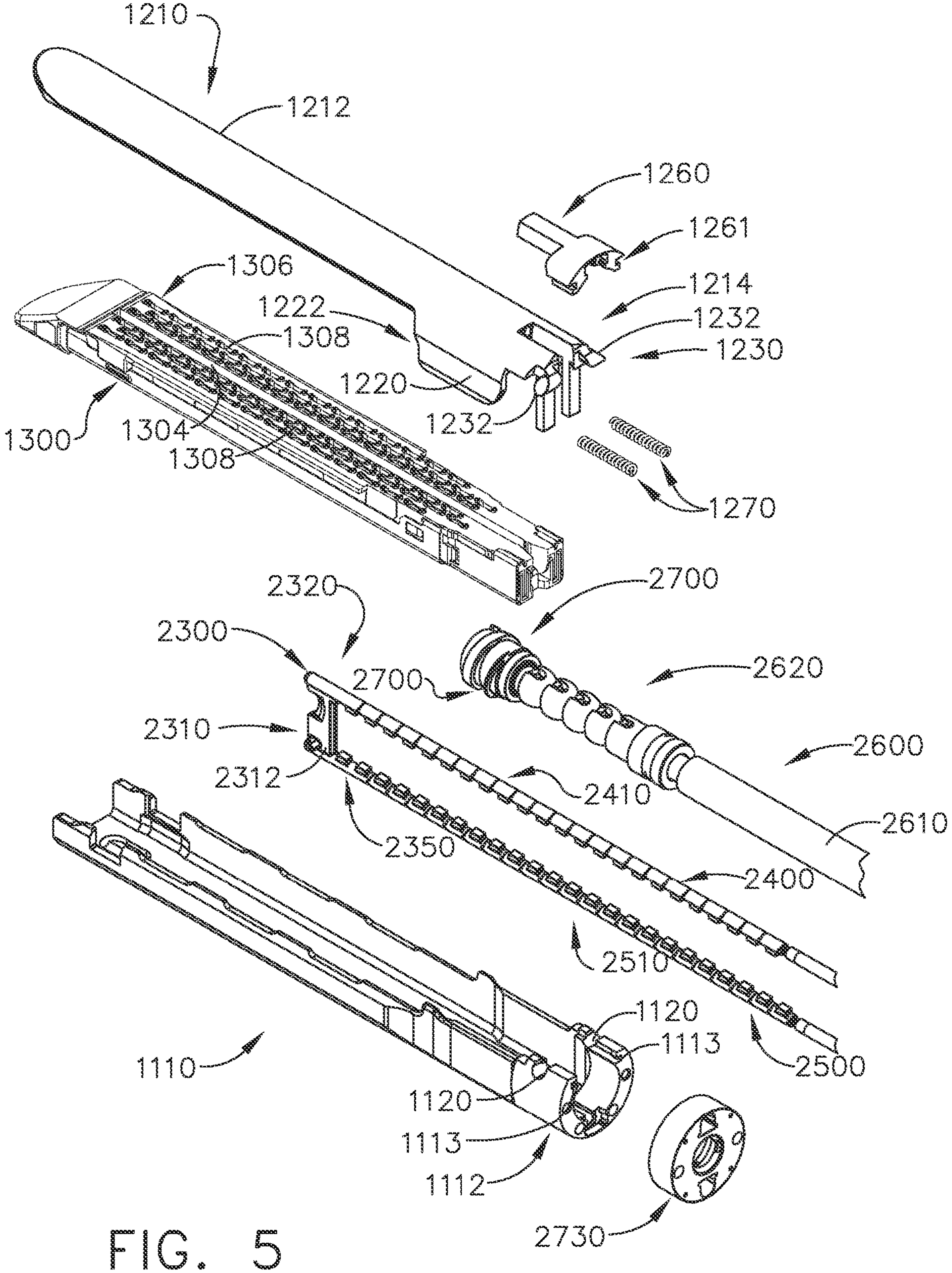
FIG. 5 is an exploded assembly view of a portion of the surgical instrument of FIG. 1.
Figure 6:
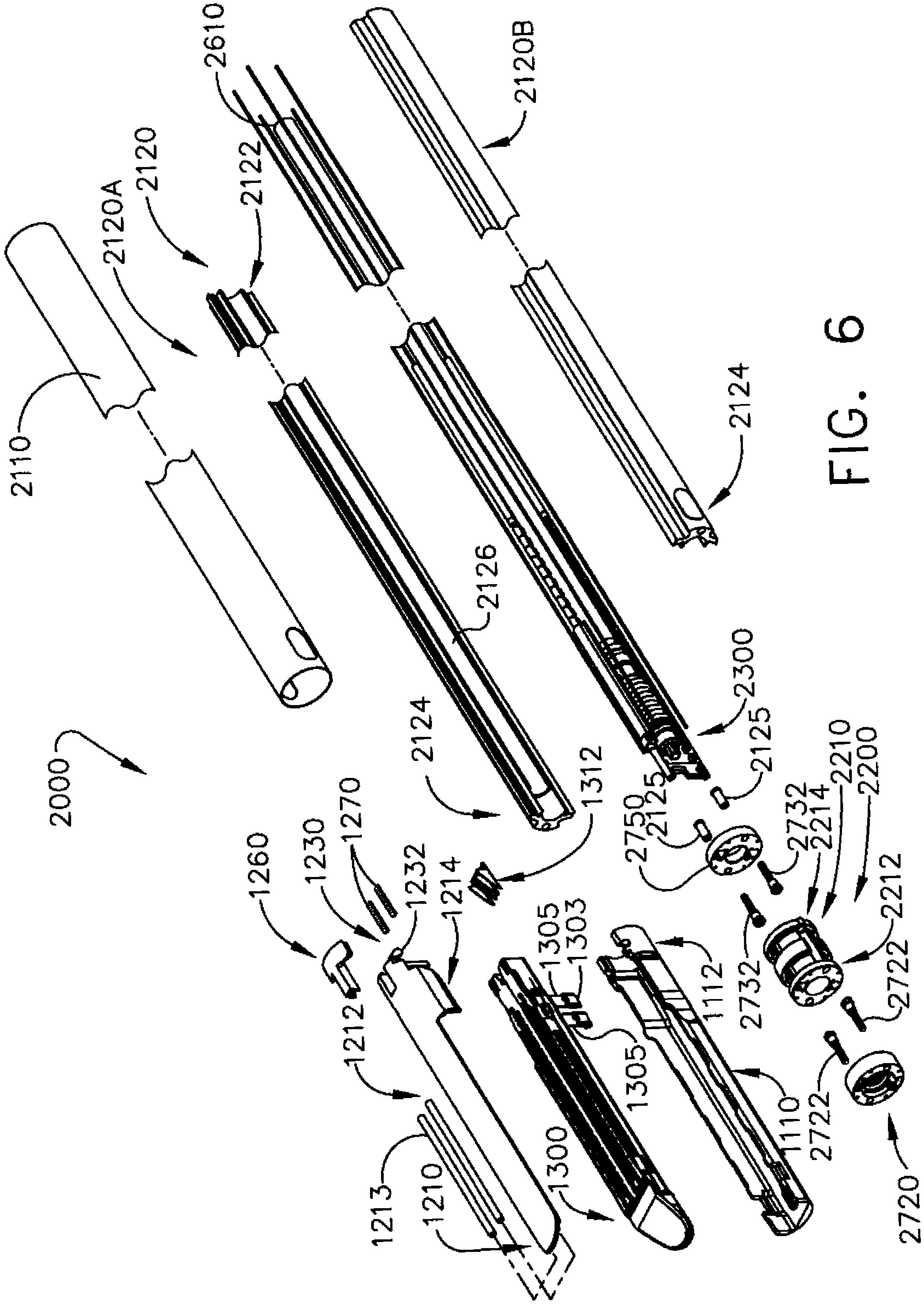
FIG. 6 is an exploded assembly view of an elongate shaft assembly of the surgical instrument of FIG. 1.

As can be seen in FIGS. 5 and 6, the proximal end 1214 of the anvil body 1212 comprises an anvil mounting portion 1230 that includes a pair of laterally extending mounting pins 1232 that are configured to be received in corresponding mounting cradles or pivot cradles 1120 formed in the proximal end 1112 of the elongate channel 1110. The mounting pins 1232 are pivotally retained within the mounting cradles 1120 by an anvil cap 1260 that may be attached to the proximal end 1112 of the elongate channel 1110 by mechanical snap features 1261 that are configured to engage retention formations 1113 on the elongate channel 1110. See FIG. 5. In other arrangements, the anvil cap 1260 may be attached to the elongate channel 1110 by welding, adhesive, etc. Such arrangement facilitates pivotal travel of the anvil 1210 relative to the surgical staple cartridge 1300 mounted in the elongate channel 1110 about a pivot axis PA between an open position (FIG. 1) and a closed position (FIGS. 2-5). Such pivot axis PA may be referred to herein as being "fixed" in that the pivot axis does not translate or otherwise move as the anvil 1200 is pivoted from an open position to a closed position.

In the illustrated arrangement, the elongate shaft assembly 2000 defines a shaft axis SA and comprises a proximal shaft portion 2100 that may operably interface with a housing of the control portion (e.g., handheld unit, robotic tool driver, etc.) of the surgical instrument 10. The elongate shaft assembly 2000 further comprises an articulation joint 2200 that is attached to the proximal shaft portion 2100 and the surgical end effector 1000. In various instances, the proximal shaft portion 2100 comprises a hollow outer tube 2110 that may be operably coupled to a housing 2002. See FIG. 2. As can be seen in FIG. 6, the proximal shaft portion 2100 may further comprise a rigid proximal support shaft 2120 that is supported within the hollow outer tube 2110 and extends from the housing to the articulation joint 2200. The proximal support shaft 2120 may comprise a first half 2120A and a second half 2120B that may be coupled together by, for example, welding, adhesive, etc. The proximal support member 2120 comprises a proximal end 2122 and a distal end 2124 and includes an axial passage 2126 that extends therethrough from the proximal end 2122 to the distal end 2124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 10 employs a firing system 2300 that may address many if not all of these issues as well as others.

As can be seen in FIGS. 5-11, in at least one embodiment, the firing system 2300 comprises a firing member 2310 that includes a vertically-extending firing member body 2312 that comprises a top firing member feature 2320 and a bottom firing member feature 2350. A tissue cutting blade 2314 is attached to or formed in the vertically-extending firing member body 2312. See FIGS. 9 and 11. In at least one arrangement, it is desirable for the firing member 2310 to pass through the anvil body 1212 with low friction, high strength and high stiffness. In the illustrated arrangement, the top firing member feature 2320 comprises a top tubular body 2322 that has a top axial passage 2324 extending therethrough. See FIG. 10. The bottom firing member feature 2350 comprises a bottom tubular body 2352 that has a bottom axial passage 2354 extending therethrough. In at least one arrangement, the top firing member feature 2320 and the bottom firing member feature 2350 are integrally formed with the vertically-extending firing member body 2312. As can be seen in FIG. 12, the anvil body 1212 comprises an axially extending anvil slot 1240 that has a cross-sectional shape that resembles a "keyhole". Similarly, the elongate channel 1110 comprises an axially extending channel slot 1140 that also has a keyhole cross-sectional shape.

Traditional firing member arrangements employ long flexible cantilever wings that extend from a top portion and a bottom portion of the firing member. These cantilever wings slidably pass through slots in the anvil and channel that are commonly cut with a rectangular t-cutter which tended to produce higher friction surfaces. Such long cantilever wings have minimum surface area contact with the anvil and channel and can result in galling of those components. The keyhole-shaped channel slot 1140 and keyhole-shaped anvil slot 1240 may be cut with a round t-cutter and may be finished with a reamer/borer which will result in the creation of a lower friction surface. In addition, the top tubular body 2322 and the bottom tubular body 2352 are stiffer than the prior cantilever wing arrangements and have increased surface area contact with the anvil and channel, respectively which can reduce galling and lead to a stronger sliding connection. Stated another way, because the anvil slot 1240 and the channel slot 1140 are keyhole-shaped and have less material removed than a traditional rectangular slot, the geometry and increased material may result in a stiffer anvil and channel when compared to prior arrangements.

Figure 9:
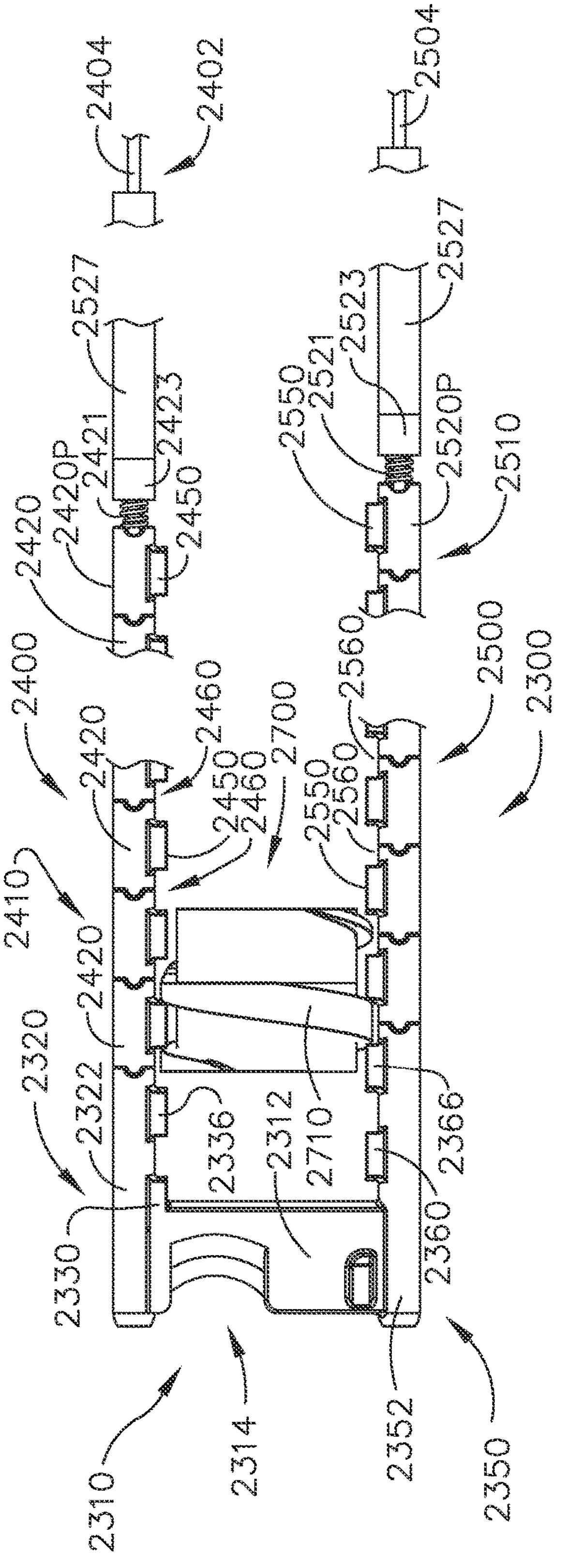
FIG. 9 is a side view of a firing member and upper and lower flexible spine assemblies of the firing system in engagement with a rotary drive screw of the rotary drive system of FIG. 8.
Figure 10:
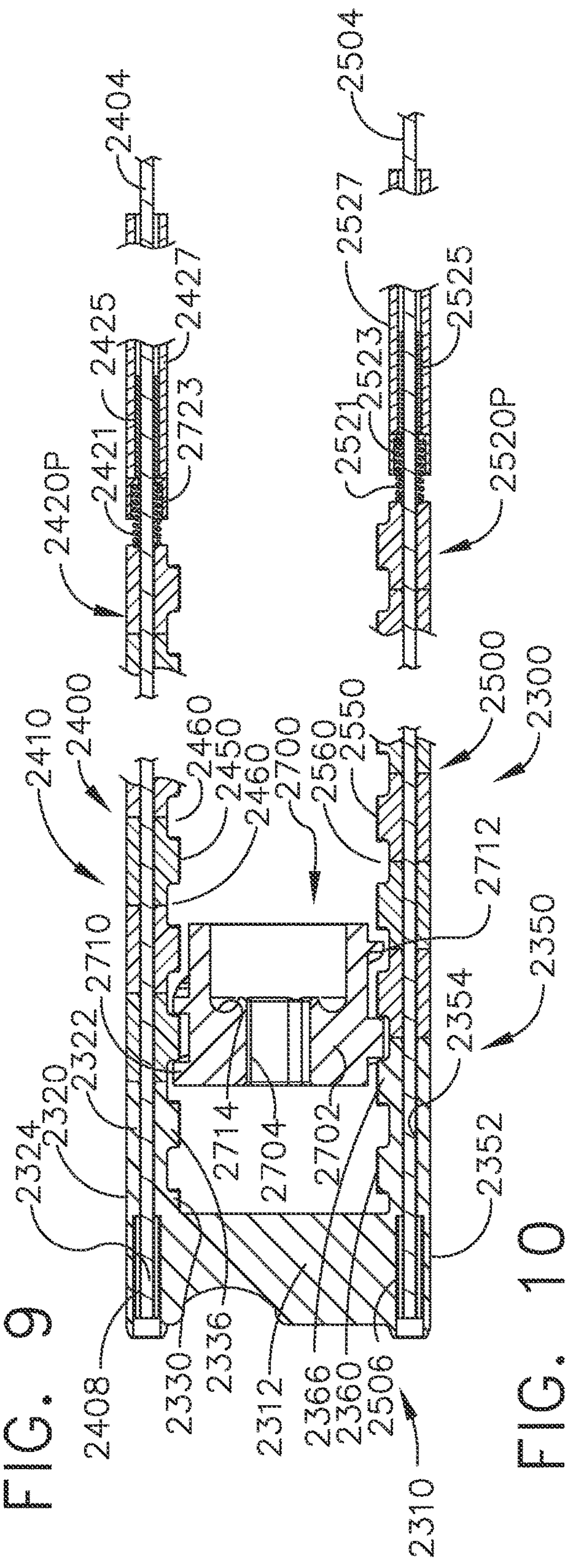
FIG. 10 is a cross-sectional view of the firing member and upper and lower flexible spine assemblies of FIG. 9.
Figure 11:
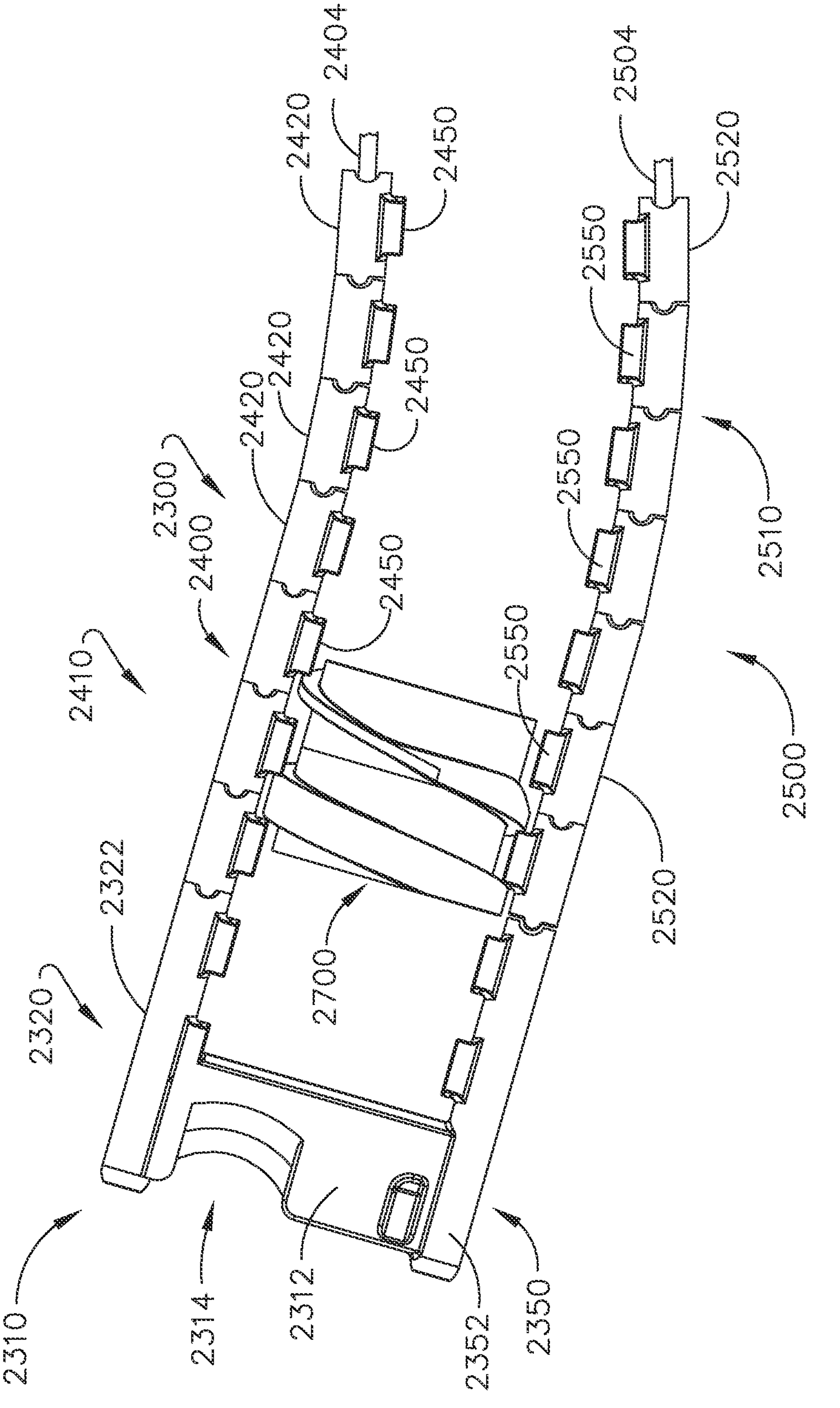
FIG. 11 is a side elevational view of the firing member and upper and lower flexible spine assemblies in engagement with the rotary drive screw of FIG. 9.
Figure 12:
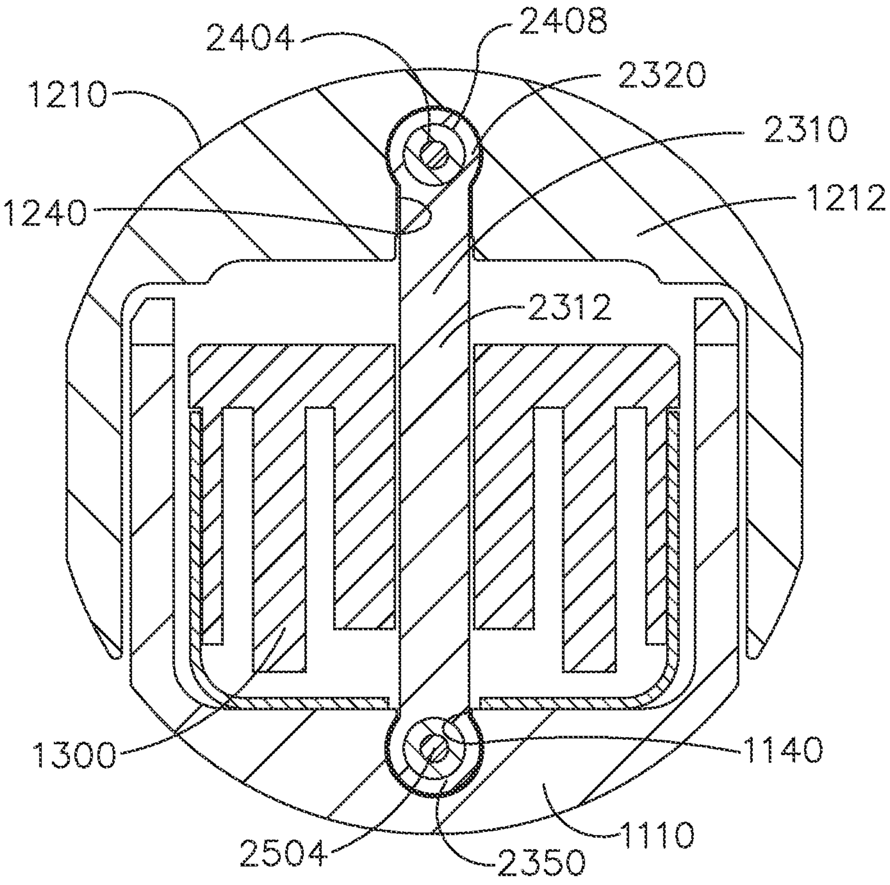
FIG. 12 is a cross-sectional end view of the surgical end effector of FIG. 4 taken along line 12-12 in FIG. 4.

Turning to FIGS. 9-11, in one arrangement, the firing system 2300 further comprises an upper flexible spine assembly 2400 that is operably coupled to the top firing member feature 2320 and a lower flexible spine assembly 2500 that is operably coupled to the bottom firing member feature 2350. In at least one embodiment, the upper flexible spine assembly 2400 comprises an upper series 2410 of upper vertebra members 2420 that are loosely coupled together by an upper flexible coupler member 2402 that is attached to the top firing member feature 2320. The upper flexible coupler member 2402 may comprises a top cable 2404 that extends through the top axial passage 2324 in the top firing member feature 2320 and a distal end 2406 of the top cable 2404 is attached to a retainer ferrule 2408 that is secured with the top axial passage 2324.

Figure 13:
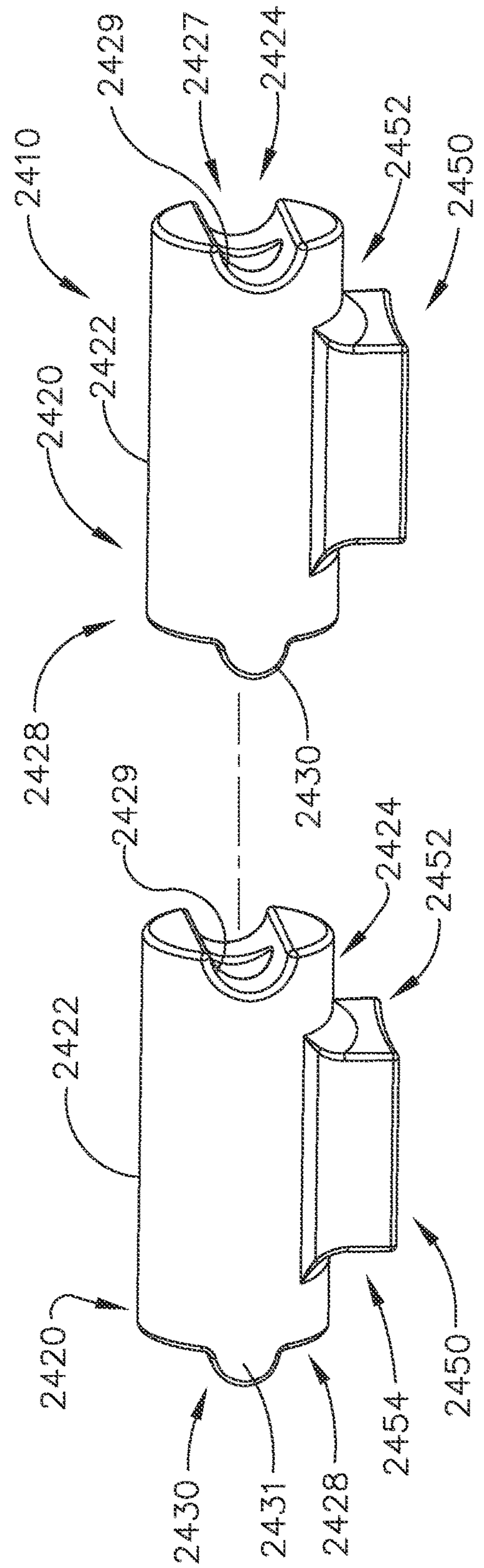
FIG. 13 is an exploded perspective view of two adjacent upper vertebra members of the upper flexible spine assembly of FIG. 10.

As can be seen in FIG. 13, each upper vertebra member 2420 comprises an upper vertebra body portion 2422 that has a proximal end 2424 and a distal end 2428. An upper hollow passage 2429 extends through the upper vertebra body portion 2422 to accommodate passage of the upper flexible coupler member 2402 therethrough. Each upper vertebra member 2420 further comprises a downwardly extending upper drive feature or upper vertebra member tooth 2450 that protrudes from the upper vertebra body portion 2422. Each upper vertebra member tooth 2450 has a helix-shaped proximal upper face portion 2452 and a helix-shaped distal upper face portion 2454. Each proximal end 2424 of the upper vertebra body portions 2422 has an upper proximal mating feature 2426 therein and each distal end 2428 has an upper distal mating feature 2430 formed therein. In at least one embodiment, the upper proximal mating feature 2426 comprises a concave recess 2427 and each upper distal mating feature 2430 comprises a convex mound 2431. When arranged in the upper series 2410, the convex mound 2431 on one upper vertebra member 2420 contacts and mates with the concave recess 2427 on an adjacent upper vertebra member 2420 in the upper series 2410 to maintain the upper vertebra members 2420 roughly in alignment so that the helix-shaped proximal upper face portion 2452 and a helix-shaped distal upper face portion 2454 on each respective upper tooth 2450 can be drivingly engaged by a rotary drive screw 2700 as will be discussed in further detail below.

Similarly, in at least one embodiment, the lower flexible spine assembly 2500 comprises a lower series 2510 of lower vertebra members 2520 that are loosely coupled together by a lower flexible coupler member 2502 that is attached to the bottom firing member feature 2350. The lower flexible coupler member 2502 may comprises a lower cable 2504 that extends through the bottom axial passage 2354 in the bottom firing member feature 2350 and a distal end 2506 of the bottom cable 2504 is attached to a retainer ferrule 2508 that is secured with the bottom axial passage 2354.

Figure 14:
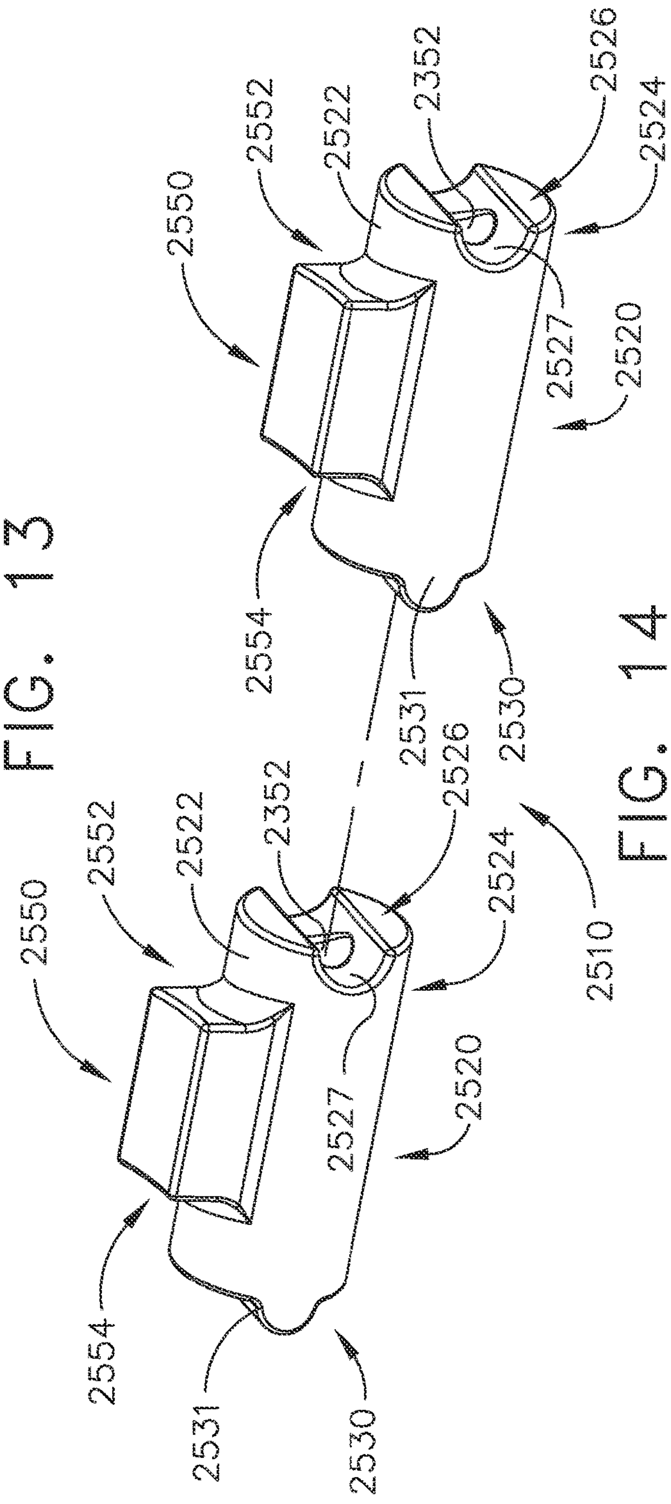
FIG. 14 is an exploded perspective view of two adjacent lower vertebra members of the lower flexible spine assembly of FIG. 10.

As can be seen in FIG. 14, each lower vertebra member 2520 comprises a lower vertebra body portion 2522 that has a proximal end 2524 and a distal end 2528. A lower hollow passage 2529 extends through the lower vertebra body portion 2522 to accommodate passage of the lower flexible coupler member 2502 therethrough. Each lower vertebra member 2520 further comprises an upwardly extending lower drive feature or lower vertebra member tooth 2550 that protrudes upward from the lower vertebra body portion 2522. Each lower vertebra member tooth 2550 has a helix-shaped proximal lower face portion 2552 and a helix-shaped distal lower face portion 2554. Each proximal end 2524 of the lower vertebra body portions 2522 has a lower proximal mating feature 2526 therein and each distal end 2528 has a lower distal mating feature 2530 formed therein. In at least one embodiment, the lower proximal mating feature 2526 comprises a concave recess 2527 and each lower distal mating feature 2530 comprises a convex mound 2531. When arranged in the lower series 2510, the convex mound 2531 on one lower vertebra member 2520 contacts and mates with the concave recess 2527 on an adjacent lower vertebra member 2520 in the lower series 2510 to maintain the lower vertebra members 2520 roughly in alignment so that the helix-shaped proximal lower face portion 2552 and a helix-shaped distal lower face portion 2554 on each respective lower vertebra member tooth 2550 can be drivingly engaged by a rotary drive screw 2700 as will be discussed in further detail below.

Figure 7:
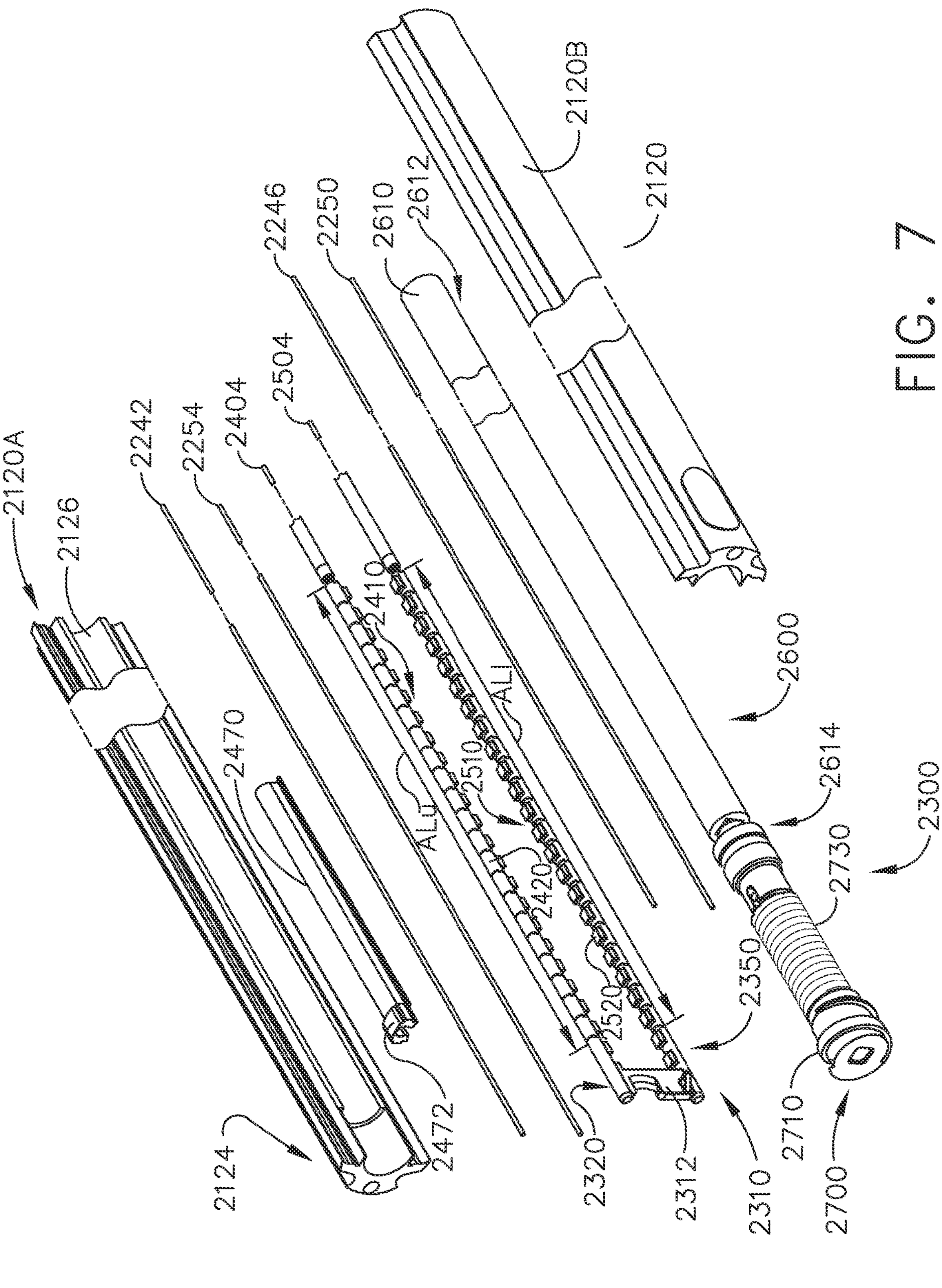
FIG. 7 is another exploded assembly view of the elongate shaft assembly of FIG. 6.
Figure 8:
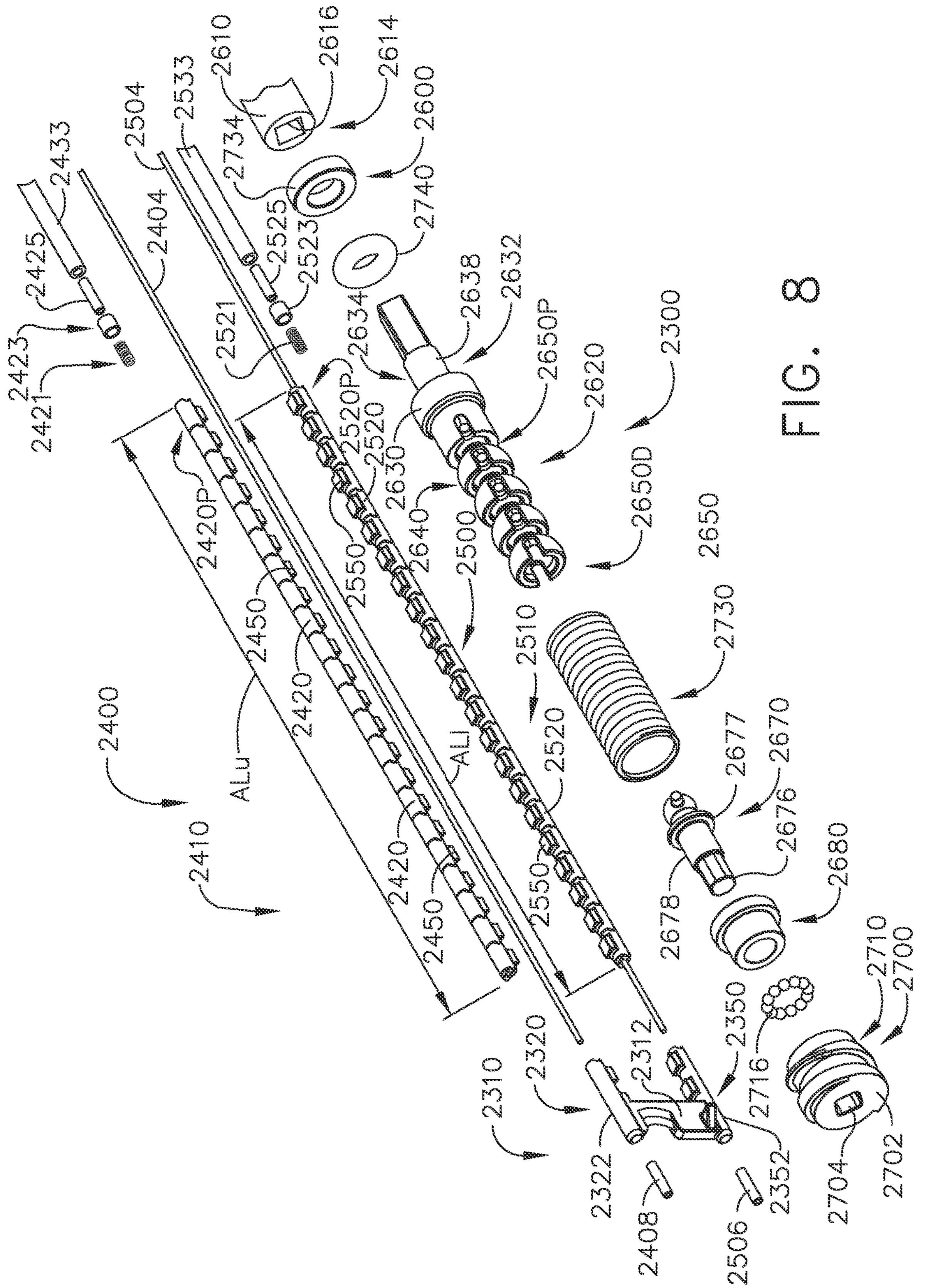
FIG. 8 is an exploded assembly view of a firing system and a rotary drive system according to at least one aspect of the present disclosure.

Now turning to FIGS. 5, 7, and 8, in at least one arrangement, the firing drive system 2300 further comprises a rotary drive screw 2700 that is configured to drivingly interface with the upper series 2410 of upper vertebra members 2420 and the lower series 2510 of lower vertebra members 2520. In the illustrated arrangement, the rotary drive screw 2700 is driven by a rotary drive system 2600 that comprises a proximal rotary drive shaft 2610 that is rotatably supported within the axial passage 2126 within the proximal support shaft 2120. See FIG. 7. The proximal rotary drive shaft 2610 comprises a proximal end 2612 and a distal end 2614. The proximal end 2612 may interface with a gear box 2004 or other arrangement that is driven by a motor 2006 or other source of rotary motion housed in the housing of the surgical instrument. See FIG. 2. Such source of rotary motion causes the proximal rotary drive shaft to rotate about the shaft axis SA within the axial passage 2126 in the proximal support shaft 2120.

Figure 16:
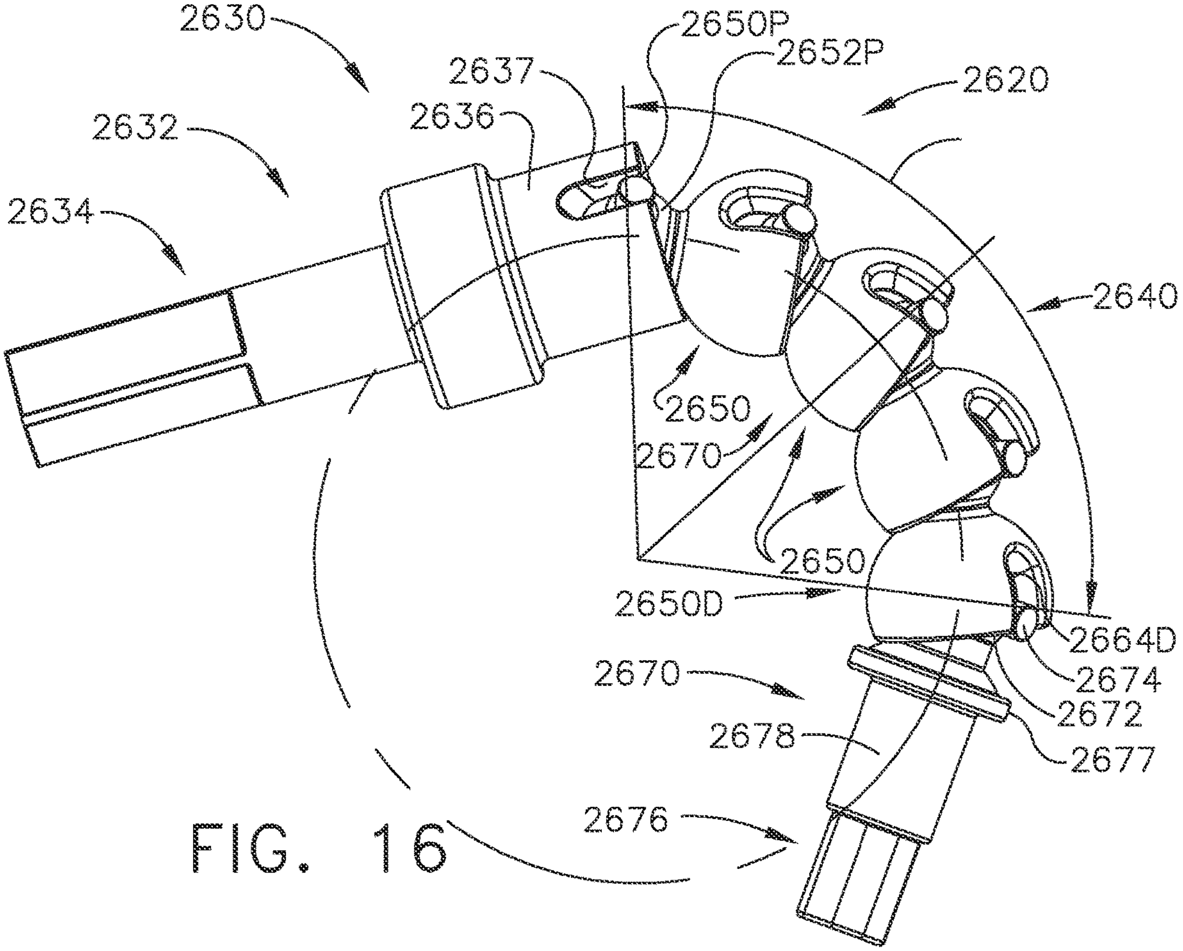
FIG. 16 is a perspective view of a CV drive shaft assembly of the rotary drive system of FIG. 8 in an articulated orientation.
Figure 17:
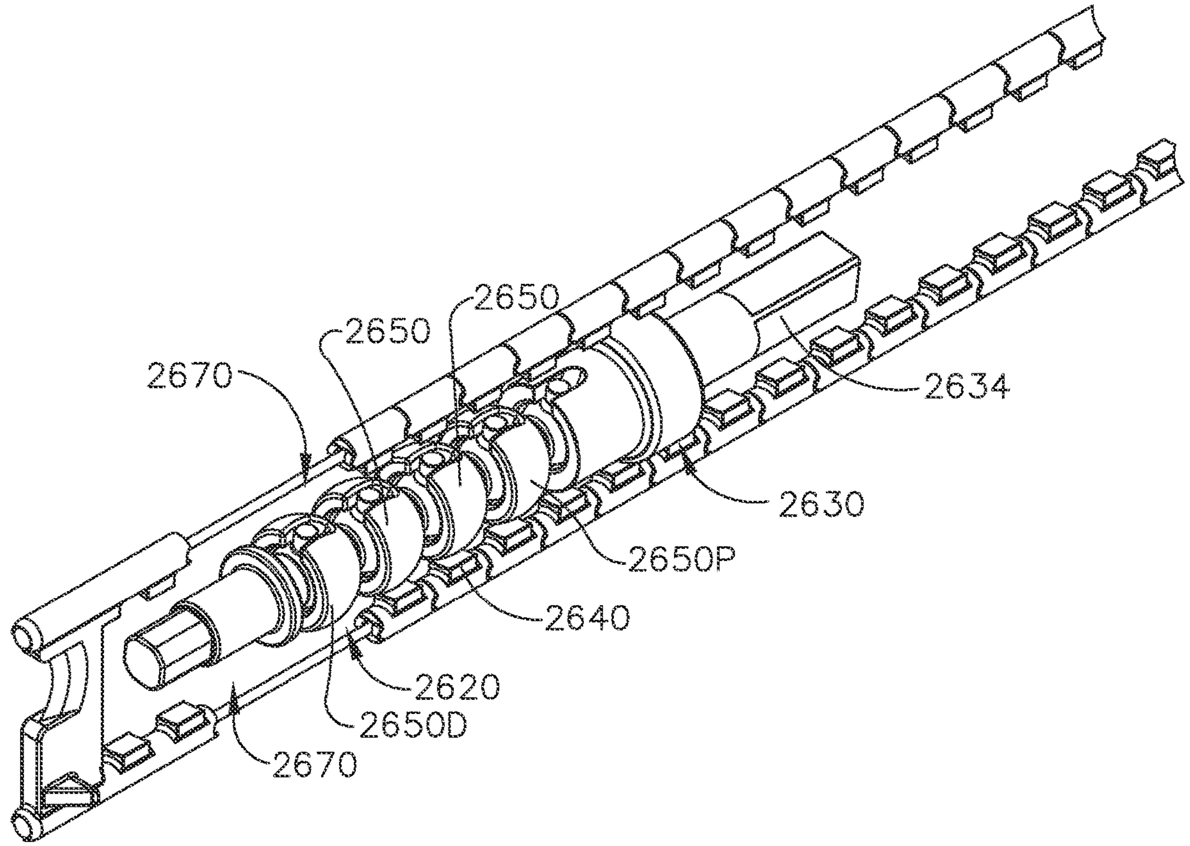
FIG. 17 is a perspective view of the firing system of FIG. 8 in driving engagement with the CV drive shaft assembly of FIG. 16 in accordance with at least one aspect of the present disclosure.

The proximal rotary drive shaft 2610 is operably supported within the elongate shaft assembly 2000 in a location that is proximal to the articulation joint 2200 and operably interfaces with a constant velocity (CV) drive shaft assembly 2620 that spans or extends axially through the articulation joint 2200. As can be seen in FIGS. 8, 16, and 17, in at least one arrangement, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650.

Figure 18:
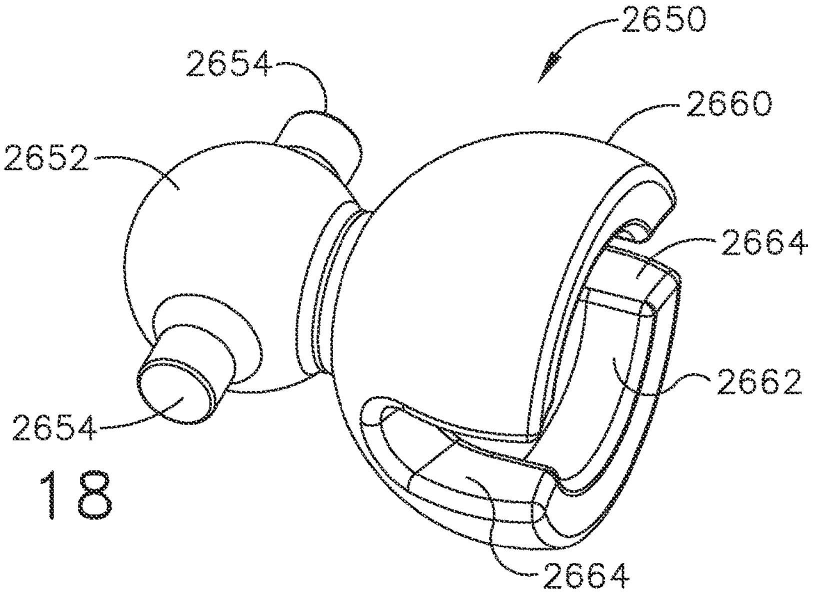
FIG. 18 is a perspective view of a drive joint of the CV drive shaft assembly of FIG. 16.

As can be seen in FIG. 18, in at least one arrangement, each drive joint 2650 comprises a first or distal sphere portion 2660 and a second or proximal sphere portion 2652. The distal sphere portion 2660 is larger than the proximal sphere portion 2652. The distal sphere portion 2660 comprises a socket cavity 2662 that is configured to rotatably receive a proximal sphere portion 2652 of an adjacent drive joint 2650 therein. Each proximal sphere portion 2652 comprises a pair of diametrically opposed joint pins 2654 that are configured to be movably received in corresponding pin slots 2664 in the distal sphere portion 2660 of an adjacent drive joint 2650 as can be seen in FIG. 16. A proximal sphere portion 2652P of a proximal-most drive joint 2650P is rotatably received in a distal socket portion 2636 of the proximal shaft segment 2632 as shown in FIG. 16. The joint pins 2654P are received within corresponding pin slots 2637 in the distal socket portion 2636. As can be further seen in FIG. 16, a distal-most drive joint 2650D in the series 2640 of movably coupled drive joints 2650 is movably coupled to a distal CV drive shaft 2670.

In at least one arrangement, the distal CV drive shaft 2670 comprises a proximal sphere portion 2672 that is sized to be movably received in the socket cavity 2662D in the distal-most drive joint 2650D. The proximal sphere portion 2672 includes joint pins 2674 that are movably received in the pin slots 2664D in the distal-most drive joint 2650D. The distal CV drive shaft 2670 further comprises a distally extending shaft stem 2676 that is configured to be non-rotatably coupled to the rotary drive screw 2700 that is positioned distal to the articulation joint 2200. The distal CV drive shaft 2670 includes a flange 2677 and a mounting barrel portion 2678 for receiving a thrust bearing housing 2680 thereon.

In the illustrated arrangement, when the series 2640 of movably coupled drive joints 2650 articulates, the joint pins 2674 remain in the corresponding pin slots 2664 of an adjacent drive joint 2650. In the example illustrated in FIG. 18, each drive joint may be capable of approximately eighteen degrees of articulation in the pitch and yaw directions. FIG. 16 illustrates an angle of the series of 2640 of drive joints 2650 when each drive joint 2650 in the series are fully articulated ninety degrees in pitch and yaw which yields an angle α of approximately 100.9 degrees. In such arrangement, the outer surface of each distal sphere portion 2660 clears the outer surface of the adjacent or adjoining proximal sphere portion 2652 allowing for unrestricted motion until the eighteen degree limit is reached. The rigid design and limited small angles allow the series 2640 of movably coupled drive joints 2650 to carry high loads torsionally at an overall large angle.

In the illustrated arrangement, the articulation joint 2200 comprises an articulation joint spring 2230 that is supported within an outer elastomeric joint assembly 2210. The outer elastomeric joint assembly 2210 comprises a distal end 2212 that is attached to the proximal end 1112 of the elongate channel 1110. For example, as can be seen in FIG. 6, the distal end 2212 of the outer elastomeric joint assembly 2210 is attached to the proximal end 1112 of the elongate channel 1110 by a pair of cap screws 2722 that extend through a distal mounting bushing 2720 to be threadably received in the proximal end 1112 of the elongate channel 1110. A proximal end 2214 of the elastomeric joint assembly 2210 is attached to the distal end 2124 of the proximal support shaft 2120. The proximal end 2214 of the elastomeric joint assembly 2210 is attached to the distal end 2124 of the proximal support member 2120 by a pair of cap screws 2732 that extend through a proximal mounting bushing 2750 to be threadably received in threaded inserts 2125 mounted within the distal end 2124 of the proximal support shaft 2120.

To prevent the drive joints 2650 from buckling during articulation, the series 2640 of movably coupled drive joints 2650 extend through at least one low friction articulation joint spring 2730 that is supported within the outer elastomeric joint assembly 2210. See FIG. 19. The articulation joint spring 2730 is sized relative to the drive joints 2650 such that a slight radial clearance is provided between the articulation joint spring 2730 and the drive joints 2650. The articulation joint spring 2730 is designed to carry articulation loads axially which may be significantly lower than the torsional firing loads. The joint spring(s) is longer than the series 2640 of drive joints 2650 such that the drive joints are axially loose. If the "hard stack" of the series 2640 of drive joints 2650 is longer than the articulation joint spring(s) 2730 hard stack, then the drive joints 2650 may serve as an articulation compression limiter causing firing loads and articulation loads to resolve axially through the series 2640 of the drive joints 2650. When the firing loads resolve axially through the series 2640 of the drive joints 2650, the loads may try to straighten the articulation joint 2200 or in other words cause de-articulation. If the hard stack of the articulation joint spring(s) 2730 is longer than the hard stack of the series 2640 of the drive joints 2650, the firing loads will then be contained within the end effector and no firing loads will resolve through the drive joints 2650 or through the springs(s) 2730.

Figure 19:
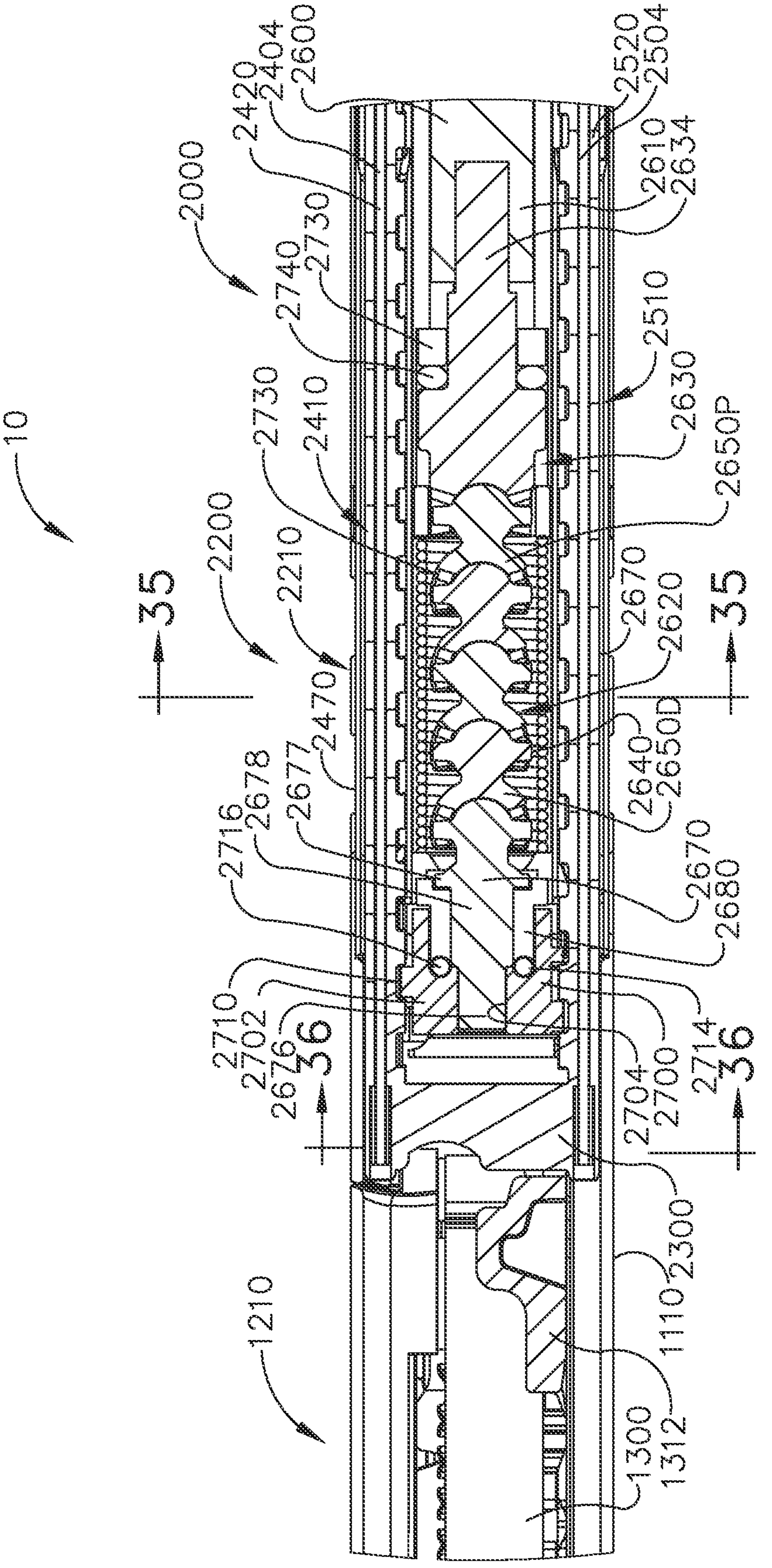
FIG. 19 is a cross-sectional view of a portion of the surgical instrument of FIG. 4 taken along line 19-19 in FIG. 4.
Figure 20:
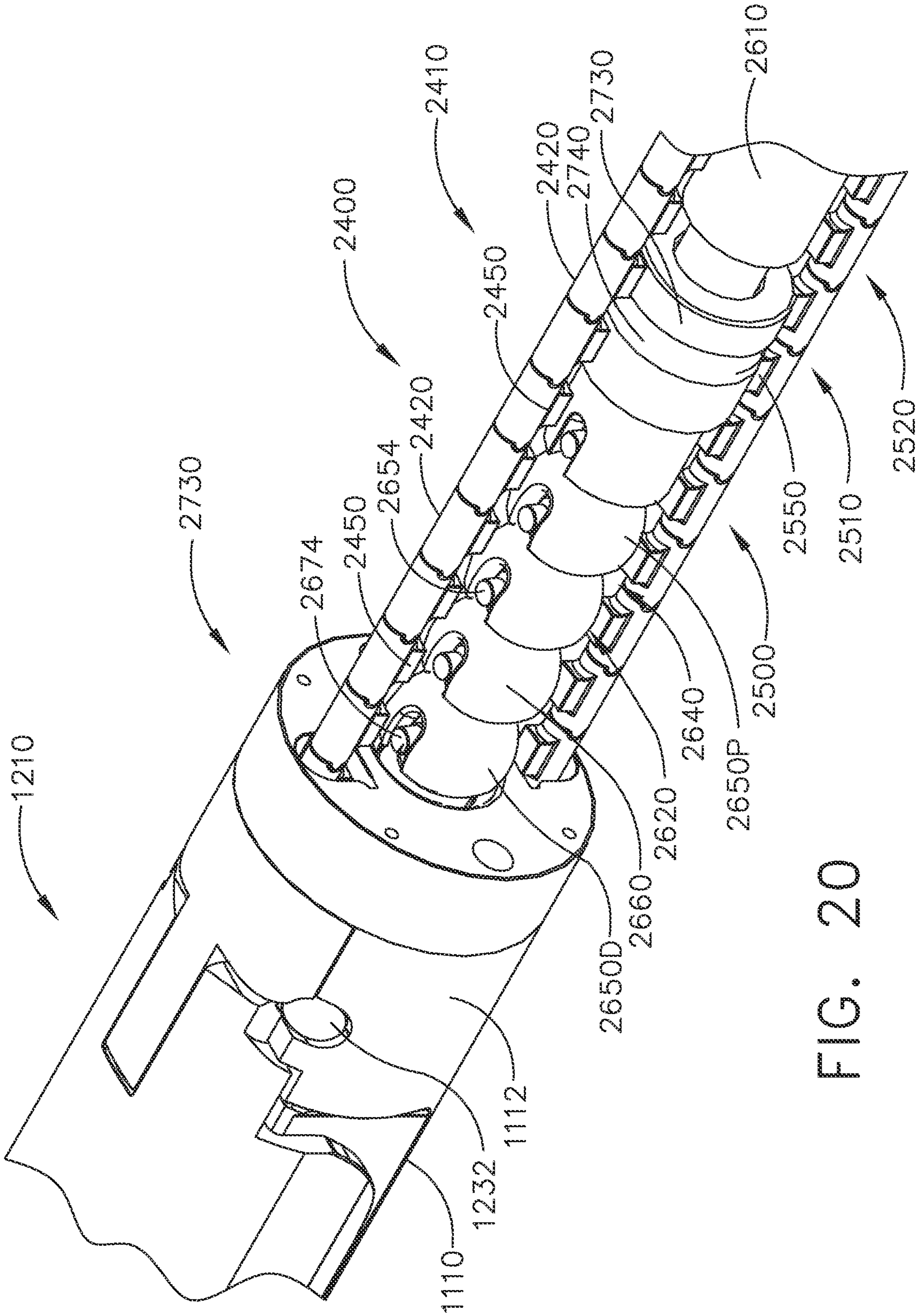
FIG. 20 is a partial perspective view of a proximal end portion of the surgical end effector and portions of the firing system and the rotary drive system of the surgical instrument of FIG. 1.
Figure 21:
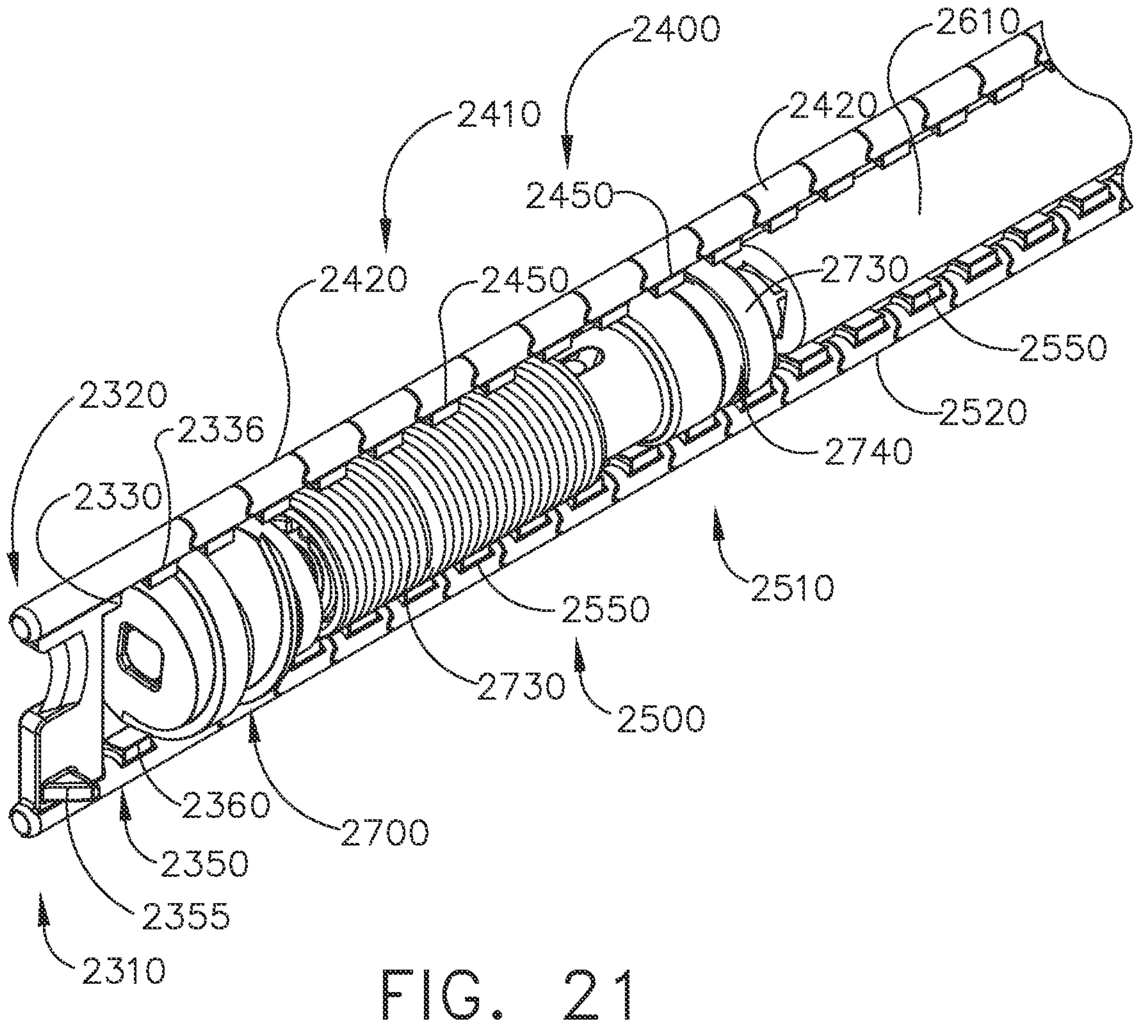
FIG. 21 is a perspective view of the rotary drive system of the surgical instrument of FIG. 1 in driving engagement with the firing system thereof in accordance with at least one aspect of the present disclosure.

To further ensure that the drive joints 2650 are always engaged with each other, a proximal drive spring 2740 is employed to apply an axial biasing force to the series 2640 of drive joints 2650. For example, as can be seen in FIGS. 8, 19, and 20, the proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring/bushing received on the proximal barrel portion 2638 of the proximal shaft segment 2632. The proximal drive spring 2740 lightly biases the drive joints 2650 together to decrease any gaps that may occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

As can be seen in FIGS. 9 and 10, the top firing member feature 2320 on the firing member 2310 comprises a distal upper firing member tooth segment 2330 that is equivalent to one half of an upper tooth 2450 on each upper vertebra member 2420. In addition, a proximal upper firing member tooth 2336 that is identical to an upper tooth 2450 on each upper vertebra member 2420 is spaced from the distal upper firing member tooth segment 2330. The distal upper firing member tooth segment 2330 and the proximal upper firing member tooth 2336 may be integrally formed with the top firing member feature 2320 of the firing member 2310. Likewise, the bottom firing member feature 2350 of the firing member 2310 comprises a distal lower firing member tooth 2360 and a proximal lower firing member tooth 2366 that are integrally formed on the bottom firing member feature 2350. For example, in at least one arrangement, the firing member 2310 with the rigidly attached teeth 2330, 2336, 2360, and 2366 may be fabricated at one time as one unitary component using conventional metal injection molding techniques.

As indicated above, each of the upper vertebra members 2520 is movably received on an upper flexible coupler member 2402 in the form of a top cable 2404. As was described above, the distal end 2406 of the top cable 2404 is secured to the top firing member feature 2320 of the firing member 2310. Similarly, each of the lower vertebra members 2520 is movably received on a lower flexible coupler member 2502 in the form of a lower cable 2504. A distal end 2506 of the lower cable 2504 is secured to the bottom firing member feature 2350 of the firing member 2310. In at least one arrangement, the top cable 2404 and the bottom cable 2504 extend through the proximal shaft portion 2100 and, as will be discussed in further detail below, may interface with a bailout arrangement supported in the housing for retracting the firing member 2310 back to its home or starting position should the firing member drive system fail.

Turning again to FIG. 8, the axial length $AL_u$ of the upper series 2410 of upper vertebra members 2420 and the axial length $AL_1$ of the lower series 2510 of lower vertebra members 2520 are equal and must be sufficiently long enough to facilitate the complete distal advancement of the firing member 2310 from the home or starting position to a distal-most ending position within the staple cartridge while the proximal-most upper vertebra members 2420 in the upper series 2410 of upper vertebra members 2420 and the proximal-most lower vertebra members 2520 in the lower series 2510 of lower vertebra members 2520 remain in driving engagement with the rotary drive screw 2700. As can be seen in FIG. 8, an upper compression limiting spring 2421 is configured to interface with a proximal-most upper vertebra member 2420P in the upper series 2410 of upper vertebra members 2420. The upper compression limiting spring 2421 is journaled on the top cable 2404 and is retained in biasing engagement with the proximal-most upper vertebra member 2420P by an upper spring holder 2423 that is retained in position by an upper ferrule 2425 that is crimped onto the top cable 2404. The top cable 2404 extends through an upper hypotube 2433 that is supported in the proximal support shaft. Likewise, a lower compression limiting spring 2521 is configured to interface with a proximal-most, lower vertebra member 2520P in the lower series 2510 of lower vertebra members 2520. The lower compression spring 2521 is journaled on the lower cable 2504 and is retained in biasing engagement with the proximal-most, lower vertebra member 2520P by a lower spring holder 2523 that is retained in position by a lower ferrule 2525 that is crimped onto the lower cable 2504. The lower cable 2504 extends through a lower hypotube 2533 that is supported in the proximal support shaft.

When the upper vertebra members 2420 and the lower vertebra members 2520 angle through the articulation joint (after the end effector has been positioned in an articulated position), the gaps between the respective vertebra members 2420, 2520 increase in each series 2410, 2510 which causes the springs 2421, 2521 to become tighter. The compression limiting springs 2421, 2521 provide enough slack in the cables 2404, 2504, respectively to enable the vertebra members 2420, 2520 angle through the most extreme articulation angles. If the cables 2404, 2504 are pulled too tight, the spring holders 2423, 2523 will contact their respective proximal-most vertebra members 2420P, 2520P. Such compression limiting arrangements ensure that the vertebra members 2420, 2520 in their respective series 2410, 2510 always remain close enough together so that the rotary drive screw 2700 will always drivingly engage them in the manner discussed in further detail below. When the vertebra members 2420, 2520 are aligned straight again, the compression limiting springs 2421, 2521 may partially relax while still maintaining some compression between the vertebra members.

As indicated above, when the upper vertebra members 2420 are arranged in the upper series 2410 and lower vertebra members 2520 are arranged in the lower series 2510, the convex mounds and concave recesses in each vertebra member as well as the compression limiter springs serve to maintain the upper and lower vertebra members in relatively linear alignment for driving engagement by the rotary drive screw 2700. As can be seen in FIGS. 9 and 10, when the upper vertebra members 2420 are in linear alignment, the upper teeth 2450 are spaced from each other by an opening space generally designated as 2460 that facilitates driving engagement with the helical drive thread 2170 on the rotary drive screw. Similarly, when the lower vertebra members 2520 are in linear alignment, the lower vertebra member teeth 2550 are spaced from each other by an opening space generally designated as 2560 that facilitates driving engagement with the helical drive thread 2170 of the rotary drive screw 2700.

Figure 22:
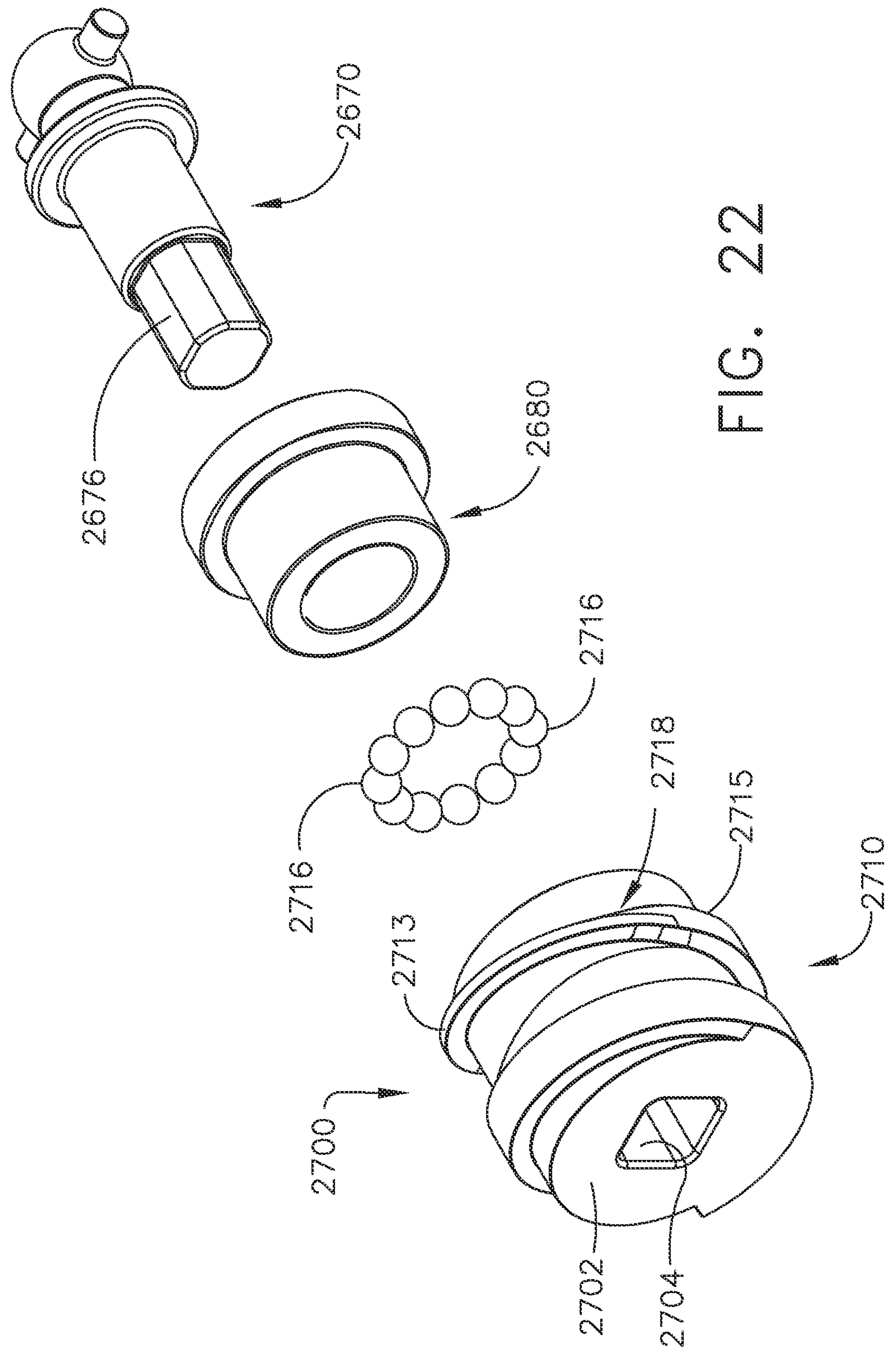
FIG. 22 is an exploded perspective view of the rotary drive screw and thrust bearing arrangement of the firing system of FIG. 21.

Turning to FIGS. 8 and 22, the rotary drive screw 2700 comprises a screw body 2702 that has a socket 2704 therein for receiving the distally extending shaft stem 2676 of the distal CV drive shaft 2670. An internal radial groove 2714 (FIG. 10) is formed in the screw body 2702 for supporting a plurality of ball bearings 2716 therein. In one arrangement, for example, 12 ball bearings 2716 are employed. The radial groove 2714 supports the ball bearings 2716 between the screw body 2702 and a distal end of the thrust bearing housing 2680. The ball bearings 2716 serve to distribute the axial load of the rotary drive screw 2700 and significantly reduce friction through the balls' rolling motion.

Figure 24:
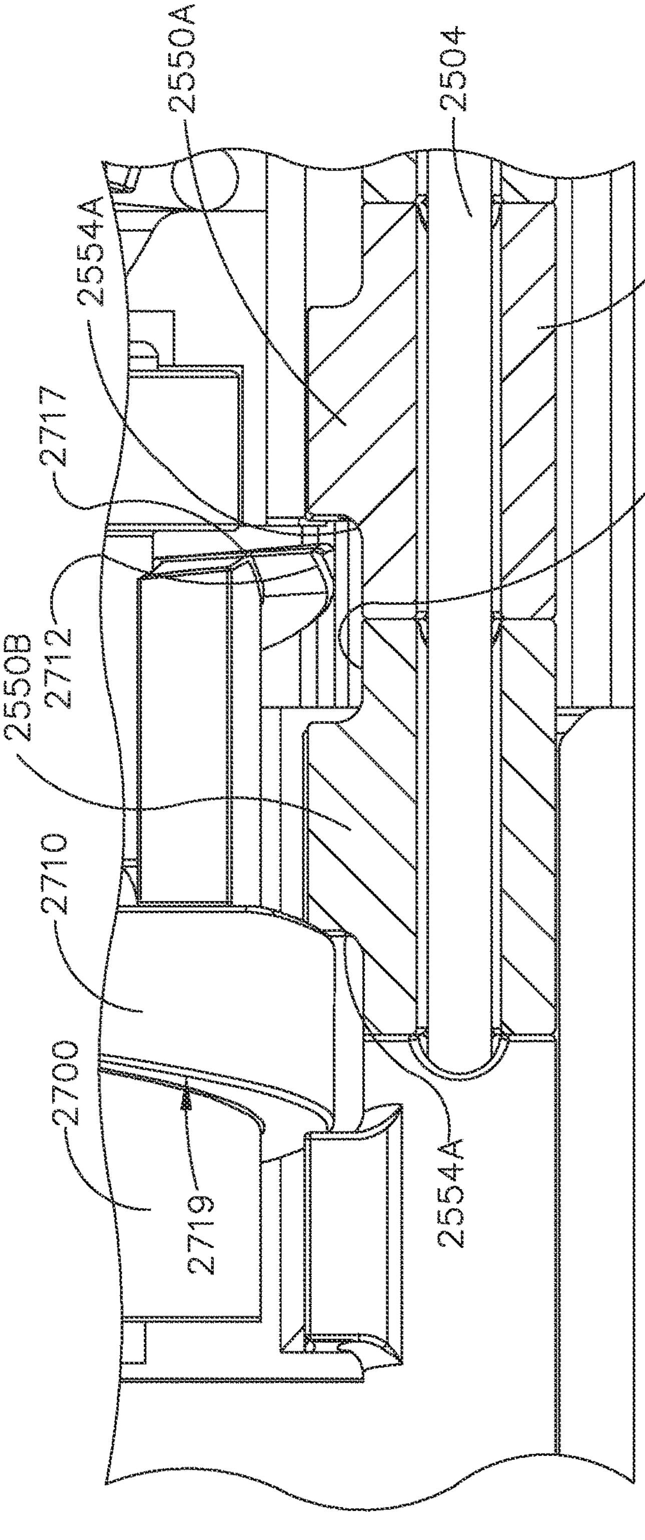
FIG. 24 is a partial cross-sectional side view of a portion of the lower flexible spine assembly and a portion of the firing member of FIG. 21 in driving engagement with a portion of the rotary drive screw.
Figure 23:
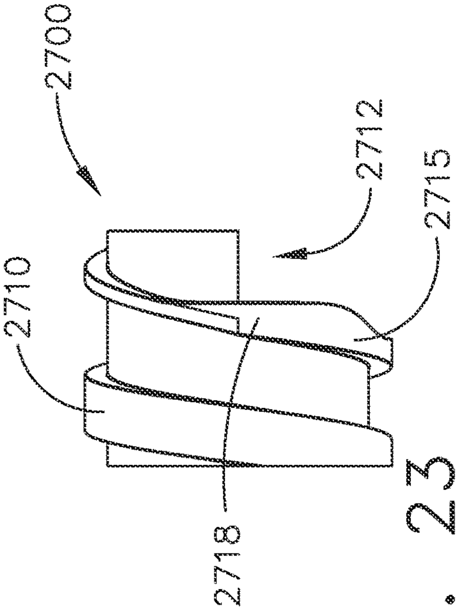
FIG. 23 is a side view of the rotary drive screw of FIG. 22.

As can be seen in FIG. 23, a helical drive thread 2710 is provided around the screw body 2702 and serves to form a proximal thread scoop feature 2712. The proximal thread scoop feature 2712 is formed with a first pitch 2713 and the remaining portion of the helical drive thread 2710 is formed with a second pitch 2715 that differs from the first pitch 2713. In FIGS. 22 and 23, area 2718 illustrates where the first pitch 2713 and the second pitch 2715 converge. In at least one embodiment, the first pitch 2713 is larger than the second pitch 2715 to ensure that the rotary drive screw 2700 captures and "scoops up" or drivingly engages every upper vertebra member 2420 and every lower vertebra member 2520. As can be seen in FIG. 24, a proximal end 2717 of the helical drive thread 2710 that has the first pitch 2713 has scooped into the into the opening space 2560 between two adjacent lower vertebra member teeth 2550A and 2550B while the center portion 2719 of the helical drive thread 2710 that has the second pitch 2715 is in driving engagement with the helix-shaped distal lower face portion 2554 on the lower vertebra member tooth 2550B and the helix-shaped proximal lower face portion 2552 on the proximal lower firing member tooth 2366. As can also be appreciated, the scoop feature 2712 may not contact the helix-shaped distal lower face portion 2554A of the lower vertebra member tooth 2550A as it scoops up the lower vertebra member tooth 2550B when driving the firing member 2310 distally. The helical drive thread 2710 interacts with the teeth 2450 of the upper vertebra members 2420 in a similar manner.

A power screw is a threaded rod with a full three hundred sixty degree nut around it. Rotation of the power screw causes the nut to advance or move longitudinally. In the present arrangements, however, due to space constraints, a full three hundred sixty degree nut cannot fit inside the end effector. In a general sense, the upper flexible spine assembly 2400 and the lower flexible spine assembly 2500 comprise a radially/longitudinally segmented "power screw nut" that is rotatably driven by the rotary drive screw 2700. When the rotary drive screw is rotated in a first rotary direction, the rotary drive screw 2700 drives one or more vertebra members in each of the upper series and lower series of vertebra members longitudinally while the vertebra members 2420, 2520 stay in the same locations radially. The upper series 2410 and lower series 2510 are constrained from rotating around the rotary drive screw 2700 and can only move longitudinally. In one arrangement, the upper vertebra members 2420 in the upper series 2410 and the lower vertebra members 2520 in the lower series 2510 only surround the rotary drive screw 2700 with less than ten degrees each.

Figure 25:
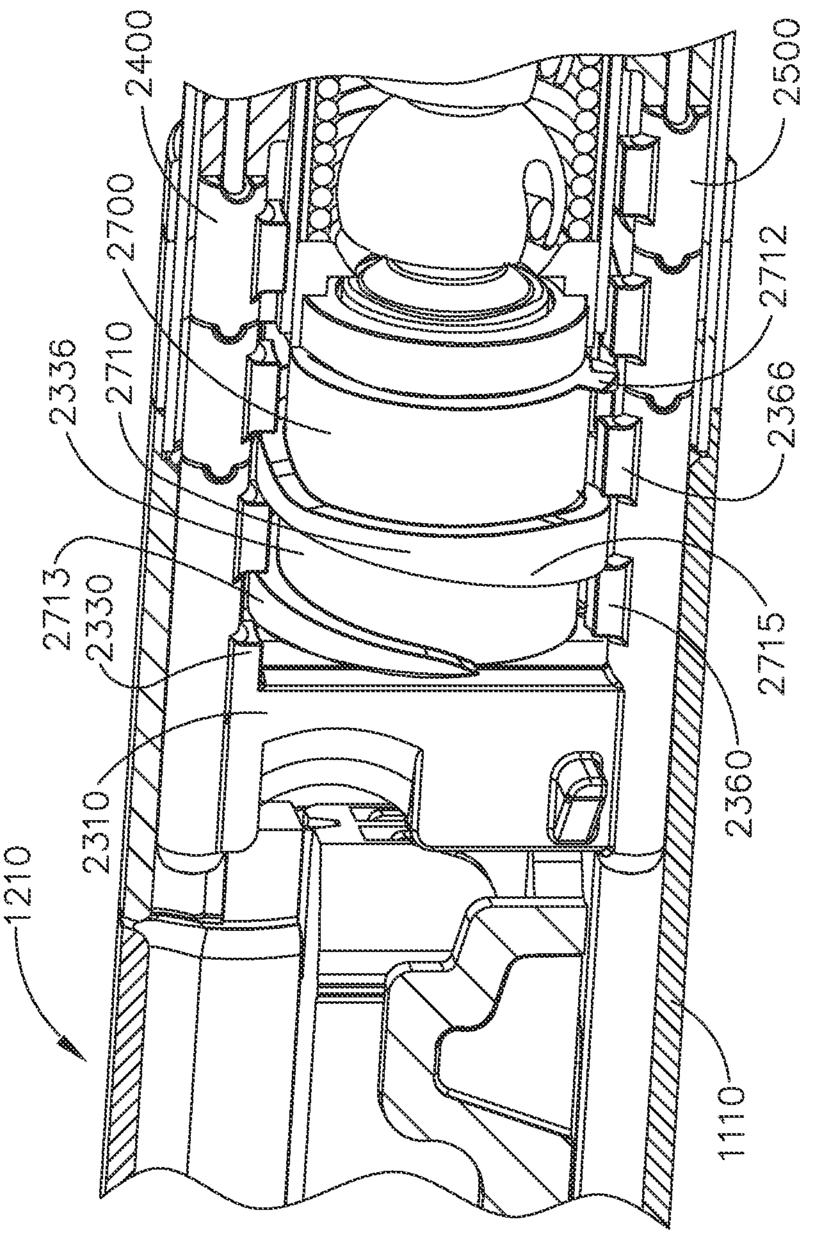
FIG. 25 is a perspective view of the firing member in a home or starting position within the surgical end effector of the surgical instrument of FIG. 1.
Figure 26:
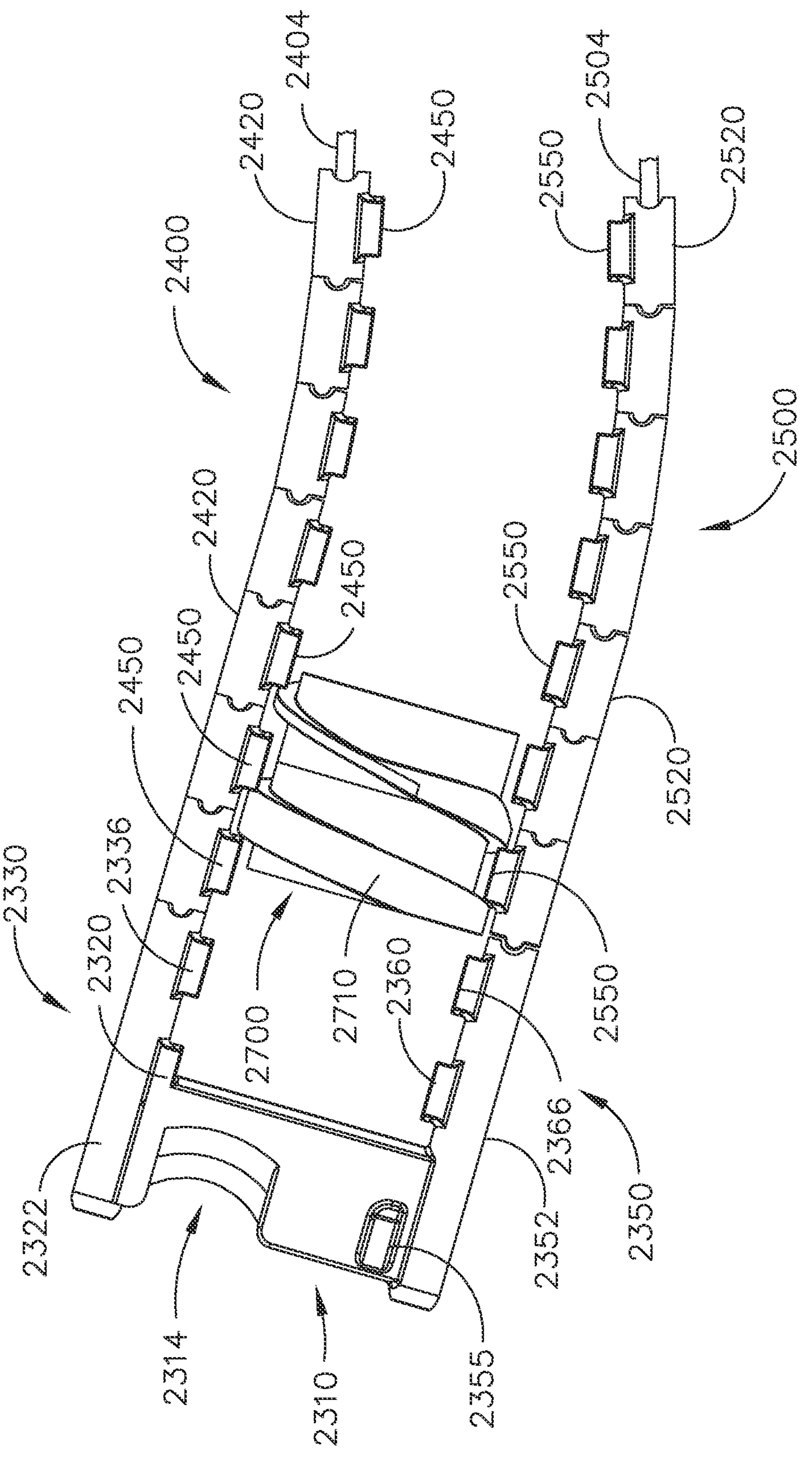
FIG. 26 is a side view illustrating the upper flexible spine assembly and the lower flexible spine assembly of FIG. 21 in driving engagement with the rotary drive screw after the firing member has been driven distally from a home or starting position.

FIG. 25 illustrates the firing member 2310 in the home or starting position. As can be seen in FIG. 25, a portion of the helical drive thread 2710 on the rotary drive screw 2700 is engaged between the distal upper firing member tooth segment 2330 and the proximal upper firing member tooth 2336 and another portion of the helical drive thread 2710 is engaged between the distal lower firing member tooth 2360 and a proximal lower firing member tooth 2366 on the firing member 2310. Such arrangement enables the rotary drive screw 2700 to precisely control the distal and proximal movement of the firing member 2310 which, as will be discussed in further detail below, can result in the precise movement of the anvil 1210. Once the firing member 2310 has been sufficiently distally advanced during a firing stroke, the helical drive thread 2710 operably engages the teeth on the upper and lower vertebras. See FIG. 26.

Figure 27:
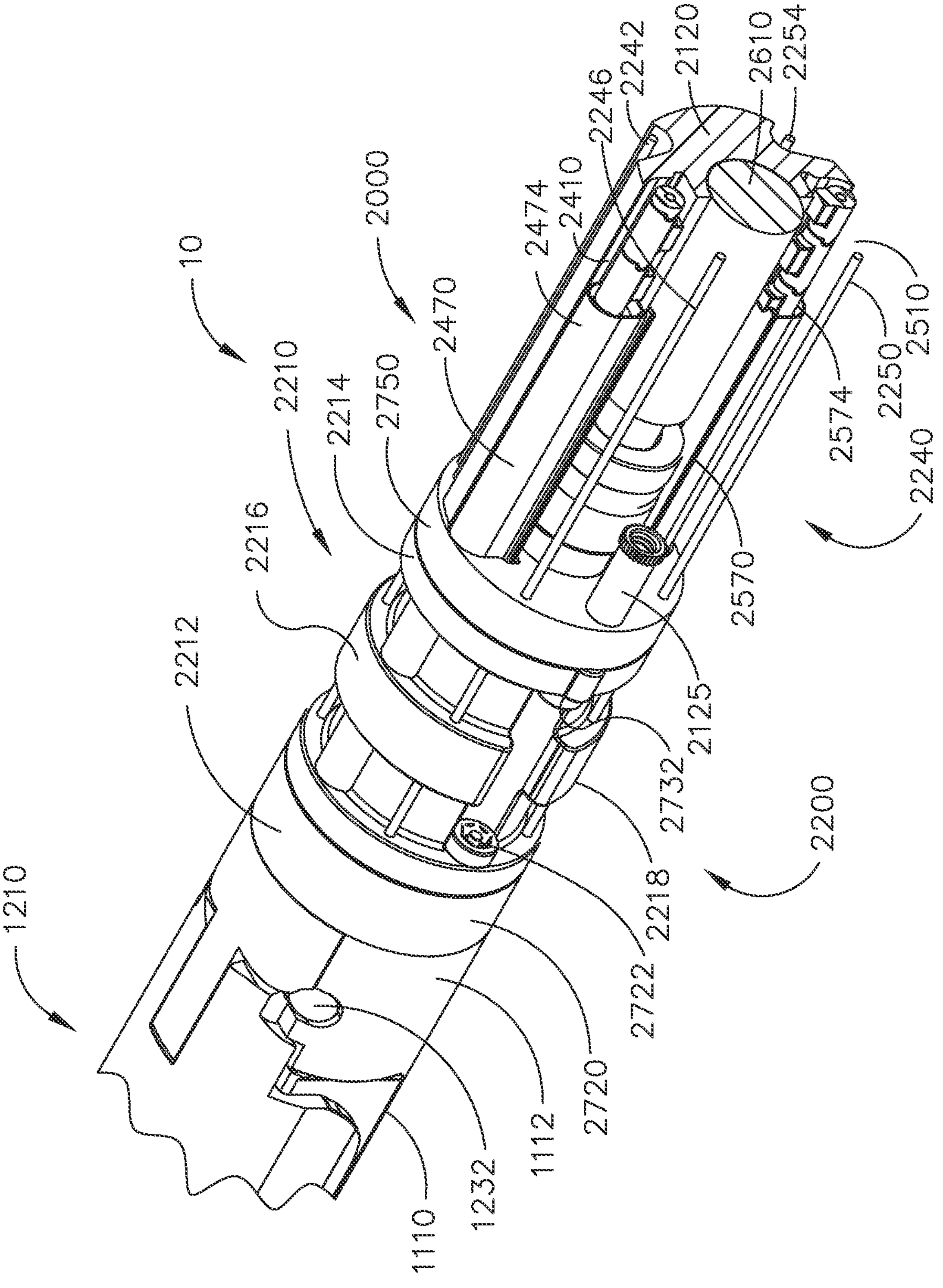
FIG. 27 is a partial cross-sectional perspective view of a portion of the surgical end effector, firing system and rotary drive system of the surgical instrument of FIG. 1 according to at least one aspect of the present disclosure with an outer elastomeric joint assembly of an articulation joint omitted for clarity.
Figure 29:
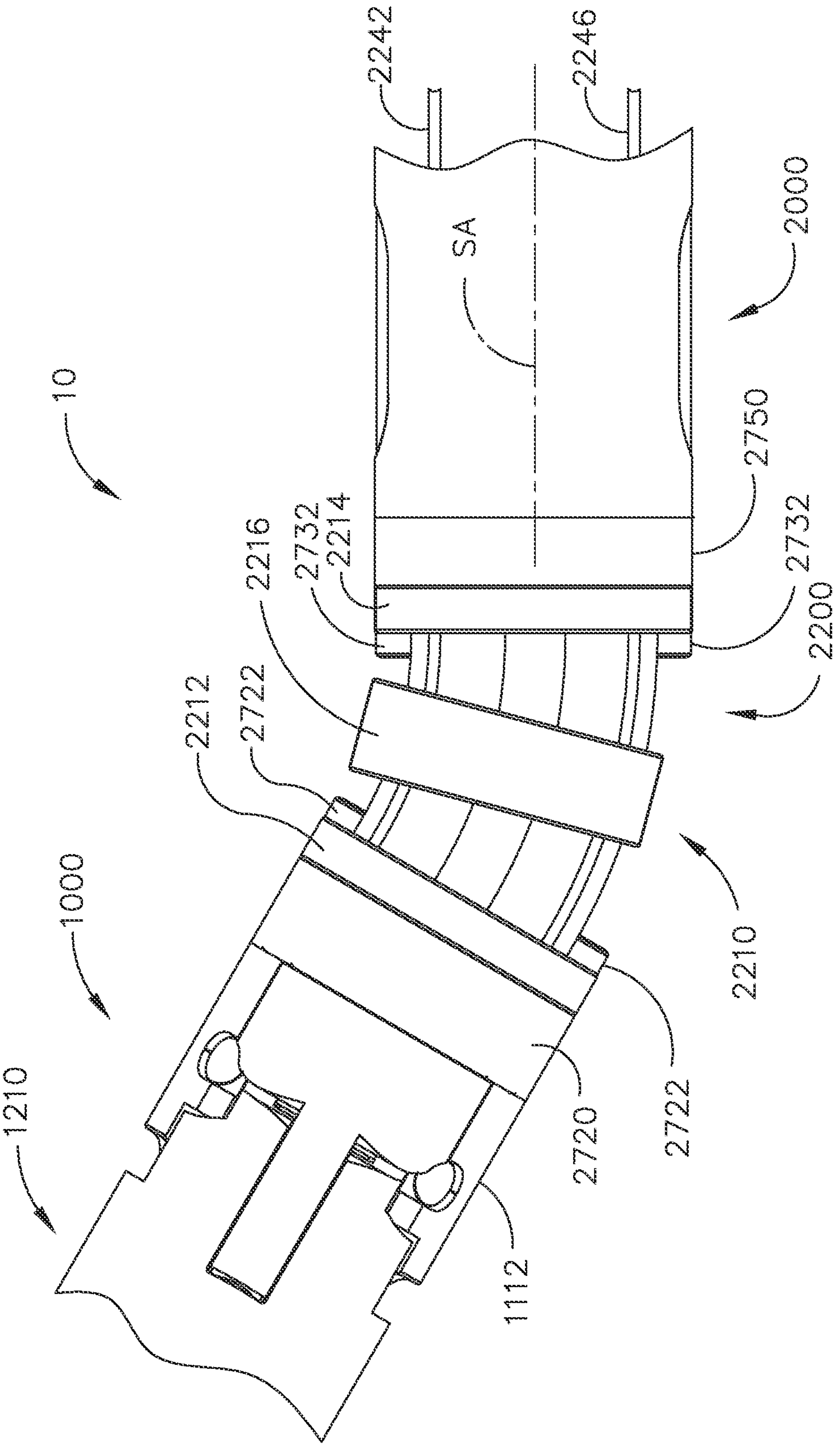
FIG. 29 is a top view of the surgical end effector of FIG. 27 articulated in a first direction relative to a portion of the elongate shaft assembly in accordance with at least one aspect of the present disclosure.
Figure 30:
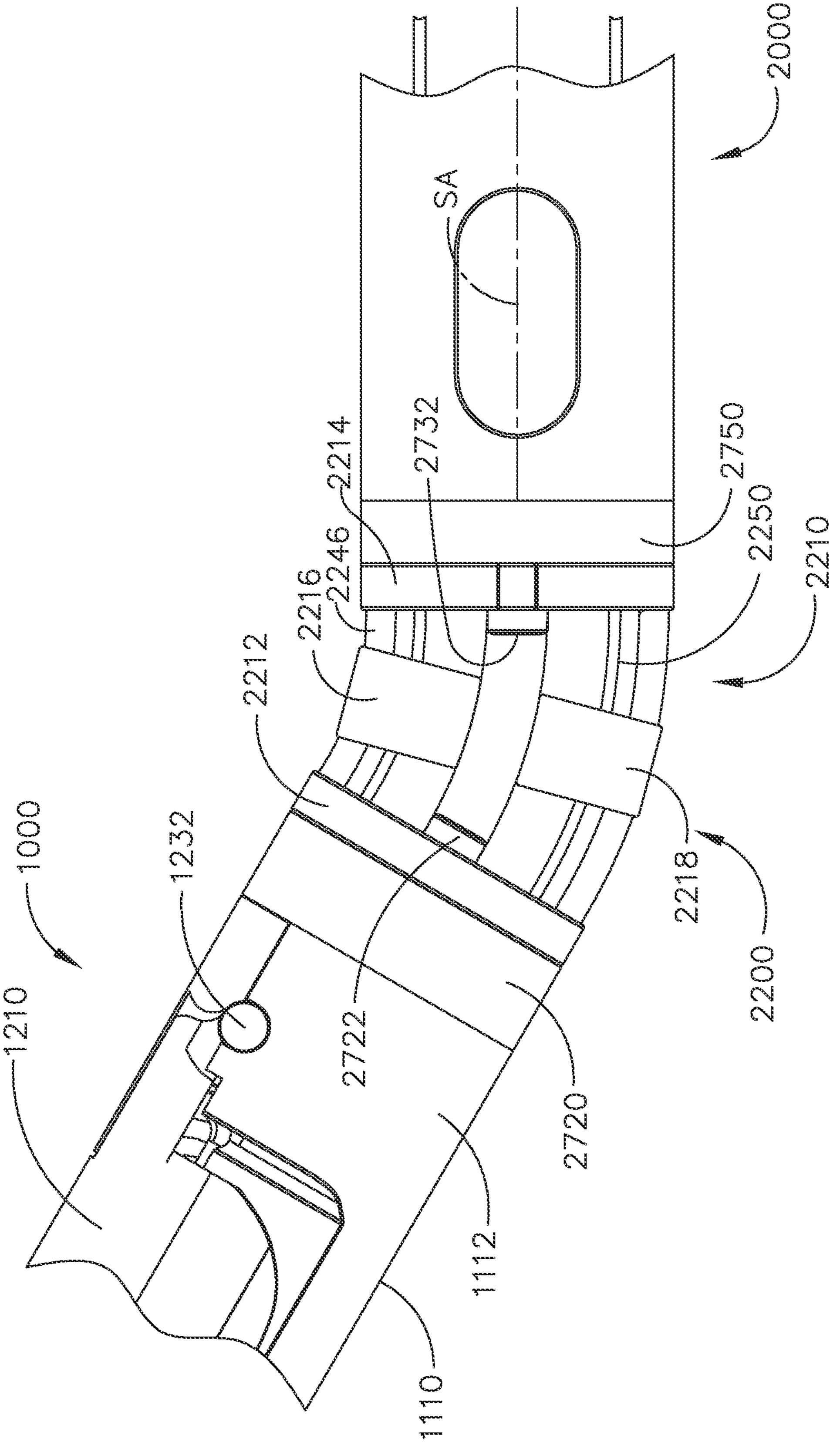
FIG. 30 is a side view of the surgical end effector of FIG. 29 articulated in another direction relative to a portion of the elongate shaft assembly in accordance with at least one aspect of the present disclosure.
Figure 31:
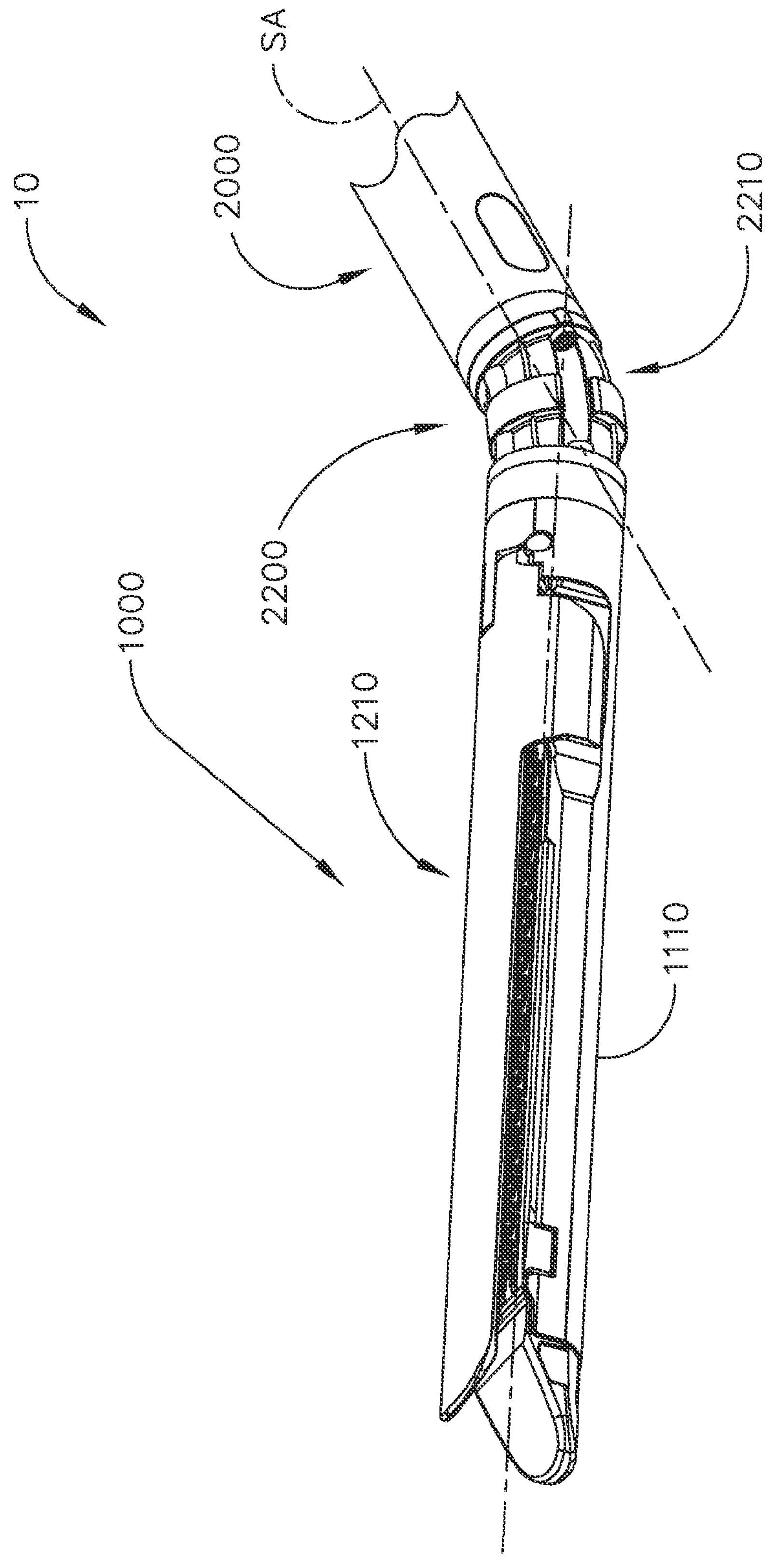
FIG. 31 is a perspective view of the surgical end effector of FIG. 29 articulated in multiple planes with respect to a portion of the elongate shaft assembly in accordance with at least one aspect of the present disclosure.

The surgical instrument 10 also comprises an articulation system 2240 that is configured to apply articulation motions to the surgical end effector 1000 to articulate the surgical end effector relative to the elongate shaft assembly 2000. In at least one arrangement, for example, the articulation system comprises four articulation cables 2242, 2246, 2250, and 2254 that extend through the elongate shaft assembly 2000. See FIG. 27. In the illustrated arrangement, the articulation cables 2242, 2246 pass through the proximal mounting bushing 2750, the proximal end 2214 of the elastomeric joint assembly 2210, as well as a central rib segment 2216 to be secured to the distal end 2212 of the elastomeric joint assembly 2210 or other portion of the surgical instrument. Likewise, the articulation cables 2250 and 2254 extend through the proximal mounting bushing 2750, the proximal end 2214 of the elastomeric joint assembly 2210, as well as a central rib segment 2218 to be secured to the distal end 2212 of the elastomeric joint assembly 2210 or other portion of the surgical end effector. The cables 2242, 2246, 2250, and 2254 operably interface with an articulation control system that is supported in the housing of the surgical instrument 10. For example, a proximal portion of each cable 2242, 2246, 2250, and 2254 may be spooled on a corresponding rotary spool or cable-management system 2007 (FIG. 2) in the housing portion of the surgical instrument 10 that is configured to payout and retract each cable 2242, 2246, 2250, and 2254 in desired manners. The spools/cable management system may be motor powered or manually powered (ratchet arrangement, etc.). FIG. 29 illustrates articulation of the surgical end effector 1000 through a first articulation plane relative to the elongate shaft assembly 2000. FIG. 30 illustrates articulation of the surgical end effector 1000 through a second articulation plane relative to the elongate shaft assembly 2000. FIG. 31 illustrates articulation of the surgical end effector 1000 through multiple articulation planes relative to the elongate shaft assembly 2000.

Figure 32:
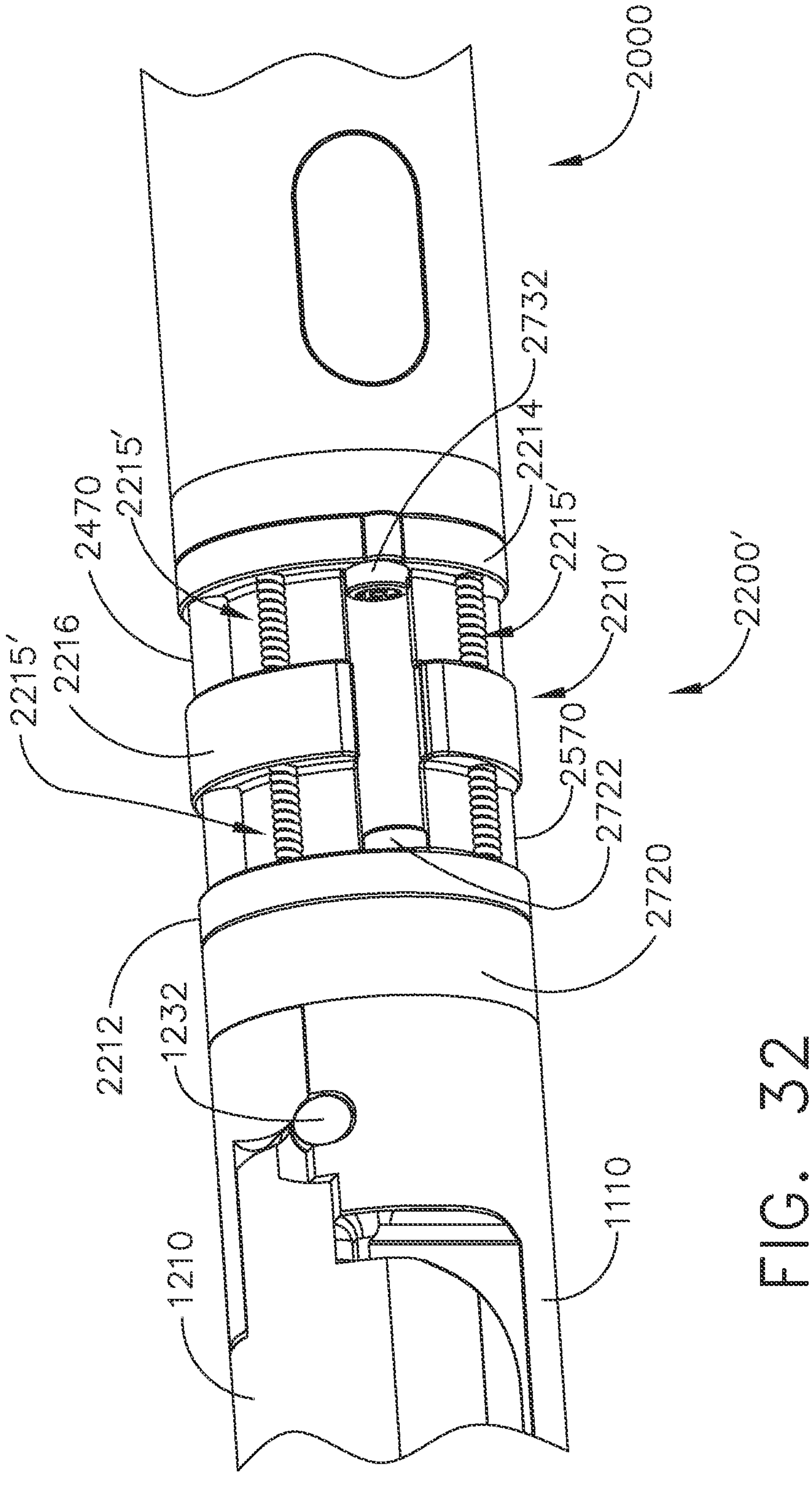
FIG. 32 is a side elevational view of a portion of another surgical instrument that employs another outer elastomeric joint assembly in accordance with at least one aspect of the present disclosure.
Figure 33:
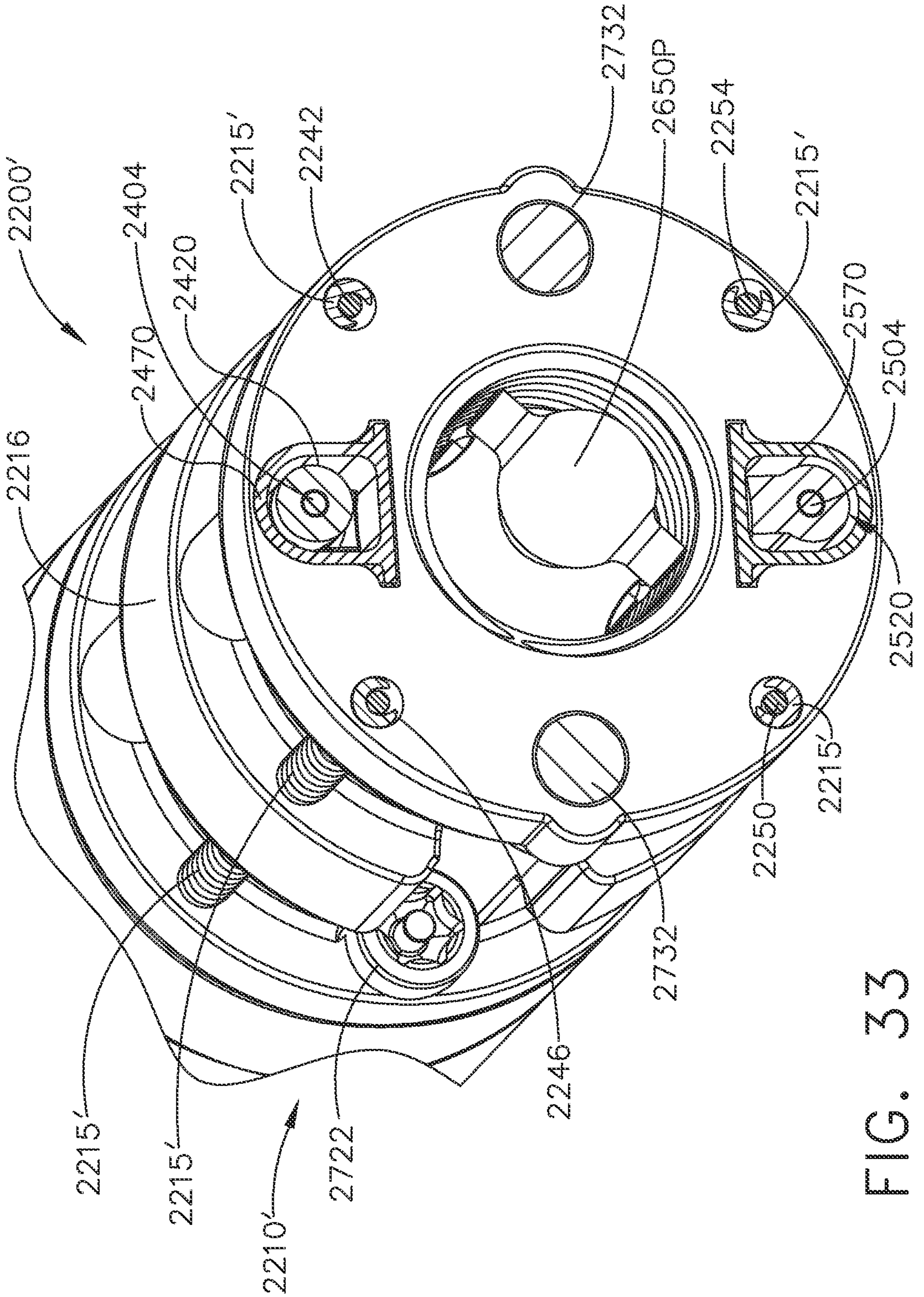
FIG. 33 is a partial cross-sectional perspective view of the surgical instrument of FIG. 32.
Figure 34:
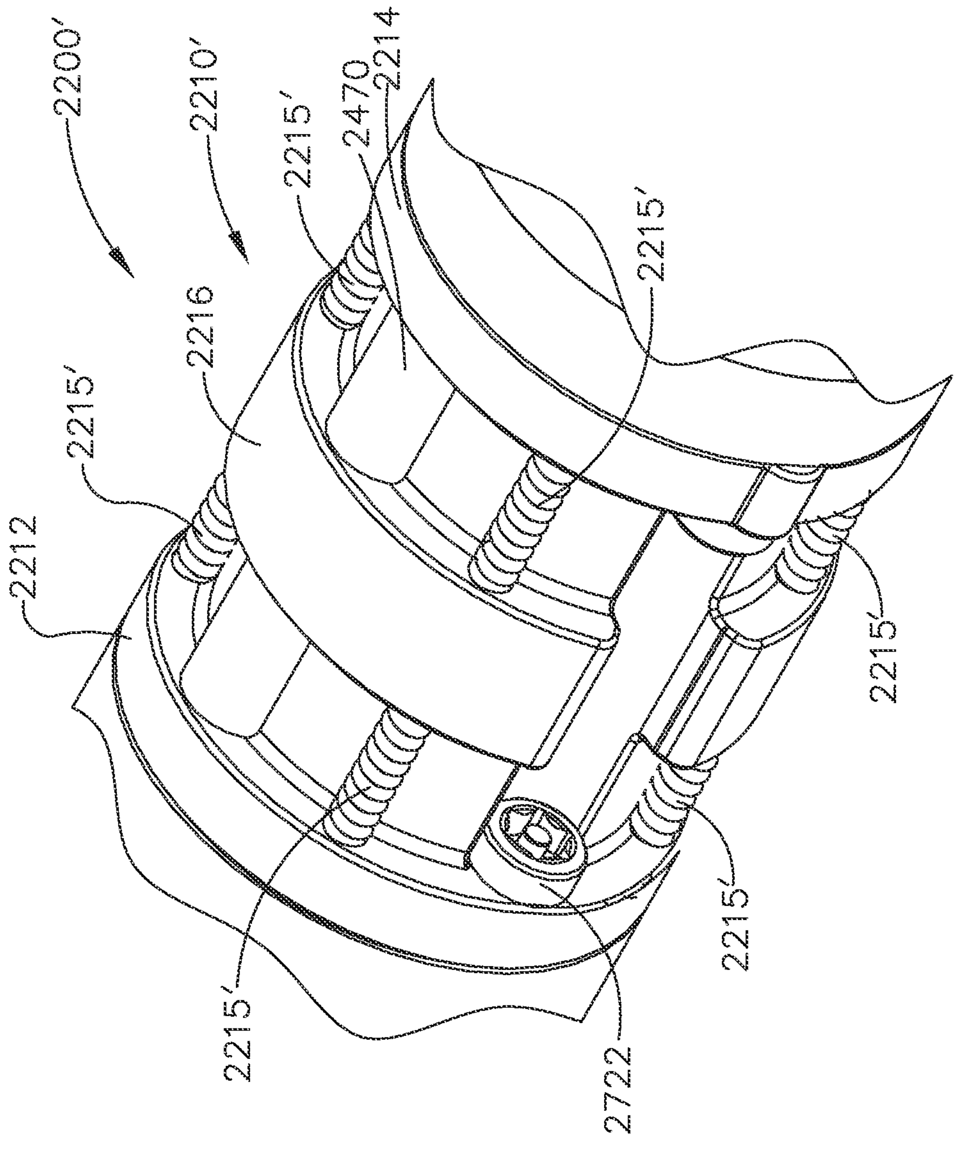
FIG. 34 is a perspective view of a portion of the outer elastomeric joint assembly of FIG. 32.

FIGS. 32-34 illustrate an alternative articulation joint 2200' in the form of an elastomeric joint assembly 2210'. As can be seen in FIG. 33, each articulation cable passes through a corresponding spring 2215' that is mounted in the ribs 2216' of the elastomeric joint assembly 2210'. For example, cable 2242 extends through spring 2244. Cable 2246 extends through spring 2248. Cable 2250 extends through spring 2252 and cable 2254 extends through spring 2256. As indicated above, the end effector is articulated by pulling on and relaxing the appropriate cables 2242, 2246, 2250 and 2254. To achieve higher articulation angles with greater joint stability, each of the springs 2244, 2248, 2252, and 2256 can slide through the ribs of the elastomeric joint to push the end effector and pull on the cables extending therethrough. The springs 2244, 2248, 2252, and 2256 will also retract into the ribs when the cables 2242, 2246, 2250, and 2254 are pulled tight. Each of the springs 2244, 2248, 2252, and 2256 loosely seat over the particular cable that passes therethrough. Each cable and corresponding spring may terminate or otherwise be coupled to a corresponding solid rod that is supported in the elongate shaft assembly 2000 and may be pushed and pulled from its proximal end. When the cable is pulled, the corresponding spring would carry little to no load. When the spring is pushed, the cable would carry little load, but will help limit the end effector movement. This interaction between the cable and spring may facilitate higher articulation angles that may approach ninety degrees, for example.

Figure 28:
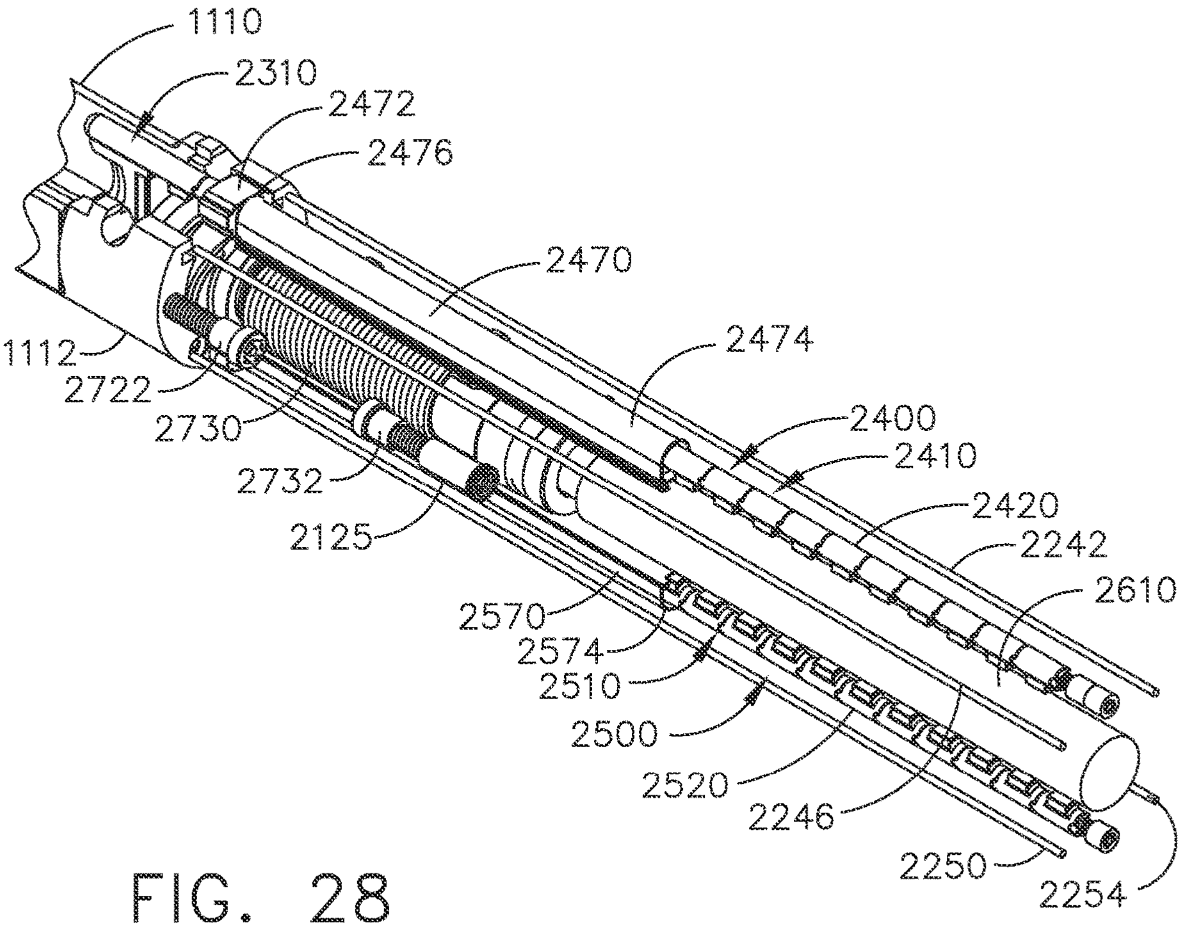
FIG. 28 is another partial perspective view of a portion of the surgical end effector, firing system and rotary drive system of FIG. 27 with an outer elastomeric joint assembly of an articulation joint and portions of the elongate shaft assembly omitted for clarity.
Figure 35:
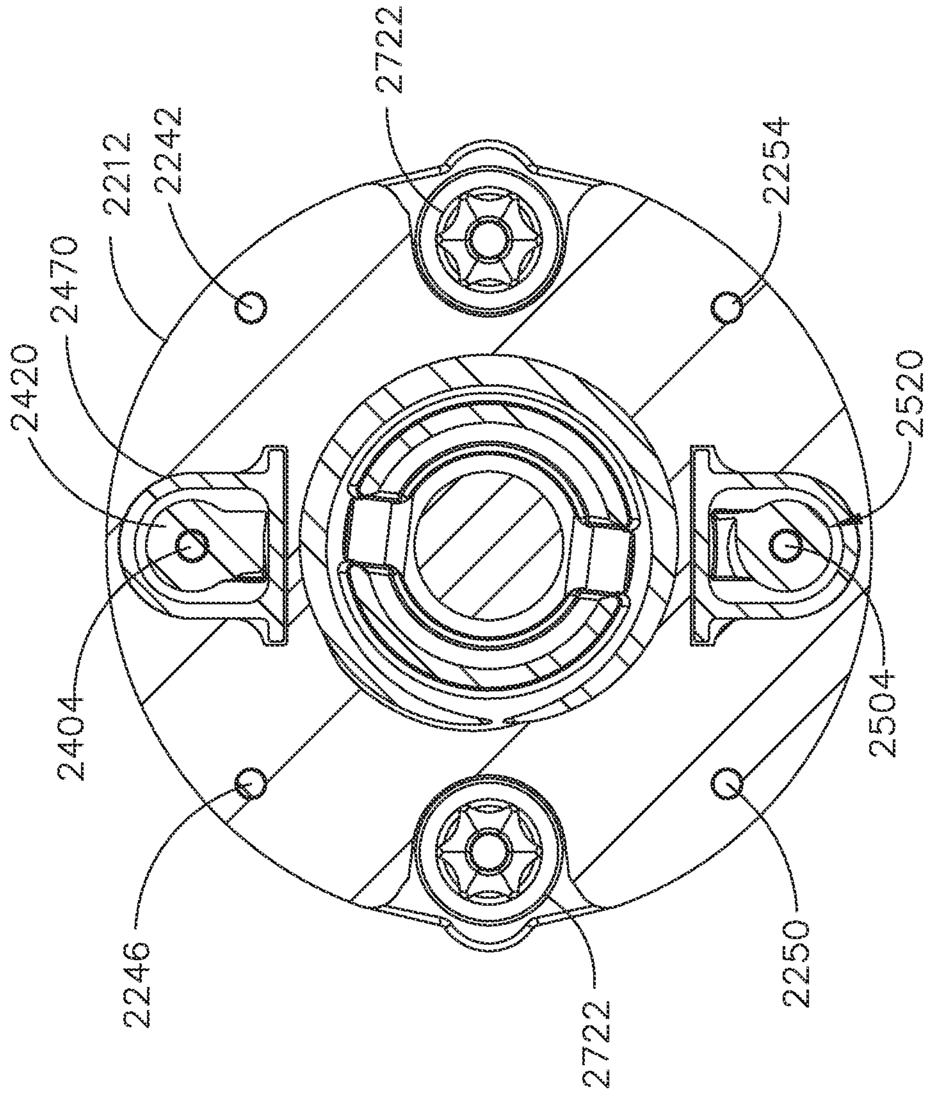
FIG. 35 is a cross-sectional end view of a portion of the surgical instrument of FIG. 19 taken along lines 35-35 in FIG. 19.

Because the radially/longitudinally segmented power screw nut arrangement disclosed herein does not have the same constraints as a three hundred sixty degree nut, the upper vertebra members 2420 in the upper series 2410 and the lower vertebra members 2520 in the lower series 2510 are constrained to ensure that their loads are transferred to the firing member in a longitudinal direction. To maintain each of the upper vertebra members 2420 in the desired orientation and to prevent the upper vertebra members 2420 from becoming snagged or disoriented when traversing through the articulation joint 2200, the upper vertebra members 2420 are aligned to pass through an upper sleeve 2470 that extends through an upper portion of the outer elastomeric joint assembly 2210 of the articulation joint 2200. See FIGS. 27, 28, and 35. A distal end 2472 of the upper sleeve 2470 is supported in the proximal end 1112 of the elongate channel 1110 and a proximal end 2474 of the upper sleeve 2470 is supported in the distal end of the proximal support shaft 2120. The upper sleeve 2470 is fabricated from a polymer or plastic material that has a low coefficient of friction and is flexible to enable the upper sleeve 2470 to flex with the outer elastomeric joint assembly 2210. The upper sleeve 2470 protects the upper vertebra members 2420 from contacting the outer elastomeric joint assembly 2210 that is fabricated from an elastomeric material that may have a higher coefficient of friction than the coefficient of friction of the material of the upper sleeve 2470. Stated another way, the upper sleeve 2470 forms a low friction, flexible, continuous, uninterrupted, and fully encapsulating path for the upper vertebra members 2420 as they traverse the articulation joint 2200.

Similarly, a lower sleeve 2570 is employed to support the lower vertebra members 2520 as they pass through the articulation joint 2200. A distal end 2572 of the lower sleeve 2570 is supported in the proximal end of the elongate channel and a proximal end of the lower sleeve 2570 is supported in the distal end of the proximal support shaft 2120. Like the upper sleeve 2470, the lower sleeve 2570 is fabricated from a polymer or plastic material that has a low coefficient of friction and is flexible to enable the lower sleeve 2570 to flex with the outer elastomeric joint assembly 2210. The lower sleeve 2570 protects the lower vertebra members 2520 from contacting the outer elastomeric joint assembly 2210 as they pass through the articulation joint 2200. Stated another way, the lower sleeve 2570 forms a low friction, flexible, continuous, uninterrupted, and fully encapsulating path for the lower vertebra members 2520 as they traverse the articulation joint 2200. In various embodiments, the upper sleeve 2470 and the lower sleeve 2570 are configured to bend freely without creating a kink. To prevent the formation of kinks in the sleeves, in at least one arrangement, the sleeves 2470, 2570 are supported within the outer elastomeric joint assembly 2210 such that the sleeves may move axially. For example, when the articulation joint angles up, the lower sleeve 2570 may slide distally and have a large bend radius; the upper sleeve 2470 in the same example, may slide proximally and have a tighter bend radius. By moving axially, the amount of material exposed outside of the joint assembly 2210 which might otherwise be susceptible to kinking under a tight bend radius is reduced. In at least one arrangement, the distal end 2472 of the upper sleeve 2470 is formed with an upper scoop 2476 that is configured to funnel the upper vertebra members 2420 into the anvil cap 1260. Similarly, the distal end of the lower sleeve 2570 may be formed with a lower scoop that is configured to funnel the lower vertebra members 2520 into the channel slot 1140 in the elongate channel 1110.

Figure 36:
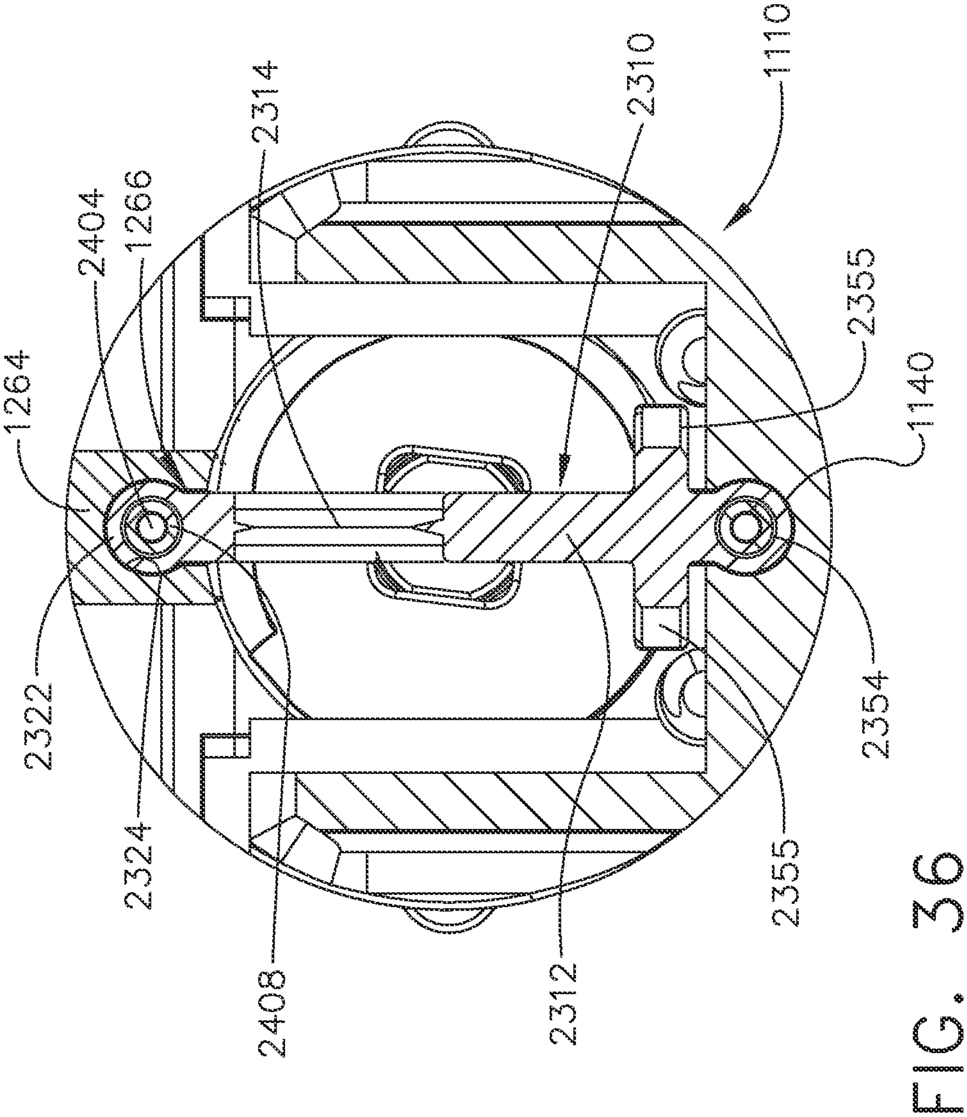
FIG. 36 is a cross-sectional end view of a portion of the surgical instrument of FIG. 19 taken along lines 36-36 in FIG. 19.
Figure 37:
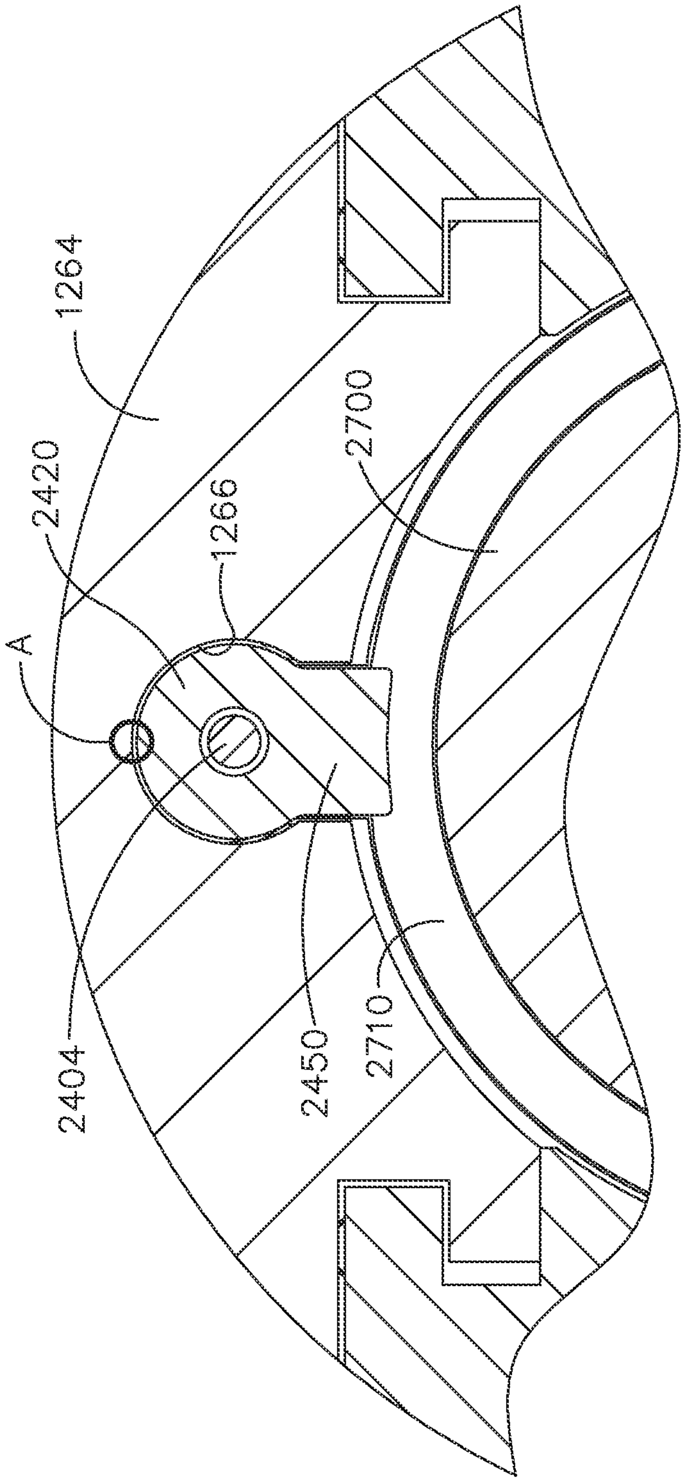
FIG. 37 is a partial cross-sectional view of a portion of an anvil cap and an upper vertebra member of the surgical instrument of FIG. 19 in accordance with at least one aspect of the present disclosure.

As indicated above, the anvil mounting portion 1230 comprises a pair of laterally extending mounting pins 1232 that are configured to be received in corresponding mounting cradles or pivot cradles 1120 that are formed in the proximal end 1112 of the elongate channel 1110. The mounting pins 1232 are pivotally retained within the mounting cradles 1120 by an anvil cap 1260 that is attached to the proximal end 1112 of the elongate channel 1110 in the above-described manners. The anvil cap 1260 comprises a proximal end 1262 and a distal end 1264 and has a keyhole-shaped vertebra passage 1266 extending therethrough to accommodate passage of the top firing member feature 2320 and upper vertebra members 2420 therethrough. FIG. 36 illustrates the vertebra passage 1266 in the anvil cap 1260. When the rotary drive screw 2700 applies load to the upper vertebra members 2420, the vertebra members 2420 will tend to tilt about the area A in FIG. 37, so the upper vertebra member tooth 2450 is no longer square with the rotary drive screw 2700 and may instead experience a higher-pressure line contact. Areas B in FIG. 37 show where the upper vertebra member 2420 stops tilting. To ensure that most of the loads stay in the longitudinal direction to perform useful work, the upper vertebra member tooth 2450 must be angled the same amount as the upper vertebra member 2420 tilts. Thus, when the upper vertebra member 2420 tilts, the upper vertebra member tooth 2450 will still maintain surface contact with the helical drive member 2710 on the rotary drive screw 2700 and all loads will be directed longitudinally and not vertically. The slightly angled upper vertebra member tooth 2450 may behave like a square thread when the vertebra member 2420 is tilted and better distributes loads to lower the pressure contact. By directing most of the loads in the longitudinal direction, vertical loads are avoided which could result in the establishment of friction that would counter the longitudinal loads. The upper vertebra members 2420 react similarly as they pass down the keyhole-shaped anvil slot 1240. Likewise, the lower vertebra members 2520 react similarly as they pass through the keyhole-shaped axially extending channel slot 1140 in the elongate channel 1110.

Figure 38:
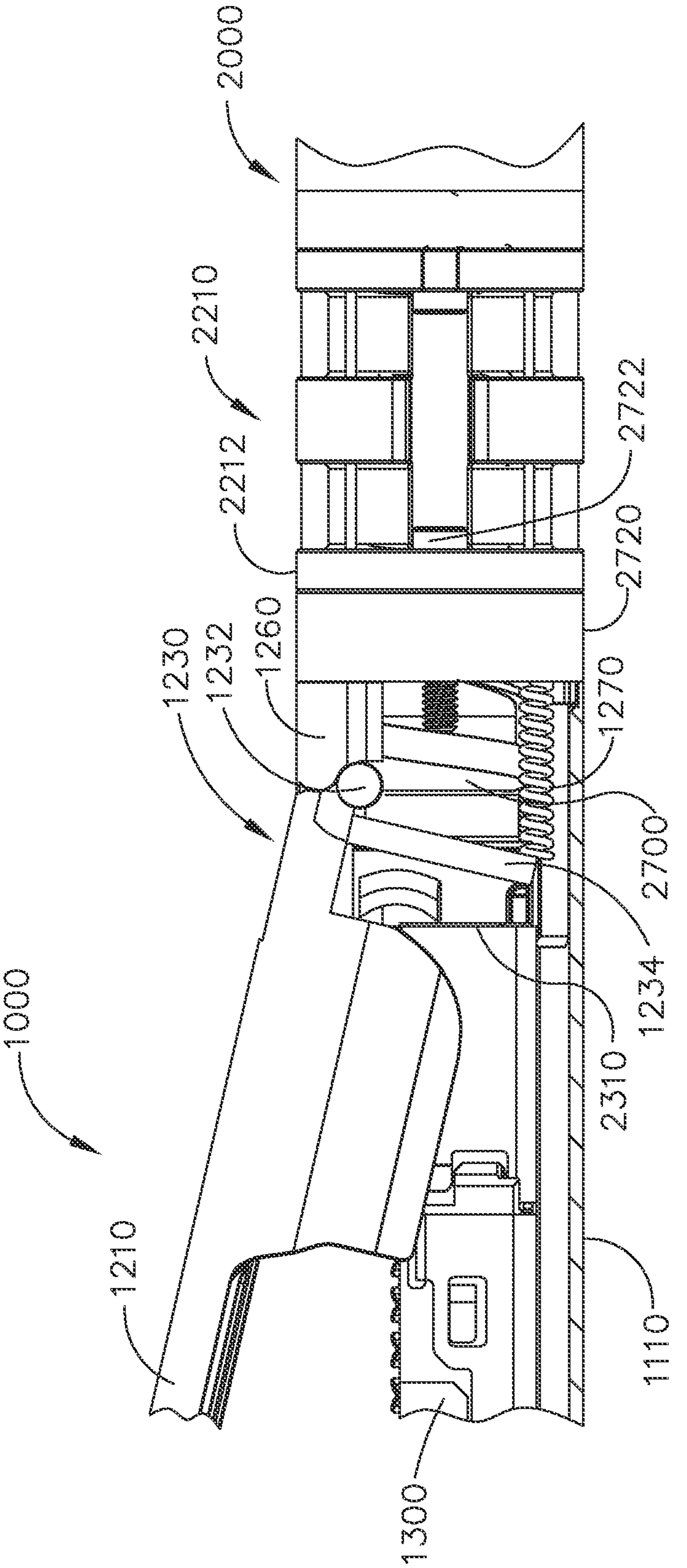
FIG. 38 is a side view of a portion of the surgical end effector of the surgical instrument of FIG. 19 with an anvil thereof in an open position in accordance with at least one aspect of the present disclosure and with portions of the surgical end effector omitted for clarity.

In the illustrated arrangement, the anvil 1210 is moved to the open position by a pair of anvil springs 1270 that are supported within the proximal end of the elongate channel. See FIGS. 38, 42, and 43. The springs 1270 are positioned to apply a pivotal biasing force to corresponding anvil control arms 1234 that may be integrally formed with anvil mounting portion 1230 and extend downwardly therefrom. See FIG. 38.

Figure 39:
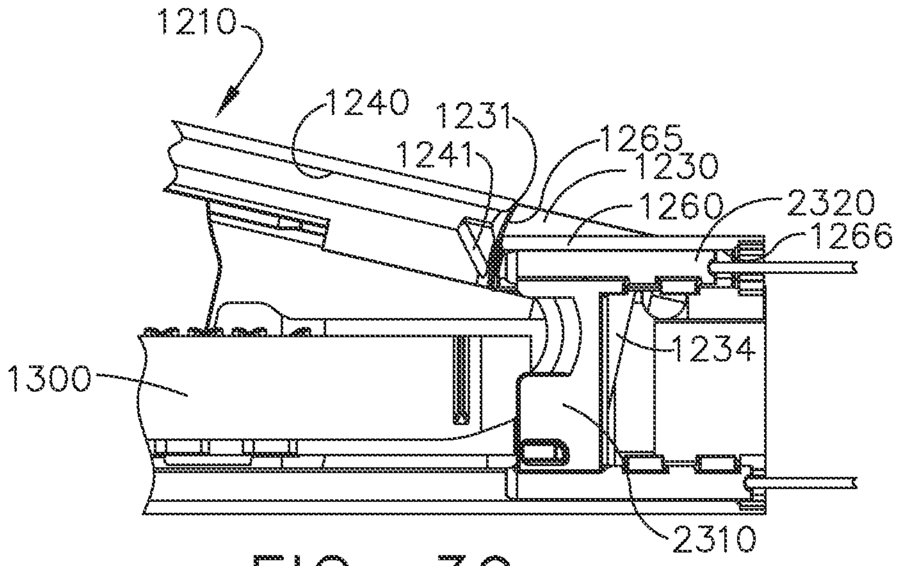
FIG. 39 is a partial cross-sectional side view of the surgical end effector of FIG. 38 with the anvil in an open position and the firing member in the home or starting position in accordance with at least one aspect of the present disclosure.
Figure 40:
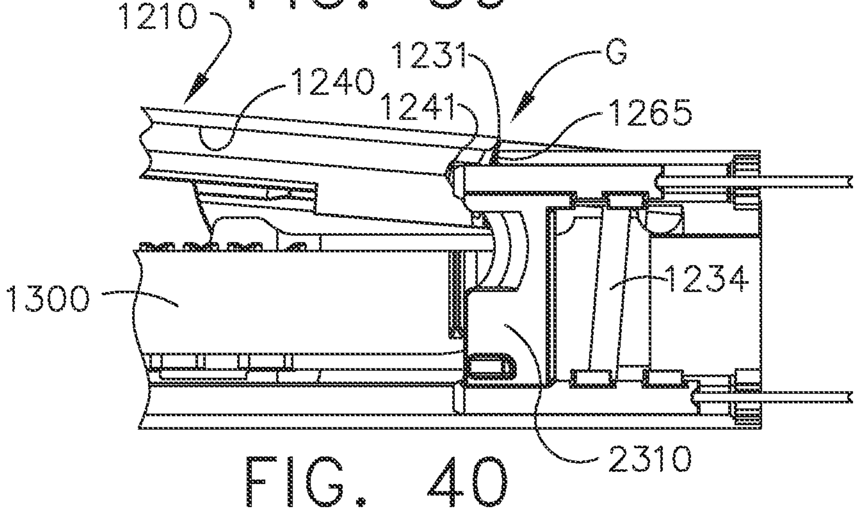
FIG. 40 is another partial cross-sectional side view of the surgical end effector of FIG. 39 with the anvil in a partially closed position.
Figure 41:
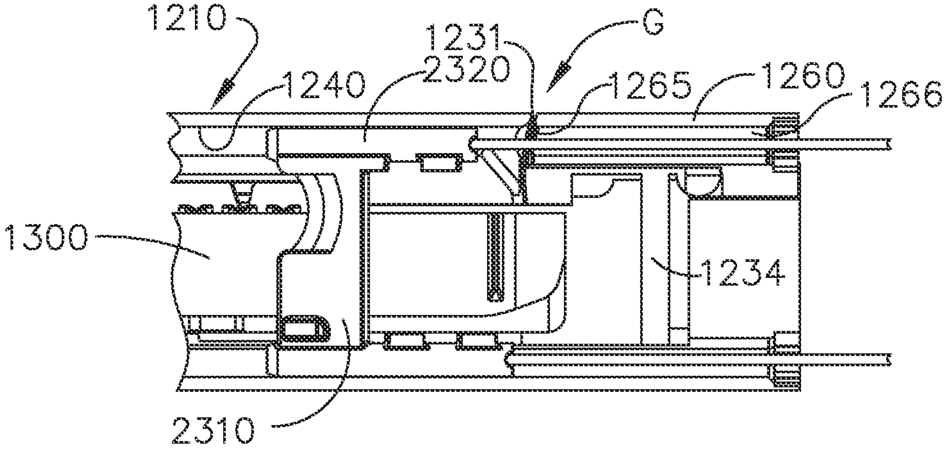
FIG. 41 is another partial cross-sectional side view of the surgical end effector of FIG. 39 with the anvil in a fully closed position and the firing member distally advancing through the surgical end effector.

FIGS. 39-41 illustrate portions of the anvil 1210, the firing member 2310, and the anvil cap 1260 when the anvil 1210 is open (FIG. 39), when the anvil 1210 is partially closed (FIG. 40) and after the firing member has been advanced distally from the home or starting position (FIG.

41). As can be seen in FIG. 39, when the firing member 2310 is in the home or starting position, the top firing member feature 2320 is completely received within the vertebra passage 1266 in the anvil cap 1260. During a firing stroke, the top firing member feature 2320 and the upper vertebra members 2420 in the upper series 2410 must transition from the vertebra passage 1266 in the anvil cap 1260 to the keyhole-shaped anvil slot 1240. Thus, it is desirable to minimize any gap "G" between the anvil mounting portion 1230 and a distal end 1264 of the anvil cap 1260. To minimize this gap G while facilitate unimpeded pivotal travel of the anvil 1210, the distal end 1264 of the anvil cap 1260 is formed with a curved cap surface 1265 that matches a curved mating surface 1231 on the anvil mounting portion 1230. Both surfaces 1265, 1231 are curved and concentric about the pivot axis PA or some other reference point. Such arrangement allows the anvil 1210 to move radially and not interfere with the anvil cap 1260 while maintaining a minimal gap G therebetween. The gap G between the anvil mounting portion 1230 and the distal end 1264 of the anvil cap 1260 is significantly shorter than a length of an upper vertebra member 2420 which facilitates easy transition of each upper vertebra member 2420 from the vertebra passage 1266 in the anvil cap 1260 to the keyhole-shaped anvil slot 1240. In addition, to further assist with the transition of the top firing member feature 2320 into the keyhole-shaped anvil slot 1240, a ramped surface 1241 is formed adjacent the curved mating surface 1231 on the anvil mounting portion 1230. As the firing member 2310 is initially advanced distally from the home or starting position, a distal end of the top firing member feature 2320 contacts the ramped surface 1241 and begins to apply a closing motion to the anvil 1210 as can be seen in FIG. 40. Further distal advancement of the firing member 2310 during the firing stroke or firing sequence causes the top firing member feature to enter the keyhole shaped anvil slot 1240 to completely close the anvil 1210 and retain the anvil 1210 in the closed position during the firing sequence. See FIG. 41.

Figure 15:
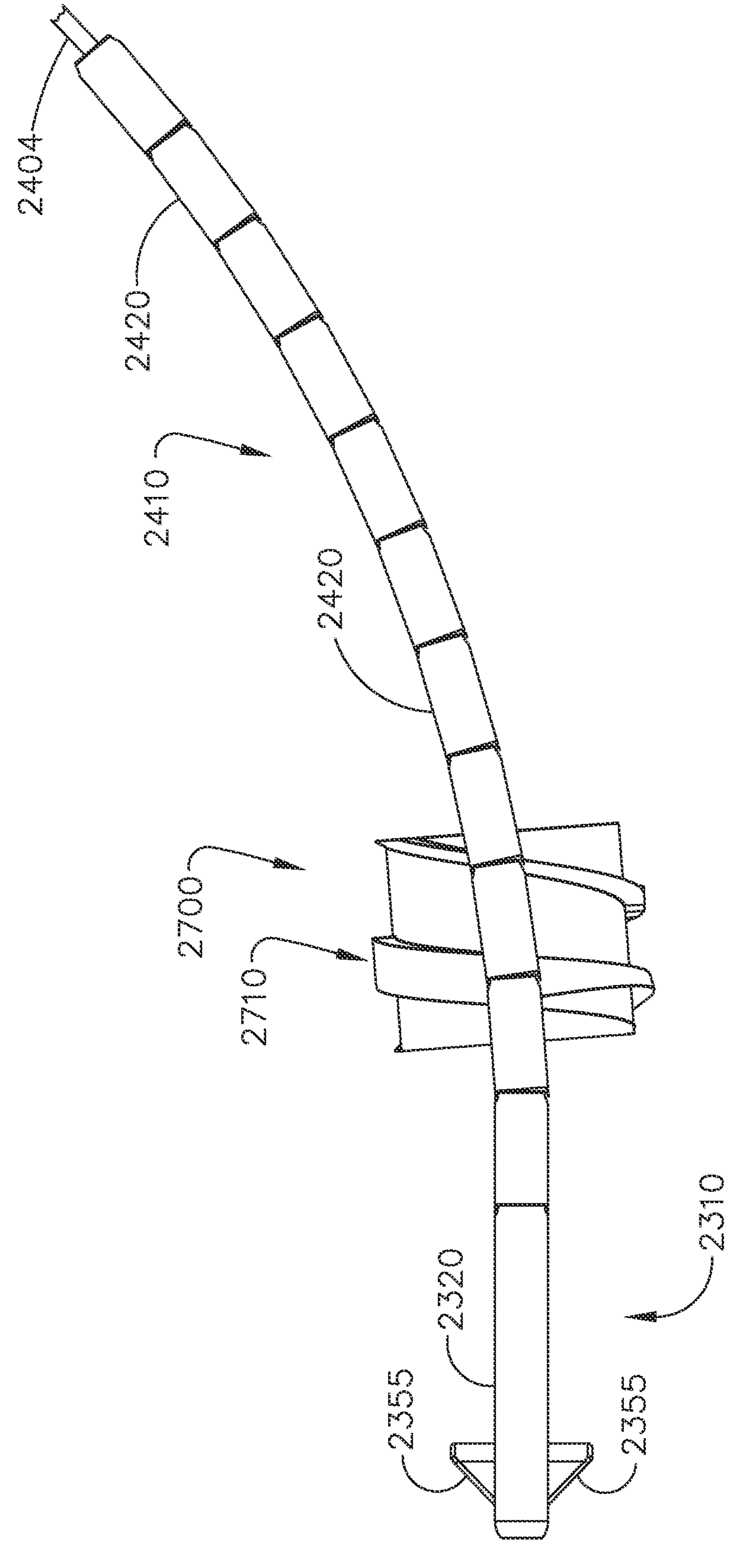
FIG. 15 is a top view of a firing member and upper and lower flexible spine assemblies in engagement with the rotary drive screw of FIG. 9.
Figure 42:
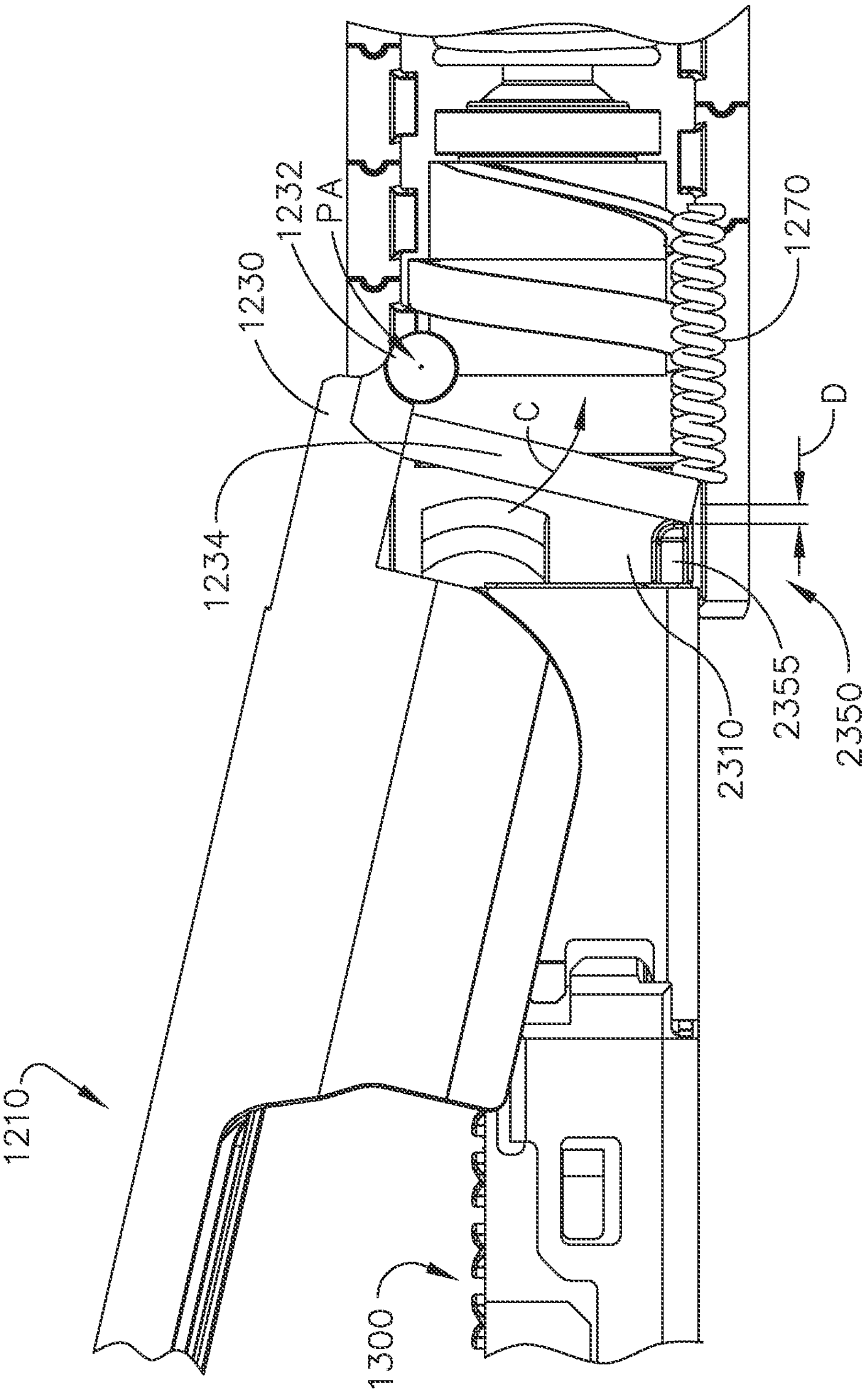
FIG. 42 is a partial side elevational view of the surgical end effector of FIG. 19 with portions thereof omitted for clarity to illustrate the anvil opening springs applying an opening motion to the anvil and with the firing member in a home or starting position.
Figure 43:
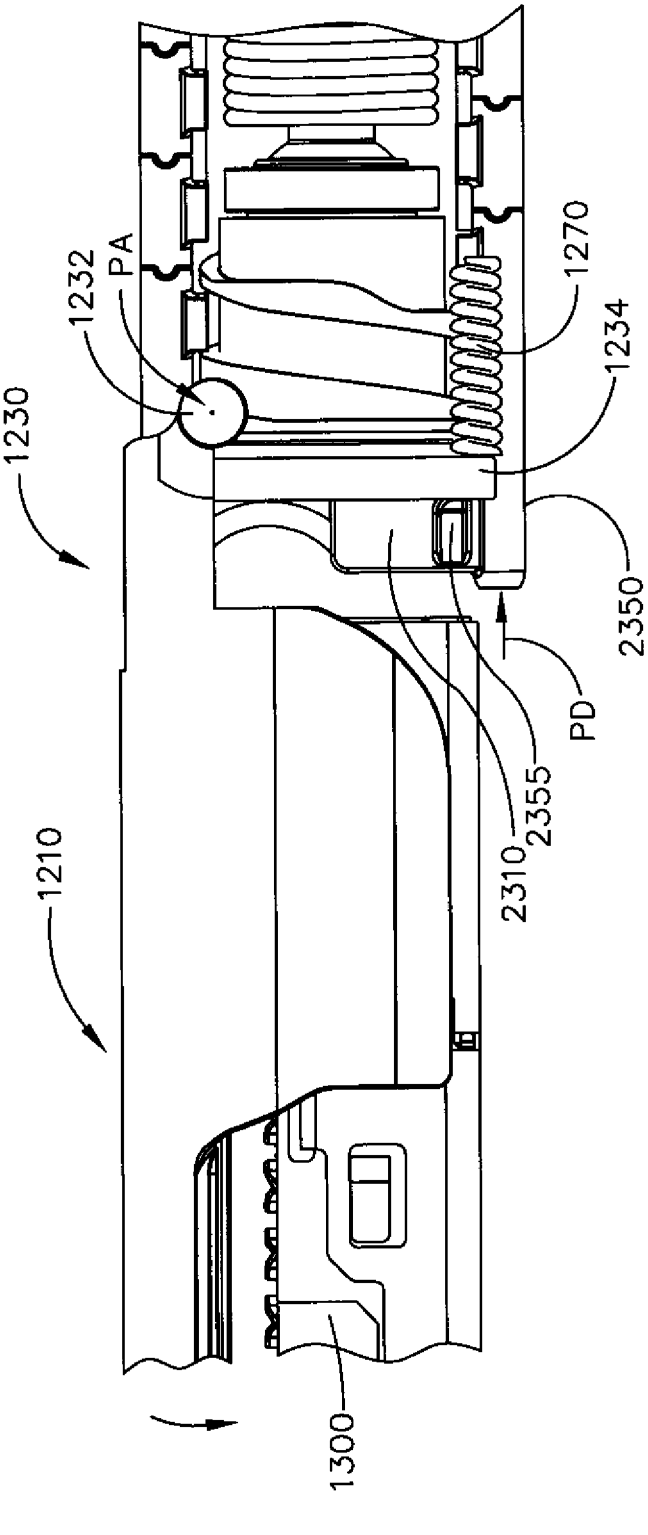
FIG. 43 is another partial side view of the surgical end effector of FIG. 42, after the firing member has moved proximally a short distance to apply a quick closure motion to the anvil for grasping purposes.

In general, the highest firing forces established in an endocutter are associated with cutting and stapling tissue. If those same forces can be used to close the anvil, then the forces generated during pre-clamping and grasping of tissue can be high as well. In at least one arrangement, the firing member body 2312 further comprises a firing member wing or tab 2355 that extends laterally from each lateral side of the firing member body 2312. See FIGS. 15 and 36. The firing member wings 2355 are positioned to contact the corresponding anvil control arms 1234 when the firing member 2310 is driven in the proximal direction PD from the home or starting position to quickly close the anvil 1210 for grasping purposes. In at least one arrangement, when the firing member 2310 is in the home or starting position, the firing member wings 2355 are located distal to the anvil control arms 1234 as shown in FIG. 42. When the firing member 3210 is moved proximally, the firing member wings 2355 push the anvil control arms 1234 (pivotal direction C) against the bias of the anvil springs 1270. See FIG. 42. In one arrangement, the firing member 2310 only has to move a short distance D to pivot the anvil 1210 to a closed position. In one embodiment, distance D may be approximately 0.070 inches long, for example. This short movement allows for a quick response. Because the anvil pivot point or pivot axis PA is relatively far from the firing member wings 2355 which creates a substantial moment arm, the proximal movement of the firing member 2310 (and firing member wings 2355) results in an application of high pre-compression torque to the anvil 1210 to move the anvil 1210 to a closed position. Thus, the firing member wings 2355 may be referred to herein as "pre-compression features". See FIG. 43. Thus, the clinician may use the surgical end effector 1000 to grasp and manipulate tissue between the anvil 1210 and the surgical staple cartridge 1300 without cutting the tissue and forming the staples, by advancing the firing member 2310 proximally the short distance D to cause the anvil 1210 to quickly pivot to a closed position.

The firing member 2310 may be moved in the proximal direction PD by rotating the rotary drive screw 2700 in a second rotary direction. Thus, when the firing member 2310 is in the "home" or starting position, the anvil 1210 may be biased into the fully open position by the anvil springs 1270. Activation of the rotary drive system 2600 to apply a rotary motion to the rotary drive screw 2700 in a first rotary direction will cause the firing member 2310 to be advanced distally from the home or starting position to apply an anvil closure motion to the anvil 1210 to move the anvil closed to clamp the target tissue between the anvil 1210 and the surgical staple cartridge 1300. Continued rotation of the rotary drive screw in the first rotary direction will cause the firing member 2310 to continue to distally advance through the surgical end effector 1000. As the firing member 2310 moves distally, the firing member 2310 (as well as the firing member wings 2355 thereon) contacts a sled 1312 (FIG. 19) that is supported in the surgical staple cartridge 1300 to drive the sled 1312 distally through the staple cartridge body 1302. When the firing member 2310 is in the home or starting position, the surgeon may wish to use the surgical end effector to grasp and manipulate tissue. To do so, the rotary drive system is actuated to apply a second rotary drive motion to the rotary drive screw 2700 in a second rotary direction that is opposite to the first rotary direction. Such rotary movement of the rotary drive screw 2700 in the second rotary direction will drive the firing member 2310 proximally from the starting position and cause the anvil 1210 to quickly pivot to the closed position. Thus, in accordance with at least one embodiment, the "home or starting position" of the firing member 2310 is not its proximal-most position.

If during the firing process, the rotary drive system 2600 quits rotating, the firing member 2310 may become stuck within the surgical end effector. In such instance, the top firing member feature 2320 may remain engaged with the anvil 1210 and the bottom firing member feature 2350 may remain engaged with the elongate channel 1110 and thereby prevent the surgeon from moving the anvil 1210 to an open position to release the tissue clamped between anvil 1210 and surgical staple cartridge 1300. This could occur, for example, if the motor or other control arrangement supplying the rotary drive motions to the rotary drive shaft 2610 fails or otherwise becomes inoperative. In such instances, the firing member 2310 may be retracted back to the home or starting position within the surgical end effector 1000 by pulling the top cable 2404 and the lower cable 2504 in a proximal direction. For example, a proximal portion of the top cable 2404 and a proximal portion of the lower cable 2505 may be spooled on a rotary spool or cable-management system 2009 (FIG. 2) in the housing portion of the surgical instrument 10 that is configured to payout the top cable 2404 and lower cable 2504 during the firing stroke and also retract the cables 2404, 2504 in a proximal direction should the firing member 2310 need to be retracted. The cable management system 2009 may be motor powered or manually powered (ratchet arrangement, etc.) to apply retraction motions to the cables 2404, 2504. When the cables 2404, 2504 are retracted, the upper vertebra members 2420 and lower vertebra members 2520 will cause the rotary drive screw 2700 to spin in reverse.

The following equation may be used to determine whether the rotary drive screw 2700 will spin in reverse depending upon the lead (L), pitch diameter ($d_p$), tooth angle ($\alpha$) and friction ($\mu$):

$$\mu \geq \frac{L}{\pi d_p} \cos\alpha$$

The rotary drive screw 2700 may self-lock if the above equation is true. For the most part, in many instances, the pitch diameter is mostly fixed for an endocutter, but the lead and tooth angle are variable. Because the upper vertebra member teeth 2450 and lower vertebra member teeth 2550 are mostly square, the rotary drive screw 2700 is more likely to be back drivable (cos (90)=1). The leads of the upper vertebra member teeth 2450 and lower vertebra member teeth 2550 may also be advantageous in that the rolling friction between the vertebra members 2420, 2520 and the rotary drive screw 2700 is more likely to enable the rotary drive screw 2700 to be back driven. Thus, in the event of an emergency, the surgeon can pull on the upper and lower cables 2404, 2504 in the proximal direction to cause the firing member 2310 to fully retract for a quick "bailout".

As indicated above, the relative control motions for the rotary drive system 2600, as well as the various cable-management systems employed in connection with the firing system 2300 and the articulation control system 2240, may be supported within a housing 2002 which may be handheld or comprise a portion of a larger automated surgical system. The firing system 2300, articulation control system 2240, and the rotary drive system 2600 may, for example, be motor-controlled and operated by one or more control circuits.

Figure 44:
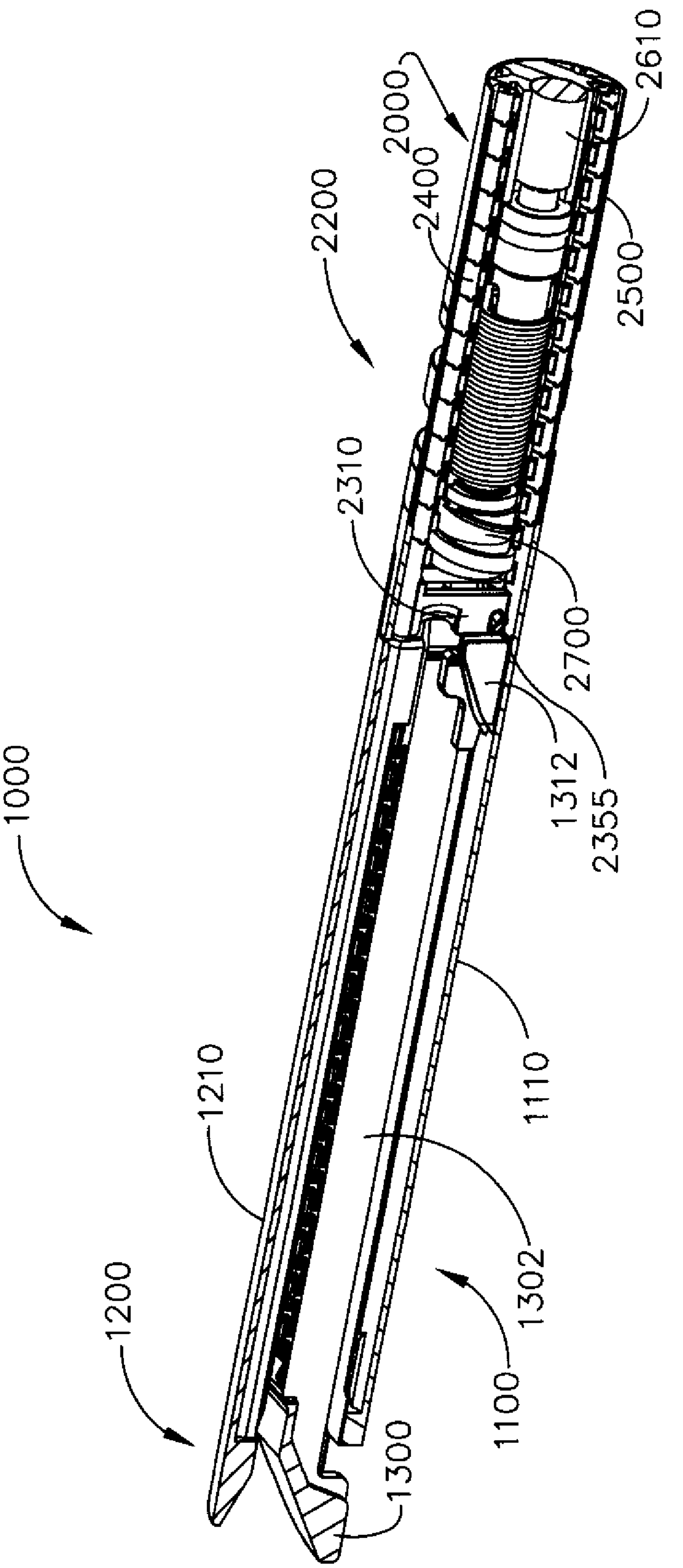
FIG. 44 is a cross-sectional view of the surgical end effector of FIG. 19 with the jaws thereof in a closed position and the firing member thereof in a proximal-most position.

One method of using the surgical instrument 10 may involve the use of the surgical instrument 10 to cut and staple target tissue within a patient using laparoscopic techniques. For example, one or more trocars may have been placed through the abdominal wall of a patient to provide access to a target tissue within the patient. The surgical end effector 1000 may be inserted through one trocar and one or more cameras or other surgical instruments may be inserted through the other trocar(s). To enable the surgical end effector 1000 to pass through the trocar cannula, the surgical end effector 1000 is positioned in an unarticulated orientation and the jaws 1100 and 1200 must be closed. To retain the jaws 1100 and 1200 in the closed position for insertion purposes, for example, the rotary drive system 2600 may be actuated to apply the second rotary motion to the rotary drive screw 2700 to cause the firing member 2310 to move proximally from the starting position to move the anvil 1210 (jaw 1200) to the closed position. See FIG. 44. The rotary drive system 2600 is deactivated to retain the firing member 2310 in that position. Once the surgical end effector has passed into the abdomen through the trocar, the rotary drive system 2600 may be activated to cause the rotary drive screw 2700 to drive the firing member 2310 distally back to the starting position wherein the anvil springs 1270 will pivot the anvil 1210 to the open position. See FIG. 38.

Once inside the abdomen and before engaging the target tissue, the surgeon may need to articulate the surgical end effector 1000 into an advantageous position. The articulation control system 2240 is then actuated to articulate the surgical end effector in one or more planes relative to a portion of the elongate shaft assembly 2000 that is received within the cannula of the trocar. Once the surgeon has oriented the surgical end effector 1000 in a desirable position, the articulation control system 2240 is deactivated to retain the surgical end effector 1000 in the articulated orientation. The surgeon may then use the surgical end effector to grasp the target tissue or adjacent tissue by activating the rotary drive system to rotate the rotary drive screw in the second rotary direction to move the firing member proximally to cause the anvil 1210 to rapidly close to grasp the tissue between the anvil 1210 and the surgical staple cartridge 1300. The anvil 1210 may be opened by reversing the rotation of the rotary drive screw 2700. This process may be repeated as necessary until the target tissue has be properly positioned between the anvil 1210 and the surgical staple cartridge 1300.

Once the target tissue has been positioned between the anvil 1210 and the surgical staple cartridge, the surgeon may commence the closing and firing process by activating the rotary drive system 2600 to drive the firing member 2310 distally from the starting position. As the firing member 2310 moves distally from the starting position, the firing member 2310 applies a closure motion to the anvil 1210 and moves the anvil 1210 from the open position to the closed position in the manners discussed above. As the firing member 2310 moves distally, the firing member 2310 retains the anvil 1210 in the closed position thereby clamping the target tissue between the anvil 1210 and the surgical staple cartridge 1300. As the firing member 2310 moves distally, the firing member 2310 contacts a sled 1312 supported in the surgical staple cartridge 1300 and also drives the sled 1312 distally through the staple cartridge body 1302. The sled 1312 serially drives rows of drivers supported in the staple cartridge toward the clamped target tissue. Each driver has supported thereon one or more surgical staples or fasteners which are then driven through the target tissue and into forming contact with the underside of the anvil 1210. As the firing member 2310 moves distally, the tissue cutting edge 2314 thereon cuts through the stapled tissue.

Figure 45:
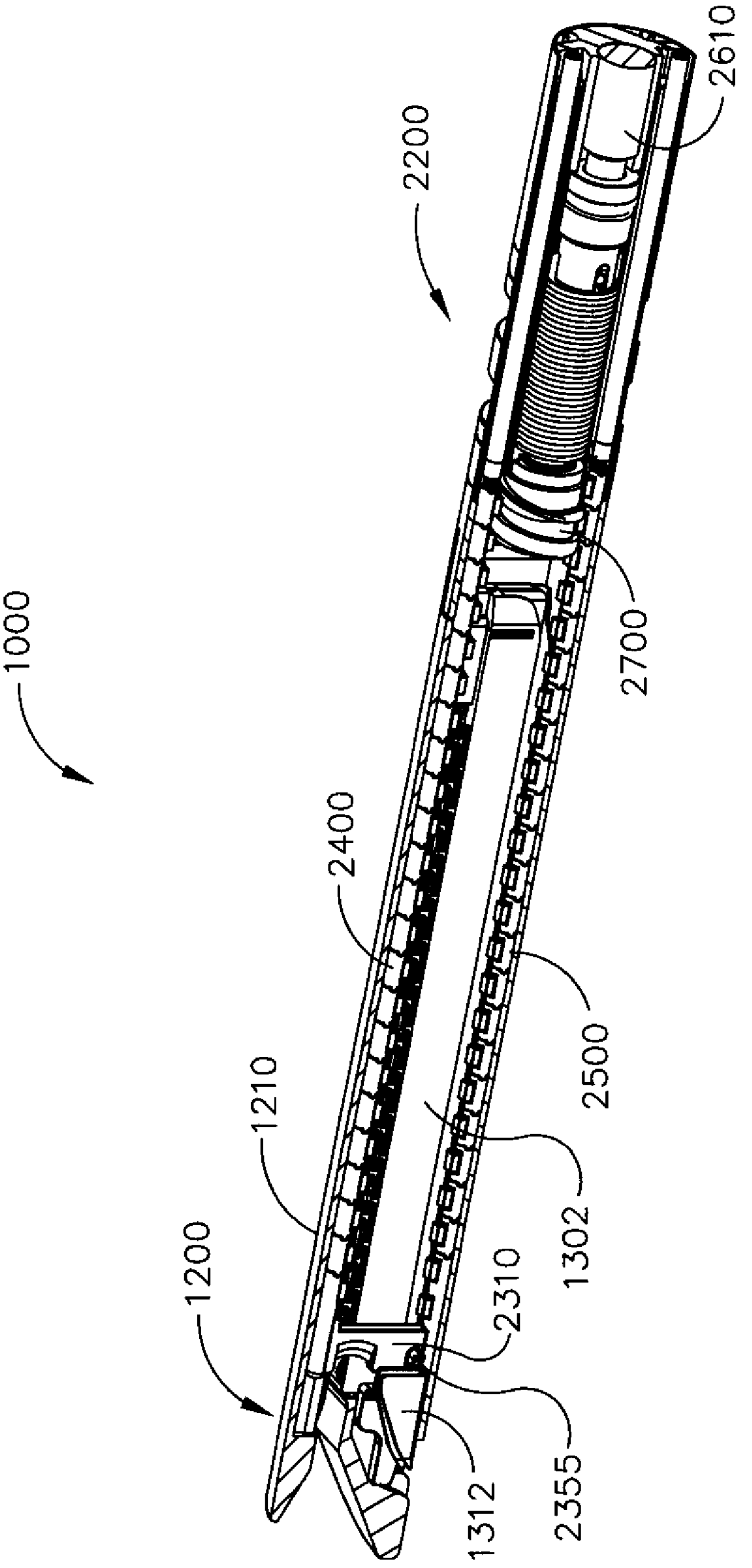
FIG. 45 is another cross-sectional view of the surgical end effector of FIG. 44, after the firing member has been distally advanced to the ending position within the surgical end effector.
Figure 46:
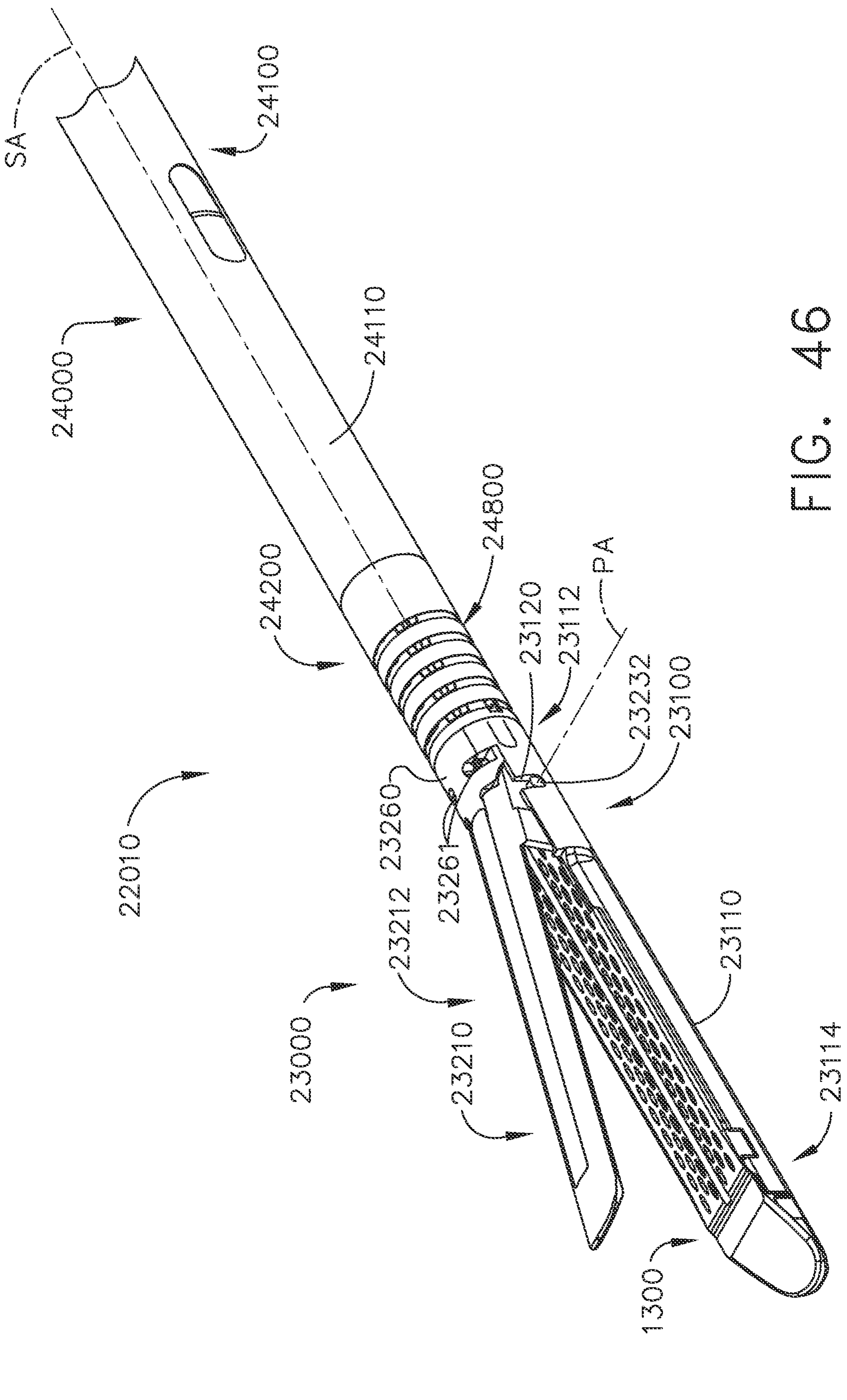
FIG. 46 is a perspective view of a portion of another surgical instrument.
Figure 47:
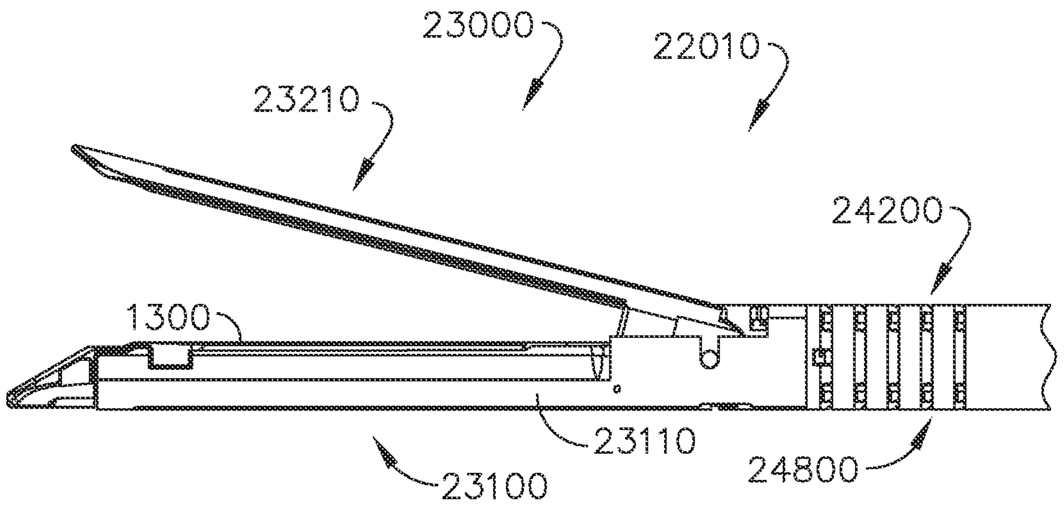
FIG. 47 is a side elevational view of a surgical end effector of the surgical instrument of FIG. 46, with the jaws thereof in an open position.

After the firing member 2310 has been driven distally to the ending position within the surgical end effector 1000 (FIG. 45), the rotary drive system 2600 is reversed which causes the firing member 2310 to retract proximally back to the home or starting position. Once the firing member 2310 has returned to the starting position, the anvil springs 1270 will pivot the anvil 1210 to the open position to enable the surgeon to release the stapled tissue from the surgical end effector 1000. Once the stapled tissue has been released, the surgical end effector may be withdrawn out of the patient through the trocar cannula. To do so, the surgeon must first actuate the articulation control system 2240 to return the surgical end effector 1000 to an unarticulated position and actuate the rotary drive system to drive the firing member 2310 proximally from the home or starting position to close the jaws. Thereafter, the surgical end effector 1000 may be withdrawn through the trocar cannula. If during the firing process or during the retraction process, the firing system becomes inoperative, the surgeon may retract the firing member 2310 back to the starting position by applying a pulling motion to the cables 2404, 2505 in the proximal direction in the various manners described herein.

FIGS. 46-68 illustrate another surgical instrument 22010 that in many aspects is identical or very similar to the surgical instrument 10 described above, except for the various differences discussed below. Like surgical instrument 10, surgical instrument 22010 may address many of the challenges facing surgical instruments with articulatable end effectors that are configured to cut and fasten tissue. In various embodiments, the surgical instrument 22010 may comprise a handheld device. In other embodiments, the surgical instrument 22010 may comprises an automated system sometimes referred to as a robotically-controlled system, for example. In various forms, the surgical instrument 22010 comprises a surgical end effector 23000 that is operably coupled to an elongate shaft assembly 24000. The elongate shaft assembly 24000 may be operably attached to a housing that is handheld or otherwise comprises a portion of a robotic system as was discussed above.

Figure 48:
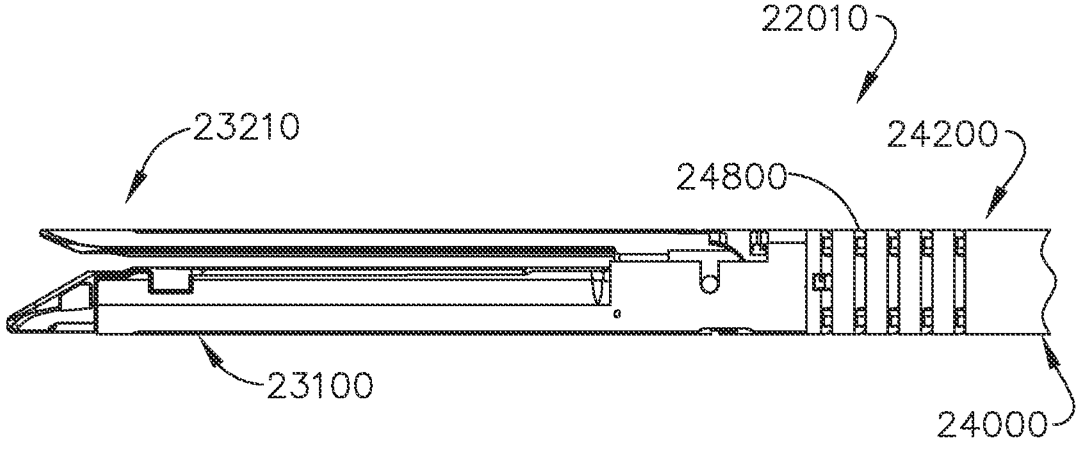
FIG. 48 is another side view of the surgical end effector of FIG. 48 with the jaws thereof in a closed position.
Figure 49:
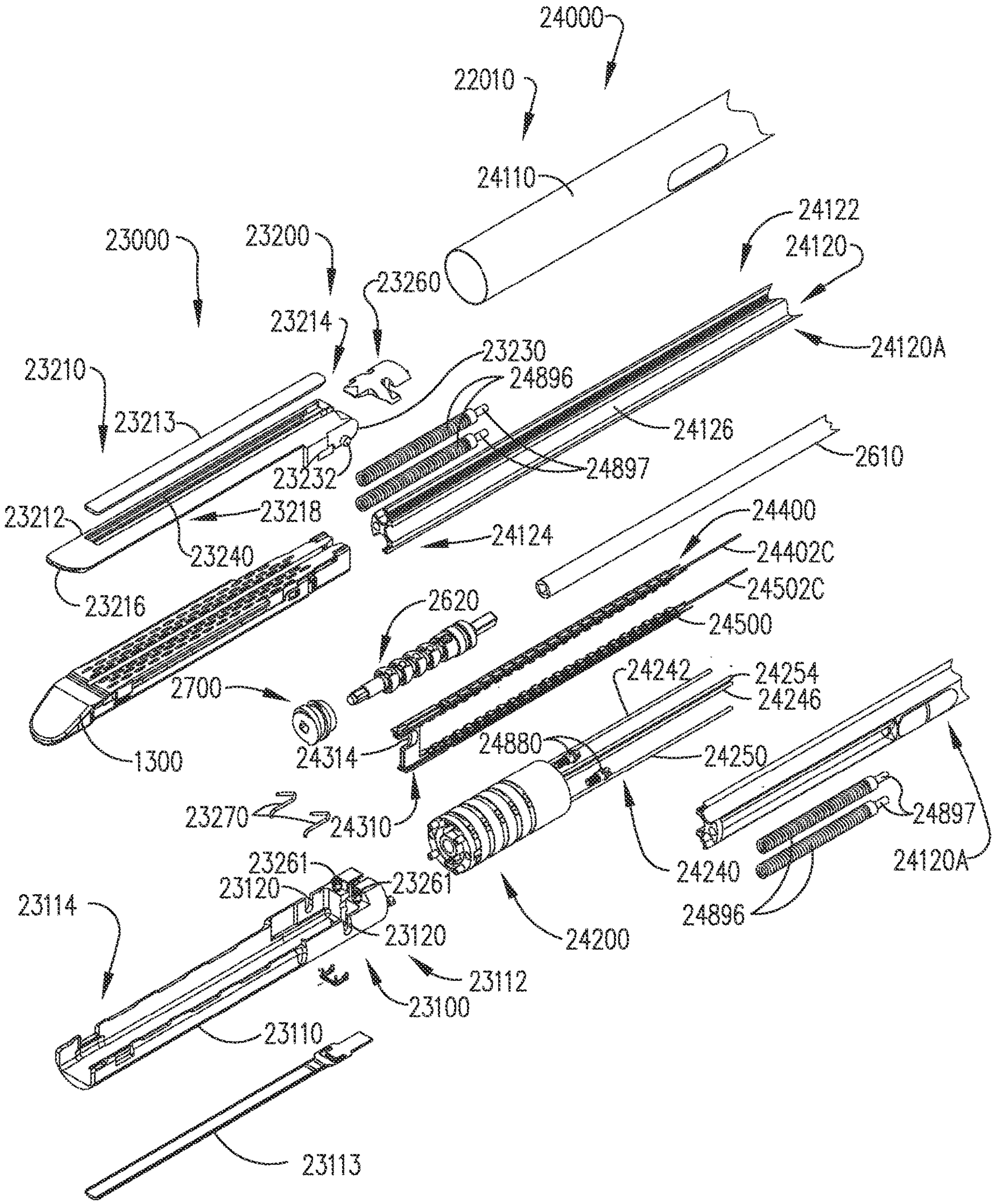
FIG. 49 is an exploded assembly view of a portion of the surgical instrument of FIG. 46.
Figure 50:
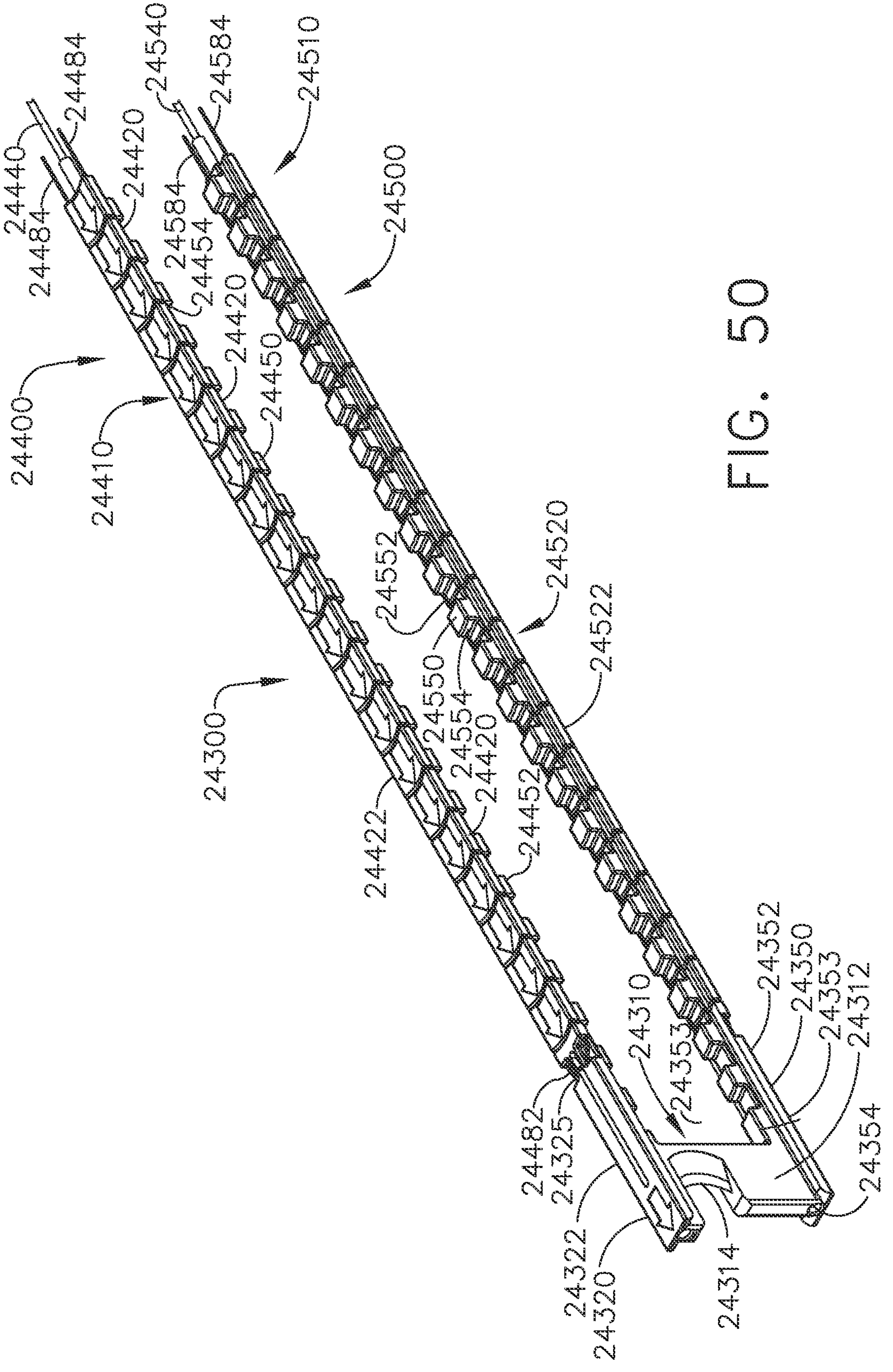
FIG. 50 is a perspective view of a firing member and portions of an upper flexible spine assembly and a lower flexible spine assembly of a firing system of the surgical instrument of FIG. 46.

As can be seen in FIG. 49, in one form, the surgical end effector 23000 comprises a first jaw 23100 and a second jaw 23200. In the illustrated arrangement, the first jaw 23100 comprises an elongate channel 23110 that comprises a proximal end 23112 and a distal end 23114 and is configured to operably support a surgical staple cartridge 1300 therein. The elongate channel 23110 has an open bottom to facilitate ease of assembly and has a channel cover 23113 that is configured to be attached thereto (welded, etc.) to cover the opening and add rigidity to the elongate channel 23110. In the illustrated arrangement, the second jaw 23200 comprises an anvil 23210 that comprises an elongate anvil body 23212 that comprises a proximal end 23214 and a distal end 23216. In one arrangement, an anvil cover 23213 is provided to facilitate assembly of the device and add rigidity to the anvil 23210 when it is attached (welded, etc.) to the anvil body 23212. The anvil body 23212 comprises a staple-forming undersurface 23218 that faces the first jaw 23100 and may include a series of staple-forming pockets (not shown) that corresponds to each of the staples or fasteners in the surgical staple cartridge 1300. The proximal end 23214 of the anvil body 23212 comprises an anvil mounting portion 23230 that includes a pair of laterally extending mounting pins 23232 that are configured to be received in corresponding mounting cradles or pivot cradles 23120 formed in the proximal end 23112 of the elongate channel 23110. The mounting pins 23232 are pivotally retained within the mounting cradles 23120 by an anvil cap 23260 that may be attached to the proximal end 23112 of the elongate channel 23110 by screws 23261. In other arrangements, the anvil cap 23260 may be attached to the elongate channel 23110 by welding, adhesive, etc. Such arrangement facilitates pivotal travel of the anvil 23210 relative to the surgical staple cartridge 1300 mounted in the elongate channel 23110 about a pivot axis PA between an open position (FIG. 47) and a closed position (FIG. 48). Such pivot axis PA may be referred to herein as being "fixed" in that the pivot axis does not translate or otherwise move as the anvil 23210 is pivoted from an open position to a closed position.

In the illustrated arrangement, the anvil 23210 is moved to the open position by a pair of anvil springs 23270 that are supported within the proximal end 23112 of the elongate channel 23110. See FIGS. 49 and 62. The springs 23270 are positioned to apply a pivotal biasing force to corresponding portions of the anvil 23210 to apply opening forces thereto. See FIG. 47.

In the illustrated arrangement, the elongate shaft assembly 24000 defines a shaft axis SA and comprises a proximal shaft portion 24100 that may operably interface with a housing of the control portion (e.g., handheld unit, robotic tool driver, etc.) of the surgical instrument 22010. The elongate shaft assembly 24000 further comprises an articulation joint 24200 that is attached to the proximal shaft portion 24100 and the surgical end effector 23000. In various instances, the proximal shaft portion 24100 comprises a hollow outer tube 24110 that may be operably coupled to a housing in the various manners discussed above. As can be seen in FIG. 49, the proximal shaft portion 24100 may further comprise a rigid proximal support shaft 24120 that is supported within the hollow outer tube 24110 and extends from the housing to the articulation joint 24200. The rigid proximal support shaft 24120 may comprise a first half 24120A and a second half 24120B that may be coupled together by, for example, welding, adhesive, etc. The rigid proximal support shaft 24120 comprises a proximal end 24122 and a distal end 24124 and includes an axial passage 24126 that extends therethrough from the proximal end 24122 to the distal end 24124.

As was discussed above, many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles. The surgical instrument 22010 employs a firing system 24300 that is identical to or very similar in many aspects as firing system 2300 described above. As such, only those aspects of the firing system 24300 needed to understand the operation of the surgical instrument 22010 will be discussed below.

Figure 54:
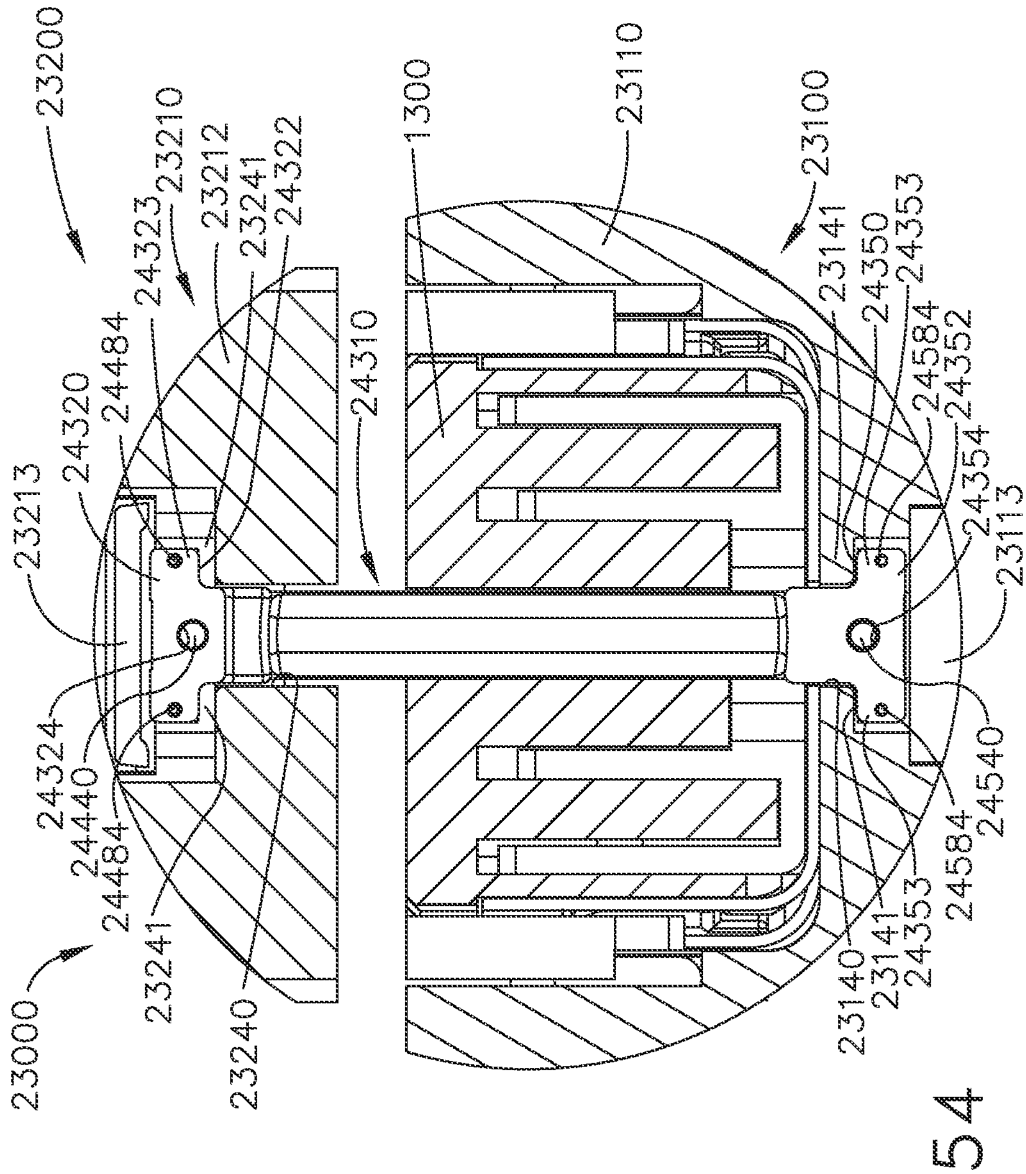
FIG. 54 is a cross-sectional end view of the surgical end effector of the surgical instrument of FIG. 46, with the jaws thereof in a closed position.

As can be seen in FIGS. 50-54, in at least one embodiment, the firing system 24300 comprises a firing member 24310 that includes a vertically-extending firing member body 24312 that comprises a top firing member feature 24320 and a bottom firing member feature 24350. A tissue cutting blade 24314 is attached to or formed in the vertically-extending firing member body 24312. See FIGS. 50 and 51. In at least one arrangement, it is desirable for the firing member 24310 to pass through the anvil body 23212 with low friction, high strength and high stiffness. In the illustrated arrangement, the top firing member feature 24320 comprises a T-shaped body 24322 that has two laterally extending tabs 24323 protruding therefrom and a top axial passage 24324 extending therethrough. See FIG. 53. The bottom firing member feature 24350 comprises a T-shaped body 24352 that has two laterally extending tabs 24353 protruding therefrom and a bottom axial passage 24354 extending therethrough. See FIG. 50. In at least one arrangement, the top firing member feature 24320 and the bottom firing member feature 24350 are integrally formed with the vertically-extending firing member body 24312. As can be seen in FIG. 54, the anvil body 23212 comprises an axially extending anvil slot 23240 that defines two opposed ledges 23241 for slidably receiving the laterally extending tabs 24323 thereon. Similarly, the elongate channel 23110 comprises an axially extending channel slot 23140 that defines axially extending channel ledges 23141 that are configured to slidably receive the laterally extending tabs 24353 thereon.

In the illustrated arrangement, the firing system 24300 comprises an upper flexible spine assembly 24400 that is operably coupled to the top firing member feature 24320 of the firing member 24310. In at least one embodiment, the upper flexible spine assembly 24400 comprises an upper series 24410 of upper vertebra members 24420 that are loosely coupled together by an upper flexible coupler member 24440 that extends through each of the upper vertebra members 24420 and is attached to the top firing member feature 24320.

Figure 52:
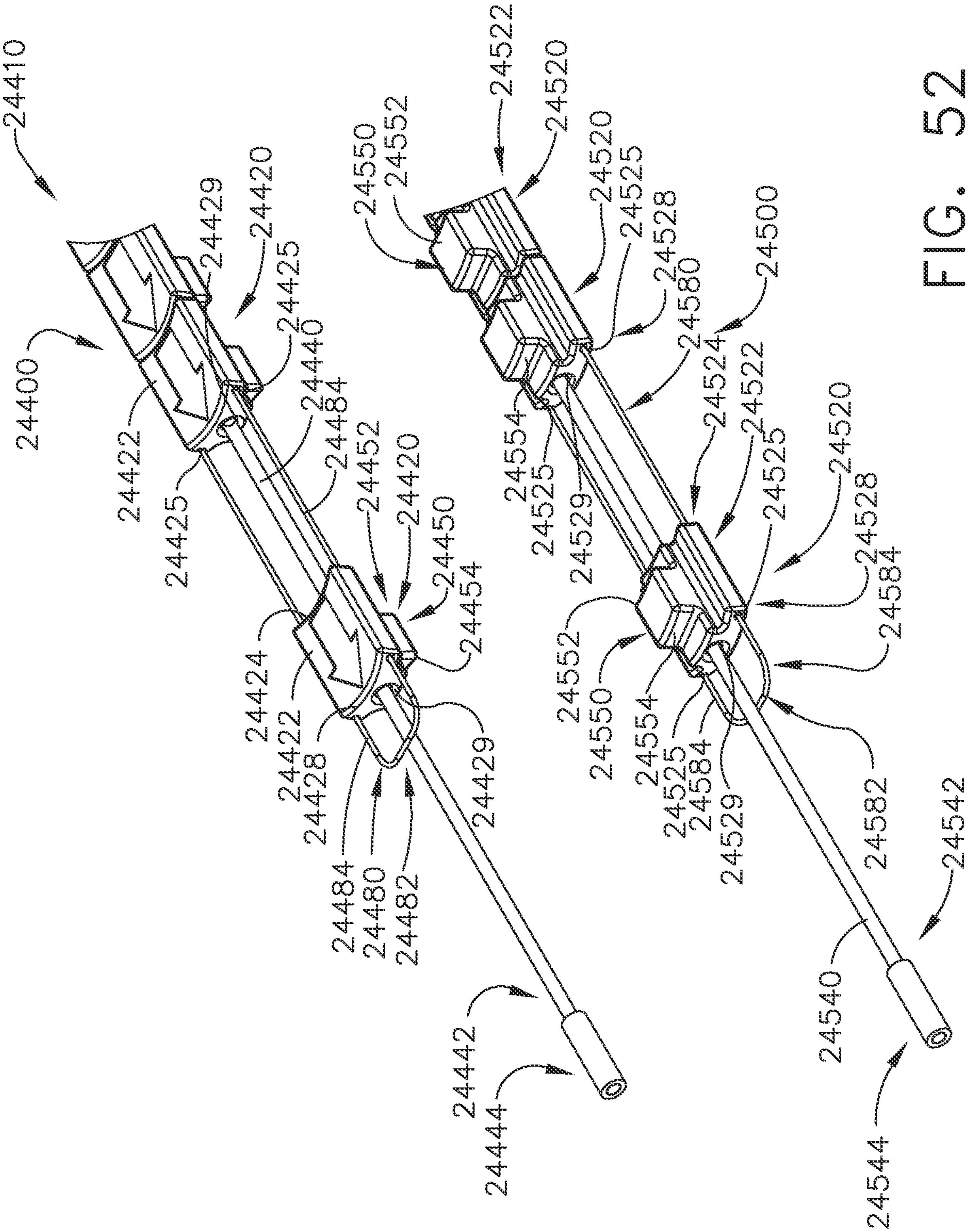
FIG. 52 is a partial exploded assembly view of the upper flexible spine assembly and lower flexible spine assembly depicted in FIG. 51.
Figure 53:
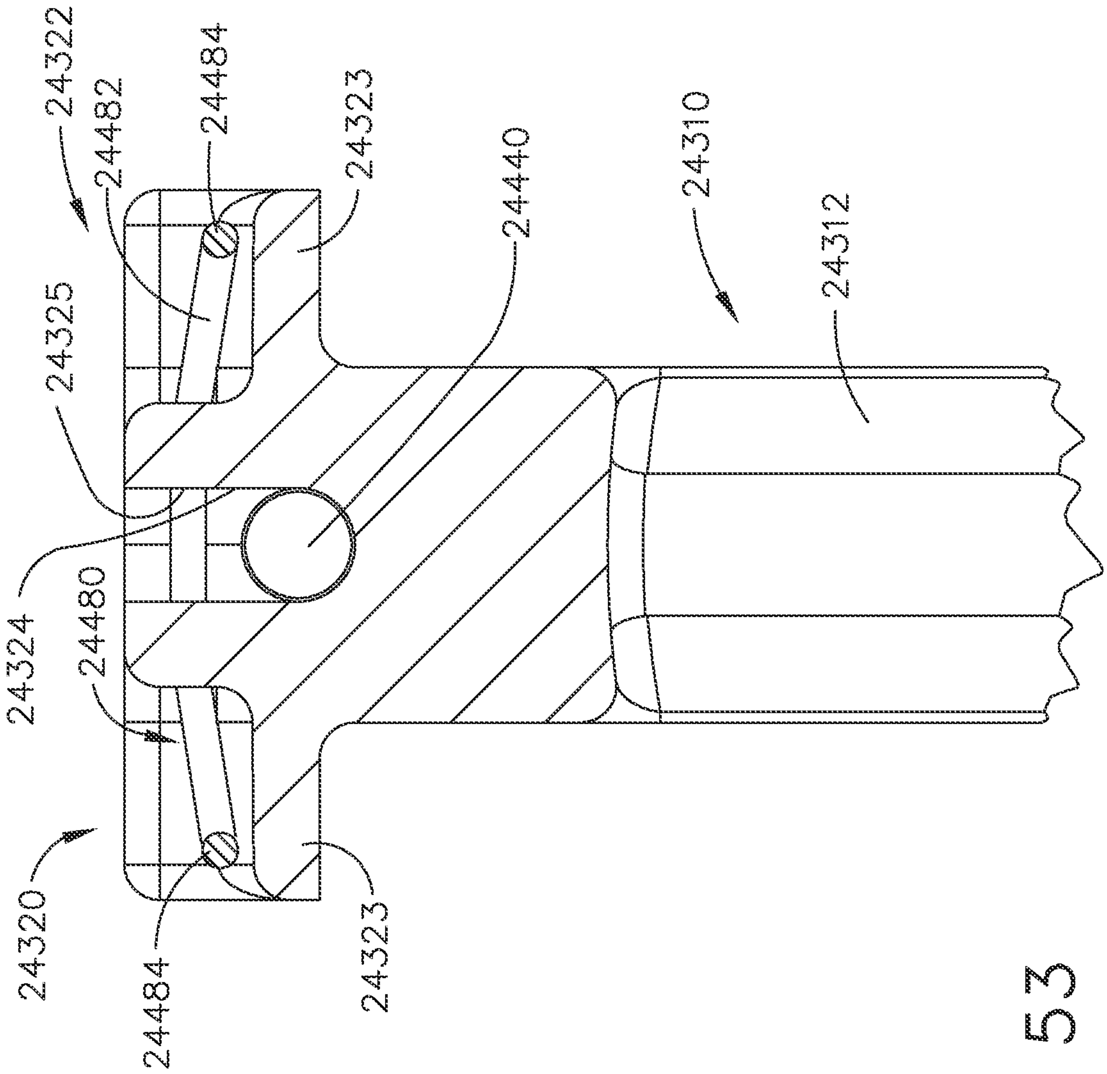
FIG. 53 is a partial cross-sectional end view of an upper portion of the firing member depicted in FIG. 50.

As can be seen in FIG. 52, each upper vertebra member 24420 is substantially T-shaped when viewed from an end thereof. In one aspect, each upper vertebra member 24420 comprises an upper vertebra body portion 24422 that has a proximal end 24424 and a distal end 24428. Each upper vertebra member 24420 further comprises a downwardly extending upper drive feature or upper vertebra member tooth 24450 that protrudes from the upper vertebra body portion 24422. Each upper vertebra member tooth 24450 has a helix-shaped proximal upper face portion 24452 and a helix-shaped distal upper face portion 24454. Each proximal end 24424 of the upper vertebra body portions 24422 has an arcuate or slightly concave curved shape and each distal end 24428 has an arcuate or slightly convex curved shape. When arranged in the upper series 24410, the convex distal end 24428 on one upper vertebra member 24420 contacts and mates with the concave proximal end 24424 on an adjacent upper vertebra member 24420 in the upper series 24410 to maintain the upper vertebra members 24420 roughly in alignment so that the helix-shaped proximal upper face portion 24452 and a helix-shaped distal upper face portion 24454 on each respective upper vertebra member tooth 24450 can be drivingly engaged by a rotary drive screw 2700 in the various manners disclosed herein. These curved mating surfaces on the upper vertebra members 24420 allow the upper vertebras members 24420 to better transfer loads between themselves even when they tilt.

In at least one embodiment, an upper alignment member 24480 is employed to assist with the alignment of the upper vertebra members 24420 in the upper series 24410. In one arrangement, the alignment member 24480 comprises a spring member or metal cable which may be fabricated from Nitinol wire, spring steel, etc., and be formed with a distal upper looped end 24482 and two upper leg portions 24484 that extend through corresponding upper passages 24425 in each upper vertebra body portion 24422. The upper flexible coupler member 24440 extends through an upper passage 24429 in each of the upper vertebra members 24420 to be attached to the firing member 24310. In particular, a distal end portion 24442 extends through the top axial passage 24324 in the top firing member feature 24320 and is secured therein by an upper retention lug 24444. A proximal portion of the upper flexible coupler member 24440 may interface with a corresponding rotary spool or cable-management system of the various types and designs disclosed herein that serve to payout and take up the upper flexible coupler member 24440 to maintain a desired amount of tension therein during operation and articulation of the surgical end effector 23000. The cable management system may be motor powered or manually powered (ratchet arrangement, etc.) to maintain a desired amount of tension in the upper flexible coupler member 24440. The amount of tension in each flexible coupler member may vary depending upon the relative positioning of the surgical end effector 23000 to the elongate shaft assembly 24000.

The firing system 24300 further comprises a lower flexible spine assembly 24500 that is operably coupled to the bottom firing member feature 24350. The lower flexible spine assembly 24500 comprises a lower series 24510 of lower vertebra members 24520 that are loosely coupled together by a lower flexible coupler member 24540 that extends through each of the lower vertebra members 24520 and is attached to the bottom firing member feature 24350. As can be seen in FIG. 52, each lower vertebra member 24520 is substantially T-shaped when viewed from an end thereof. In one aspect, each lower vertebra member 24520 comprises a lower vertebra body portion 24522 that has a proximal end 24524 and a distal end 24528. Each lower vertebra member 24520 further comprises an upwardly extending lower drive feature or lower vertebra member tooth 24550 that protrudes from the lower vertebra body portion 24522. Each lower vertebra member tooth 24550 has a helix-shaped proximal lower face portion 24552 and a helix-shaped distal lower face portion 24554. The proximal end 24524 of each lower vertebra body portions 24522 has an arcuate or slightly concave curved shape and each distal end 24528 has an arcuate or slightly convex curved shape. When arranged in the lower series 24510, the convex distal end 24528 on one lower vertebra member 24520 contacts and mates with the concave proximal end 24524 on an adjacent lower vertebra member 24520 in the lower series 24510 to maintain the lower vertebra members 24520 roughly in alignment so that the helix-shaped proximal lower face portion 24552 and a helix-shaped distal lower face portion 24554 on each respective lower vertebra member tooth 24550 can be drivingly engaged by the rotary drive screw 2700 in the various manners disclosed herein. These curved mating surfaces on the lower vertebra members 24520 allow the lower vertebra members 24520 to better transfer loads between themselves even when they tilt.

In at least one embodiment, a lower alignment member 24580 is employed to assist with the alignment of the lower vertebra members 24520 in the lower series 24510. In one arrangement, the lower alignment member 24580 comprises a spring member or metal cable which may be fabricated from Nitinol wire, spring steel, etc., and be formed with a distal lower looped end 24582 and two lower leg portions 24584 that extend through corresponding lower passages 24525 in each lower vertebra body portion 24522. The lower flexible coupler member 24540 extends through the bottom axial passage 24529 in each of the lower vertebra members 24520 to be attached to the firing member 24310. In particular, a distal end portion 24542 of the lower flexible coupler member 24540 extends through the bottom axial passage 24354 in the bottom firing member feature 24350 and is secured therein by a lower retention lug 24544. A proximal portion of the lower flexible coupler member 24540 may interface with a corresponding rotary spool or cable-management system of the various types and designs disclosed herein that serve to payout and take up the lower flexible coupler member 24540 to maintain a desired amount of tension therein during operation and articulation of the surgical end effector 23000. The cable management system may be motor powered or manually powered (ratchet arrangement, etc.) to maintain a desired amount of tension in the lower flexible coupler member 24540. The amount of tension in each flexible coupler member may vary depending upon the relative positioning of the surgical end effector 23000 to the elongate shaft assembly 24000.

In accordance with at least one aspect, a large surface area is advantageous for distributing the force between the vertebra members when they push so that the vertebra members cannot twist relative to each other. The available area in the anvil and channel is limited and the anvil and channel must remain stiff. The T-shaped upper vertebra members 24420 and the T-shaped lower vertebra members 24520 are designed to fit in the limited spaces available in the anvil 23210 and the elongate channel 23110 while ensuring that there is a large amount of area to distribute the firing loads. The curved surfaces on each upper vertebra member 24420 and each lower vertebra member 24520 allow each of those vertebras to better transfer loads between themselves even when they tilt. The upper alignment member 24480 and the lower alignment member 24580 may also serve to prevent the upper vertebra members 24420 and the lower vertebra members 24520 from twisting relative to each other. The large surface area may also help to prevent galling of the vertebra members and/or the anvil and channel. The upper flexible spine assembly 24400 and the lower flexible spine assembly 24500 otherwise operably interface with the rotary drive screw 2700 arrangements as disclosed herein. The upper flexible coupler member 24440 and the lower flexible coupler member 24540 may also be used in the manners discussed above to retract the firing member 24310 back to its starting position if, during a firing stroke, the firing drive system 24300 fails.

Figure 51:
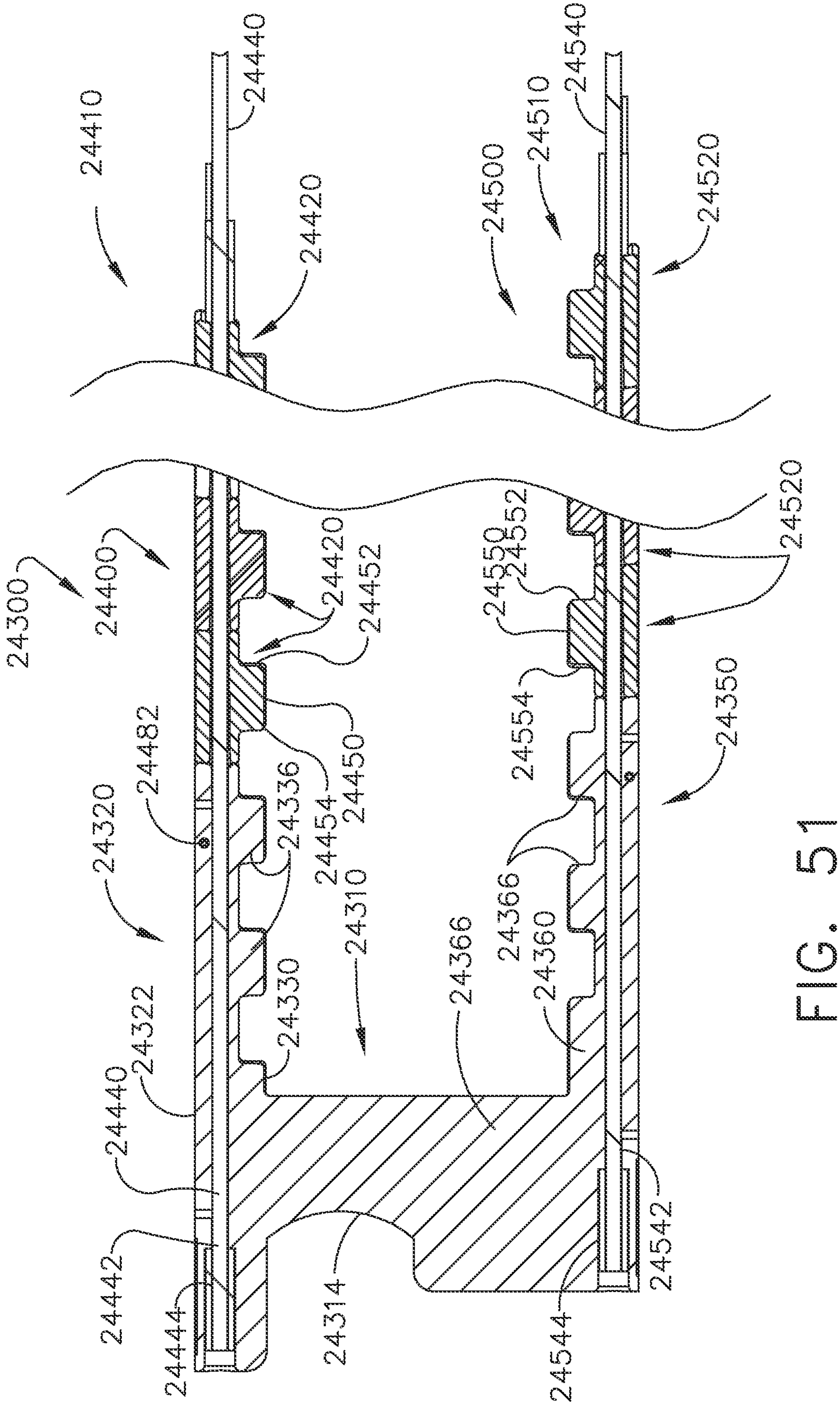
FIG. 51 is a cross-sectional side view of the portions of the firing system depicted in FIG. 50.

As can be seen in FIG. 51, the top firing member feature 24320 on the firing member 24310 comprises a distal upper firing member tooth segment 24330 that is equivalent to one half of an upper vertebra member tooth 24450 on each upper vertebra member 24420. In addition, two proximal upper firing member teeth 24336 that are identical to an upper vertebra member tooth 24450 on each upper vertebra member 24420 are spaced from the distal upper firing member tooth segment 24330. The distal upper firing member tooth segment 24330 and the proximal upper firing member teeth 24336 may each be integrally formed with the top firing member feature 24320 of the firing member 24310. Likewise, the bottom firing member feature 24350 of the firing member 24310 comprises a distal lower firing member tooth 24360 and two proximal lower firing member teeth 24366 that are integrally formed on the bottom firing member feature 24350. For example, in at least one arrangement, the firing member 24310 with the rigidly attached teeth 24330, 24336, 24360, and 24366 may be fabricated at one time as one unitary component using conventional metal injection molding techniques. The person of ordinary skill in the art will recognize that the firing member 24310 operates in essentially the same manner as the firing member 2310 as was described in detail herein.

Figure 55:
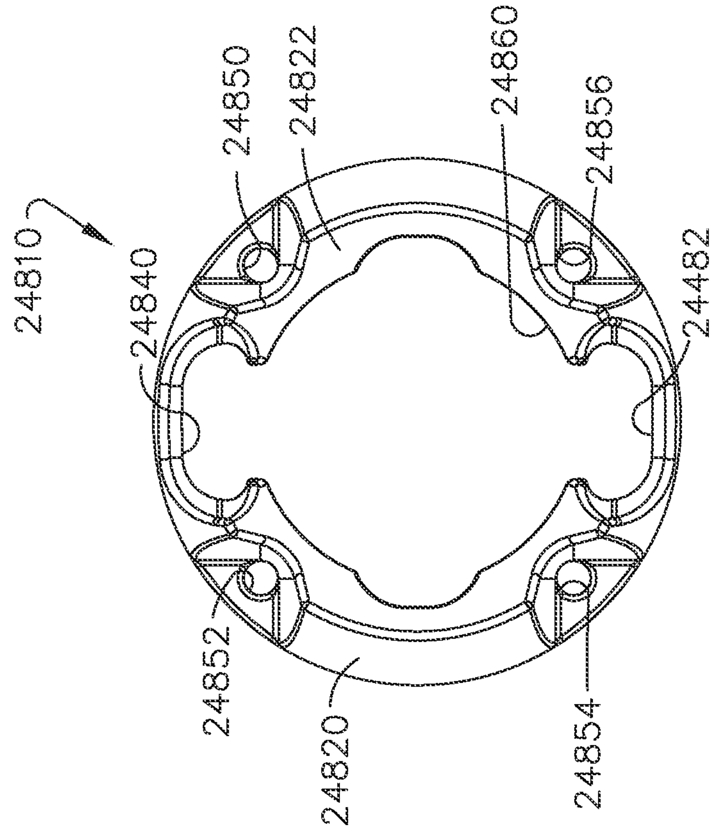
FIG. 55 is a view of a proximal face of an annular rib member of a movable exoskeleton assembly of the surgical instrument of FIG. 46.
Figure 56:
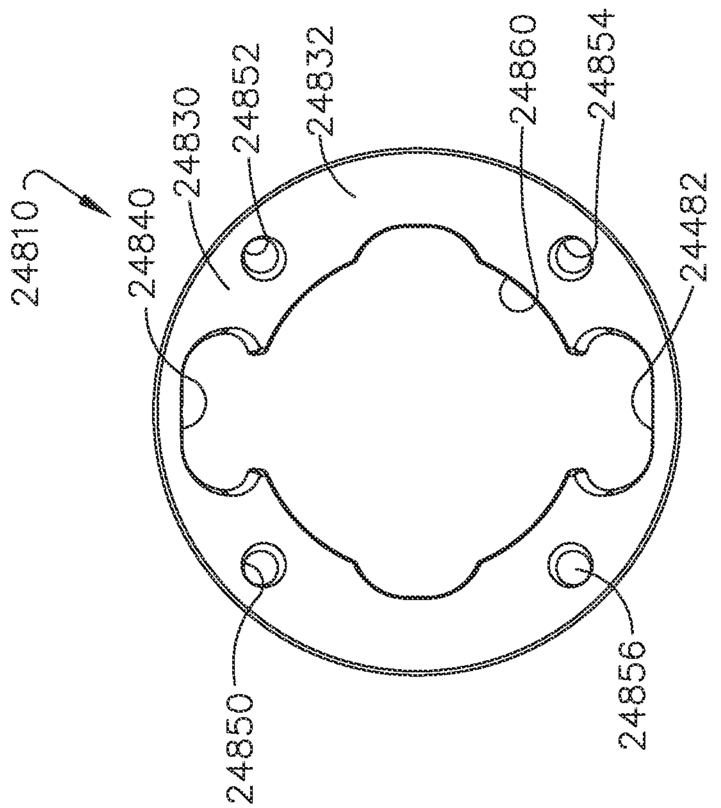
FIG. 56 is a view of a distal face of the annular rib member of FIG. 55.
Figure 57:
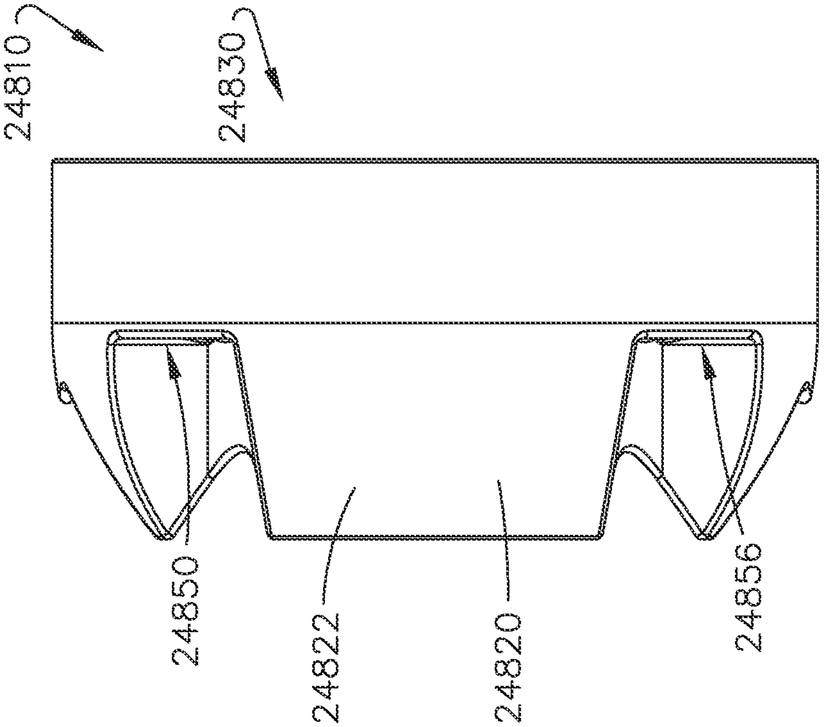
FIG. 57 is a side view of the annular rib member of FIGS. 55 and 56.

Turning now to FIGS. 55-58, in accordance with at least one aspect, the articulation joint 24200 comprises a movable exoskeleton assembly 24800. In one form, the movable exoskeleton assembly 24800 comprises a series 24802 of movably interfacing annular rib members 24810. As can be seen in FIGS. 55-57, each annular rib member 24810 comprises a first or proximal face 24820 that comprises a convex or domed portion 24822. Each annular rib member 24810 further comprises a second or distal face 24830 that is concave or dished. Each annular rib member 24810 further comprises an upper spine passage 24840 that is configured to accommodate passage of the upper flexible spine assembly 24400 therethrough and a lower spine passage 24842 that is configured to accommodate passage of the lower flexible spine assembly 24500 therethrough. In addition, each annular rib member 24810 further comprises four articulation passages 24850, 24852, 24854, and 24856 to accommodate passage of articulation actuators in the form of articulation cables 24242, 22446, 24250, and 24254 therethrough. See FIG. 49. Each annular rib member 24810 further comprises a central drive passage 24860 that is configured to accommodate passage of the constant velocity (CV) drive shaft assembly 2620 therethrough.

Figure 58:
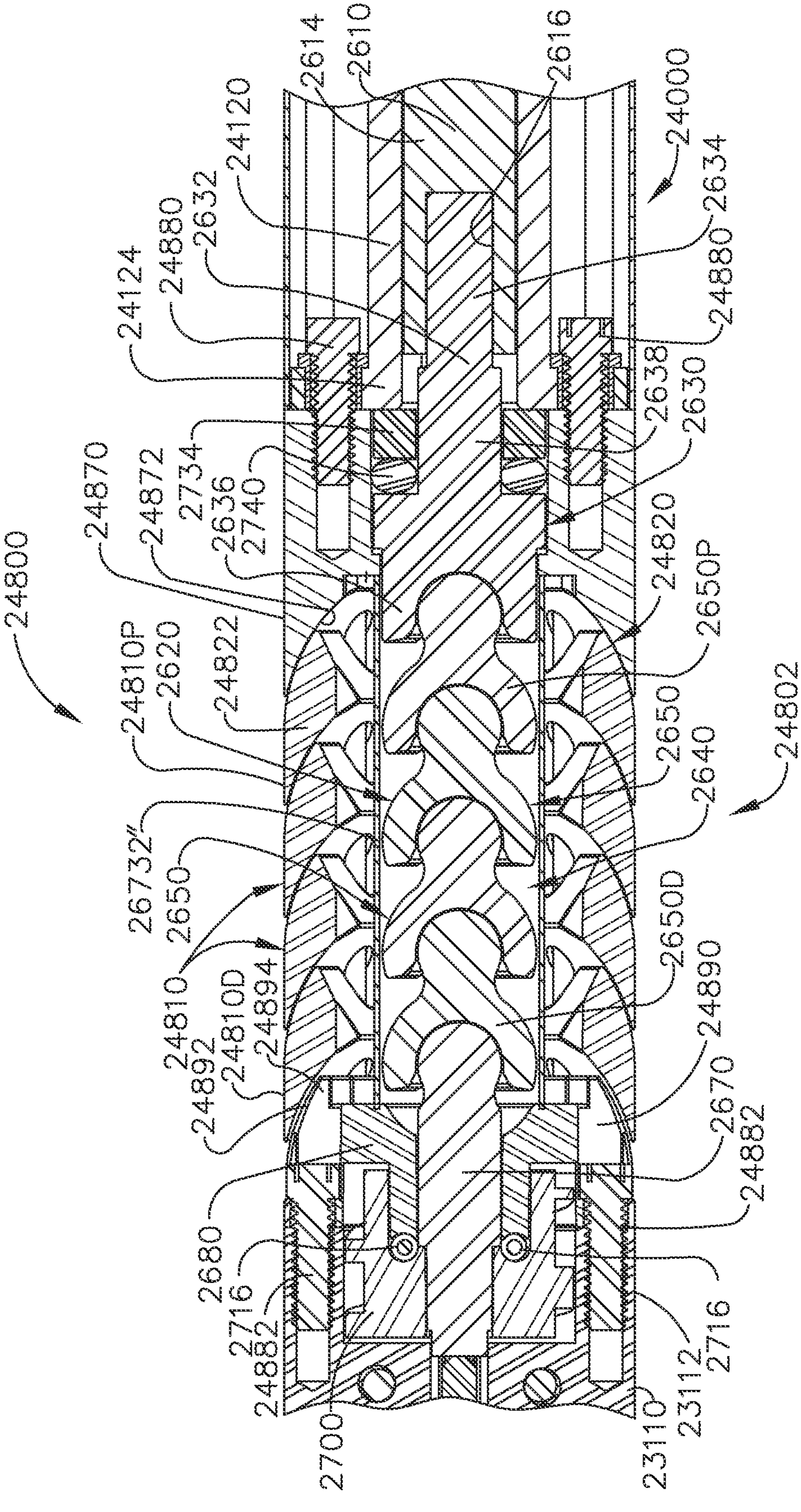
FIG. 58 is a partial cross-sectional view of a portion of the surgical instrument of FIG. 46.

As can be seen in FIG. 58, the movable exoskeleton assembly 24800 comprises a proximal attachment rib 24870 that is configured to attach the movable exoskeleton assembly 24800 to the distal end 24124 of the proximal support shaft 24120 by cap screws 24880 or other suitable fastener arrangements. The proximal attachment rib 24870 comprises a first or distal face 24872 that is concave or dished to receive or movably interface with the convex or domed portion 24822 of the proximal face 24820 of a proximal-most annular rib member 24810P. Similarly, the movable exoskeleton assembly 24800 comprises a distal attachment rib 24890 that is configured to attach the movable exoskeleton assembly 24800 to the proximal end 23112 of the elongate channel 23110 by cap screws 24882 or other suitable fasteners. The distal attachment rib 24890 comprises a first or proximal face 24892 that comprises a convex or domed portion 24894 that configured to be received in or movably interface with the concave or dished distal face 24832 of a distal-most annular rib member 24810D. In various embodiments, the annular rib members 24810, 24810P, and 24810D may be fabricated from any suitable metal (e.g., stainless steel, titanium, etc.) or other suitable material. The annular rib members 24810, 24810P, and 24810D may be formed by suitable drawing or forming operations, by machining or casting. The proximal faces 24820 and the distal faces 24830 may be polished or otherwise finished to a desirable smooth finish to reduce friction and facilitate movement between the annular rib members 24810, 24810P, and 24810D. In accordance with one aspect, all edges on each annular rib member 24810, 24810P, 24810D are rounded to facilitate relative movement between the annular rib members. The proximal attachment rib 24870 and the distal attachment rib 24890 may be formed with similar attributes.

The surgical instrument 22010 also comprises an articulation system 24240 that is configured to apply articulation motions to the surgical end effector 23000 to articulate the surgical end effector 23000 relative to the elongate shaft assembly 24000. In at least one arrangement, for example, as mentioned above, the articulation system 24240 comprises four articulation cables 24242, 24246, 24250, and 24254 that extend through the elongate shaft assembly 2400. See FIG. 49. In the illustrated arrangement, the articulation cables 24242, 24246 pass through the proximal attachment rib 24870 and through each of the annular rib members 24810P, 24810, and 24810D to be secured to the distal attachment rib 24890. In one arrangement for example, each of the articulation cables 24242, 24246 are secured to the distal attachment rib 24890 by corresponding attachment lugs 24243. See FIGS. 61 and 63. Likewise, the articulation cables 24250 and 24254 extend through the proximal attachment rib 24870 and through each of the annular rib members 24810P, 24810, and 24810D to be secured to the distal attachment rib 24890 by corresponding attachment lugs 24243.

Figure 59:
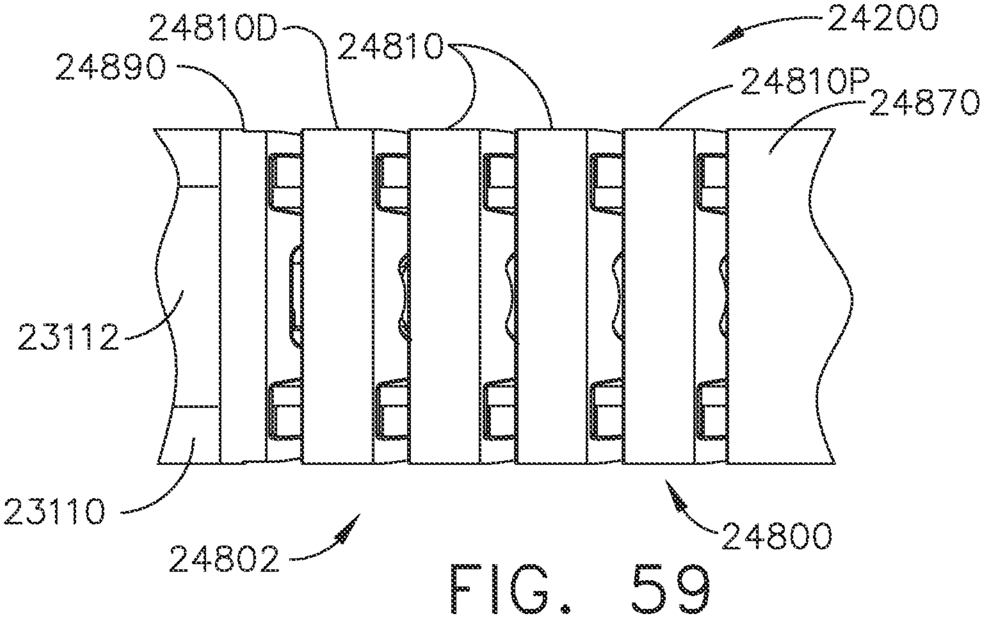
FIG. 59 is a side view of an articulation joint of the surgical instrument of FIG. 46 when the surgical end effector thereof is in an unarticulated position.
Figure 60:
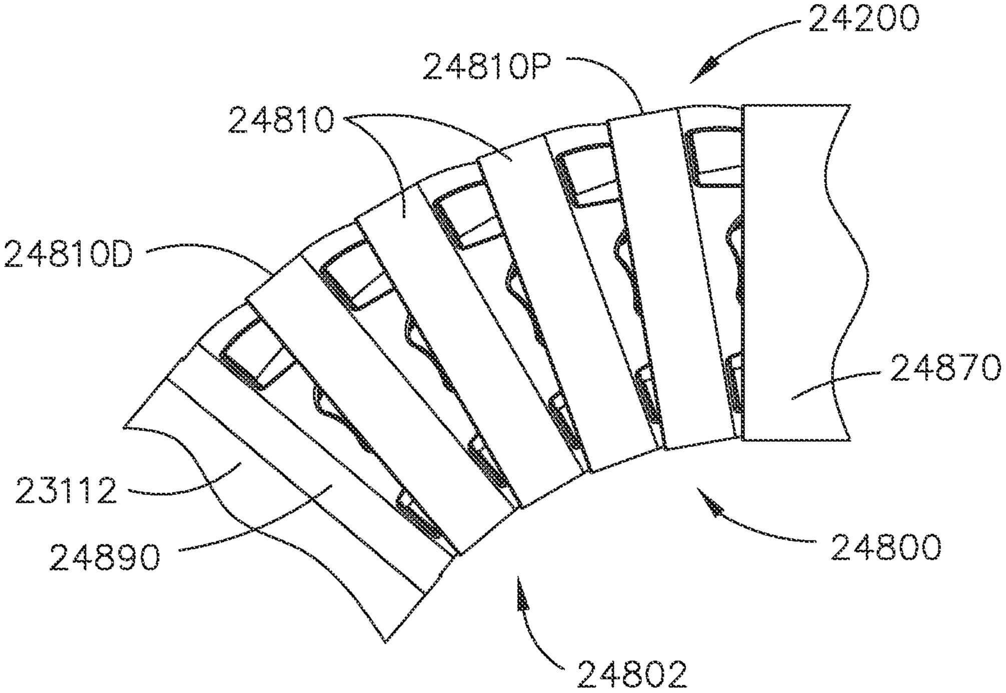
FIG. 60 is another side view of the articulation joint of FIG. 59 when the surgical end effector is in an articulated position.
Figure 61:
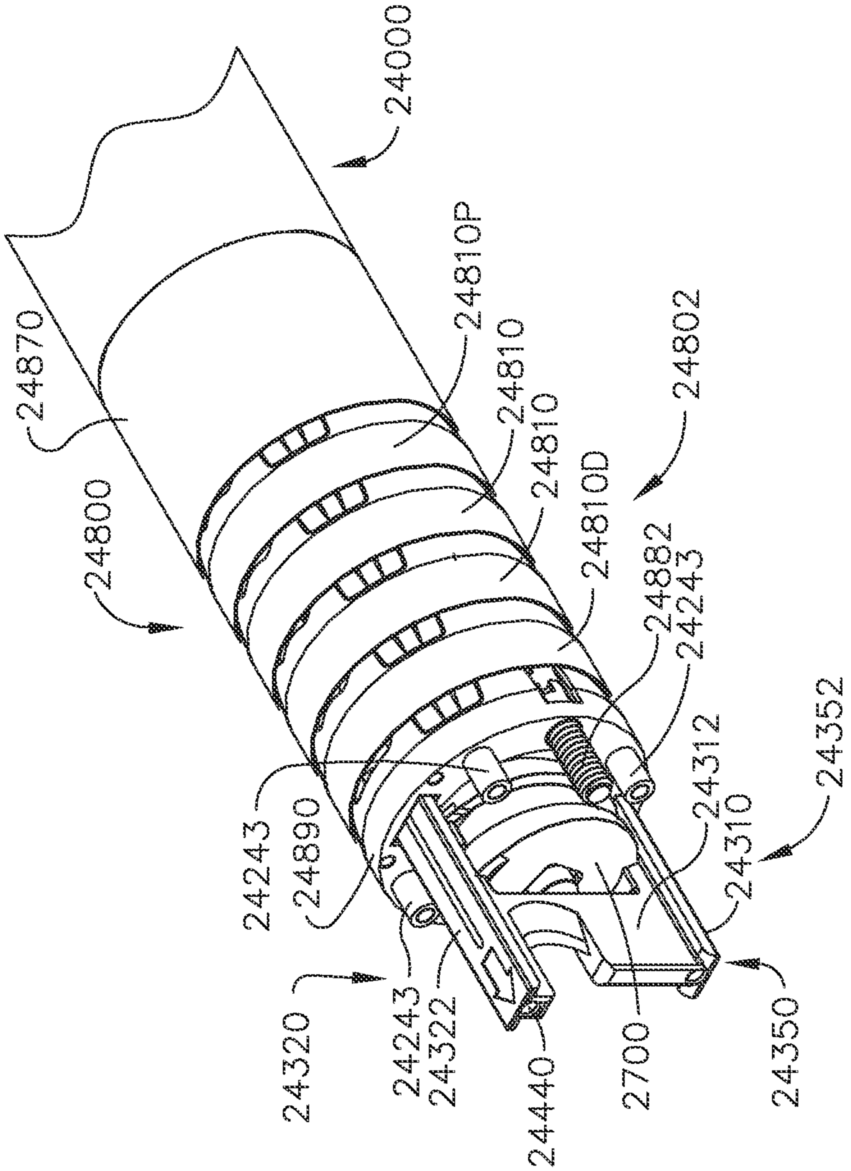
FIG. 61 is partial perspective view of a portion of the surgical instrument of FIG. 46 with the surgical end effector omitted for clarity.
Figure 62:
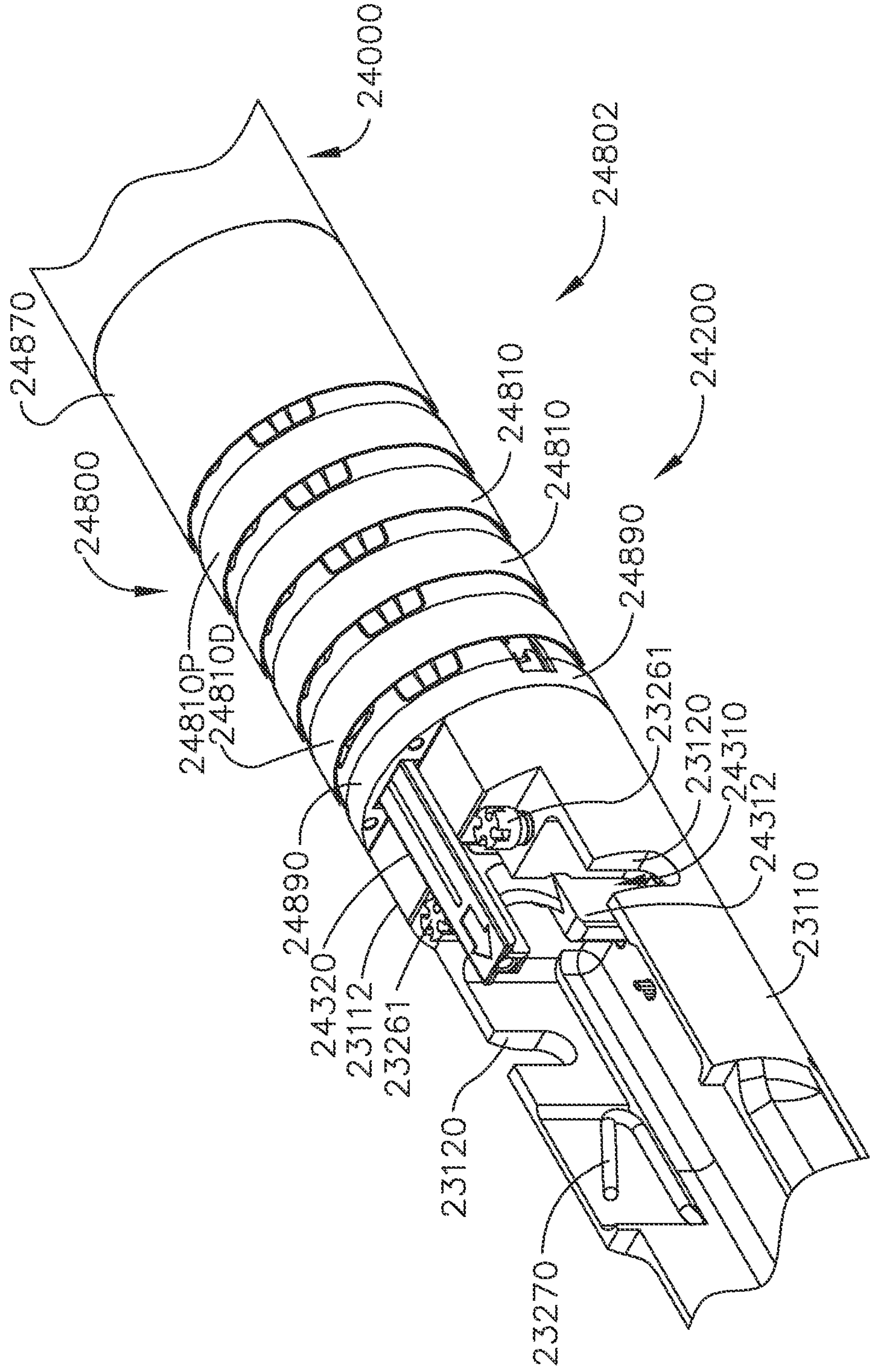
FIG. 62 is another partial perspective view of a portion of the surgical instrument of FIG. 46.
Figure 63:
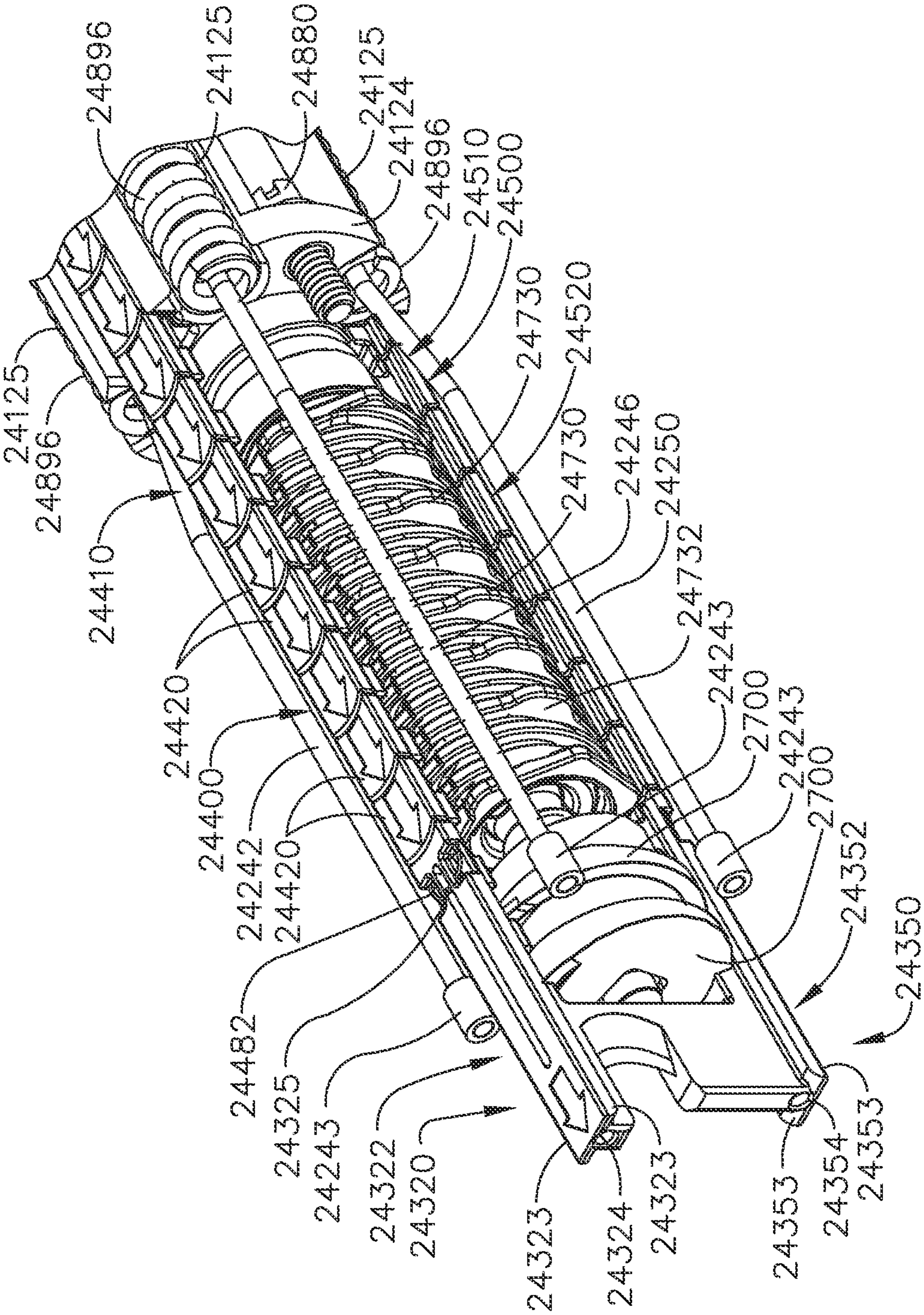
FIG. 63 is another partial perspective view of a portion of the surgical instrument of FIG. 46.

In one arrangement, each of the articulation cables 24242, 24246, 24250, and 24254 extend through corresponding coil springs 24896 that are supported in cavities 24125 in the distal end 24124 of the rigid proximal support shaft 24120. In addition, each coil spring 24896 is associated with a tensioning lug 24897 that is also journaled onto each respective articulation cable 24242, 24246, 24250, and 24524 and is secured thereon to attain a desired amount of compression in each spring 24896 which serves to retain the annular rib members 24810P, 24810, and 24810D in movable engagement with each other and with the proximal attachment rib 24870 and the distal attachment rib 24890. The cables 24242, 24246, 24250, and 24254 operably interface with an articulation control system that is supported in the housing of the surgical instrument 22010. For example, as was discussed above, a proximal portion of each cable 24242, 24246, 24250, and 24254 may be spooled on a corresponding rotary spool or cable-management system 2007 (FIG. 2) in the housing portion of the surgical instrument 22010 that is configured to payout and retract each cable 24242, 24246, 24250, and 24254 in desired manners. The spools/cable management system may be motor powered or manually powered (ratchet arrangement, etc.). FIG. 59 illustrates the articulation joint 24200 in an unarticulated position and FIG. 60 illustrates the articulation joint in one articulated configuration. Such arrangement permits the surgical end effector 23000 to be articulated through multiple articulation planes relative to the elongate shaft assembly 24000.

Figure 64:
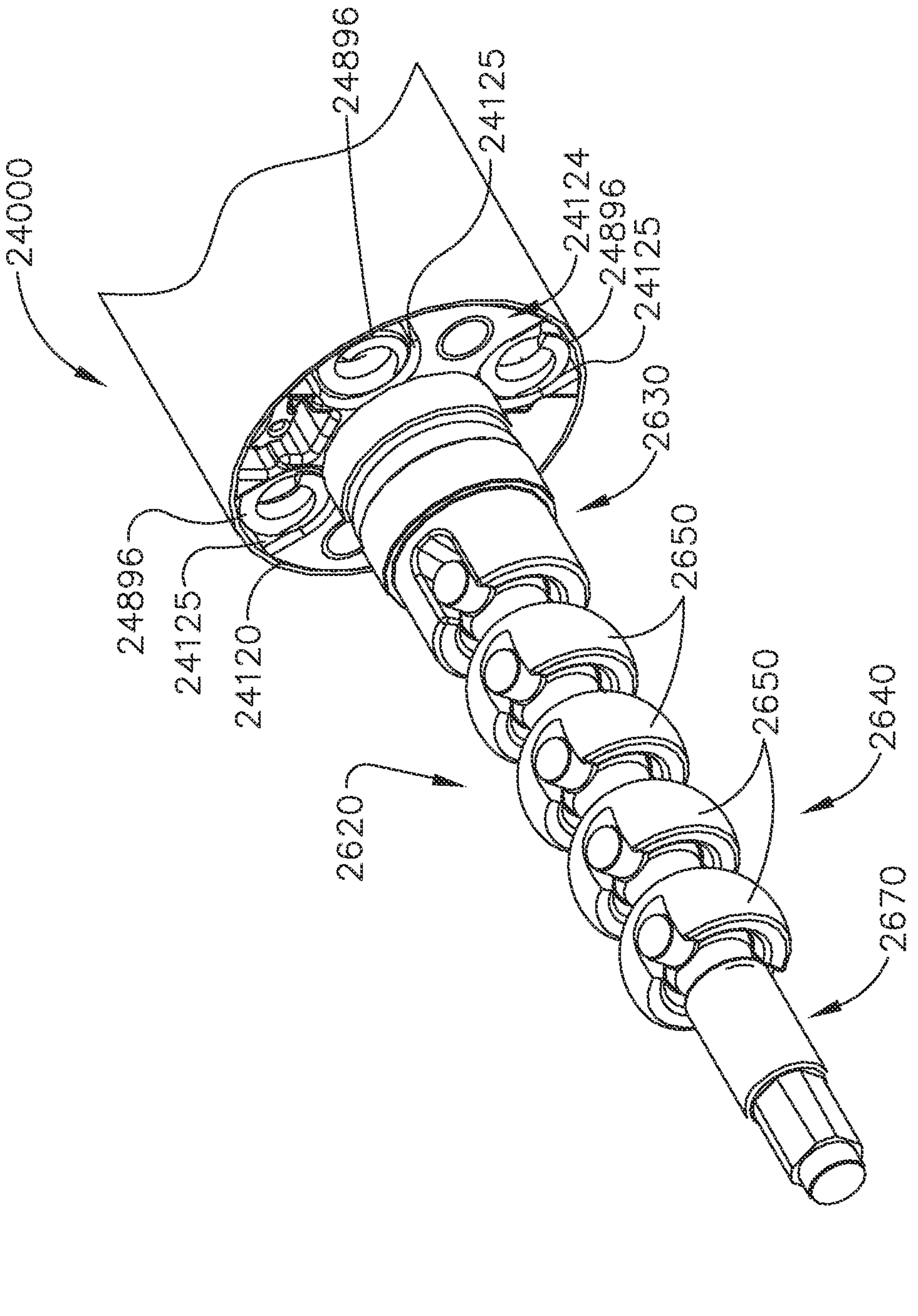
FIG. 64 is a perspective view of a CV drive shaft assembly and a portion of the elongate shaft assembly of the surgical instrument of FIG. 46.
Figure 65:
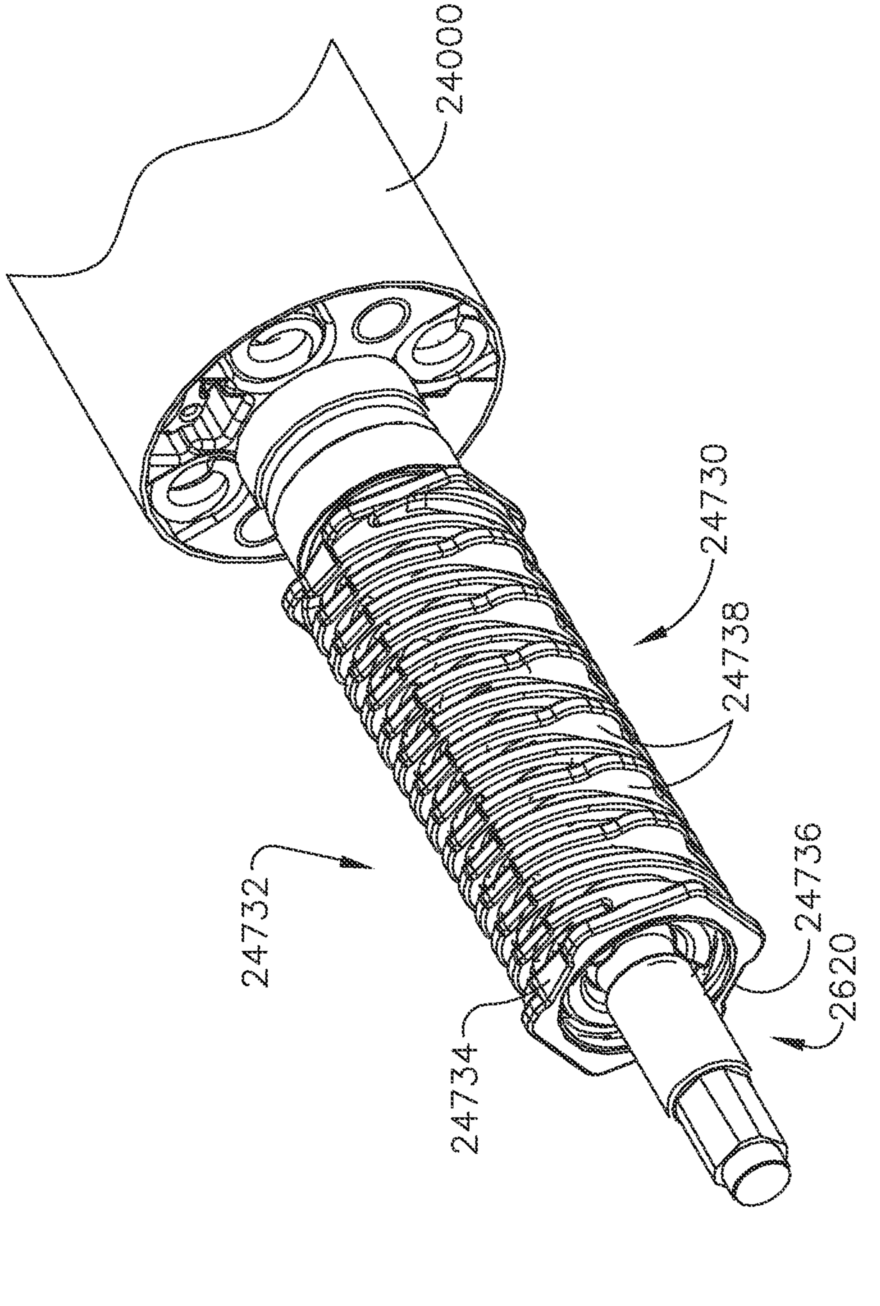
FIG. 65 is another perspective view of the CV drive shaft assembly and elongated shaft assembly of FIG. 64 with a drive cover embodiment installed around the CV drive shaft assembly.

As can be seen in FIGS. 49, 58, and 64, the surgical instrument 22010 employs a constant velocity (CV) drive shaft assembly 2620 that spans or extends axially through the articulation joint 24200. The operation and construction of the CV drive shaft assembly 2620 was described in detail above and will not be repeated here beyond what is necessary to understand the operation of the surgical instrument 22010. Briefly as described above, the CV drive shaft assembly 2620 comprises a proximal CV drive assembly 2630 and a distal CV drive shaft 2670. The proximal CV drive assembly 2630 comprises a proximal shaft segment 2632 that consists of an attachment shaft 2634 that is configured to be non-rotatably received within a similarly-shaped coupler cavity 2616 in the distal end 2614 of the proximal rotary drive shaft 2610. The proximal shaft segment 2632 operably interfaces with a series 2640 of movably coupled drive joints 2650. As can be seen in FIG. 58 as was also described previously, to ensure that the drive joints 2650 are engaged with each other, a proximal drive spring 2740 is employed to apply an axial biasing force to the series 2640 of drive joints 2650. For example, as can be seen in FIG. 58, proximal drive spring 2740 is positioned between the proximal mounting bushing 2734 and a support flange that is formed between the distal socket portion 2636 and a proximal barrel portion 2638 of the proximal shaft segment 2632. In one arrangement, the proximal drive spring 2740 may comprise an elastomeric O-ring received on the proximal barrel portion 2638 of the proximal shaft segment 2632. The proximal drive spring 2740 lightly biases the drive joints 2650 together to decrease any gaps that occur during articulation. This ensures that the drive joints 2650 transfer loads torsionally. It will be appreciated, however, that in at least one arrangement, the proximal drive spring 2740 does not apply a high enough axial load to cause firing loads to translate through the articulation joint 2200.

Figure 66:
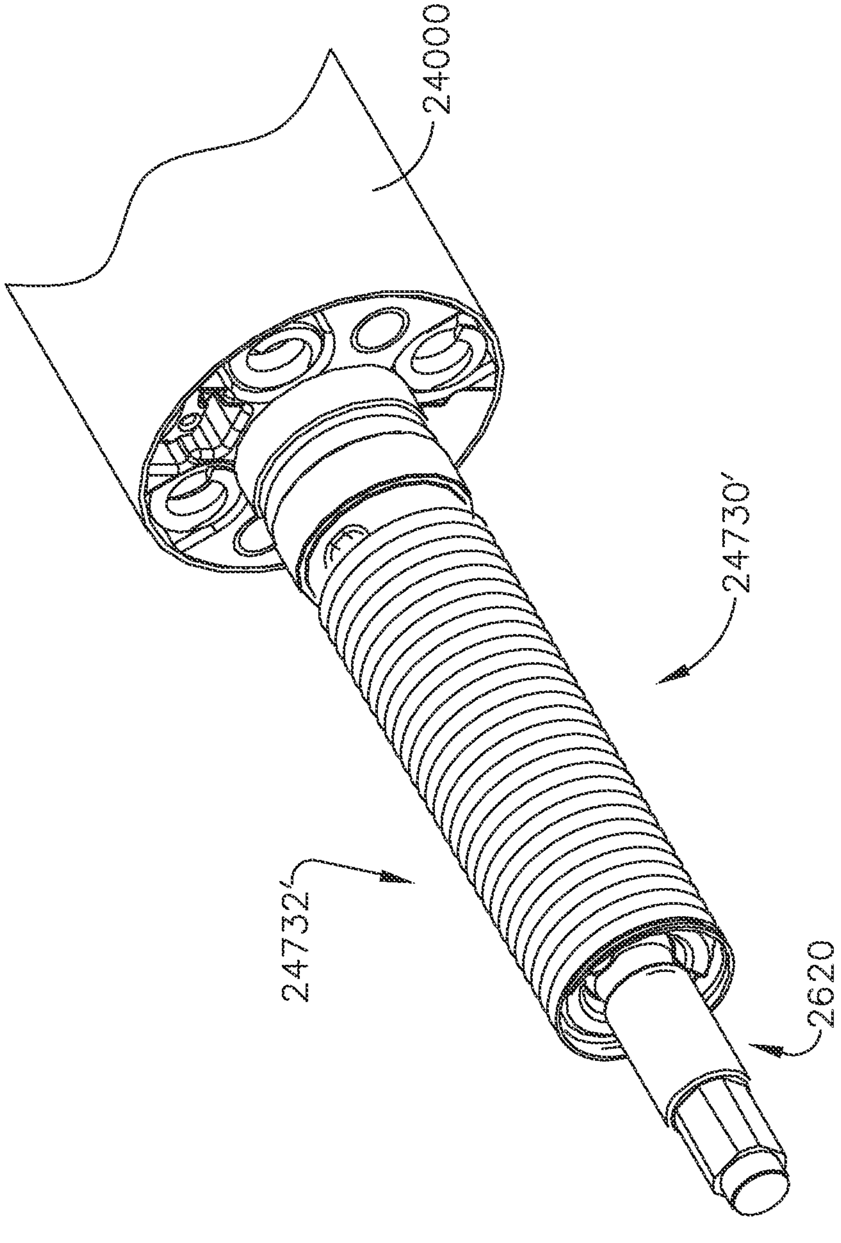
FIG. 66 is another perspective view of the CV drive shaft assembly and elongated shaft assembly of FIG. 64 with another drive cover embodiment installed around the CV drive shaft assembly.
Figure 67:
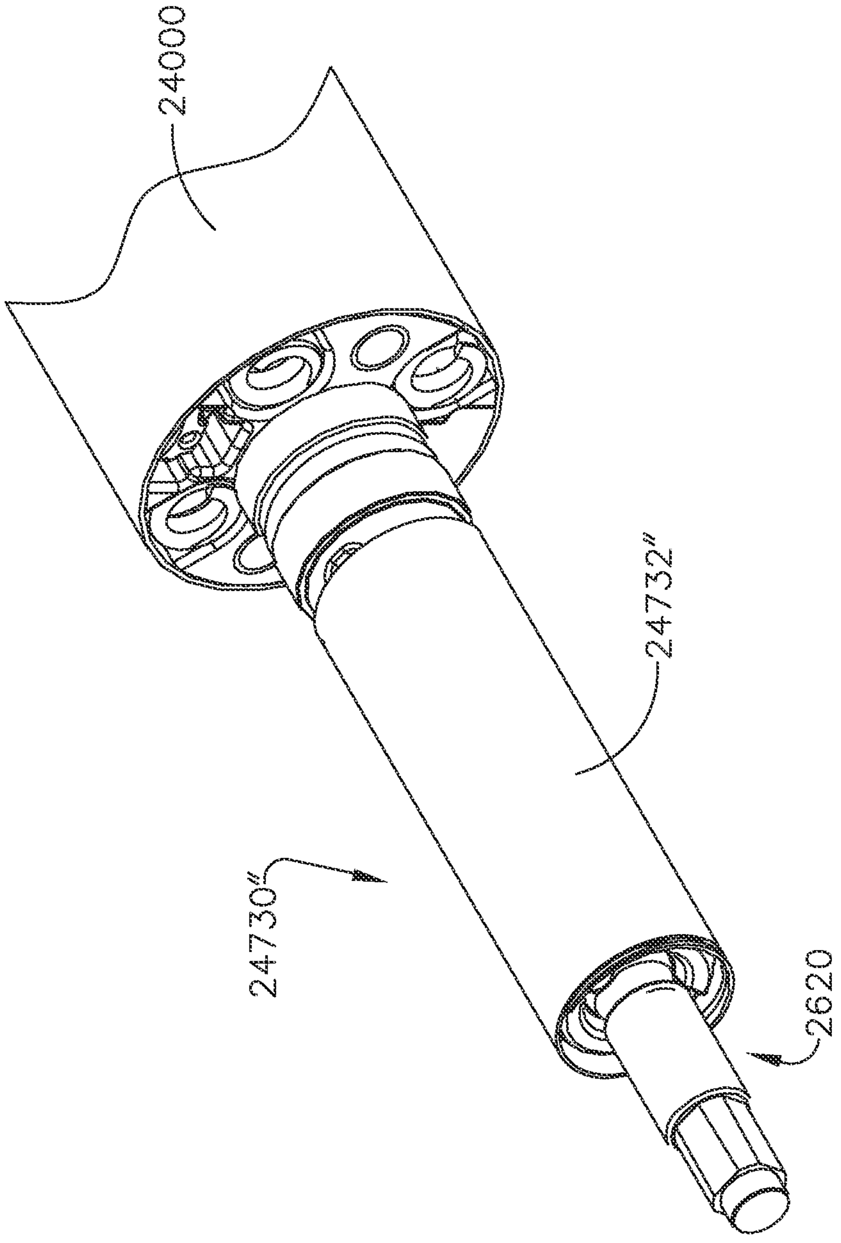
FIG. 67 is another perspective view of the CV drive shaft assembly and elongated shaft assembly of FIG. 64 with another drive cover embodiment installed around the CV drive shaft assembly.
Figure 68:
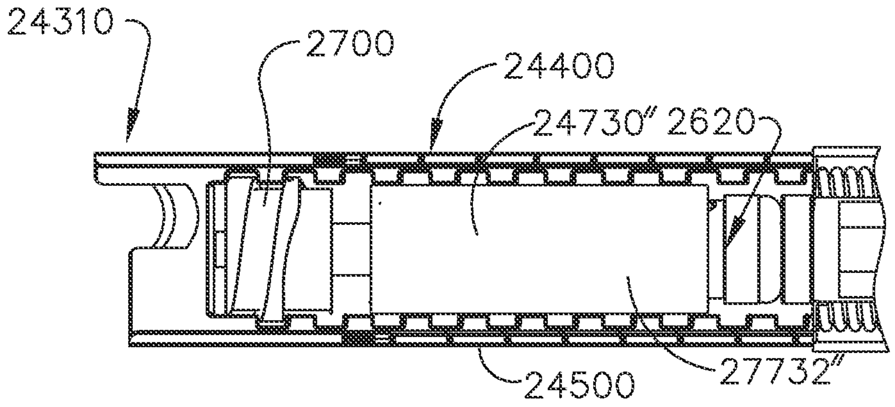
FIG. 68 is a side view of a portion of the firing system of the surgical instrument of FIG. 46 with the drive cover of FIG. 67 installed around the CV drive shaft assembly.
Figure 69:
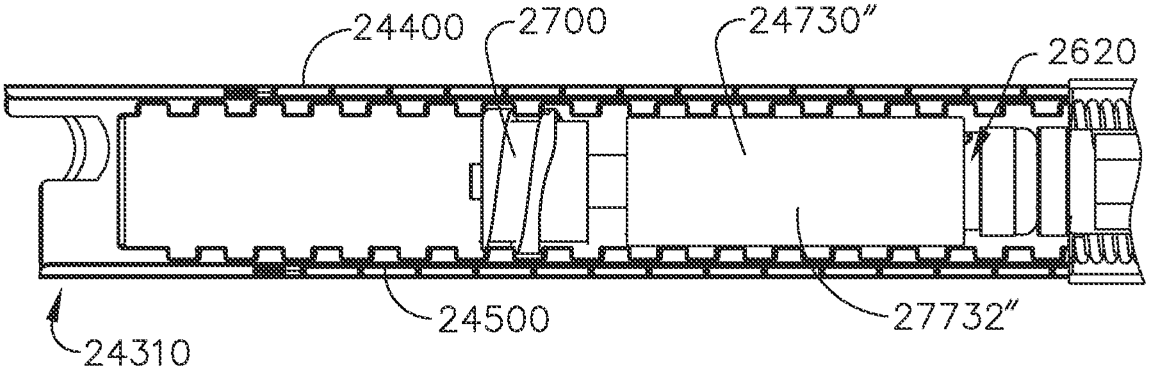
FIG. 69 is another side view of the portion of the firing system and drive cover of FIG. 68.

To further prevent the drive joints 2650 from buckling during articulation, the series 2640 of movably coupled drive joints 2650 extend through at least one low friction drive cover 24730 that extends through the central drive passage 24860 in each of the annular rib members 24810. In the arrangement depicted in FIGS. 63 and 65, the drive cover 24730 comprises an outer and inner cut hypotube 24732. Such hypotube 24732 may be fashioned from metal (e.g., stainless steel, etc.) and have multiple series of cuts or slits therein that may be made using laser cutter arrangements. In the illustrated arrangement, the hypotube 24732 may be fabricated with an upper relief passage 24734 that provides clearance for the upper flexible spine assembly 24400 to pass thereover during operation while the surgical end effector 23000 is in an articulated position and articulated positions. In addition, the hypotube 24732 may have a lower relief passage 24736 to provide similar clearance for the lower flexible spine assembly 24500. As can also be seen in FIG. 65, the hypotube 24732 may be shaped with diametrically opposed lateral tab portions 24738 to provide lateral stability during articulation. FIG. 66 illustrates an alternative drive cover 24730' that comprises an inner cut hypotube 24732'. FIGS. 58, 67, 68, and 69 illustrate an alternative drive cover 24730" that comprises flexible heat shrink tubing 24732" that is applied over the constant velocity (CV) drive shaft assembly 2620. In still other arrangements, the drive cover may comprise a coiled spring or coiled member as well.

Various embodiments of the present disclosure provide advantages over previous surgical endocutter configurations that are capable of articulation. For example, pushing a firing member forward in an articulating end effector generally requires a lot of force and that force must be balanced. For example, when firing the firing member at an angle of greater than sixty degrees, it becomes very difficult to push a beam through the articulation joint. The joint also experiences significant loads which may cause the articulation joint to de-articulate. By employing an upper flexible drive arrangement and a lower flexible drive arrangement that are each flexible through the articulation joint, but then become rigid when they are distal to the articulation joint can allow for a large degree of articulation (e.g., articulation angles over seventy degrees) while applying balanced loads to the firing member that are constrained to the firing member and not to the articulation joint. Stated another way, torsional loads are applied proximal to the articulation joint instead of longitudinal loads which could lead to de-articulation of the end effector. The torsional loads are converted to longitudinal loads at a position that is distal to the articulation joint. Thus, the rotary drive screw serves to actually convert torsional motion or loads to longitudinal loads that are applied to the firing member at a location that is distal to the articulation joint.

Further, by longitudinally breaking up the threaded drive arrangements, the threaded drive arrangements pass through the articulation joint while also effectively decreasing the length of the surgical end effector. For example, each single vertebra tooth is significantly shorter than multiple pitches rigidly connected. The vertebra can angle as they pass through the articulation joint. This flexible interconnection enables the rotary drive screw to be closely positioned to the articulation joint as compared to being significantly spaced therefrom if all of the pitches were rigidly connected.

Example 1—A surgical end effector comprising a first jaw and a second jaw that is configured to move relative to the first jaw between an open position and a closed position. A firing member is supported for axial travel within the surgical end effector between a home position corresponding to the open position of the second jaw and an ending position. The firing member is configured to apply a first closure motion to the second jaw to move the second jaw from the open position to the closed position as the firing member is moved in a distal direction from the home position to the ending position. The firing member is further configured to apply a second closure motion to the second jaw to move the second jaw towards the first jaw when the firing member is moved in a proximal direction from the home position.

Example 2—The surgical end effector of Example 1, wherein the firing member comprises a vertically-extending firing member body that includes a top firing member feature that is configured to apply the first closure motion to the second jaw. The firing member further comprises a bottom firing member feature that is configured to slidably engage the first jaw as the firing member is moved between the home position and the ending position. At least one pre-compression feature is configured to contact a portion of the second jaw when the firing member is moved in a proximal direction from the home position.

Example 3—The surgical end effector of Example 2, wherein the second jaw is supported for pivotal travel between the open position and the closed position relative to the first jaw about a jaw pivot axis. At least one pre-compression feature is configured to contact the portion of the second jaw at a pre-compression location that is distal to the jaw pivot axis.

Example 4—The surgical end effector of Examples 1, 2 or 3, wherein the second jaw comprises a second jaw body that includes a proximal end and a distal end. The second jaw further comprises pivot features on the proximal end that define the jaw pivot axis. A portion of the second jaw comprises a jaw closure arm that protrudes from the proximal end and is configured to be contacted by at least one pre-compression feature as the firing member is moved proximally from the home position.

Example 5—The surgical end effector of Examples 2, 3 or 4, wherein the top firing member feature comprises a top tubular feature that protrudes from a top end of the vertically-extending firing member body and wherein the bottom firing member feature comprises a bottom tubular feature that protrudes from a bottom end of the vertically-extending firing member body.

Example 6—The surgical end effector of Example 5, wherein the first jaw comprises a bottom keyhole-shaped passage that is configured to slidably accommodate the bottom tubular feature on the firing member when the firing member is moved between the home position and the ending position, and wherein the second jaw comprises a top keyhole-shaped passage that is configured to slidably accommodate the top tubular feature on the firing member when the firing member is moved between the home position and the ending position.

Example 7—The surgical end effector of Examples 1, 2, 3, 4, 5 or 6, wherein the firing member is configured to operably engage a rotary drive member that is configured to apply an initial drive motion to the firing member to drive the firing member distally from the home position to a closure position wherein the firing member applies the first closure motion to the second jaw. The rotary drive member is further configured to apply a reversing drive motion to the firing member to drive the firing member in the proximal direction from the home position.

Example 8—The surgical end effector of Example 5, wherein the firing member is configured to operably engage a rotary drive member that is configured to apply an initial drive motion to the firing member to drive the firing member distally from the home position to a closure position wherein the firing member applies the first closure motion to the second jaw. The rotary drive member is further configured to apply a reversing drive motion to the firing member to drive the firing member in the proximal direction.

Example 9—The surgical end effector of Examples 5, 6 or 8, wherein the top tubular feature comprises an upper tooth that is configured to interface with the rotary drive member, and wherein the bottom tubular feature comprises at least one lower tooth that is configured to interface with the rotary drive member.

Example 10—The surgical end effector of Examples 7, 8 or 9, further comprising means for applying a bailout motion to the firing member to move the firing member from a position that is distal to the home position in a proximal direction to the home position without applying the reversing drive motion to the firing member with the rotary drive member.

Example 11—The surgical end effector of Examples 1, 2, 3, 4, 5, 6, 7, 8, 9 or 10, wherein the surgical end effector is configured to be operably coupled to a surgical instrument that comprises an upper flexible spine assembly that is attached to a top portion of the firing member and a lower flexible spine assembly that is attached to a bottom portion of the firing member. The surgical instrument further comprises a rotary drive member that operably interfaces with the upper flexible spine assembly and the lower flexible spine assembly such that the rotary drive member causes the upper flexible spine assembly and the lower flexible spine assembly to apply axial drive motions to the firing member to move the firing member between the home position and the ending position.

Example 12—The surgical end effector of Example 11, wherein the upper flexible spine assembly comprises an upper series of upper vertebra members that are loosely coupled together, and wherein the lower flexible spine assembly comprises a lower series of lower vertebra members that are loosely coupled together.

Example 13—The surgical end effector of Example 12, wherein the upper vertebra members are movably supported relative to each other by an upper flexible coupler member that is coupled to the top portion of the firing member and extends through each upper vertebra member, and wherein the lower vertebra members are movably supported relative to each other by a lower flexible coupler member that is coupled to the bottom portion of the firing member and extends through each lower vertebra member.

Example 14—The surgical end effector of Examples 2, 3, 4, 5, 6, 8, 9, 10, 11, 12 or 13, wherein the first jaw comprises a channel that is configured to operably support a surgical staple cartridge that comprises a cartridge body that operably supports a plurality of surgical staples therein. A cartridge sled is movably supported in the cartridge body and is configured to move between a beginning position and a finished position in the cartridge body to drive the surgical staples from the cartridge body. The second jaw comprises an anvil that is supported for pivotal travel between the open position and the closed position relative to the surgical staple cartridge. At least one pre-compression feature on the firing member is configured to drive the cartridge sled from the beginning position to the finished position when the firing member is distally driven from the home position to the ending position.

Example 15—A surgical instrument that comprises an elongate shaft that operably supports a firing drive system therein. A surgical end effector is operably coupled to the elongate shaft and comprises a first jaw and a second jaw that is configured to move relative to the first jaw between an open position and a closed position. A firing member operably interfaces with the firing drive system such that the firing drive system is configured to move the firing member between a home position that corresponds to the open position of the second jaw and an ending position. When the firing member is moved distally from the home position, the firing member applies a first closure motion to the second jaw to move the second jaw from the open position to the closed position. The firing drive system is configured to move the firing member proximally from the home position such that, when the firing member moves proximally from the home position, the firing member applies a second closure motion to the second jaw to move the second jaw towards the first jaw.

Example 16—The surgical instrument of Example 15, wherein the firing drive system comprises a rotary drive member that is configured to apply axial drive motions to the firing member.

Example 17—The surgical instrument of Example 16, further comprising an upper flexible spine assembly that is attached to a top portion of the firing member and operably interfaces with the rotary drive member such that rotation of the rotary drive member causes the upper flexible spine assembly to apply an upper axial drive motion to the firing member. A lower flexible spine assembly is attached to a bottom portion of the firing member and operably interfaces with the rotary drive member such that said rotation of the rotary drive member causes the lower flexible spine assembly to apply a lower axial drive motion to the firing member.

Example 18—The surgical instrument of Example 17, wherein the upper flexible spine assembly comprises an upper series of upper vertebra members that are loosely coupled together, and wherein the lower flexible spine assembly comprises a lower series of lower vertebra members that are loosely coupled together.

Example 19—A surgical instrument comprising an elongate shaft that operably supports a firing drive system therein. A surgical end effector is operably coupled to the elongate shaft and comprises a first jaw and a second jaw that is configured to move relative to the first jaw between an open position and a closed position. A firing member operably interfaces with the firing drive system such that the firing drive system is configured to move the firing member between a home position that corresponds to the open position of the second jaw and an ending position. When the firing member is moved distally from the home position, the firing member applies a first closure motion to the second jaw to move the second jaw from the open position to the closed position. When the firing member is moved proximally from the home position, the firing member applies a second closure motion to the second jaw. The surgical instrument further comprises means for applying a rotary motion to the firing member to move the firing member distally from the home position and proximally from the home position. The means for applying is further configured to apply additional rotary motions to a drive arrangement that interfaces with the firing member to apply axial drive motions to the firing member.

Example 20—The surgical instrument of Example 19, further comprising means for applying a retraction force to the firing member to move the firing member from a position that is distal to the home position to the home position without actuating the means for applying.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical end effector, comprising:

a first jaw;

a second jaw, wherein said second jaw is configured to move relative to said first jaw between an open position and a closed position about a jaw pivot axis, and wherein said second jaw comprises at least one anvil control portion extending from said second jaw; and a firing member supported for axial travel within said surgical end effector between a home position distal to said jaw pivot axis and corresponding to said open position of said second jaw and an ending position adjacent a distal end of said surgical end effector, wherein said firing member is configured to apply a first closure motion to said second jaw to move said second jaw from said open position to said closed position as said firing member is moved in a distal direction from said home position to said ending position, and wherein said firing member is further configured to apply a second closure motion to said at least one anvil control portion at a location that is below and distal to said jaw pivot axis to move said second jaw towards said first jaw when said firing member is moved in a proximal direction from said home position.

2. The surgical end effector of claim 1, wherein said firing member comprises:

a vertically-extending firing member body comprising:

a top firing member feature configured to apply said first closure motion to said second jaw;

a bottom firing member feature configured to slidably engage said first jaw as said firing member is moved between said home position and said ending position; and at least one pre-compression feature configured to contact said at least on anvil control portion at said location when said firing member is moved in a proximal direction from said home position.

3. The surgical end effector of claim 2, wherein said top firing member feature comprises a top tubular feature protruding from a top end of said vertically-extending firing member body and wherein said bottom firing member feature comprises a bottom tubular feature protruding from a bottom end of said vertically-extending firing member body.

4. The surgical end effector of claim 3, wherein said first jaw comprises a bottom keyhole-shaped passage configured to slidably accommodate said bottom tubular feature on said firing member when said firing member is moved between said home position and said ending position, and wherein said second jaw comprises a top keyhole-shaped passage configured to slidably accommodate said top tubular feature on said firing member when said firing member is moved between said home position and said ending position.

5. The surgical end effector of claim 3, wherein said firing member is configured to operably engage a rotary drive member configured to apply an initial drive motion to said firing member to drive said firing member distally from said home position to ft said ending position wherein said firing member applies the first closure motion to said second jaw, and wherein said rotary drive member is configured to apply a reversing drive motion to said firing member to drive said firing member in said proximal direction.

6. The surgical end effector of claim 5, wherein said top tubular feature comprises an upper tooth configured to interface with said rotary drive member, and wherein said bottom tubular feature comprises at least one lower tooth configured to interface with said rotary drive member.

7. The surgical end effector of claim 6, further comprising means for applying a bailout motion to said firing member to move said firing member from a position distal to said home position proximally to said home position without applying said reversing drive motion to said firing member with said rotary drive member.

8. The surgical end effector of claim 2, wherein said surgical end effector is configured to be operably coupled to a surgical instrument comprising:

an upper flexible spine assembly attached to a top portion of said firing member;

a lower flexible spine assembly attached to a bottom portion of said firing member; and a rotary drive member, wherein said rotary drive member operably interfaces with said upper flexible spine assembly, wherein said rotary drive member operably interfaces with said lower flexible spine assembly, and wherein said rotary drive member causes said upper flexible spine assembly and said lower flexible spine assembly to apply axial drive motions to said firing member to move said firing member between said home position and said ending position.

9. The surgical end effector of claim 8, wherein said upper flexible spine assembly comprises an upper series of upper vertebra members that are loosely coupled together, and wherein said lower flexible spine assembly comprises a lower series of lower vertebra members that are loosely coupled together.

10. The surgical end effector of claim 9, wherein said upper vertebra members are movably supported relative to each other by an upper flexible coupler member that is coupled to said top portion of said firing member and extends through each said upper vertebra member, and wherein said lower vertebra members are movably supported relative to each other by a lower flexible coupler member that is coupled to said bottom portion of said firing member and extends through each said lower vertebra member.

11. The surgical end effector of claim 1, wherein said second jaw comprises:

a second jaw body comprising a second jaw proximal end and a second jaw distal end; and pivot features on said second jaw proximal end, wherein said pivot features define said jaw pivot axis.

12. The surgical end effector of claim 1, wherein said first jaw comprises a channel configured to operably support a surgical staple cartridge, wherein said surgical staple cartridge comprises:

a cartridge body operably supporting a plurality of surgical staples therein; and a cartridge sled movably supported in said cartridge body, wherein said cartridge sled is configured to move between a beginning position and a finished position in said cartridge body to drive said surgical staples from said cartridge body, and wherein said second jaw comprises an anvil supported for pivotal travel between said open position and said closed position relative to said surgical staple cartridge, and wherein said at least one pre-compression feature on said firing member is configured to contact and drive said cartridge sled from said beginning position to said finished position when said firing member is distally driven from said home position to said ending position.

13. The surgical end effector of claim 1, wherein said firing member is configured to operably engage a rotary drive member configured to apply an initial drive motion to said firing member to drive said firing member distally from said home position to said ending position wherein said firing member applies the first closure motion to said second jaw, and wherein said rotary drive member is configured to apply a reversing drive motion to said firing member to drive said firing member in said proximal direction from said home position.

14. The surgical end effector of claim 13, further comprising means for applying a retraction force to said firing member to move said firing member from a position distal to said home position to said home position without actuating said rotary drive member.

15. A surgical instrument, comprising:

an elongate shaft operably supporting a firing drive system therein; and a surgical end effector operably coupled to said elongate shaft, wherein said surgical end effector comprises:

a first jaw;

a second jaw, wherein said second jaw is configured to move relative to said first jaw between an open position and a closed position about a jaw pivot axis, and wherein said second jaw comprises at least one anvil control portion extending downward from said second jaw such that said at least one anvil control portion extends below said jaw pivot axis at a location that is distal to said jaw pivot axis; and a firing member operably interfacing with said firing drive system, wherein said firing drive system is configured to move said firing member between a home position distal to said jaw pivot axis and corresponding to said open position of said second jaw and an ending position adjacent a distal end of said surgical instrument, wherein when said firing member is moved distally from said home position, said firing member is configured to apply a first closure motion to said second jaw to move said second jaw from said open position to said closed position, and wherein said firing drive system is configured to move said firing member proximally from said home position such that, when said firing member moves proximally from said home position, said firing member applies a second closure motion to said at least one anvil control portion at said location to move said second jaw towards said first jaw.

16. The surgical instrument of claim 15, wherein said firing drive system comprises a rotary drive member configured to apply axial drive motions to said firing member.

17. The surgical instrument of claim 16, further comprising:

an upper flexible spine assembly attached to a top portion of said firing member, wherein said upper flexible spine assembly operably interfaces with said rotary drive member, such that rotation of said rotary drive member causes said upper flexible spine assembly to apply an upper axial drive motion to said firing member; and a lower flexible spine assembly attached to a bottom portion of said firing member, wherein said lower flexible spine assembly operably interfaces with said rotary drive member such that said rotation of said rotary drive member causes said lower flexible spine assembly to apply a lower axial drive motion to said firing member.

18. The surgical instrument of claim 17, wherein said upper flexible spine assembly comprises an upper series of upper vertebra members that are loosely coupled together, and wherein said lower flexible spine assembly comprises a lower series of lower vertebra members that are loosely coupled together.

19. A surgical end effector, comprising:

a first jaw;

a second jaw, wherein said second jaw is configured to move relative to said first jaw between an open position and a closed position; and a firing member supported for axial travel within said surgical end effector between a home position corresponding to said open position of said second jaw and an ending position, wherein said firing member comprises:

a vertically-extending firing member body comprising:

a top tubular feature protruding from a top end of said vertically-extending firing member body, wherein said top tubular feature is configured to apply a first closure motion to said second jaw to move said second jaw from said open position to said closed position as said firing member is moved in a distal direction from said home position to said ending position;

a bottom tubular feature protruding from a bottom end of said vertically-extending firing member, wherein said bottom tubular feature is configured to slidably engage said first jaw as said firing member is moved between said home position and said ending position; and at least one pre-compression feature configured to apply a second closure motion to said second jaw to move said second jaw towards said first jaw when said firing member is moved in a proximal direction from said home position.

20. The surgical end effector of claim 19, wherein said first jaw comprises a bottom keyhole-shaped passage configured to slidably accommodate said bottom tubular feature on said firing member when said firing member is moved between said home position and said ending position, and wherein said second jaw comprises a top keyhole-shaped passage configured to slidably accommodate said top tubular feature on said firing member when said firing member is moved between said home position and said ending position.

21. The surgical end effector of claim 19, wherein said firing member is configured to operably engage a rotary drive member configured to apply an initial drive motion to said firing member to drive said firing member distally from said home position to said ending position wherein said firing member applies the first closure motion to said second jaw, and wherein said rotary drive member is configured to apply a reversing drive motion to said firing member to drive said firing member in said proximal direction.

22. The surgical end effector of claim 21, wherein said top tubular feature comprises an upper tooth configured to interface with said rotary drive member, and wherein said bottom tubular feature comprises at least one lower tooth configured to interface with said rotary drive member.

23. The surgical end effector of claim 21, further comprising means for applying a bailout motion to said firing member to move said firing member from a position distal to said home position proximally to said home position without applying said reversing drive motion to said firing member with said rotary drive member.

24. The surgical end effector of claim 19, wherein said surgical end effector is configured to be operably coupled to a surgical instrument comprising:

an upper flexible spine assembly attached to a top portion of said firing member;

a lower flexible spine assembly attached to a bottom portion of said firing member; and a rotary drive member, wherein said rotary drive member operably interfaces with said upper flexible spine assembly, wherein said rotary drive member operably interfaces with said lower flexible spine assembly, and wherein said rotary drive member causes said upper flexible spine assembly and said lower flexible spine assembly to apply axial drive motions to said firing member to move said firing member between said home position and said ending position.

25. The surgical end effector of claim 24, wherein said upper flexible spine assembly comprises an upper series of upper vertebra members that are loosely coupled together, and wherein said lower flexible spine assembly comprises a lower series of lower vertebra members that are loosely coupled together.

26. The surgical end effector of claim 25, wherein said upper vertebra members are movably supported relative to each other by an upper flexible coupler member that is coupled to said top portion of said firing member and extends through each said upper vertebra member, and wherein said lower vertebra members are movably supported relative to each other by a lower flexible coupler member that is coupled to said bottom portion of said firing member and extends through each said lower vertebra member.

27. The surgical end effector of claim 19, wherein said first jaw comprises a channel configured to operably support a surgical staple cartridge, wherein said surgical staple cartridge comprises:

a cartridge body operably supporting a plurality of surgical staples therein; and a cartridge sled movably supported in said cartridge body, wherein said cartridge sled is configured to move between a beginning position and a finished position in said cartridge body to drive said surgical staples from said cartridge body, and wherein said second jaw comprises an anvil supported for pivotal travel between said open position and said closed position relative to said surgical staple cartridge, and wherein said at least one pre-compression feature on said firing member is configured to contact and drive said cartridge sled from said beginning position to said finished position when said firing member is distally driven from said home position to said ending position.

28. A surgical end effector, comprising:

a first jaw;

a second jaw, wherein said second jaw is configured to move relative to said first jaw between an open position and a closed position; and a firing member supported for axial travel within said surgical end effector between a home position corresponding to said open position of said second jaw and an ending position;

an upper flexible spine assembly attached to a top portion of said firing member;

a lower flexible spine assembly attached to a bottom portion of said firing member such that said lower flexible spine assembly is permanently spaced from said upper flexible spine assembly out of engagement therewith; and a rotary drive member, wherein said rotary drive member operably interfaces with said upper flexible spine assembly, wherein said rotary drive member operably interfaces with said lower flexible spine assembly, and wherein said rotary drive member causes said upper flexible spine assembly and said lower flexible spine assembly to apply axial drive motions to said firing member to move said firing member between said home position and said ending position.

29. The surgical end effector of claim 28, wherein said firing member comprises:

a vertically-extending firing member body comprising:

a top firing member feature configured to apply a first closure motion to said second jaw to move said second jaw from said open position to said closed position as said firing member is moved in a distal direction from said home position to said ending position;

a bottom firing member feature configured to slidably engage said first jaw as said firing member is moved between said home position and said ending position; and at least one pre-compression feature configured to apply a second closure motion to said second jaw to move said second jaw towards said first jaw when said firing member is moved in a proximal direction from said home position.

30. The surgical end effector of claim 29, wherein said upper flexible spine assembly comprises an upper series of upper vertebra members that are loosely coupled together, and wherein said lower flexible spine assembly comprises a lower series of lower vertebra members that are loosely coupled together.

31. The surgical end effector of claim 30, wherein said upper vertebra members are movably supported relative to each other by an upper flexible coupler member that is coupled to said top portion of said firing member and extends through each said upper vertebra member, and wherein said lower vertebra members are movably supported relative to each other by a lower flexible coupler member that is coupled to said bottom portion of said firing member and extends through each said lower vertebra member.

32. The surgical end effector of claim 29, wherein said first jaw comprises a channel configured to operably support a surgical staple cartridge, wherein said surgical staple cartridge comprises:

a cartridge body operably supporting a plurality of surgical staples therein; and a cartridge sled movably supported in said cartridge body, wherein said cartridge sled is configured to move between a beginning position and a finished position in said cartridge body to drive said surgical staples from said cartridge body, and wherein said second jaw comprises an anvil supported for pivotal travel between said open position and said closed position relative to said surgical staple cartridge, and wherein said at least one pre-compression feature on said firing member is configured to contact and drive said cartridge sled from said beginning position to said finished position when said firing member is distally driven from said home position to said ending position.

* * * * *